(12) United States Patent
Theuer

(10) Patent No.: US 9,926,375 B2
(45) Date of Patent: Mar. 27, 2018

(54) ANTI-ENDOGLIN ANTIBODIES AND USES THEREOF

(71) Applicant: Tracon Pharmaceuticals, Inc., San Diego, CA (US)

(72) Inventor: Charles Theuer, La Jolla, CA (US)

(73) Assignee: TRACON PHARMACEUTICALS, INC., San Diego, CA (US)

( * ) Notice: Subject to any disclaimer, the term of this patent is extended or adjusted under 35 U.S.C. 154(b) by 39 days.

(21) Appl. No.: 15/131,312

(22) Filed: Apr. 18, 2016

(65) Prior Publication Data
US 2016/0257755 A1 Sep. 8, 2016

Related U.S. Application Data

(63) Continuation-in-part of application No. PCT/US2015/060136, filed on Nov. 11, 2015.

(60) Provisional application No. 62/078,788, filed on Nov. 12, 2014, provisional application No. 62/161,669, filed on May 14, 2015.

(51) Int. Cl.
| A61K 39/395 | (2006.01) |
| C07K 16/18 | (2006.01) |
| C07K 16/28 | (2006.01) |
| A61K 39/00 | (2006.01) |

(52) U.S. Cl.
CPC .... *C07K 16/2896* (2013.01); *A61K 2039/505* (2013.01); *C07K 2317/24* (2013.01); *C07K 2317/76* (2013.01)

(58) Field of Classification Search
None
See application file for complete search history.

(56) References Cited

U.S. PATENT DOCUMENTS

| 928,641 A | 7/1909 | Levi |
| 4,472,509 A | 9/1984 | Gansow et al. |
| 4,683,202 A | 7/1987 | Mullis |
| 4,816,567 A | 3/1989 | Cabilly et al. |
| 4,868,103 A | 9/1989 | Stavrianopoulos et al. |
| 4,938,948 A | 7/1990 | Ring et al. |
| 5,021,236 A | 6/1991 | Gries et al. |
| 5,391,377 A | 2/1995 | Barnwell |
| 5,530,101 A | 6/1996 | Queen et al. |
| 5,591,828 A | 1/1997 | Bosslet et al. |
| 5,631,169 A | 5/1997 | Lakowicz et al. |
| 5,756,097 A | 5/1998 | Landucci et al. |
| 5,796,097 A | 8/1998 | Lawrence |
| 5,928,641 A | 7/1999 | Seon |
| 6,096,289 A | 8/2000 | Goldenberg |
| 6,096,871 A | 8/2000 | Presta et al. |
| 6,190,660 B1 | 2/2001 | Seon |
| 6,200,566 B1 | 3/2001 | Seon |
| 6,267,958 B1 | 7/2001 | Andya et al. |
| 6,350,861 B1 | 2/2002 | Co et al. |
| 6,407,213 B1 | 6/2002 | Carter et al. |
| 6,610,293 B1 | 8/2003 | Fischer et al. |
| 6,737,056 B1 | 5/2004 | Presta |
| 6,881,557 B2 | 4/2005 | Foote |
| 7,091,321 B2 | 8/2006 | Gillies et al. |
| 7,097,836 B1 | 8/2006 | Seon |
| 7,112,412 B1 | 9/2006 | Bander |
| 7,115,716 B2 | 10/2006 | Watkins |
| 7,217,798 B2 | 5/2007 | Hinton et al. |
| 8,221,753 B2 | 7/2012 | Theuer et al. |
| 8,609,094 B2 | 12/2013 | Theuer et al. |
| RE45,499 E | 4/2015 | Schneider et al. |
| 9,150,652 B2 | 10/2015 | Theuer et al. |
| 9,518,122 B2 | 12/2016 | Theuer et al. |
| 2002/0136725 A1 | 9/2002 | Blackburn et al. |
| 2003/0003048 A1 | 1/2003 | Li et al. |
| 2003/0129193 A1 | 7/2003 | Thorpe et al. |
| 2003/0185832 A1 | 10/2003 | Thorpe et al. |
| 2004/0023313 A1 | 2/2004 | Boyle et al. |
| 2004/0033228 A1 | 2/2004 | Krause et al. |
| 2004/0175756 A1 | 9/2004 | Kolkman et al. |
| 2005/0037421 A1 | 2/2005 | Honda et al. |
| 2005/0048512 A1 | 3/2005 | Kolkman et al. |
| 2005/0053973 A1 | 3/2005 | Kolkman et al. |
| 2005/0089932 A1 | 4/2005 | Kolkman et al. |
| 2005/0164301 A1 | 7/2005 | Kolkman et al. |
| 2005/0221384 A1 | 10/2005 | Kolkman et al. |
| 2005/0238646 A1 | 10/2005 | Ledbetter et al. |

(Continued)

FOREIGN PATENT DOCUMENTS

| CN | 101084015 A | 12/2007 |
| CN | 102414221 A | 4/2012 |

(Continued)

OTHER PUBLICATIONS

Al-Lazikani et al, Standard conformations for the canonical structures of immunoglobulins. J. Mol Biology, 273(4):927-948, (1997).
Altschul et al., "Basic Local Alignment Search Tool," J. Mol. Biol. 215:403-410 (1990).
Altschul et al., "Gapped BLAST and PSI-BLAST: a new generation of protein database search programs," Nucl. Acids. Res. 25(17):3389-3402 (1997).
Bird, et al. Single-chain antigen-binding proteins. Science. 242(4877):423-6 (1998).
Burrows, et al. Up-regulation of endoglin on vascular endothelial cells in human solid tumors: implications for diagnosis and therapy. Clin Cancer Res. 1(12):1623-34 (1995).
Carillo and Lipman, "The Multiple Sequence Alignment Problem in Biology," SIAM J. Appl. Math 48(5):907-1082 (1988).

(Continued)

*Primary Examiner* — Christine J Saoud
*Assistant Examiner* — Jon M Lockard
(74) *Attorney, Agent, or Firm* — Wilson Sonsini Goodrich & Rosati

(57) ABSTRACT

The present application relates to compositions of humanized and deimmunized anti-endoglin antibodies and antigen-binding fragments thereof. One aspect relates to antibodies having one or more modifications in at least one amino acid residue of at least one of the framework regions of the variable heavy chain, the variable light chain or both. Another aspect relates to anti-endoglin antibodies which inhibit or treat fibrosis.

16 Claims, 25 Drawing Sheets

(56) References Cited

U.S. PATENT DOCUMENTS

| | | | |
|---|---|---|---|
| 2006/0147379 | A1 | 7/2006 | Bornhop et al. |
| 2006/0223096 | A1 | 10/2006 | Umana et al. |
| 2006/0292643 | A1 | 12/2006 | Goletz et al. |
| 2007/0008238 | A1 | 1/2007 | Liu et al. |
| 2007/0071761 | A1 | 3/2007 | Seon |
| 2007/0072797 | A1 | 3/2007 | Robinson et al. |
| 2007/0077310 | A1 | 4/2007 | Zemel et al. |
| 2007/0082380 | A1 | 4/2007 | Pardridge et al. |
| 2008/0199464 | A1 | 8/2008 | Plowman et al. |
| 2009/0142343 | A1 | 6/2009 | Fuh et al. |
| 2010/0015157 | A1 | 1/2010 | Andya et al. |
| 2010/0098692 | A1 | 4/2010 | Theuer et al. |
| 2011/0076263 | A1 | 3/2011 | Theuer et al. |
| 2012/0244147 | A1 | 9/2012 | Theuer et al. |
| 2012/0294864 | A1 | 11/2012 | Theuer et al. |
| 2014/0234319 | A1 | 8/2014 | Kapur et al. |
| 2015/0209430 | A1 | 7/2015 | Benedict et al. |
| 2016/0009811 | A1 | 1/2016 | Theuer et al. |

FOREIGN PATENT DOCUMENTS

| | | |
|---|---|---|
| CN | 104788562 A | 7/2015 |
| EP | 0404097 A2 | 12/1990 |
| EP | 0404097 A3 | 10/1991 |
| EP | 0404097 B1 | 9/1996 |
| EP | 2892559 A1 | 7/2015 |
| WO | WO-9311161 A1 | 6/1993 |
| WO | WO-9745450 A1 | 12/1997 |
| WO | WO-9856418 A1 | 12/1998 |
| WO | WO00-42012 A1 | 7/2000 |
| WO | WO-0230463 A2 | 4/2002 |
| WO | WO-02069232 A2 | 9/2002 |
| WO | WO-02072824 A2 | 9/2002 |
| WO | WO-02069232 A3 | 2/2003 |
| WO | WO-03068260 A1 | 8/2003 |
| WO | WO-03070234 A1 | 8/2003 |
| WO | WO-2008038127 A2 | 4/2008 |
| WO | WO-2008045373 A2 | 4/2008 |
| WO | WO-2008154351 A1 | 12/2008 |
| WO | WO-2009033581 A1 | 3/2009 |
| WO | WO-2009091810 A1 | 7/2009 |
| WO | WO-2010032059 A2 | 3/2010 |
| WO | WO-2010039873 A2 | 4/2010 |
| WO | WO-2010039875 A2 | 4/2010 |
| WO | WO-2010066762 A1 | 6/2010 |
| WO | WO-2010102241 A1 | 9/2010 |
| WO | WO-2011022339 A1 | 2/2011 |
| WO | WO-2011041441 A1 | 4/2011 |
| WO | WO-2012003470 A2 | 1/2012 |
| WO | WO-2012145539 A1 | 10/2012 |
| WO | WO-2013019805 A1 | 2/2013 |
| WO | WO-2014039682 A1 | 3/2014 |
| WO | WO-2015042269 A1 | 3/2015 |
| WO | WO-2016077451 A1 | 5/2016 |

OTHER PUBLICATIONS

Castonguay et al., Soluble endoglin specifically binds bone morphogenetic proteins 9 and 10 via its orphan domain, inhibits blood vessel formation, and suppresses tumor growth. Journal of Biological Chemistry, 286(34):30034-30046 (2011).
Chothia, et al. Canonical structures for the hypervariable regions of immunoglobulins. J Mol Biol. 196(4):901-17 (1997).
Chothia et al., Structural repertoire of the human VH segments J.Mol.Biol. 227:799-817, (1992).
Clackson, et al. Making antibody fragments using phage display libraries. Nature. 352(6336):624-8 (1991).
Devereux et al., "A comprehensive set of sequence analysis programs for the VAX," Nucl. Acids Res. 12(1):387-395 (1984).
Edge, et al. Total synthesis of a human leukocyte interferon gene. Nature. 292(5825):756-62 (1981).
Fix et al., "Oral controlled release technology for peptides: status and future prospects," Pharm Res. 13:1760-1764 (1996).
Francis, et al. PEGylation of cytokines and other therapeutic proteins and peptides: the importance of biological optimisation of coupling techniques. Int J Hematol. 68(1):1-18 (1998).
GE and Butcher, Cloning and expression of a cDNA encoding mouse endoglin, an endothelial cell TGF-β ligand. 138(1-2):201-206, (1994).
Ghetie, et al. Immunotoxins in the therapy of cancer: from bench to clinic. Pharmacol Ther. 63(3):209-34 (1994).
Heeley, et al. Mutations flanking the polyglutamine repeat in the modulatory domain of rat glucocorticoid receptor lead to an increase in affinity for hormone. Endocr Res. 28(3):217-29 (2002).
Henikoff et al., "Amino acid substitution matrices from protein blocks," PNAS USA 89:10915-10919 (1992).
Holliger, et al. "Diabodies": small bivalent and bispecific antibody fragments. Proc Natl Acad Sci U S A. 90(14):6444-8 (1993).
Huston, et al. Protein engineering of antibody binding sites: recovery of specific activity in an anti-digoxin single-chain Fv analogue produced in Escherichia coli. Proc Natl Acad Sci U S A. 85(16):5879-83 (1988).
Jay, et al. Chemical synthesis of a biologically active gene for human immune interferon-gamma. Prospect for site-specific mutagenesis and structure-function studies. J Biol Chem. 259(10):6311-7 (1984).
Jones and Segal, "Antibody-Dependent Cell Mediated Cytolysis (ADCC) with Antibody-Coated Effectors: New Methods for Enhancing Antibody Binding and Cytolysis," J. Immunol. 125:926-933 (1980).
Kabat et al., Sequences of Proteins in Immunological Interest, 5th ed., Public Health Service, National Institutes of Health, Bethesda MD 1991, pp. 647-669.
Kapur et al., Reduced endoglin activity limits cardiac fibrosis and improves survival in heart failure Circulation, 125:2728-2738 (2012).
Kapur et al., Reducing endoglin activity limits calcineurin and TRPC-6 expression and improves survival in a mouse model of right ventricular pressure overload. Journal of the American Heart Association, 3:e000965, 17 pages, (2014), downloaded from the internet: http://jaha.ahajournals.org/.
Kohler, et al. Continuous cultures of fused cells secreting antibody of predefined specificity. Nature. 256(5517):495-7 (1975).
Leatherbarrow, et al. Effector functions of a monoclonal aglycosylated mouse IgG2a: binding and activation of complement component C1 and interaction with human monocyte Fc receptor. Mol Immunol. 22(4):407-15 (1985).
Liljeblad, et al. Analysis of agalacto-IgG in rheumatoid arthritis using surface plasmon resonance. Glycoconj J. 17(5):323-9 (2000).
Liu et al., Modulation of circulating protein biomarkers following TRC105 (anti-endoglin antibody) treatment in patients with advanced cancer. Cancer Medicine, published by John Wiley & Sons, 2014, 12 pages.
Marks et al., "By-Passing Immunization Human Antibodies from V-gene Libraries Displayed on Phage," J. Mol. Biol. 222:581-597 (1991).
Martin and Thornton, Structural families in loops of homologous proteins: automatic classification, modelling and application to antibodies. J.Mol.Biol., 263(5):800-815, (1996).
Muraoka, et al. Structural requirements for IgM assembly and cytolytic activity. Effects of mutations in the oligosaccharide acceptor site at Asn402. J Immunol. Jan. 15, 1989;142(2):695-701.
Muyldermans et al., "Sequence and structure of Vh domain from naturally occurring camel heavy chain immunoglobulins lacking light chains," Protein Engineering 7(9):1129-1135 (1994).
Nambiar, et al. Total synthesis and cloning of a gene coding for the ribonuclease S protein. Science. Mar. 23, 1984;223(4642):1299-301.
Noren et al., "A general method for site-specific incorpation of unnatural amino acids into proteins," Science 244:182-188 (1989).
Osbourn et al., "Directed selection of MIP-1α neutralizing CCR5 antibodies from a phage display human antibody library" Nature Biotechnology, vol. 16, pp. 778-781 (1998).
Pluckthun, "Antibodies from Escherichia coli," in Handbook of Experimental Pharmacology;The Pharmacology of Monoclonal

(56) References Cited

OTHER PUBLICATIONS

Antibodies; vol. 113, Chapter 11, pp. 269-315 (1994), Rosenburg and Moore eds., Springer-Verlag, New York.
Pluckthun. Antibody engineering: advances from the use of *Escherichia coli* expression systems. Biotechnology (N Y). 9(6):545-51 (1991).
Presta, "Antibody engineering," Curr. Op. Struct. Biol. 2:593-596 (1992).
Reff, "High-level production of recombinant immunoglobulins in mammalian cells," Curr. Op. Biotech. 4:573-576 (1993).
Reiter, et al. Engineering antibody Fv fragments for cancer detection and therapy: disulfide-stabilized Fv fragments. Nat Biotechnol. Oct. 1996;14(10):1239-45.
Riechmann, et al. Reshaping human antibodies for therapy. Nature. Mar. 24, 1988;332(6162):323-7.
Samanen, et al. Chemical approaches to improve the oral bioavailability of peptidergic molecules. J Pharm Pharmacol. Feb. 1996;48(2):119-35.
Sanyal et al., Endpoints and clinical trial design for nonalcoholic steatohepatitis. Hepatology, 54(1):344-353 (2011).
Silverman et al., "Corrigendum: Multivalent avimer proteins evolved by exon shuffling of a family of human receptor domains," Nat. Biotech. 24(2):220 (2006).
Silverman et al., "Multivalent avimer proteins evolved by exon shuffling of a family of human receptor domains," Nat. Biotech. 23:1493-1494 (2005).
Sox and Hood, "Attachment of Carbohydrate to the Variable Region of Myeloma Immunoglobulin Light Chains," PNAS 66(3):975-982 (1970).
Tao et al., "Studies of anlycosylated chimeric mouse-human IgG. Role of carbohydrate in the structure and effector functions mediated by the human IgG constant region," J. Immunol. 143:2595-2601 (1989).
Taylor, et al. Selective removal of alpha heavy-chain glycosylation sites causes immunoglobulin A degradation and reduced secretion. Mol Cell Biol. Oct. 1988;8(10):4197-203.
Tomlinson et al., The Structural repertoire of the human VK domain. The EMBO Journal, 14(18):4628-4638, (1995).
Trill, et al. Production of monoclonal antibodies in COS and CHO cells. Curr Opin Biotechnol. Oct. 1995;6(5):553-60.
Ward et al., "Binding activities of a repertoire of single immunoglobulin variable domains secreted from *Escherichia coli*," Nature 341:544-546 (1989).
Altman et al., "The American College of Rheumatology criteria for the classification and reporting of osteoarthritis of the hip," Arthritis Rheum. 34:505-514 (1991).
Antitope, "Meeting Report" 5th Annual Monoclonal Antibodies Conference, Aug. 2000, pp. 308-317.
Argarana et al., "Molecular cloning and nucleotide sequences of the streptavidin gene," Nucl. Acids Res. 14(4):1871-1882 (1986).
Baker, et al. "Identification and Removal of Immunogenicity in Therapeutic Proteins." Current Opinion in Drug Discovery and Development, vol. 10, No. 2, Jan. 1, 2007, pp. 219-227.
Bernebeu et al., "Novel biochemical pathways of endoglin in vascular cell physiology," J. Cell Biochem. 102(6)1375-1388 (2007).
Blood et al., "Tumor interactions with the vasculature: angiogenesis and tumore metastasis," Biochim. Biophys. Acta 1032:89-118 (1990).
Bockhorn, et al. "Differential Vascular and Transcriptional Responses to Anti-Vascular Endothelial Growth Factor Antibody in Orthotopic Human Pancreatic Cancer Xenografts." Clinical Cancer Research: An Official Journal of the American Association for Cancer Research, vol. 9, No. 11, Sep. 15, 2003, pp. 4221-4226.
Bonnet & Walsh, "Osteoarthritis, angiogenesis and inflammation," Rheumotol. 44:7-16 (2005).
Brooks, et al. Insulin-like growth factor receptor cooperates with integrin alpha v beta 5 to promote tumor cell dissemination in vivo. J Clin Invest. 99(6):1390-8, 1997.

Chad and Chamow, "Therapeutic antibody expression technology," Curr Opin Biotechnol. 12(2):188-94, 2001.
Chidlow, et al. Pathogenic angiogenesis in IBD and experimental colitis: new ideas and therapeutic avenues. Am J Physiol Gastrointest Liver Physiol. 293(1):G5-G18, 2007.
D'Amato, et al. Thalidomide is an inhibitor of angiogenesis. Proc Natl Acad Sci U S A. 26;91(9):4082-5, 1994.
Davis, et al."Regional effects of an antivascular endothelial growth factor receptor monoclonal antibody on receptor phosphorylation and apoptosis in human 253J B-V bladder cancer xenografts." Cancer Research, vol. 64, No. 13, pp. 4601-4610, 2004.
Derbalian et al., "Fluorescein labeling of fab while preserving single thiol," Anal. Biochem. 173:59-63 (1988).
Dobeli et al., "Recombinant Fusion Proteins for the Industrial Production of Disulfide Bridge Containin Peptides: Purification, Oxidation without Concatamer Formation, and Selective Cleavage," Protein Expression and Purification 12(3):404-414 (1998).
Du et al., Crystal structure of chimeric antibody C2H7 Fab in complex with a CD20 peptide. Molecular Immunology, 45:2861-2868, 2008.
Duff et al., "CD105 is important for angiogenesis evidence and potential applications," FASEB J. 17:984-992 (2003).
Exinger et al., Multitargeted antifolate (Pemetrexed): A comprehensive review of its mechanisms of action, recent results and future prospects. Cancer Therapy, 1:315-322 (2003).
Ferrara et al., Discovery and development of Bevacizumab, an anti-VEGF antibody for treating cancer. Nature Reviews, Drug Discovery, 3:391-400, 2004.
Furstenberger, et al. Insulin-like growth factors and cancer. Lancet Oncol. 3(5):298-302, 2002.
Gao, et al. Cross-linked polyacrylamide coating for capillary isoelectric focusing. Anal Chem 76(24) :7179-718, 20046.
Gigli, et al. The stoichiometric measurement of the serum inhibition of the first component of complement by the inhibition of immune hemolysis. J Immunol. 100(6):1154-64, 1968.
Gilles et al., "Stability of water-soluble carbodiimides in aqueous solution," Anal. Biochem. 184(2):244-248 (1990).
Glazer et al., "Emerging Techniques: Phycofluor probes," Trends Biochem. Sci. 9:423-427 (1984).
Green, "A spectrophotometric assay for avidin and biotin based on binding of dyes by avidin," Biochem J. 94:23c-24c (1965).
Green, "Avidin" in Advances in Protein Chemistry, Academic Press, New York 39:85-133 (1975).
Green, "The use of bifunctional biotinyl compoounds to determine the arrangement of subunits in avidin," Biochem J. 125:781-791 (1971).
Greenberg et al., "Characteristics of the Effector Cells Mediating Cytotoxicity Against Antibody-Coated Target Cells," Immunol. 21:719 (1975).
Hardy et al., "Demonstration of B-cell maturation in X-linked immunodeficient mice by simultaneous three-colour immunofluorescence," Nature 306:270-272 (1983).
Hardy et al., "Murine B Cell Differentiation Lineages," J. Exp. Med. 159:1169-1188 (1984).
Haywood, et al. Inflammation and angiogenesis in osteoarthritis. Arthritis & Rheumatism. 48(8): 2173-2177 (2003).
Houck, et al. The vascular endothelial growth factor family: identification of a fourth molecular species and characterization of alternative splicing of RNA. Mol Endocrinol. 5(12):1806-14, 1991.
International preliminary report on patentability dated Apr. 14, 2011 for PCT/US2009/059086.
Jeong, et al. Avimers hold their own. Nat Biotechnol. 23(12):1493-4, 2005.
Jones et al., Analysis of polypeptides and proteins. Adv. Drug Delivery Rev. 10:29-90 (1993).
Jones, et al. Replacing the complementarity-determining regions in a human antibody with those from a mouse. Nature. 321(6069):522-5, 1986.
Kelland et al., Telomere targeting agents—clinical development candidates, European Journal of Cancer, Supplements, 4(12):140-141 (2006).

(56) References Cited

OTHER PUBLICATIONS

Kim et al., "Three-dimensional in vitro tissue culture models of breast cancer—a review," Breast Cancer Research Treatment 85(3):281-291 (2004).
Koch and Distler, "Vaculopathy and disordered angiogenesis in selected rheumatic diseases: rheumatoid arthritis and systemic sclerosis," Arthritis Res. and Ther. 9(Supp.2):1-9 (2007).
Kroll et al., "A Multifunctional Prokaryotic Protein Expression System: Overproduction, Affinity Purification, and Selective Detection," DNA Cell Biol. 12:441-453 (1993).
Kronick et al., "Immunoassay Techniques with Fluorescent Phycobiliprotein Conjugates," Clin. Chem. 29:1582-1586 (1983).
Kronick et al., "The use of phycobiliproteins as fluorescent labels in immunoassay," J. Immunol Meth. 92:1-13 (1986).
Lahn, et al. Aerosolized anti-T-cell-receptor antibodies are effective against airway inflammation and hyperreactivity. Int Arch Allergy Immunol. May 2004;134(1):49-55.
Lanier et al, "Human Lymphocyte Subpopulations Identified by Using Three-Color Immunofluorescence and Flow Cytometry Analysis: Correlation of Leu-2, Leu-3, Leu-7, Leu-8, and Leu-11 Cell Surface Antigen Expression," J. Immunol 132:151-156 (1984).
Leung, et al. Vascular endothelial growth factor is a secreted angiogenic mitogen. Science. 246(4935):1306-9, 1989.
Liu et al., ENDOGLIN is dispensable for Vasculogenesis, but required for vascular endothelial growth factor-induced angiogenesis. PLOS/One, 9(1):e86273, 12 pages, 2014.
Lowe et al., Aggregation, stability and formulation of human antibody therapeutics, Advances I Protein Chemistry and Structural Biology, 84:41-61, 2011.
Ma et al., A Phase II trial of a combination of pemetrexed and gemcitabine in patients with metastatic breast cancer: an NCCTG study. Annals of Oncology, 17(2):226-231 (2006).
Mack, et al. A systematic study in CIEF: Defining and optimizing experimental parameters critical of method reproducibility and robustness. Electrophoresis 30:(23), 4049-4058, 2009.
MacKay et al., "Effect on Natural Killer and Antibody-Dependent Cellular Cytotoxicity of Adjuvant Cytotoxic .Chemotherapy Including Melphalan in Breast Cancer," Cancer Immunol. Immunother. 16:98-100 (1983).
MacLennan. Competition for receptors for immunoglobulin on cytotoxic lymphocytes. Clin Exp Immunol. 10(2):275-83, 1972.
Maio et al., "Is it the primetime for endoglin (CD105) in the clinical setting?" Cardiovascular Research 69(4):781-783 (2006).
Matsuno, et al. "Induction of Lasting Complete Regression of Preformed Distinct Solid Tumors by Targeting the Tumor Vasculature Using Two New Anti-Endoglin Monoclonal Antibodies." Clinical Cancer Research, vol. 5, No. 2, Feb. 1, 1999, pp. 371-382.
Mirsalis et al., Preclinical toxicity studies of Methoxyamine (MX) and Terozolamide (TMZ). Proceedings of the American Association Cancer Res., vol. 45, 2 pages (2004).
Montesano, et al. In vitro rapid organization of endothelial cells into capillary-like networks is promoted by collagen matrices. J Cell Biol. 97(5 Pt 1):1648-52, 1983.
Nakajima et al., "Mechanism of amide formation by carbodiimide for bioconjugation in aqueous media," Bioconjugate Chem. 6(1):123-130 (1995).
Nilsson et al., "p-Tolueneslfonyl chloride as an activating agent of agarose for the preparation of immonobilized affinity ligands and proteins," Eur. J. Biochem. 112:397-402 (1980).
Pahler et al., "Characterization and Chrystallization of Core Streptavidin," J. Biol. Chem. 262:13933-13937 (1987).
Parks et al., "Three-Color Immunofluorescence Analysis of Mouse B-Lymphocyte Subpopulations," Cytometry 5:159-168 (1984).
PCT Patent Application No. PCT/US2009/059086 International search report and written opinion dated Aug. 18, 2010.
PCT Patent Application No. PCT/US2010/045651 International Preliminary Report on Patentability dated Feb. 21, 2012.
PCT Patent Application No. PCT/US2010/045651 International search report and written opinion dated Nov. 23, 2010.
PCT Patent Application No. PCT/US2010/050759 International preliminary report on patentability dated Apr. 3, 2012.
PCT Patent Application No. PCT/US2013/058265 International preliminary report on patentability dated Mar. 19, 2015.
PCT Patent Application No. PCT/US2013/058265 International Search Report dated Oct. 14, 2013.
PCT Patent Application No. PCT/US2013/058265 Written Opinion dated Oct. 14, 2013.
PCT Patent Application No. PCT/US2015/060136 International Preliminary Report on Patentability dated May 26, 2017.
PCT Patent Application No. PCT/US2010/050759 International search report and written opinion dated Feb. 23, 2011.
Perry, et al. "New Approaches to Prediction of Immune Responses to Therapeutic Proteins during Preclinical Development." Drugs in R & D, vol. 9, No. 6, Jan. 1, 2008, pp. 386-396.
Pinals, et al. Preliminary criteria for clinical remission in rheumatoid arthritis Arthritis Rheum. (10)1308-15, 1981.
Presta, et al. Humanization of an anti-vascular endothelial growth factor monoclonal antibody for the therapy of solid tumors and other disorders. Cancer Res. 57(20):4593-9, 1997.
Rosen. Early evidence of tolerability and clinical activity from a phase 1 study oftrc105 (ant-cd105 antibody) in patients with advanced refractory cancer. 2009 ASCO Annual Meeting. Jun. 2, 2009. Retrieved from the internet: www.traconpharma.com/pdfs/105ST101_TRC105_EORTC_MCI_AACR_Poster.pdf.
Rosen, et al. Early evidence of tolerability and clinical activity from a phase 1 study of TRC105 (anti-CD105 antibody) in patients with advanced refractory cancer, EORTC-NCI-AACR symposium on molecular targets and cancer therapeutics, Geneva, Switzerland, Oct. 21-24, 2008, EJC supplements. 2008; 6(12): 126: poster 400.
Roy-Chaudhury et al., "Endoglin, a transforming growth factor-beta-binding protein, is upregulated in chronic progressive renal disease," Exp. Nephrol. 5:55-60 (1997).
Rudikoff, et al. Single amino acid substitution altering antigen-binding specificity. Proc Natl Acad Sci U S A. 79(6):1979-83, 1982.
Salesi, et al. Clinical experience with bevacizumab in colorectal cancer. Anticancer Research, 25: 3619-3623, 2005.
Schnaper, et al. Type IV collagenase(s) and TIMPs modulate endothelial cell morphogenesis in vitro. J Cell Physiol. 156(2):235-46, 1993.
Sehgal et al., "A Method for the High Efficiency of Water-Soluble Carbodiimide-Mediated Amidation," Anal. Biochem. 218(1):87-91 (1994).
She et al., "Synergy between anti-endoglin (CD205) monoclonal antibodies and TGF-β in suppression of growth of human endothelial cells," Int. J. Cancer 108:251-257 (2004).
Shiozaki et al., "Antiangiogenic chimeric anti-endoglin(CD105) antibody: pharmacokinetics and immunogenicity in nonhuman primates and effects of doxor ubicin," Cancer Immunology, Immunotherapy 55(2):140-150 (2005).
Silverman et al., "Multivalent avimer proteins evolved by exon shuffling of a family of human receptor domains," Nat. Biotech. 23:1556-1561 (2005).
Sjolander and Urbaniczky, "Integrated Fluid Handling System for Biomolecular Interaction Analysis," Anal. Chem. 63:2338-2345 (1991).
Stahle, et al. Multivariate data analysis and experimental design in biomedical research. Prog. Med. Chem., vol. 25, Chapter 6, 291-338, 1988.
Stefansson, et al. Inhibition of angiogenesis in vivo by plasminogen activator inhibitor-1. J Biol Chem. 276(11):8135-41, 2001.
Su et al., "PTEN and Phosphatidylinositol 3'-Kinase Inhibitors Up-Regulate p53 and Block Tumor-induced Angiogenesis: Evidence for an Effect on the Tumor and Endothelial Compartment," Cancer Res. 63:3585-3592 (2003).
Szabo et al., "Surface plasmon resonance and its use in biomolecular interaction analysis (BIA)," Curr. Op. Struct. Biol. 5:699-705 (1995).
Szajani et al, "Effects of carbodiimide structure on the immobilization of enzymes," Appl. Biochem. Biotech. 30(2):225-231 (1991).
Tracon Pharmaceuticals. Tracon pharmaceuticals announces dosing of initial three cancer patients in a Phase 1 clinical trial with

(56) References Cited

OTHER PUBLICATIONS

TRC105, a human chimeric antibody. Company News. Jan. 8, 2008. www.traconpharma.com/content/pr_01_9_08.html.
Tsujie et al., "Effective anti-angiogenic therapy of established tumors inmice by naked anti-human endoglin (CD105) antibody: Differences in growth rate and therapeutic response between tumors growing at different sites," Int. J. Oncology 29:1087-1094 (2006).
Uneda et al., Anti-endoglin monoclonal antibodies are effective for suppressing metastasis and the primary tumors by targeting tumor vasculature. Int. J. Cancer, 125(6):1446-1453 (2009).
U.S. Appl. No. 12/570,918 Office action dated Mar. 28, 2012.
U.S. Appl. No. 12/570,918 Office action dated Oct. 17, 2012.
U.S. Appl. No. 12/751,907 Office action dated Sep. 30, 2011.
U.S. Appl. No. 13/390,896 Office action dated Nov. 21, 2014.
U.S. Appl. No. 13/390,896 Office Action dated Aug. 23, 2017.
U.S. Appl. No. 13/390,896 Office Action dated Nov. 3, 2016.
U.S. Appl. No. 13/485,702 Notice of Allowance dated Sep. 3, 2013.
U.S. Appl. No. 14/054,446 Office Action dated Jun. 12, 2015.
U.S. Appl. No. 14/421,108 Office Action dated Aug. 16, 2017.
U.S. Appl. No. 14/838,006 Notice of Allowance dated Aug. 29, 2016.
U.S. Appl. No. 14/838,006 Office Action dated May 20, 2016.
U.S. Appl. No. 15/337,113 Office Action dated Jul. 12, 2017.
U.S. Appl. No. 15/337,113 Restriction Requirement dated Jan. 13, 2017.
Varner et al., "Review: The Integrin auß3: Angiogenesis and Apoptosis," Cell Adh. Commun. 3:367-374 (1995).
Vogelzang et al., Phase III study of pemetrexed in combination with cisplatin versus cisplatin alone in patients with malignant pleural mesothelioma. Journal of Clinical Oncology, 21(14): 2636-2644 (2003).
Volpert et al., "Idl regulates angiogenesis through transcriptional repression of thrombospondin-1," Cancer Cell 2(6):473-483 (2002).
Weidner et al., "Tumor Angiogenesis: A New Significant and Independent Prognostic Indicator in Early-Stage Breast Carcinoma," J. Natl. Cancer Inst. 84:1875-1887 (1992).
Williams, "Dissection of the extracellular human interferon gamma receptor into two immunoglobulin-like domains," Biochem. 34:1787-1797 (1995).
Wold, et al. PLS-regression: a basic tool of chemometrics. Chemom. Intell. Lab Syst. 58: 109-130 (2001).
Yan et al., "Human/Severe Combined Immunodeficient Mouse Chimeras," J. Clin. Invest. 91:986-996 (1993).
Yan et al., Methoxyamine potentiates iododeoxyuridine-induced radiosensitization by altering cell cycle kinetics and enhancing senescence. Mol. Cancer Therapy, 5(4): 893-902 (2006).
Zent et al., "Angiogenesis in Diabetic Nephropathy," Seminars in Nephrology 27(2):161-171 (2007).
Bussolati et al., Identification of a tumor-initiating stem cell population in human renal carcinomas. FASEB Journal, 22:3696-3705, 2008.
Liu et al., Effects of the combination of TRC105 and bevacizumab on endothelial cell biology. Invest New Drugs, 9 pages, published online Jul. 5, 2014.
European Patent Application No. 17194562.9 extended European Search Report dated Nov. 8, 2017.
Wood et al., PTK787/ZK 222584, A novel and potent inhibitor of vascular endothelial growth factor receptor tyrosine kinases, impairs vascular endothelial growth factor-induced responses and tumor growth after oral administration. Cancer Research, AACR—American Association for Cancer Research, US, 60(8):2178-2189, 2000.
Akagi, A. et al., Expression of Type XVI collagen in human skin fibroblasts: Enhanced expression in fibrotic skin diseases. J. Invest. Dermatol., 113:246-250, 1999.
Appleton, I., et al., Short Communication: Apoptosis, necrosis, and proliferation. Possible implications in the etiology of keloids. Am. J. Pathol., 149(5):1441-1447, 1996.
Flaherty et al., Steroids in idiopathic pulmonary fibrosis: A prospective assessment of adverse reactions, response to therapy, and survival. Am. J. Med., 110:278-282, 2001.
Girogescu, Non-invasive Biochemical Markers of Liver Fibrosis, J. Gastrointestin. Liver Dis., 15(2): 149-159, 2006.
Gougos and Letarte, Identification of a human endothelial cell antigen with monoclonal antibody 44G4 produced against a pre-B leukemic cell line. J. Immunol. 141:1925-1933, 1988.
Gougos and Letarte, Primary structure of endoglin, an RGD-containing Glycoprotein of human endothelial cells. J. Biol. Chem. 265(15):8361-8364, 1990.
Haruta and Seon, Distinct human leukemia-associated cell surface glycoprotein GP160 defined by monoclonal antibody SN6. Proc. Natl. Acad. Sci. USA 83:7898-7902, 1986.
Lahn et al., Aerosolized Anti-T-cell-Receptor Antibodies are Effective against Airway Inflammation and Hyperreactivity, Int. Arch. Allergy Immuno., 134:49-55, 2004.
Lasky and Brody, Interstitial fibrosis and growth factors. Environ. Health Perspect., 108 Suppl 4:751-762, 2000.
Li and Friedman, Liver fibrogenesis and the role of hepatic stellate cells: New insights and prospects for theraphy. Gastroenterol. Hepatol. 14:618-633, 1999.
Liu et al., Effects of the combination of TRC105 and bevacizumab on endothelial cell biology. Investigational New Drugs, 32(5):851-859, 2014.
Martinez, Hampton et al., Mortality in idiopathic pulmonary fibrosis (IPF): Predictors prior to high dose corticosteroid therapy. Am. J. Respir. Crit. Care Med., 149:A878, 1994.
Morris et al., Endoglin promotes TGF-beta/Smad1 signaling in scleroderma fibroblasts. Journal of Cellular Physiology, 226(12):3340-3348, 2011. (Abstract only).
Nolan-Stevaux et al., Endoglin requirement for BMP9 signaling in endothelial cells reveals new mechanism of action for selective anti-endoglin antibodies. PLOS/One, 7(12):350920, 12 pages, 2012.
PCT/US2015/060136 International Search Report and Written Opinion dated Feb. 3, 2016.
Ryu et al., Idiopathis pulmonary fibrosis: Current concepts. Mayo Clin. Proc., 73:1085-1101, 1998.
Schena, F. and Gesualdo, L., Pathogenic Mechanisms of Diabetic Nephropathy, J. Am. Soc. Nephrol., 16:S30-33, 2005.
Travis et al., Idiopathic nonspecific interstitial pneumonia: Prognostic significance of cellular and fibrosing patterns. Survival comparison with usual interstitial pneumonia and desquamative interstitial pneumonia. Am. J. Surg. Path., 24(1):19-33, 2000.
Wang et al., A Monoclonal antibody detects heterogeneity in vascular endothelium of tomours and normal tissues. Int. J. Cancer 54:363-370, 1993.
Whaley-Connell and Sower, Chronic Kidney Disease and the Cardiometabolic Syndrome, J. Clin. Hypert., 8(8):546-48, 2006.

FIG. 1

O2-VK1-39 variable (V_L) light chain with TRC105 V_L grafted CDRs underlined [SEQ ID NO: 4]

FIG. 2

VH3-15 variable (V_H) heavy chain with TRC105 V_H grafted CDRs underlined [SEQ ID NO: 42]

| E | V | Q | L | V | E | S | G | G | G | L | V | K | P | G | G | S | L | R | L | S | C | A | A | S | G | F | T |

| | | | | | | | | | | | | | | | | 49 | | | | | | | | | | | |
| F | S | D | A | W | M | D | W | V | R | Q | A | P | G | K | G | L | E | W | V | G | E | I | R | S | K | A | S |
| | | | | | | | | | | | | | | | | | | | | | A | | | | | | S |

| | | | | | | | | | | | | | | | | | | 76 | 77 | 78 | | | | | | | |
| N | H | A | T | Y | Y | A | E | S | V | K | G | R | F | T | I | S | R | D | D | S | K | N | T | L | Y | L | Q |
| | | | | | | | | | | | | | | | | | | | | | | S | R | V | | | |

| 82a | | | | | | | 89 | | | | | 94 | | | | | | | | | | | | | | | |
| M | N | S | L | K | T | E | D | T | A | V | Y | Y | C | T | R | W | R | R | F | F | D | S | W | G | Q | G | T |
| | I | | | | | | | | | L | I | | | T | | | | | | | | | | | | | |
| | | | | | | | | | | | L | | | G | | | | | | | | | | | | | |

| 108 | 109 | | | 113 |
| L | V | T | V | S | S |
| | L | | | | A |

FIG. 3A

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 31A | 31B | 31C | 31D | 31E | 31F | 32 | 33 | 34 | 35 | 36 | 37 | 38 | 39 | 40 | 41 | 42 | 43 | 44 | 45 | 46 | 47 | 48 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Mouse_VK | Q | I | V | L | S | Q | S | P | A | I | L | S | A | S | P | G | E | K | V | T | M | T | C | R | A | S | S | S | V | S | - | - | - | - | - | - | - | Y | M | H | W | Y | Q | Q | K | P | G | S | S | P | K | P | W | - |
| V1-39-O2/O12+JK4 | D | I | Q | M | T | Q | S | P | S | S | L | S | A | S | V | G | D | R | V | T | I | T | C | R | A | S | Q | S | I | S | S | - | - | - | - | - | - | Y | L | N | W | Y | Q | Q | K | P | G | K | A | P | K | L | L | - |
| HuVK_v0 | D | I | Q | M | T | Q | S | P | S | S | L | S | A | S | V | G | D | R | V | T | I | T | C | R | A | S | S | S | V | S | - | - | - | - | - | - | - | Y | M | H | W | Y | Q | Q | K | P | G | K | A | P | K | L | L | - |
| HuVK_v1 | D | I | Q | M | T | Q | S | P | S | S | L | S | A | S | V | G | D | R | V | T | I | T | C | R | A | S | S | S | V | S | - | - | - | - | - | - | - | Y | M | H | W | Y | Q | Q | K | P | G | K | A | P | K | PW | - |
| HuVK_v2 | D | I | Q | L | T | Q | S | P | S | S | L | S | A | S | V | G | D | R | V | T | I | T | C | R | A | S | S | S | V | S | - | - | - | - | - | - | - | Y | M | H | W | Y | Q | Q | K | P | G | K | A | P | K | PW | - |

| | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Mouse_VK | Y | A | T | S | N | L | A | S | G | V | P | V | R | F | S | G | S | G | S | G | T | D | Y | S | L | T | I | S | R | V | E | A | E | D | A | A | T | Y | Y | C | Q | Q | W | S | S | N | P | L | T | F | G | A | G | T |
| V1-39-O2/O12+JK4 | Y | A | A | S | S | L | Q | S | G | V | P | S | R | F | S | G | S | G | S | G | T | D | F | T | L | T | I | S | S | L | Q | P | E | D | F | A | T | Y | Y | C | Q | Q | S | Y | S | T | P | L | T | F | G | G | G | T |
| HuVK_v0 | Y | A | T | S | N | L | A | S | G | V | P | S | R | F | S | G | S | G | S | G | T | D | F | T | L | T | I | S | S | L | Q | P | E | D | F | A | T | Y | Y | C | Q | Q | W | S | S | N | P | L | T | F | G | G | G | T |
| HuVK_v1 | Y | A | T | S | N | L | A | S | G | V | P | S | R | F | S | G | S | G | S | G | T | D | Y | T | L | T | I | S | S | L | Q | P | E | D | F | A | T | Y | Y | C | Q | Q | W | S | S | N | P | L | T | F | G | G | G | T |
| HuVK_v2 | Y | A | T | S | N | L | A | S | G | V | P | S | R | F | S | G | S | G | S | G | T | D | Y | T | L | T | I | S | S | L | Q | P | E | D | F | A | T | Y | Y | C | Q | Q | W | S | S | N | P | L | T | F | G | G | G | T |

| | 103 | 104 | 105 | 106 | 107 |
|---|---|---|---|---|---|
| Mouse_VK | K | L | E | L | K |
| V1-39-O2/O12+JK4 | K | V | E | I | K |
| HuVK_v0 | K | V | E | I | K |
| HuVK_v1 | K | V | E | I | K |
| HuVK_v2 | K | V | E | I | K |

|  | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 31A | 31B | 31C | 31D | 31E | 31F | 32 | 33 | 34 | 35 | 36 | 37 | 38 | 39 | 40 | 41 | 42 | 43 | 44 | 45 | 46 | 47 | 48 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| TRC105-VK | Q | I | V | L | S | Q | S | P | A | I | L | S | A | S | P | G | E | K | V | T | M | T | C | R | A | S | S | S | V | S | - | - | - | - | - | - | - | Y | M | H | W | Y | Q | Q | K | P | G | S | S | P | K | P | W | - |
| V3-11-L6+JK4 | E | I | V | L | T | Q | S | P | A | T | L | S | L | S | P | G | E | R | A | T | L | S | C | R | A | S | Q | S | V | S | - | - | - | - | - | - | - | Y | L | N | W | Y | Q | Q | K | P | G | Q | A | P | R | L | L | - |
| SuperVK_v0 | E | I | V | L | T | Q | S | P | A | T | L | S | L | S | P | G | E | R | A | T | L | S | C | R | A | S | S | S | V | S | - | - | - | - | - | - | - | Y | M | H | W | Y | Q | Q | K | P | G | Q | A | P | R | L | L | - |
| SuperVK_v1 | E | I | V | L | T | Q | S | P | A | T | L | S | L | S | P | G | E | R | A | T | L | S | C | R | A | S | S | S | V | S | - | - | - | - | - | - | - | Y | M | H | W | Y | Q | Q | K | P | G | Q | A | P | R | P | W | - |
| SuperVK_v2 | E | I | V | L | T | Q | S | P | A | T | L | S | L | S | P | G | E | R | A | T | L | S | C | R | A | S | S | S | V | S | - | - | - | - | - | - | - | Y | M | H | W | Y | Q | Q | K | P | G | Q | A | P | R | P | W | - |

|  | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| TRC105-VK | Y | A | T | S | N | L | A | S | G | V | P | V | R | F | S | G | S | G | S | G | T | S | Y | S | L | T | I | S | R | V | E | A | E | D | A | A | T | Y | Y | C | Q | Q | W | S | S | N | P | L | T | F | G | A | G |
| V3-11-L6+JK4 | Y | D | A | S | N | R | A | T | G | I | P | A | R | F | S | G | S | G | S | G | T | D | F | T | L | T | I | S | S | L | E | P | E | D | F | A | V | Y | Y | C | Q | Q | R | S | N | W | P | L | T | F | G | G | G |
| SuperVK_v0 | Y | A | T | S | N | L | A | S | G | I | P | A | R | F | S | G | S | G | S | G | T | D | F | T | L | T | I | S | S | L | E | P | E | D | F | A | V | Y | Y | C | Q | Q | W | S | S | N | P | L | T | F | G | G | G |
| SuperVK_v1 | Y | A | T | S | N | L | A | S | G | I | P | A | R | F | S | G | S | G | S | G | T | D | Y | T | L | T | I | S | S | L | E | P | E | D | F | A | V | Y | Y | C | Q | Q | W | S | S | N | P | L | T | F | G | G | G |
| SuperVK_v2 | Y | A | T | S | N | L | A | S | G | V | P | A | R | F | S | G | S | G | S | G | T | D | Y | T | L | T | I | S | S | L | E | P | E | D | F | A | V | Y | Y | C | Q | Q | W | S | S | N | P | L | T | F | G | G | G |

|  | 102 | 103 | 104 | 105 | 106 | 107 |
|---|---|---|---|---|---|---|
| TRC105-VK | T | K | L | E | L | K |
| V3-11-L6+JK4 | T | K | V | E | I | K |
| SuperVK_v0 | T | K | V | E | I | K |
| SuperVK_v1 | T | K | V | E | I | K |
| SuperVK_v2 | T | K | V | E | I | K |

FIG. 4B

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 31A | 31B | 32 | 33 | 34 | 35 | 36 | 37 | 38 | 39 | 40 | 41 | 42 | 43 | 44 | 45 | 46 | 47 | 48 | 49 | 50 | 51 | 52 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| TRC105-VH | E | V | K | L | E | E | S | G | G | G | L | V | Q | P | G | G | S | M | K | L | S | C | A | A | S | G | F | T | F | S | D | - | - | A | W | M | D | W | V | R | Q | S | P | E | K | G | L | E | W | V | A | E | I | R |
| VH3-3-73+JH4 | E | V | Q | L | V | E | S | G | G | G | L | V | Q | P | G | G | S | L | K | L | S | C | A | A | S | G | F | T | F | S | N | - | - | S | A | M | H | W | V | R | Q | A | S | G | K | G | L | E | W | V | G | R | I | K |
| SuperVH_v0 | E | V | Q | L | V | E | S | G | G | G | L | V | Q | P | G | G | S | L | K | L | S | C | A | A | S | G | F | T | F | S | D | - | - | A | W | M | D | W | V | R | Q | A | S | G | K | G | L | E | W | V | G | E | I | R |
| SuperVH_v1 | E | V | Q | L | V | E | S | G | G | G | L | V | Q | P | G | G | S | L | K | L | S | C | A | A | S | G | F | T | F | S | D | - | - | A | W | M | D | W | V | R | Q | A | S | G | K | G | L | E | W | V | A | E | I | R |

| | 52A | 52B | 52C | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 | 95 | 96 | 97 | 98 | 99 | 101 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| TRC105-VH | S | K | A | S | N | H | A | T | Y | Y | A | E | S | V | K | G | R | F | T | I | S | R | D | D | D | S | K | S | S | V | Y | L | Q | M | N | S | L | R | A | E | D | T | G | I | Y | Y | C | T | R | W | R | R | F | D |
| VH3-3-73+JH4 | S | K | A | N | S | Y | A | T | A | Y | A | A | S | V | K | G | R | F | T | I | S | R | D | D | D | S | K | N | T | A | Y | L | Q | M | N | S | L | K | T | E | D | T | A | V | Y | Y | C | T | R | - | - | Y | F | D |
| SuperVH_v0 | S | K | A | S | N | H | A | T | Y | Y | A | E | S | V | K | G | R | F | T | I | S | R | D | D | D | S | K | N | T | A | Y | L | Q | M | N | S | L | K | T | E | D | T | A | V | Y | Y | C | T | R | W | R | R | F | D |
| SuperVH_v1 | S | K | A | S | N | H | A | T | Y | Y | A | E | S | V | K | G | R | F | T | I | S | R | D | D | D | S | K | N | T | V | Y | L | Q | M | N | S | L | K | T | E | D | T | A | V | Y | Y | C | T | R | W | R | R | F | D |

| | 102 | 103 | 104 | 105 | 106 | 107 | 108 | 109 | 110 | 111 | 112 | 113 |
|---|---|---|---|---|---|---|---|---|---|---|---|---|
| TRC105-VH | S | W | G | Q | G | T | T | L | T | V | S | S |
| VH3-3-73+JH4 | Y | W | G | Q | G | T | L | V | T | V | S | S |
| SuperVH_v0 | S | W | G | Q | G | T | L | V | T | V | S | S |
| SuperVH_v1 | S | W | G | Q | G | T | L | V | T | V | S | S |

FIG. 5

```
              1                                                                                                    56
Mouse_VK    Q I V L S Q S P A I L S A S P G E K V T M T C R A S S S V S Y M H W Y Q Q K P G S S P K P W I Y A T S N L A S
HuVK_v0     D I Q M T Q S P S S L S A S V G D R V T I T C R A S S S V S Y M H W Y Q Q K P G K A P K L L I Y A T S N L A S
SuperVK_v0  E I V L T Q S P A T L S L S P G E R A T L S C R A S S S V S Y M H W Y Q Q K P G Q A P R L L I Y A T S N L A S 57                                                                                  107
Mouse_VK    G V P V R F S G S G S G T S Y S L T I S R V E A E D A A T Y Y C Q Q W S S N P L T F G A G T K L E L K
HuVK_v0     G V P S R F S G S G S G T D F T L T I S S L Q P E D F A T Y Y C Q Q W S S N P L T F G G G T K V E I K
SuperVK_v0  G I P A R F S G S G S G T D F T L T I S S L E P E D F A V Y Y C Q Q W S S N P L T F G G G T K V E I K 1                                                                                              52A
Mouse_VK    E V K L E E S G G G L V Q P G G S M K L S C A A S G F T F S D - - A W M D W V R Q S P E K G L E W V A E I R S
HuVK_v0     E V Q L V E S G G G L V K P G G S L R L S C A A S G F T F S D - - A W M D W V R Q A P G K G L E W V G E I R S
SuperVK_v0  E V Q L V E S G G G L V Q P G G S L K L S C A A S G F T F S D - - A W M D W V R Q A S G K G L E W V G E I R S 52B                                                                                        98
Mouse_VK    K A S N H A T Y Y A E S V K G R F T I S R D D D S K S S V Y L Q M N S L R A E D T G I Y Y C T R W R R F
HuVK_v0     K A S N H A T Y Y A E S V K G R F T I S R D D D S K N T L Y L Q M N S L K T E D T A V Y Y C T T W R R F
SuperVK_v0  K A S N H A T Y Y A E S V K G R F T I S R D D D S K N T A Y L Q M N S L K T E D T A V Y Y C T R W R R F 99                        113
Mouse_VK    F D S W G Q G T T L T V S S
HuVK_v0     F D S W G Q G T L V T V S S
SuperVK_v0  F D S W G Q G T L V T V S S
```

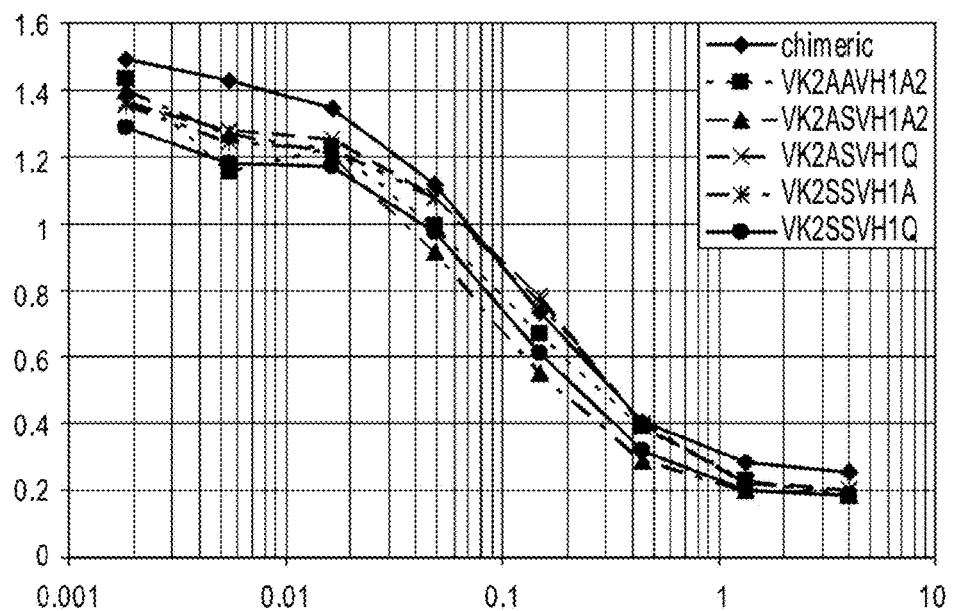
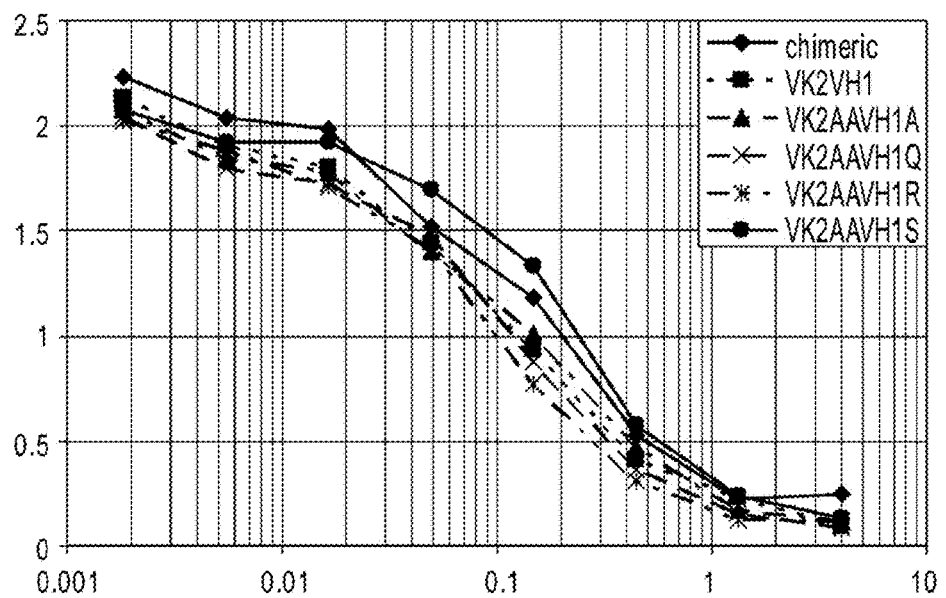

FIG. 7

Humanized Deimmunized VH1A2 [SEQ ID NO: 89] Lead Variant and Modifications Thereof with CDRs underlined

| | | | | | | | | | | | | | | | | | | | | | | | | |
|---|---|---|---|---|---|---|---|---|---|---|---|---|---|---|---|---|---|---|---|---|---|---|---|---|
| E | V | Q | L | V | E | S | G | G | G | L | V | K | P | G | G | S | L | R | L | S | C | A | A | S | G | F | T |

| | | | | | | | | | | | | | | | | | | | |
|---|---|---|---|---|---|---|---|---|---|---|---|---|---|---|---|---|---|---|---|
| | | | | | | | | | 49 | | 51 | 52b | | | | | | | |
| F | S | D | A | W | M | D | W | V | R | Q | A | P | G | K | G | L | E | W | V |
| | | | | | | | | | | | G | E | A | R | S | K | A | S | |
| | | | | | | | | | | | A | | I | | | Q | | | |
| | | | | | | | | | | | S | | | | | R | | | |

| | | | | | | | | | | | | | | | | | | | |
|---|---|---|---|---|---|---|---|---|---|---|---|---|---|---|---|---|---|---|---|
| | | | | | | | | | | | | | | | 78 | | | | |
| N | H | A | T | Y | Y | A | E | S | V | K | G | R | F | T | I | S | R | D | D |
| | | | | | | | | | | | | | | | | | | | S | K | N | T | L | Y | L | Q |
| | | | | | | | | | | | | | | | | | | V | |

| | | | | | | | | | | | | | | | | | | | |
|---|---|---|---|---|---|---|---|---|---|---|---|---|---|---|---|---|---|---|---|
| | | | | | | | | | 94 | | | | | | | | | | |
| M | N | S | L | K | T | E | D | T | A | V | Y | Y | C | T | R | W | R | R | F | F | D | S | W | G | Q | G | T |

| | | | | | | |
|---|---|---|---|---|---|---|
| L | V | T | V | S | S | |

FIG. 8

Humanized Deimmunized VH1AA [SEQ ID NO: 93] Lead Variant and Modifications Thereof with CDRs underlined

| | | | 4 | | | | | | | | | | | | | | | 19 | | | 22 | | | | |
|---|---|---|---|---|---|---|---|---|---|---|---|---|---|---|---|---|---|---|---|---|---|---|---|---|---|
| D | I | Q | M | T | Q | S | P | S | S | L | S | A | S | V | G | D | R | A | T | I | T | C | R | A | S |
|   |   |   | L |   |   |   |   |   |   |   |   |   |   |   |   |   |   | V |   |   | S |   |   |   |   |

| | | | | | | | | | | | | | | | | 48 | | 51 | | | | |
|---|---|---|---|---|---|---|---|---|---|---|---|---|---|---|---|---|---|---|---|---|---|---|
| S | S | S | S | V | S | Y | M | H | W | Y | Q | Q | K | P | G | K | A | P | K | P | W | A | Y |
|   |   |   |   |   |   |   |   |   |   |   |   |   |   |   |   |   |   | I |   |   |   |   |   |   |   |

Continuing row additions showing: A T S N L A S G
with S under T.

| V | P | S | R | F | S | G | S | G | S | G | T | D | Y | T | L | T | I | S | S | L | Q | P | E | D | F | A | T |

| Y | Y | C | Q | Q | W | S | S | N | P | L | T | F | G | G | G | T | K | V | E | I | K |

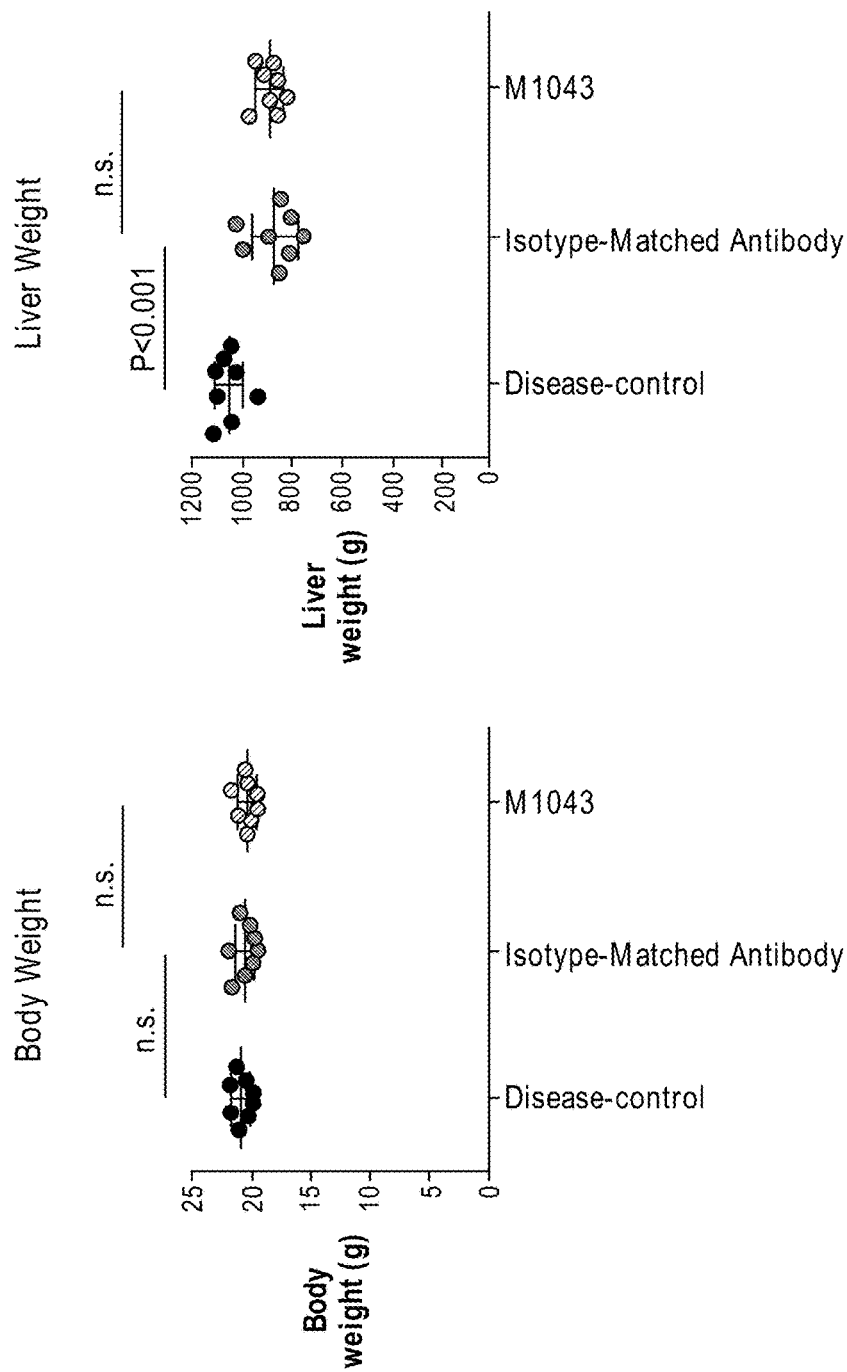

ANTI-ENDOGLIN ANTIBODIES AND USES THEREOF

CROSS-REFERENCE

This application is a continuation-in-part of International Application No. PCT/US15/60136, filed Nov. 11, 2015, which claims the benefit of U.S. Provisional Application No. 62/078,788, filed Nov. 12, 2014, which application is incorporated herein by reference in its entirety; and also claims the benefit of U.S. Provisional Application No. 62/161,669, filed May 14, 2015, which application is incorporated herein by reference in its entirety.

BACKGROUND OF THE INVENTION

Endoglin, also known as, inter alia, CD105 or edg-1, is a type I homodimeric membrane glycoprotein which is expressed at high levels in proliferating vascular endothelial cells (Burrows et al., 1995, *Clin. Cancer Res.* 1:1623-1634). However, there is some expression of endoglin by the vascular endothelium of normal tissues (Burrows et al., Id; Wang et al., 1993, *Int. J. Cancer* 54:363-370). Human endoglin is known to specifically bind transforming growth factor-β (TGF-β), and the deduced amino acid sequence of endoglin has strong homology to β-glycan, a type of TGF-β receptor.

Several anti-endoglin antibodies, in particular anti-endoglin monoclonal antibodies ("mAb"), have been described. mAb SN6j is a monoclonal antibody generated from immunization of mice with glycoprotein mixtures of cell membranes of human leukemia cells (Haruta and Seon, 1986, *Proc. Natl. Acad. Sci. USA* 83:7898-7902). SN6 is a murine mAb that recognizes human endoglin. C-SN6j is a chimeric form of SN6j which has mouse variable regions and a human constant region. mAb 44G4 is an antibody generated from immunization of mice with whole cell suspensions of human pre-B leukemia cells (Gougos and Letarte, 1988, *J. Immunol.* 141:1925-1933; 1990, *J. Biol. Chem.* 265:8361-8364). 44G4 is also a murine mAb that recognizes human endoglin. mAb MJ7/18 is an antibody generated from immunization of rats with inflamed mouse skins (Ge and Butcher, 1994, Id). MJ7/18 is a mAb that recognizes murine endoglin. mAb Tec-11 is an antibody generated from immunization of mice with human umbilical vein endothelial cells (Burrows et al., 1995, *Clin. Cancer Res.* 1:1623-1634). Tec-11 is a murine mAb with reactivity restricted to human endoglin (Burrows et al., *Clin. Cancer Res.*, 1995; 1(12): 1623-34).

SUMMARY OF THE INVENTION

Provided herein are humanized and deimmunized antibodies or antigen-binding fragments thereof that bind to endoglin. Such antibodies have uses in purification, detection, diagnostic and therapeutic applications. Also provided herein are humanized and deimmunized antibodies or antigen-binding fragments thereof that bind to one or more species or variants of endoglin and treat, inhibit, or ameliorate fibrosis.

The humanized and deimmunized antibodies and antigen-binding fragments which bind endoglin and are described herein can be used to treat, inhibit, or ameliorate fibrosis including, but not limited to, pulmonary, liver, cardiac, or kidney fibrosis. The humanized and deimmunized antibodies and antigen-binding fragments described herein can also be used in medicaments for the treatment, inhibition, or amelioration of fibrosis.

Provided herein are humanized and deimmunized antibodies that specifically bind to endoglin. Also provided herein are humanized and deimmunized antibodies that specifically bind to endoglin to prevent binding by the endoglin ligand BMP. Also provided herein are humanized and deimmunized antibodies that specifically bind to endoglin and inhibit downstream signaling of the Smad 1/5/8 pathway.

Also provided herein are antibodies of an IgG1 isotype. Also provided herein are antibodies of an IgG4 isotype. Also provided herein are antibodies of an IgG2 isotype.

Provided herein are antibodies to endoglin that inhibit the BMP9 signaling pathway and interrupt SMAD 1/5/8 signaling in fibroblasts to inhibit fibrosis.

Provided herein are methods for treating, inhibiting, or ameliorating fibrosis comprising administering a composition comprising a humanized and deimmunized antibody or antigen-binding fragment described herein that binds to endoglin associated with the disease or disorder and prevents fibrosis (i.e., preventing, treating, ameliorating, or lessening the severity of fibrosis).

Provided herein are methods for treating, inhibiting, or ameliorating treating fibrosis, comprising administering a composition comprising a humanized and deimmunized antibody or antigen-binding fragment described herein that binds to endoglin treats fibrosis.

Provided herein are methods for treating, inhibiting, or ameliorating treating fibrosis, comprising administering a composition comprising a humanized and deimmunized antibody or antigen-binding fragment described herein that binds to a endoglin receptor and blocks BMP9 binding to endoglin.

Provided herein are methods for treating, inhibiting, or ameliorating treating fibrosis, comprising administering a composition comprising a humanized and deimmunized antibody or antigen-binding fragment described herein that binds to an endoglin receptor and inhibits Smad 1/5/8 signaling.

Provided herein is a method of treating or inhibiting fibrosis in a subject in need thereof, comprising administering to the subject a composition comprising an antibody, or antigen-binding fragment thereof, comprising a heavy chain variable region having an amino acid sequence set forth as SEQ ID NO: 89 and a light chain variable region having an amino acid sequence set forth as SEQ ID NO: 93 and a pharmaceutically acceptable excipient, whereby fibrosis is treated or inhibited.

Provided herein is a method of treating or inhibiting fibrosis in a subject in need thereof, comprising administering to the subject a composition comprising an antibody, or antigen-binding fragment thereof, that binds endoglin, comprising a heavy chain variable region having an amino acid sequence set forth as SEQ ID NO: 89 and a light chain variable region having an amino acid sequence set forth as SEQ ID NO: 93, wherein: said heavy chain variable region further comprises one or more modifications selected from the group consisting of a substitution of glycine (G) by alanine (A) or serine (S) at position 49; a substitution of alanine (A) by isoleucine (I) at position 51; a substitution of lysine (K) by arginine (R) or asparagine (Q) at position 52b; a substitution of leucine (L) by valine (V) at position 78 utilizing the Kabat numbering system; and the light chain variable region further comprises one or more modifications selected from the group consisting of a substitution of methionine (M) by leucine (L) at position 4; a substitution of alanine (A) by valine (V) at position 19; a substitution of threonine (T) by serine (S) at position 22; a substitution of alanine (A) by isoleucine (I) at position 48; and a substitution of threonine (T) by serine (S) at position 51 utilizing the Kabat numbering system; and a pharmaceutically acceptable excipient, whereby fibrosis is treated or inhibited.

In such methods, the antibody, or antigen-binding fragment thereof, can comprise a heavy chain variable region having an amino acid sequence set forth as SEQ ID NO: 88, 89, 90, 91 or 92; and a light chain variable region having an amino acid sequence set forth as SEQ ID NO: 93, 94, 95, 96, 97, 100, 102, or 103.

In such methods, the antigen-binding fragment can be a Fab fragment, a Fab' fragment, a F(ab')$_2$ fragment, an Fv fragment, an scFv fragment, a single chain binding polypeptide, a Fd fragment, a variable heavy chain, a variable light chain or a dAb fragment.

The antibody, or antigen-binding fragment thereof, can be further labeled with a therapeutic label.

In one aspect, fibrosis is liver fibrosis. Liver fibrosis includes, but is not limited to, cirrhosis and associated conditions such as chronic viral hepatitis, non-alcoholic fatty liver disease (NAFLD), alcoholic steatohepatitis (ASH), non-alcoholic steatohepatitis (NASH), primary biliary cirrhosis (PBC), biliary cirrhosis, autoimmune hepatitis.

In some instances, liver fibrosis can be caused by a chronic insult to the liver from a parasite or a virus. A parasite or virus can be, for example, Hepatitis B Virus (HBV), Hepatitis B Virus (HCV), Human Immunodeficiency Virus (HIV), or schistosomiasis.

In another aspect, fibrosis is kidney fibrosis. Kidney fibrosis can be caused by chronic kidney disease, metabolic syndrome, vesicoureteral reflux, tubulointerstitial renal fibrosis, diabetes, glomerulonephritis or glomerular nephritis (GN), focal segmental glomerulosclerosis and membranous glomerulonephritis, or mesangiocapillary GN.

In another aspect, fibrosis is pulmonary fibrosis. Pulmonary fibrosis includes, but is not limited to idiopathic pulmonary fibrosis (IPF) or cryptogenic fibrosing alveolitis, chronic fibrosing interstitial pneumonia, interstitial lung disease (ILD), diffuse parenchymal lung disease (DPLD), idiopathic interstitial pneumonia, acute respiratory distress syndrome (ARDS).

In another aspect, fibrosis is a neurofibromatosis. Neurofibromatosis includes, but is not limited to, a neurofibromatosis type 1 and a neurofibromatosis type 2. In one instance, neurofibromatosis is a neurofibromatosis type 1. In another instance, neurofibromatosis is a neurofibromatosis type 2.

In another aspect, fibrosis is myelofibrosis.

Any of the methods described herein may further comprise administering one or more fibrosis inhibitors.

In some instances, the anti-endoglin antibody, or antigen-binding fragment and one or more fibrosis inhibitors are administered at the same site.

In other instances, the anti-endoglin antibody, or antigen-binding fragment and one or more fibrosis inhibitors are administered at different sites.

In other instances, the anti-endoglin antibody, or antigen-binding fragment and one or more fibrosis inhibitors are administered sequentially.

In other instances, the anti-endoglin antibody, or antigen-binding fragment and one or more fibrosis inhibitors are administered concurrently.

An antibody or antigen-binding fragment thereof can be administered in an amount of about 0.01 mg/kg, about 0.05 mg/kg, about 0.1 mg/kg, about 0.5 mg/kg, about 1 mg/kg, about 5 mg/kg, about 10 mg/kg, about 20 mg/kg, about 30 mg/kg, about 40 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, or about 200 mg/kg per patient.

Provided herein is a method of inhibiting BMP signaling comprising contacting cells with an antibody, or antigen-binding fragment thereof, wherein the antibody, or antigen-binding fragment thereof, comprises a heavy chain variable region having an amino acid sequence set forth as SEQ ID NO: 89 and a light chain variable region having an amino acid sequence set forth as SEQ ID NO: 93.

Provided herein is a method of inhibiting BMP signaling in fibroblasts comprising contacting cells with an antibody, or antigen-binding fragment thereof, wherein the antibody, or antigen-binding fragment thereof, comprises a heavy chain variable region having an amino acid sequence set forth as SEQ ID NO: 89 and a light chain variable region having an amino acid sequence set forth as SEQ ID NO: 93, wherein said heavy chain variable region further comprises one or more modifications selected from the group consisting of a substitution of glycine (G) by alanine (A) or serine (S) at position 49; a substitution of alanine (A) by isoleucine (I) at position 51; a substitution of lysine (K) by arginine (R) or asparagine (Q) at position 52b; a substitution of leucine (L) by valine (V) at position 78 utilizing the Kabat numbering system; and the light chain variable region further comprises one or more modifications selected from the group consisting of a substitution of methionine (M) by leucine (L) at position 4; a substitution of alanine (A) by valine (V) at position 19; a substitution of threonine (T) by serine (S) at position 22; a substitution of alanine (A) by isoleucine (I) at position 48; and a substitution of threonine (T) by serine (S) at position 51 utilizing the Kabat numbering system, wherein BMP signaling is inhibited.

In such methods, an antibody, or antigen-binding fragment thereof, can comprise a heavy chain variable region having an amino acid sequence set forth as SEQ ID NO: 88, 89, 90, 91 or 92; and a light chain variable region having an amino acid sequence set forth as SEQ ID NO: 93, 94, 95, 96, 97, 100, 102, or 103.

Provided herein is a method of inhibiting SMAD 1/5/8 phosphorylation in fibroblasts comprising contacting cells with an antibody, or antigen-binding fragment thereof, wherein the antibody, or antigen-binding fragment thereof, comprises a heavy chain variable region having an amino acid sequence set forth as SEQ ID NO: 89 and a light chain variable region having an amino acid sequence set forth as SEQ ID NO: 93, wherein SMAD 1/5/8 phosphorylation is inhibited.

Provided herein is a method of inhibiting SMAD 1/5/8 phosphorylation in fibroblasts comprising contacting cells with an antibody, or antigen-binding fragment thereof, wherein the antibody, or antigen-binding fragment thereof, comprises a heavy chain variable region having an amino acid sequence set forth as SEQ ID NO: 89 and a light chain variable region having an amino acid sequence set forth as SEQ ID NO: 93, wherein said heavy chain variable region further comprises one or more modifications selected from the group consisting of a substitution of glycine (G) by alanine (A) or serine (S) at position 49; a substitution of alanine (A) by isoleucine (I) at position 51; a substitution of lysine (K) by arginine (R) or asparagine (Q) at position 52b; a substitution of leucine (L) by valine (V) at position 78 utilizing the Kabat numbering system; and the light chain variable region further comprises one or more modifications selected from the group consisting of a substitution of methionine (M) by leucine (L) at position 4; a substitution of alanine (A) by valine (V) at position 19; a substitution of threonine (T) by serine (S) at position 22; a substitution of alanine (A) by isoleucine (I) at position 48; and a substitution of threonine (T) by serine (S) at position 51 utilizing the Kabat numbering system, wherein SMAD 1/5/8 phosphorylation is inhibited.

In such methods, an antibody, or antigen-binding fragment thereof, can comprise antibody, or antigen-binding fragment thereof, comprises a heavy chain variable region having an amino acid sequence set forth as SEQ ID NO: 88, 89, 90, 91 or 92; and a light chain variable region having an amino acid sequence set forth as SEQ ID NO: 93, 94, 95, 96, 97, 100, 102, or 103.

In any of such methods, the antibody can block binding of BMP9 to endoglin.

In one aspect, the humanized and deimmunized antibodies and antigen-binding fragments described herein can be any isotype. Also encompassed herein are AVIMERs, diabodies, and heavy chain dimers (including camelids and shark heavy chain constructs).

The terms "antigen-binding portion of an antibody," "antigen-binding fragment," "antigen-binding domain," "antibody fragment" or a "functional fragment of an antibody" are used interchangeably herein to refer to one or more fragments of an antibody that retain the ability to specifically bind to an antigen. Non-limiting examples of antibody fragments included within such terms include, but are not limited to, (i) a Fab fragment, a monovalent fragment consisting of the $V_L$, $V_H$, $C_L$ and $C_H1$ domains; (ii) a $F(ab')_2$ fragment, a bivalent fragment containing two Fab fragments linked by a disulfide bridge at the hinge region; (iii) a Fd fragment consisting of the $V_H$ and $C_H1$ domains; (iv) a Fv fragment containing the $V_L$ and $V_H$ domains of a single arm of an antibody, (v) a dAb fragment (Ward et al., (1989) Nature 341:544 546), which containing a $V_H$ domain; and (vi) an isolated CDR. Additionally included in this definition are "one-half" antibodies comprising a single heavy chain and a single light chain that retain binding functions. Other forms of single chain antibodies, such as diabodies are also encompassed herein.

An antigen-binding fragment can be any of those described herein including, but not limited to, a Fab fragment, a Fab', a $F(ab')_2$ fragment, an Fv fragment (including non-covalently and covalently linked Fv fragments), an scFv fragment, a single chain binding polypeptide, an Fd fragment, an Fv fragment or a dAb fragment. In one non-limiting embodiment, the antigen-binding fragment is a scFv which can, optionally, be further fused to a human Fc portion of an antibody.

In one aspect, the humanized and deimmunized antibodies and antigen-binding fragments described herein can be modified. For example, in one embodiment, the compound can be modified to alter a pharmacokinetic property of the compound such as, for example, in vivo stability, solubility, bioavailability or half-life. Such modifications include, but are not limited to, PEGylation and/or glycosylation.

The humanized and deimmunized antibodies and antigen-binding fragments described herein can be formulated for rapid or extended delivery using conventional means. In one non-limiting embodiment, rapid delivery is, for example, by intravenous injection. In another non-limiting embodiment, extended delivery is, for example, by subcutaneous deposition.

Compositions can be administered locally, regionally or systemically, such as, for example, administration by subcutaneous, subcutaneous, intravitreal, intradermal, intravenous, intra-arterial, intraperitoneal or intramuscular injection.

Provided herein are compositions of the humanized and deimmunized antibodies and antigen-binding fragments described herein and an acceptable carrier or excipient.

Antibodies and antigen-binding fragments thereof as described herein can be used to treat various fibrosis and symptoms associated with fibrosis. Additionally, these humanized and deimmunized antibodies and antigen-binding fragments thereof described herein can be used in the formulation of a medicament for the prophylaxis, treatment, inhibition, or amelioration of fibrosis and symptoms associated with fibrosis. Fibrosis in some instances is liver fibrosis. In other instances, fibrosis is kidney fibrosis. Fibrosis in yet other instances is pulmonary fibrosis. Fibrosis in yet other instances is cardiac fibrosis.

Provided herein is a method of treating, inhibiting or ameliorating fibrosis in a subject by administering a composition provided herein to a patient. Fibrosis includes, but is not limited to, liver, kidney, lung, heart, skin, intestines, eye (ocular), joints, etc. In one embodiment, fibrosis is liver fibrosis. In another embodiment, fibrosis is kidney fibrosis. In another embodiment, fibrosis is skin fibrosis. In another embodiment, fibrosis is intestinal fibrosis. In another embodiment, fibrosis is ocular fibrosis. In another embodiment, fibrosis is fibrosis of the joints.

The method can further include one or more supplemental treatments of fibrosis. An anti-fibrotic agent can be administered prior to, concomitant with, or subsequent to, administration of the pharmaceutical composition containing a humanized and deimmunized anti-endoglin antibody. If an anti-fibrotic agent is administered on the same day as the pharmaceutical composition, administration can be concomitant or sequential. An anti-fibrotic agent can be administered at the same site, or at a different site than administration of the pharmaceutical composition containing a humanized and deimmunized anti-endoglin antibody.

The invention further provides a composition comprising an endoglin binding antibody or binding fragment thereof and a pharmaceutically acceptable excipient for use in treating fibrosis, wherein the antibody or the antigen binding fragment thereof comprises a heavy chain variable region and a light chain variable region wherein: the heavy chain variable region comprises an amino acid sequence as set forth in SEQ ID NO: 89 optionally comprising one or more modifications selected from the group consisting of a substitution of glycine (G) by alanine (A) or serine (S) at position 49; a substitution of alanine (A) by isoleucine (I) at position 51; a substitution of lysine (K) by arginine (R) or asparagine (Q) at position 52b; a substitution of leucine (L) by valine (V) at position 78 utilising the Kabat number system; and wherein the light chain variable region comprises an amino acid sequence as set forth in SEQ ID NO: 89 optionally comprising one or more modifications selected from the group consisting of a substitution of methionine (M) by leucine (L) at position 4; a substitution of alanine (A) by valine (V) at position 19; a substitution of threonine (T) by serine (S) at position 22; a substitution of alanine (A) by isoleucine (I) at position 48; and a substitution of threonine (T) by serine(S) at position 51 utilising the Kabat number system; and a pharmaceutically acceptable excipient, whereby fibrosis is treated or inhibited.

The said antibody or fragment may comprise a heavy chain variable region having an amino acid sequence as set forth in SEQ ID NO: 89.

The said antibody or fragment may comprise a light chain variable region having an amino acid sequence as set forth in SEQ ID NO: 93.

The said antibody or fragment may comprise a heavy chain variable region having an amino acid sequence as set forth in SEQ ID NO: 89 as modified as set forth above.

The said antibody or fragment may comprise a light chain variable region having an amino acid sequence as set forth in SEQ ID NO: 93 as modified as set forth above.

In one preferred aspect, the said antibodies or fragments are for use in the treatment of liver fibrosis.

In another preferred aspect, the said antibodies or fragments are for use in the treatment of kidney fibrosis.

In another preferred aspect, the said antibodies or fragments are for use in the treatment of skin fibrosis.

In another preferred aspect, the said antibodies or fragments are for use in the treatment of intestinal fibrosis.

In another preferred aspect, the said antibodies or fragments are for use in the treatment of ocular fibrosis.

In another preferred aspect, the said antibodies or fragments are for use in the treatment of fibrosis of joints.

The antibodies and antigen binding fragments thereof may be humanized and deimmunized and the preparation of antibodies having these characteristics has been described in U.S. Pat. No. 8,221,753.

The antibodies may be humanized to contain an IgG1, an IgG2, an IgG3 or an IgG4 isotype. In one embodiment, an antibody may be humanized to contain an IgG1 isotype. In one embodiment, an antibody may be humanized to contain an IgG2 isotype. In one embodiment, an antibody may be humanized to contain an IgG3 isotype. In one embodiment, an antibody may be humanized to contain an IgG4 isotype.

In the methods provided herein, the subject can be a human or a non-human subject. Compositions and the anti-fibrotic agent or treatments provided herein can be administered once or multiple times depending on the health of the patient, the progression of the disease or condition, and the efficacy of the treatment. Adjustments to therapy and treatments can be made throughout the course of treatment.

Provided herein is a method of monitoring the efficacy of one or more of any of the methods provided herein to determine whether treatment should be maintained, increased, or decreased.

One embodiment of the present application contemplates the use of any of the compositions of the present invention to formulate a medicament for treating, inhibiting, or ameliorating fibrosis. Medicaments can be formulated based on the physical characteristics of the subject needing treatment, and can be formulated in single or multiple formulations based on the site of fibrosis. Medicaments of the present invention can be packaged in a suitable pharmaceutical package with appropriate labels for the distribution to hospitals and clinics wherein the label is for the indication of treating a disorder as described herein in a subject. Medicaments can be packaged as a single or multiple units. Instructions for the dosage and administration of the pharmaceutical compositions of the present invention can be included with the pharmaceutical packages.

INCORPORATION BY REFERENCE

All publications and patent applications mentioned in this specification are herein incorporated by reference to the same extent as if each individual publication or patent application was specifically and individually indicated to be incorporated by reference in its entirety unless otherwise specifically noted.

U.S. Pat. No. 8,221,753, issued Jul. 17, 2012, is hereby incorporated by reference is its entirety.

International Application No. PCT/US2013/058265, filed Sep. 5, 2013, published as WO 2014/039682, is hereby incorporated by reference is its entirety.

SEQUENCE LISTING

The instant application contains a Sequence Listing which has been submitted electronically in ASCII format and is hereby incorporated by reference in its entirety. Said ASCII copy, created on Mar. 30, 2016, is named 35882-718.501_SL.txt and is 74,853 bytes in size.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 provides a humanized O2-Vκ1-39 variable ($V_L$) light chain having the monoclonal murine chimeric TRC105 $V_L$ CDRs (underlined) grafted between the framework regions (FRs) 1-3 of the human sequence O2-Vκ1-39 and a framework region 4 from the human Jκ4 sequence (SEQ ID NO: 4) (all in bold). Variations that can be made to the human FRs are indicated at positions 1, 3, 4, 5, 36, 46, 47, 60, 70, 71, 100, and 106 of the sequence (sequence disclosed at SEQ ID NO: 86) utilizing the Kabat numbering system (shown in italics beneath the humanized sequence).

FIG. 2 provides a humanized VH3-15 variable ($V_H$) heavy chain having the monoclonal murine monoclonal murine chimeric TRC105 $V_H$ CDRs (underlined) grafted between the framework regions (FRs) 1-3 of the human sequence VH3-15 and a framework region 4 from the human JH4 sequence (SEQ ID NO: 42) (all in bold). One or more variations that can be made to the human FRs are indicated at positions 49, 76, 77, 78, 82a, 89, 94, 108, 109, and 113 of the sequence (sequence disclosed at SEQ ID NO: 87) utilizing the Kabat numbering system (shown in italics beneath the humanized sequence).

Figure 3B:
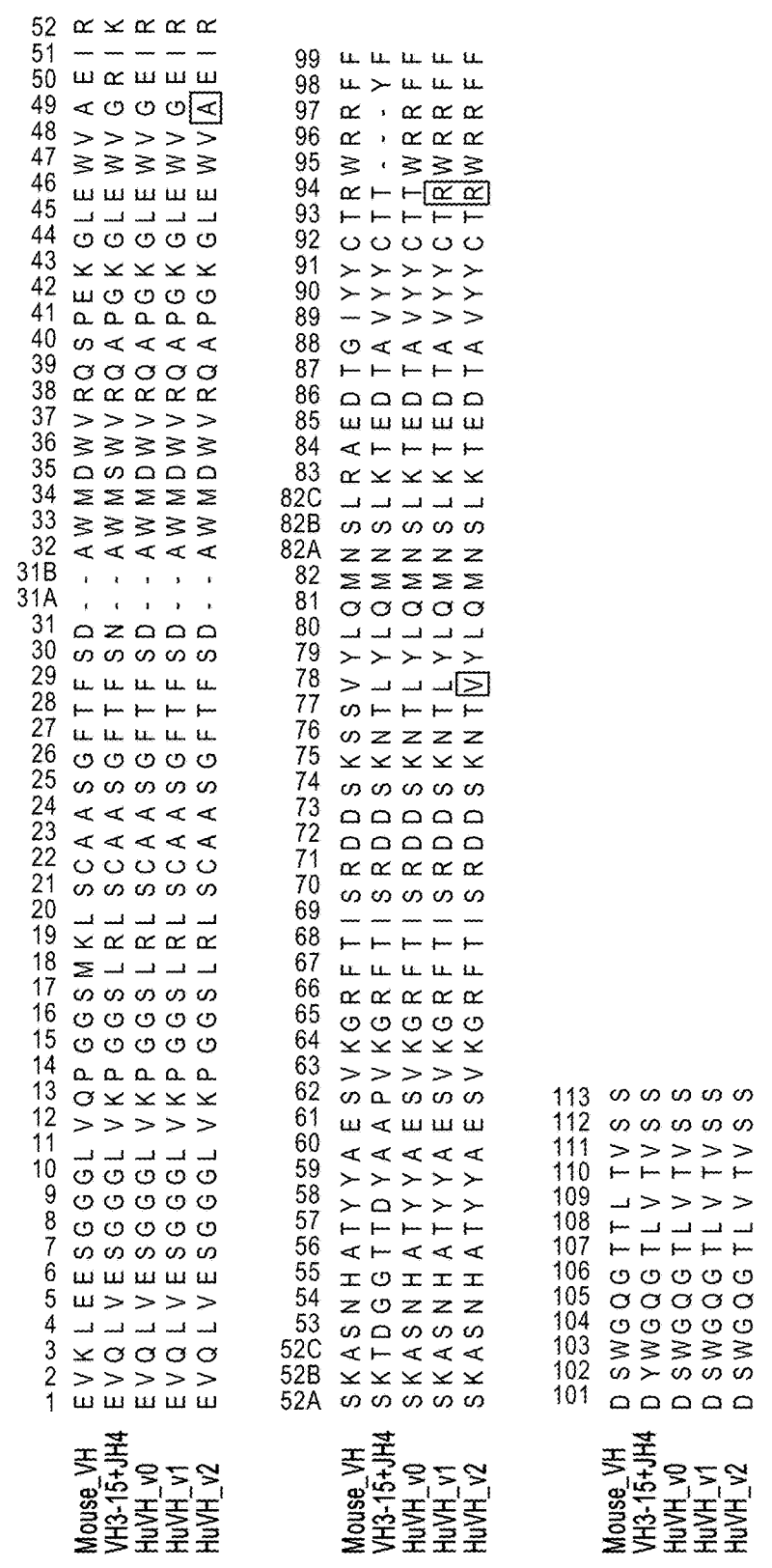

FIGS. 3A-3B provide an amino acid sequence alignment of exemplary mouse and humanized VK chains (FIG. 3A; SEQ ID NOS 1-5, respectively, in order of appearance) and $V_H$ chains (FIG. 3B; SEQ ID NOS 39-43, respectively, in order of appearance) produced according the invention described herein.

FIGS. 4A-4B provide an amino acid sequence alignment of exemplary mouse and super-humanized VK chains (FIG. 4A; SEQ ID NOS 1 and 69-72, respectively, in order of appearance) and $V_H$ chains (FIG. 4B; SEQ ID NOS 39 and 73-75, respectively, in order of appearance) produced according the invention described herein.

FIG. 5 provides an amino acid sequence alignment and comparison of exemplary mouse and humanized and super-humanized VK chains (SEQ ID NOS 1, 3 and 70, respectively, in order of appearance) and $V_H$ chains (SEQ ID NOS 39, 41 and 74, respectively, in order of appearance) produced according the invention described herein.

FIGS. 6A-6F. Anti-CD105 competition ELISA with humanized and humanized/deimmunized antibodies. Varying concentrations of each antibody were mixed with a fixed concentration of biotinylated reference anti-CD105 antibody (6.25 ng/ml) and bound to CD105 (100 ng/ml) captured on a Nunc MaxiSorp plate. Binding was detected via streptavidin-HRP and TMB substrate. Absorbance (OD) at 450 nm was measured on a plate reader and this was plotted against the test antibody concentration. FIG. 6A provides the results from the chimeric control compared to VK1VH1, VK1VH2, VK2VH1 and VK2VH2. FIG. 6B provides the results from the chimeric control compared to VK1VH1, VK2AVH1A, VK2SAVH1Q, VK2SAVH1R and VK2SAVH1S. FIG. 6C provides the results from the chimeric control compared to VK2AAVH1A2, VK2ASVH1A2, VK2ASVH1Q, VK2SSVH1A and VK2SSVH1Q. FIG. 6D provides the results from the chimeric control compared to VK2VH1, VK2AAVH1A, VK2AAVH1Q, VK2AAVH1R and VK2AAVH1S. FIG. 6E provides the results from the chimeric control compared to VK2VH1, VK2ASVH1A, VK2ASVH1R, VK2ASVH1S, and VK2SAVH1A2. FIG. 6F provides the results from the chimeric control compared to VK2VH1, VK2SSVH1Q, VK2SSVH1A2, VK2SSVH1R and VK2SSVH1S.

FIG. 7 illustrates the lead humanized deimmunized heavy chain variable region with CDRs in bold and underlined (sequence disclosed at SEQ ID NO: 89). Variations that can be made are indicated at the identified positions of the sequence utilizing the Kabat numbering system (sequence disclosed at SEQ ID NO: 116) (shown in italics beneath the humanized sequence). Variations may be made as a single mutation or as more than one mutation, and variations can be made with mutations in any combination.

FIG. 8 illustrates the lead humanized deimmunized light chain variable region with CDRs in bold and underlined (sequence disclosed at SEQ ID NO: 93). Variations that can be made are indicated at the identified positions of the sequence utilizing the Kabat numbering system (sequence disclosed at SEQ ID NO: 117) (shown in italics beneath the humanized sequence). Variations may be made as a single mutation or as more than one mutation, and variations can be made with mutations in any combination.

FIGS. 11A-B illustrate body weight and liver weight. FIG. 11A provides a graph of body weight for the three groups. FIG. 11B provides a graph of liver weight for the three groups.

FIG. 12A is a ×100 picture of a liver section from disease-control animals. FIG. 12B is a ×200 picture of a liver section from disease-control animals. FIG. 12C is a ×100 picture of a liver section of animals treated with an isotype-matched antibody. FIG. 12D is a ×200 picture of a liver section of animals treated with an isotype-matched antibody. FIG. 12E is a ×100 picture of a liver section of animals treated with M1043 Antibody. FIG. 12F is a ×200 picture of a liver section of animals treated with M1043 Antibody.

FIG. 14A. Lung hydroxyproline was quantified by a hydrolysis method. FIG. 14B. Histological analysis of lung sections was conducted by practitioners who are not aware of the Group identity. Masson's Trichrome staining is conducted and an Ashcroft Score estimate was determined. FIG. 14C. There were no significant differences in body weight between the five treatment groups by Bonferroni Multiple Comparison Testing (p>0.05 comparing the isotype control antibody group versus each other group). FIG. 14D. There were no significant differences in survival between the five treatment groups by Bonferroni Multiple Comparison Testing (p>0.05 comparing the isotype control antibody group versus each other group). FIG. 14E. Ashcroft scores.

DETAILED DESCRIPTION OF THE INVENTION

Figure 6A:
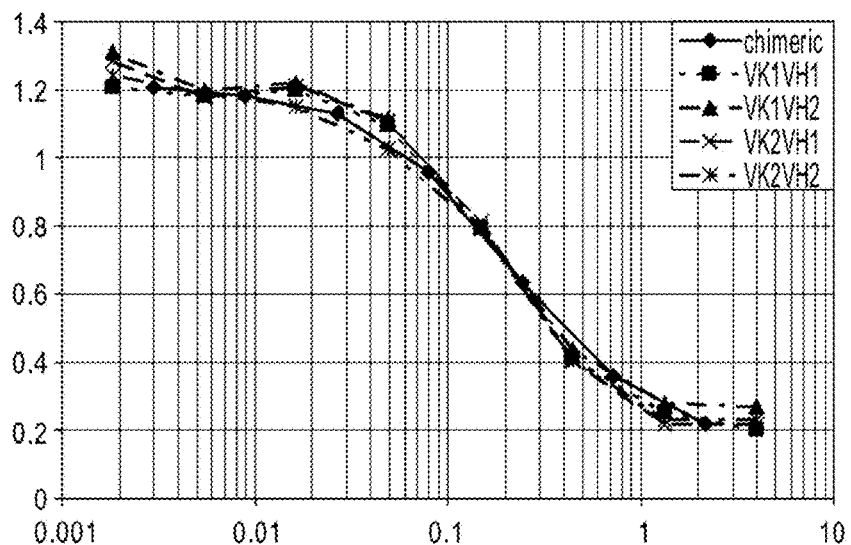
Figure 6B:
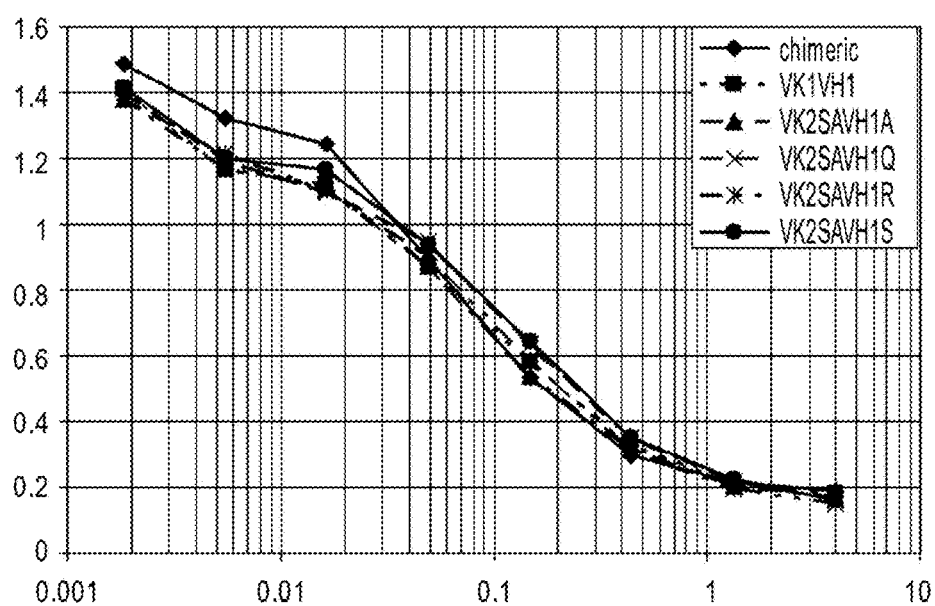
Figure 6E:
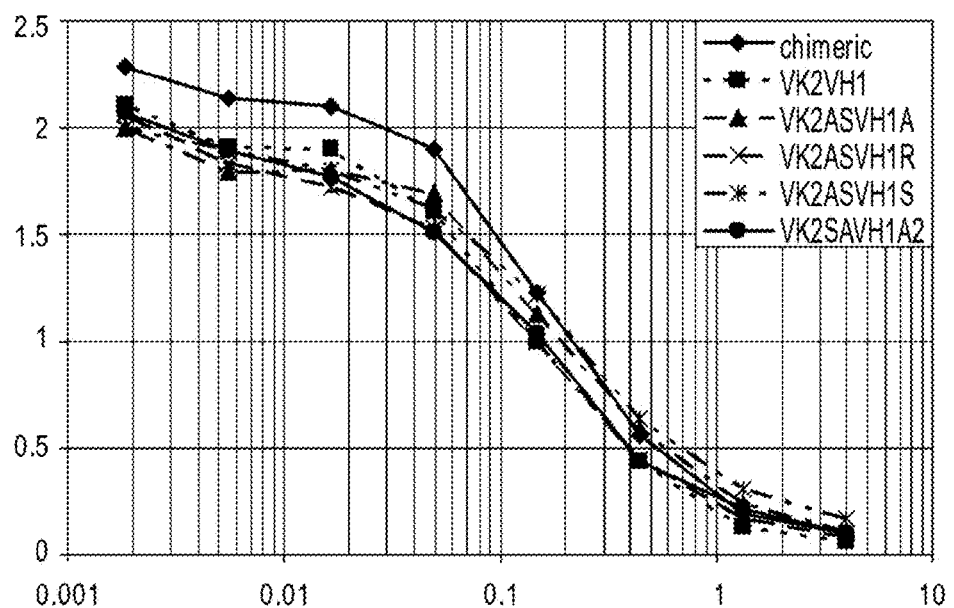
Figure 6F:
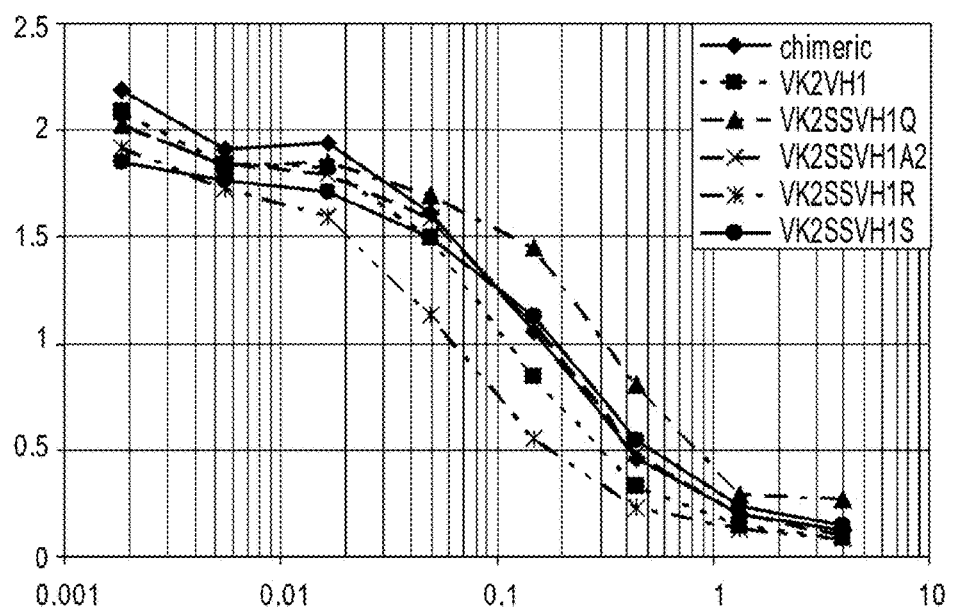
Figure 9:
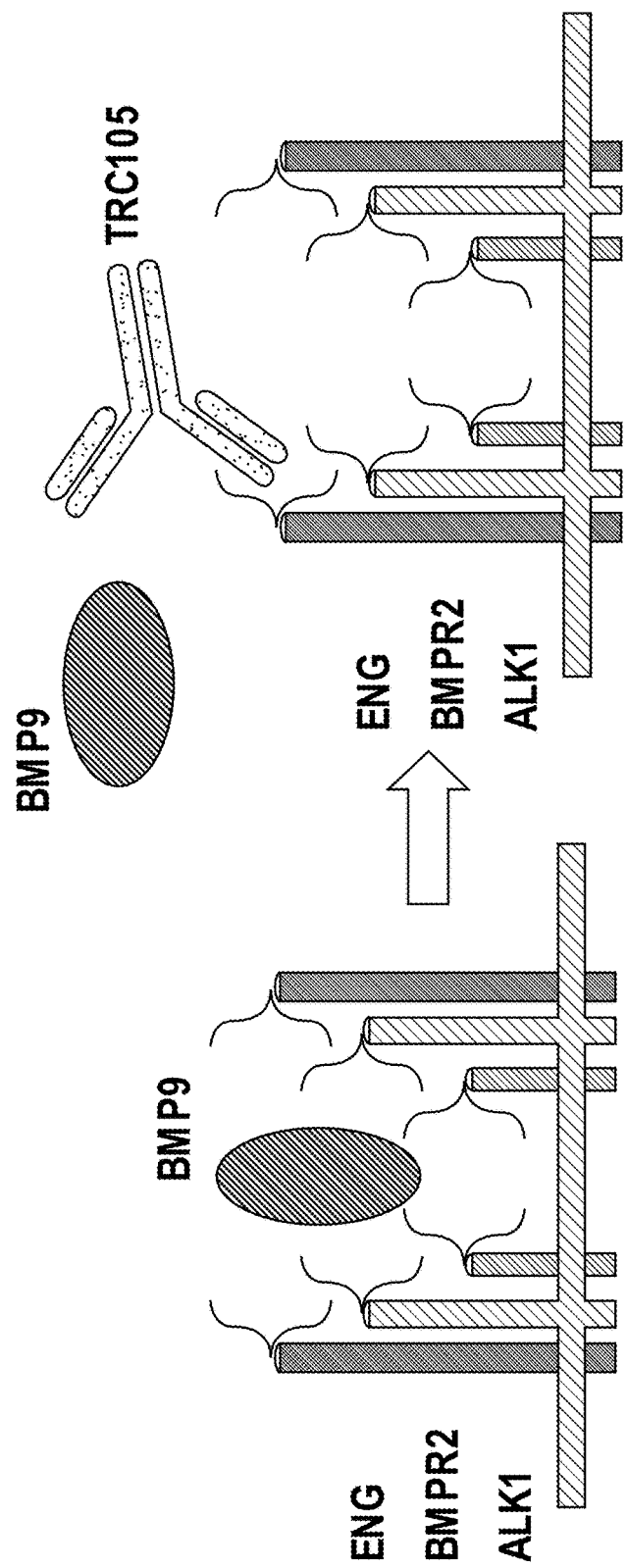
FIG. 9 illustrates binding illustrates binding of BMP 9 to the substrate binding site of endoglin (left panel) and illustrates binding of a humanized and deimmunized anti-endoglin antibody binding to endoglin and preventing binding of BMP9 (right panel).

It is to be understood that this application is not limited to particular formulations or process parameters, as these may, of course, vary. It is also to be understood that the terminology used herein is for the purpose of describing particular embodiments only, and is not intended to be limiting. Further, it is understood that a number of methods and materials similar or equivalent to those described herein can be used in the practice of the present inventions.

In accordance with the present application, there may be employed conventional molecular biology, microbiology, and recombinant DNA techniques within the skill of the art. Such techniques are explained fully in the literature. See, e.g., Sambrook et al., "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984), each of which is specifically incorporated herein by reference in its entirety.

I. Anti-Endoglin Antibodies

Provided herein are humanized antibodies, and antigen-binding fragments thereof that bind endoglin. Humanized and deimmunized antibodies described herein exhibit reduced immunogenicity while maintaining and/or improving their specificity. These humanized and deimmunized endoglin antibodies are useful for the treatment, inhibition or amelioration of fibrosis as well as for purification and detection of endoglin, in vitro assays, and treatment of subjects suffering from fibrosis.

The present inventors have identified that a neutralizing antibody or antigen-binding fragment thereof that specifically binds to endoglin can bind to endoglin and inhibit binding of BMP9 to a receptor in the TGF beta family.

The inventors have also newly described a method of inhibiting BMP signaling in fibroblasts by virtue of the antibody or fragment thereof blocking binding of BMP9 to endoglin.

Also described herein is a method of inhibiting fibrosis by administering an antibody or antigen-binding fragment thereof that specifically binds to an endoglin receptor and inhibits Smad 1/5/8 signaling.

A. Antibody Terminology

As used herein, the term "antibody" refers to an immunoglobulin (Ig) whether natural or partly or wholly synthetically produced. The term also covers any polypeptide or protein having a binding domain which is, or is homologous to, an antigen-binding domain. The term further includes "antigen-binding fragments" and other interchangeable terms for similar binding fragments such as described below. Complementarity determining region (CDR) grafted antibodies and other humanized antibodies (including CDR modifications and framework region modifications) are also contemplated by this term.

Hereinafter, a reference to the terms "antibody" or "antibodies" are to be considered inclusive of any of the antigen-binding fragments described herein and the terms are to be interchangeable where applicable. In addition to their use for purification of endoglin, these antibodies are useful for purification, detection and diagnostic purposes as well as therapeutic purposes. The antibodies provided herein can be used for the formulation of medicaments for the treatment of fibrosis.

Native antibodies and native immunoglobulins are usually heterotetrameric glycoproteins of about 150,000 Daltons, composed of two identical light (L) chains and two identical heavy (H) chains. Each light chain is typically linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ("$V_H$") followed by a number of constant domains ("$C_H$"). Each light chain has a variable domain at one end ("$V_L$") and a constant domain ("$C_L$") at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The terms "synthetic polynucleotide," "synthetic gene" or "synthetic polypeptide," as used herein, mean that the corresponding polynucleotide sequence or portion thereof, or amino acid sequence or portion thereof, is derived, from a sequence that has been designed, or synthesized de novo, or modified, compared to an equivalent naturally-occurring sequence. Synthetic polynucleotides (antibodies or antigen binding fragments) or synthetic genes can be prepared by methods known in the art, including but not limited to, the chemical synthesis of nucleic acid or amino acid sequences. Synthetic genes are typically different from naturally-occurring genes, either at the amino acid, or polynucleotide level, (or both) and are typically located within the context of synthetic expression control sequences. For example, synthetic gene sequences can include amino acid, or polynucleotide, sequences that have been changed, for example, by the replacement, deletion, or addition, of one or more, amino acids, or nucleotides, thereby providing an antibody amino acid sequence, or a polynucleotide coding sequence that is different from the source sequence. Synthetic gene polynucleotide sequences, may not necessarily encode proteins with different amino acids, compared to the natural gene; for example, they can also encompass synthetic polynucleotide sequences that incorporate different codons but which encode the same amino acid (i.e., the nucleotide changes represent silent mutations at the amino acid level).

With respect to antibodies, the term "variable domain" refers to the variable domains of antibodies that are used in the binding and specificity of each particular antibody for its particular antigen. However, the variability is not evenly distributed throughout the variable domains of antibodies. Rather, it is concentrated in three segments called hypervariable regions (also known as CDRs) in both the light chain and the heavy chain variable domains. More highly conserved portions of variable domains are called the "framework regions" or "FRs." The variable domains of unmodified heavy and light chains each contain four FRs (FR1, FR2, FR3 and FR4), largely adopting a β-sheet configuration interspersed with three CDRs which form loops connecting and, in some cases, part of the β-sheet structure. The CDRs in each chain are held together in close proximity by the FRs and, with the CDRs from the other chain, contribute to the formation of the antigen-binding site of antibodies (see Kabat et al., Sequences of Proteins of Immunological Interest, 5th Ed. Public Health Service, National Institutes of Health, Bethesda, Md. (1991), pages 647-669).

The terms "hypervariable region" and "CDR" when used herein, refer to the amino acid residues of an antibody which are responsible for antigen-binding. The CDRs comprise amino acid residues from three sequence regions which bind in a complementary manner to an antigen and are known as CDR1, CDR2, and CDR3 for each of the $V_H$ and $V_L$ chains. In the light chain variable domain, the CDRs typically correspond to approximately residues 24-34 (CDRL1), 50-56 (CDRL2) and 89-97 (CDRL3), and in the heavy chain variable domain the CDRs typically correspond to approximately residues 31-35 (CDRH1), 50-65 (CDRH2) and 95-102 (CDRH3) according to Kabat et al., Sequences of Proteins of Immunological Interest, 5th Ed. Public Health Service, National Institutes of Health, Bethesda, Md. (1991)). It is understood that the CDRs of different antibodies may contain insertions, thus the amino acid numbering may differ. The Kabat numbering system accounts for such insertions with a numbering scheme that utilizes letters attached to specific residues (e.g., 27A, 27B, 27C, 27D, 27E, and 27F of CDRL1 in the light chain) to reflect any insertions in the numberings between different antibodies. Alternatively, in the light chain variable domain, the CDRs typically correspond to approximately residues 26-32 (CDRL1), 50-52 (CDRL2) and 91-96 (CDRL3), and in the heavy chain variable domain, the CDRs typically correspond to approximately residues 26-32 (CDRH1), 53-55 (CDRH2) and 96-101 (CDRH3) according to Chothia and Lesk, J. Mol. Biol., 196: 901-917 (1987)).

As used herein, "framework region" or "FR" refers to framework amino acid residues that form a part of the antigen binding pocket or groove. In some embodiments, the framework residues form a loop that is a part of the antigen binding pocket or groove and the amino acids residues in the loop may or may not contact the antigen. Framework regions generally comprise the regions between the CDRs. In the light chain variable domain, the FRs typically correspond to approximately residues 0-23 (FRL1), 35-49 (FRL2), 57-88 (FRL3), and 98-109 and in the heavy chain variable domain the FRs typically correspond to approximately residues 0-30 (FRH1), 36-49 (FRH2), 66-94 (FRH3), and 103-133 according to Kabat et al., Sequences of Proteins of Immunological Interest, 5th Ed. Public Health Service, National Institutes of Health, Bethesda, Md. (1991)). As discussed above with the Kabat numbering for the light chain, the heavy chain too accounts for insertions in a similar manner (e.g., 35A, 35B of CDRH1 in the heavy chain). Alternatively, in the light chain variable domain, the FRs typically correspond to approximately residues 0-25 (FRL1), 33-49 (FRL2) 53-90 (FRL3), and 97-109 (FRL4), and in the heavy chain variable domain, the FRs typically correspond to approximately residues 0-25 (FRH1), 33-52 (FRH2), 56-95 (FRH3), and 102-113 (FRH4) according to Chothia and Lesk, J. Mol. Biol., 196: 901-917 (1987)).

The loop amino acids of a FR can be assessed and determined by inspection of the three-dimensional structure of an antibody heavy chain and/or antibody light chain. The three-dimensional structure can be analyzed for solvent accessible amino acid positions as such positions are likely to form a loop and/or provide antigen contact in an antibody variable domain. Some of the solvent accessible positions can tolerate amino acid sequence diversity and others (e.g., structural positions) are, generally, less diversified. The three dimensional structure of the antibody variable domain can be derived from a crystal structure or protein modeling.

Constant domains (Fc) of antibodies are not involved directly in binding an antibody to an antigen but, rather, exhibit various effector functions, such as participation of the antibody in antibody-dependent cellular toxicity via interactions with, for example, Fc receptors (FcR). Fc domains can also increase bioavailability of an antibody in circulation following administration to a patient.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., IgG1, IgG2, IgG3, IgG4, IgA1, and IgA2. The heavy-chain constant domains (Fc) that correspond to the different classes of immunoglobulins are called α, δ, ε, γ, and μ, respectively. The subunit structures and three-dimensional configurations of different classes of immunoglobulins are well known. The functional characteristics of the different classes of immunoglobulins are also known.

The "light chains" of antibodies (immunoglobulins) from any vertebrate species can be assigned to one of two clearly distinct types, called kappa or ("κ" or "K") and lambda or ("λ"), based on the amino acid sequences of their constant domains.

The terms "antigen-binding portion of an antibody," "antigen-binding fragment," "antigen-binding domain," "antibody fragment" or a "functional fragment of an antibody" are used interchangeably herein to refer to one or more fragments of an antibody that retain the ability to specifically bind to an antigen. Non-limiting examples of antibody fragments included within such terms include, but are not limited to, (i) a Fab fragment, a monovalent fragment consisting of the $V_L$, $V_H$, $C_L$ and $C_{H1}$ domains; (ii) a F(ab')$_2$ fragment, a bivalent fragment containing two Fab fragments linked by a disulfide bridge at the hinge region; (iii) a Fd fragment consisting of the $V_H$ and $C_{H1}$ domains; (iv) a Fv fragment containing the $V_L$ and $V_H$ domains of a single arm of an antibody, (v) a dAb fragment (Ward et al., (1989) Nature 341:544 546), which containing a $V_H$ domain; and (vi) an isolated CDR. Additionally included in this definition are "one-half" antibodies comprising a single heavy chain and a single light chain. Other forms of single chain antibodies, such as diabodies are also encompassed herein.

"F(ab')$_2$" and "Fab'" moieties can be produced by treating an Ig with a protease such as pepsin and papain, and include antibody fragments generated by digesting immunoglobulin near the disulfide bonds existing between the hinge regions in each of the two heavy chains. For example, papain cleaves IgG upstream of the disulfide bonds existing between the hinge regions in each of the two heavy chains to generate two homologous antibody fragments in which an light chain composed of $V_L$ and $C_L$ (light chain constant region), and a heavy chain fragment composed of $V_H$ and $C_{H\gamma1}$ (γ1) region in the constant region of the heavy chain) are connected at their C terminal regions through a disulfide bond. Each of these two homologous antibody fragments is called Fab'. Pepsin also cleaves IgG downstream of the disulfide bonds existing between the hinge regions in each of the two heavy chains to generate an antibody fragment slightly larger than the fragment in which the two above-mentioned Fab' are connected at the hinge region. This antibody fragment is called F(ab')$_2$.

The Fab fragment also contains the constant domain of the light chain and the first constant domain ($C_H1$) of the heavy chain. Fab' fragments differ from Fab fragments by the addition of a few residues at the carboxyl terminus of the heavy chain $C_H1$ domain including one or more cysteine(s) from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Fv" refers to an antibody fragment which contains a complete antigen-recognition and antigen-binding site. This region consists of a dimer of one heavy chain and one light chain variable domain in tight, non-covalent or covalent association (disulfide linked Fv's have been described in the art, Reiter et al. (1996) Nature Biotechnology 14:1239-1245). It is in this configuration that the three CDRs of each variable domain interact to define an antigen-binding site on the surface of the $V_H$-$V_L$ dimer. Collectively, a combination of one or more of the CDRs from each of the $V_H$ and $V_L$ chains confer antigen-binding specificity to the antibody. For example, it would be understood that, for example, the CDRH3 and CDRL3 could be sufficient to confer antigen-binding specificity to an antibody when transferred to $V_H$ and $V_L$ chains of a recipient antibody or antigen-binding fragment thereof and this combination of CDRs can be tested for binding, affinity, etc. using any of the techniques described herein. Even a single variable domain (or half of an Fv comprising only three CDRs specific for an antigen) has the ability to recognize and bind antigen, although likely at a lower affinity than when combined with a second variable domain. Furthermore, although the two domains of a Fv fragment ($V_L$ and $V_H$), are coded for by separate genes, they can be joined using recombinant methods by a synthetic linker that enables them to be made as a single protein chain in which the $V_L$ and $V_H$ regions pair to form monovalent molecules (known as single chain Fv (scFv); Bird et al. (1988) Science 242:423-426; Huston et al. (1988) Proc. Natl. Acad. Sci. USA 85:5879-5883; and Osbourn et al. (1998) Nat. Biotechnol. 16:778). Such scFvs are also intended to be encompassed within the term "antigen-binding portion" of an antibody. Any $V_H$ and $V_L$ sequences of specific scFv can be linked to an Fc region cDNA or genomic sequences, in order to generate expression vectors encoding complete Ig (e.g., IgG) molecules or other isotypes. $V_H$ and $V_L$ can also be used in the generation of Fab, Fv or other fragments of Igs using either protein chemistry or recombinant DNA technology.

"Single-chain Fv" or "sFv" antibody fragments comprise the $V_H$ and $V_L$ domains of an antibody, wherein these domains are present in a single polypeptide chain. In some embodiments, the Fv polypeptide further comprises a polypeptide linker between the $V_H$ and $V_L$ domains which enables the sFv to form the desired structure for antigen binding. For a review of sFvs, see, e.g., Pluckthun in The Pharmacology of Monoclonal Antibodies, Vol. 113, Rosenburg and Moore eds. Springer-Verlag, New York, pp. 269-315 (1994).

The term "AVIMER™" refers to a class of therapeutic proteins of human origin, which are unrelated to antibodies and antibody fragments, and are composed of several modular and reusable binding domains, referred to as A-domains (also referred to as class A module, complement type repeat, or LDL-receptor class A domain). They were developed from human extracellular receptor domains by in vitro exon shuffling and phage display (Silverman et al., 2005, *Nat. Biotechnol.* 23:1493-1494; Silverman et al., 2006, Nat. Biotechnol. 24:220). The resulting proteins can contain multiple independent binding domains that can exhibit improved affinity (in some cases, sub-nanomolar) and specificity compared with single-epitope binding proteins. See, for example, U.S. Patent Application Publ. Nos. 2005/0221384, 2005/0164301, 2005/0053973 and 2005/0089932, 2005/0048512, and 2004/0175756, each of which is hereby incorporated by reference herein in its entirety.

Each of the known 217 human A-domains comprises ~35 amino acids (~4 kDa); and these domains are separated by linkers that average five amino acids in length. Native A-domains fold quickly and efficiently to a uniform, stable structure mediated primarily by calcium binding and disulfide formation. A conserved scaffold motif of only 12 amino acids is required for this common structure. The end result is a single protein chain containing multiple domains, each of which represents a separate function. Each domain of the proteins binds independently and the energetic contributions of each domain are additive. These proteins were called "AVIMERs™" from avidity multimers.

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA* 90:6444 6448 (1993).

Antigen-binding polypeptides also include heavy chain dimers such as, for example, antibodies from camelids and sharks. Camelid and shark antibodies comprise a homodimeric pair of two chains of V-like and C-like domains (neither has a light chain). Since the $V_H$ region of a heavy chain dimer IgG in a camelid does not have to make hydrophobic interactions with a light chain, the region in the heavy chain that normally contacts a light chain is changed to hydrophilic amino acid residues in a camelid. $V_H$ domains of heavy-chain dimer IgGs are called $V_{HH}$ domains. Shark Ig-NARs comprise a homodimer of one variable domain (termed a V-NAR domain) and five C-like constant domains (C-NAR domains). In camelids, the diversity of antibody repertoire is determined by the CDRs 1, 2, and 3 in the $V_H$ or $V_{HH}$ regions. The CDR3 in the camel $V_{HH}$ region is characterized by its relatively long length, averaging 16 amino acids (Muyldermans et al., 1994, *Protein Engineering* 7(9): 1129). This is in contrast to CDR3 regions of antibodies of many other species. For example, the CDR3 of mouse $V_H$ has an average of 9 amino acids. Libraries of camelid-derived antibody variable regions, which maintain the in vivo diversity of the variable regions of a camelid, can be made by, for example, the methods disclosed in U.S. Patent Application Ser. No. 20050037421.

"Humanized" forms of non-human (e.g., murine) antibodies include chimeric antibodies which contain minimal sequence derived from a non-human Ig. For the most part, humanized antibodies are human Igs (recipient antibody) in which one or more of the CDRs of the recipient are replaced by CDRs from a non-human species antibody (donor antibody) such as mouse, rat, rabbit or non-human primate having the desired specificity, affinity and binding function. In some instances, one or more FR amino acid residues of the human Ig are replaced by corresponding non-human amino acid residues. Furthermore, humanized antibodies can contain residues which are not found in the recipient antibody or in the donor antibody. These modifications can be made to refine antibody performance, if needed. A humanized antibody can comprise substantially all of at least one and, in some cases two, variable domains, in which all or substantially all of the hypervariable regions correspond to those of a non-human immunoglobulin and all, or substantially all, of the FRs are those of a human immunoglobulin sequence. The humanized antibody optionally can also include at least a portion of an immunoglobulin constant region (Fc), typically that of a human immunoglobulin. For details, see Jones et al., Nature 321: 522-525 (1986); Reichmann et al., *Nature* 332: 323-329 (1988); and Presta, *Curr. Op. Struct. Biol.* 2: 593-596 (1992).

A humanized antibody also includes antibodies in which part, or all of the CDRs of the heavy and light chain are derived from a non-human monoclonal antibody, substantially all the remaining portions of the variable regions are derived from human variable region (both heavy and light chain), and the constant regions are derived from a human constant region. In one embodiment, the CDR1, CDR2 and CDR3 regions of the heavy and light chains are derived from a non-human antibody. In yet another embodiment, at least one CDR (e.g., a CDR3) of the heavy and light chains is derived from a non-human antibody. Various combinations of CDR1, CDR2, and CDR3 can be derived from a non-human antibody and are contemplated herein. In one non-limiting example, one or more of the CDR1, CDR2 and CDR3 regions of each of the heavy and light chains are derived from a murine chimeric monoclonal antibody clone TRC105.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations, which can include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, monoclonal antibodies can be made by the hybridoma method first described by Kohler et al., Nature 256:495 (1975), or can be made by recombinant DNA methods (see, e.g., U.S. Pat. No. 4,816,567). In certain embodiments, the monoclonal antibodies can be isolated from phage antibody libraries using the techniques described in Clackson et al., Nature 352:624-628 (1991) and Marks et al., J. Mol. Biol. 222:581-597 (1991), for example.

Antibodies can be isolated and purified from the culture supernatant or ascites mentioned above by saturated ammonium sulfate precipitation, euglobulin precipitation method, caproic acid method, caprylic acid method, ion exchange chromatography (DEAE or DE52), or affinity chromatography using anti-Ig column or a protein A, G or L column such as described in more detail below.

Exemplary antibodies for use in the compositions and methods described herein are intact immunoglobulin molecules, such as, for example, a humanized antibody or those portions of a humanized Ig molecule that contain the antigen binding site (i.e., paratope) or a single heavy chain and a single light chain, including those portions known in the art as Fab, Fab', F(ab)', F(ab')$_2$, Fd, scFv, a variable heavy domain, a variable light domain, a variable NAR domain, bi-specific scFv, a bi-specific Fab$_2$, a tri-specific Fab$_3$ and a single chain binding polypeptides and others also referred to as antigen-binding fragments. When constructing an immunoglobulin molecule or fragments thereof, variable regions or portions thereof may be fused to, connected to, or otherwise joined to one or more constant regions or portions thereof to produce any of the antibodies or fragments thereof described herein. This may be accomplished in a variety of ways known in the art, including but not limited to, molecular cloning techniques or direct synthesis of the nucleic acids encoding the molecules. Exemplary non-limiting methods of constructing these molecules can also be found in the examples described herein.

In one exemplary embodiment, the application contemplates a single chain binding polypeptide having a heavy chain variable region, and/or a light chain variable region which binds endoglin and has, optionally, an immunoglobulin Fc region. In one exemplary embodiment, the application contemplates a single chain binding polypeptide having a heavy chain variable region, and/or a light chain variable region which binds endoglin and has, optionally, an immunoglobulin Fc region. Such a molecule is a single chain variable fragment optionally having effector function or increased half-life through the presence of the immunoglobulin Fc region. Methods of preparing single chain binding polypeptides are known in the art (e.g., U.S. Patent Application No. 2005/0238646).

The terms "germline gene segments" or "germline sequences" refer to the genes from the germline (the haploid gametes and those diploid cells from which they are formed). The germline DNA contains multiple gene segments that encode a single Ig heavy or light chain. These gene segments are carried in the germ cells but cannot be transcribed and translated into heavy and light chains until they are arranged into functional genes. During B-cell differentiation in the bone marrow, these gene segments are randomly shuffled by a dynamic genetic system capable of generating more than $10^8$ specificities. Most of these gene segments are published and collected by the germline database.

As used herein, "immunoreactive" refers to binding agents, antibodies or fragments thereof that are specific to a sequence of amino acid residues ("binding site" or "epitope"), yet if are cross-reactive to other peptides/proteins, are not toxic at the levels at which they are formulated for administration to human use. The term "binding" refers to a direct association between two molecules, due to, for example, covalent, electrostatic, hydrophobic, and ionic and/or hydrogen-bond interactions under physiological conditions, and including interactions such as salt bridges and water bridges and any other conventional binding means. The term "preferentially binds" means that the binding agent binds to the binding site with greater affinity than it binds unrelated amino acid sequences. Preferably such affinity is at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater than the affinity of the binding agent for unrelated amino acid sequences. The terms "immunoreactive" and "preferentially binds" are used interchangeably herein.

As used herein, the term "affinity" refers to the equilibrium constant for the reversible binding of two agents and is expressed as $K_D$. Affinity of a binding protein to a ligand such as affinity of an antibody for an epitope can be, for example, from about 100 nanomolar (nM) to about 0.1 nM, from about 100 nM to about 1 picomolar (pM), or from about 100 nM to about 1 femtomolar (fM). As used herein, the term "avidity" refers to the resistance of a complex of two or more agents to dissociation after dilution. Apparent affinities can be determined by methods such as an enzyme linked immunosorbent assay (ELISA) or any other technique familiar to one of skill in the art. Avidities can be determined by methods such as a Scatchard analysis or any other technique familiar to one of skill in the art.

"Epitope" refers to that portion of an antigen or other macromolecule capable of forming a binding interaction with the variable region binding pocket of an antibody. Such binding interactions can be manifested as an intermolecular contact with one or more amino acid residues of one or more CDRs. Antigen binding can involve, for example, a CDR3 or a CDR3 pair or, in some cases, interactions of up to all six CDRs of the $V_H$ and $V_L$ chains. An epitope can be a linear peptide sequence (i.e., "continuous") or can be composed of noncontiguous amino acid sequences (i.e., "conformational" or "discontinuous"). An antibody can recognize one or more amino acid sequences; therefore an epitope can define more than one distinct amino acid sequence. Epitopes recognized by antibodies can be determined by peptide mapping and sequence analysis techniques well known to one of skill in the art. Binding interactions are manifested as intermolecular contacts with one or more amino acid residues of a CDR. TRC105 is a chimeric antibody which is the same variable amino acid sequence as the murine antibody described as Y4-2F1 or SN6j in U.S. Pat. Nos. 5,928,641; 6,200,566; 6,190,660; and 7,097,836. Epitopes recognized by Y4-2F1 and SN6j, and thus TRC105, have been previously identified.

The term "specific" refers to a situation in which an antibody will not show any significant binding to molecules other than the antigen containing the epitope recognized by the antibody. The term is also applicable where for example, an antigen binding domain is specific for a particular epitope which is carried by a number of antigens, in which case the antibody or antigen-binding fragment thereof carrying the antigen binding domain will be able to bind to the various antigens carrying the epitope. The terms "preferentially binds" or "specifically binds" mean that the antibodies or fragments thereof bind to an epitope with greater affinity than it binds unrelated amino acid sequences, and, if cross-reactive to other polypeptides containing the epitope, are not toxic at the levels at which they are formulated for administration to human use. In one aspect, such affinity is at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater than the affinity of the antibody or fragment thereof for unrelated amino acid sequences. The terms "immunoreactive," "binds," "preferentially binds" and "specifically binds" are used interchangeably herein. The term "binding" refers to a direct association between two molecules, due to, for example, covalent, electrostatic, hydrophobic, and ionic and/or hydrogen-bond interactions under physiological conditions, and includes interactions such as salt bridges and water bridges, as well as any other conventional means of binding.

The phrase "conservative amino acid substitution" refers to grouping of amino acids on the basis of certain common properties. A functional way to define common properties between individual amino acids is to analyze the normalized frequencies of amino acid changes between corresponding proteins of homologous organisms (Schulz, G. E. and R. H. Schirmer, Principles of Protein Structure, Springer-Verlag). According to such analyses, groups of amino acids may be defined where amino acids within a group exchange preferentially with each other, and therefore resemble each other most in their impact on the overall protein structure (Schulz, G. E. and R. H. Schirmer, Principles of Protein Structure, Springer-Verlag). Examples of amino acid groups defined in this manner include:

(i) a charged group, consisting of Glu and Asp, Lys, Arg and His,
(ii) a positively-charged group, consisting of Lys, Arg and His,
(iii) a negatively-charged group, consisting of Glu and Asp,
(iv) an aromatic group, consisting of Phe, Tyr and Trp,
(v) a nitrogen ring group, consisting of His and Trp,
(vi) a large aliphatic non-polar group, consisting of Val, Leu and Ile,
(vii) a slightly-polar group, consisting of Met and Cys,
(viii) a small-residue group, consisting of Ser, Thr, Asp, Asn, Gly, Ala, Glu, Gln and Pro,
(ix) an aliphatic group consisting of Val, Leu, Ile, Met and Cys, and
(x) a small hydroxyl group consisting of Ser and Thr.

In addition to the groups presented above, each amino acid residue may form its own group, and the group formed by an individual amino acid may be referred to simply by the one and/or three letter abbreviation for that amino acid commonly used in the art as described above.

A "conserved residue" is an amino acid that is relatively invariant across a range of similar proteins. Often conserved residues will vary only by being replaced with a similar amino acid, as described above for "conservative amino acid substitution."

A "non-conservative amino acid substitution" refers to a change from one amino acid in a group identified above into a different group.

The letter "x" or "xaa" as used in amino acid sequences herein is intended to indicate that any of the twenty standard amino acids may be placed at this position unless specifically noted otherwise. For the purposes of peptidomimetic design, an "x" or a "xaa" in an amino acid sequence may be replaced by a mimic of the amino acid present in the target sequence, or the amino acid may be replaced by a spacer of essentially any form that does not interfere with the activity of the peptidomimetic.

"Homology" or "identity" or "similarity" refers to sequence similarity between two peptides or between two nucleic acid molecules. Homology and identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. A sequence which is "unrelated" or "non-homologous" shares less than 40% identity, though preferably less than 25% identity with a sequence of the present invention. In comparing two sequences, the absence of residues (amino acids or nucleic acids) or presence of extra residues also decreases the identity and homology/similarity.

The term "homology" describes a mathematically based comparison of sequence similarities which is used to identify genes or proteins with similar functions or motifs. The nucleic acid (nucleotide, oligonucleotide) and amino acid (protein) sequences of the present invention may be used as a "query sequence" to perform a search against public databases to, for example, identify other family members, related sequences or homologs. Such searches can be performed using the NBLAST and(BLAST programs (version 2.0) of Altschul, et al. (1990) *J. Mol. Biol.* 215:403-10. BLAST nucleotide searches can be performed with the NBLAST program, score=100, word length=12 to obtain nucleotide sequences homologous to nucleic acid molecules of the invention. BLAST amino acid searches can be performed with the(BLAST program, score=50, word length=3 to obtain amino acid sequences homologous to protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and BLAST) can be used (see, world wide web site ncbi.nlm.nih.gov).

As used herein, "identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in (Computational Molecular Biology, Lesk, A. M., Ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., *SIAM J. Applied Math.*, 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., *Nucleic Acids Research* 12(1): 387 (1984)), BLASTP, BLASTN, and FASTA (Altschul, S. F. et al., J. Molec. Biol. 215: 403-410 (1990) and Altschul et al. *Nuc. Acids Res.* 25: 3389-3402 (1997)). The BLAST X program is publicly available from NCBI and other sources (BLAST Manual, Altschul, S., et al., NCBI NLM NIH Bethesda, Md. 20894; Altschul, S., et al., *J. Mol. Biol.* 215: 403-410 (1990). The well known Smith Waterman algorithm may also be used to determine identity.

"Isolated" (used interchangeably with "substantially pure") when applied to polypeptides means a polypeptide or a portion thereof which, by virtue of its origin or manipulation: (i) is present in a host cell as the expression product of a portion of an expression vector; or (ii) is linked to a protein or other chemical moiety other than that to which it is linked in nature; or (iii) does not occur in nature, for example, a protein that is chemically manipulated by appending, or adding at least one hydrophobic moiety to the protein so that the protein is in a form not found in nature. By "isolated" it is further meant a protein that is: (i) synthesized chemically; or (ii) expressed in a host cell and purified away from associated and contaminating proteins. The term generally means a polypeptide that has been separated from other proteins and nucleic acids with which it naturally occurs. Preferably, the polypeptide is also separated from substances such as antibodies or gel matrices (polyacrylamide) which are used to purify it.

"Inducing a host immune response" means that a patient experiences alleviation or reduction of signs or symptoms of illness, and specifically includes, without limitation, prolongation of survival. In certain preferred embodiments of the methods according to the invention, a CD8+ IFN-γ producing T cell is activated to induce a cytotoxic T lymphocyte (CTL) immune response in the patient administered the antagonist. In certain embodiments of the methods according to the invention, a CD4+ IFN-γ producing T cell is activated to induce a helper T cell immune response in the patient administered with the composition. These activated CD4+ IFN-γ producing T cells (i.e., helper T cells) provide necessary immunological help (e.g., by release of cytokines) to induce and maintain not only CTL, but also a humoral immune response mediated by B cells. Thus, in certain embodiments of the methods according to the invention, a humoral response to the antigen is activated in the patient administered with the composition. In one aspect, an adjuvant may be added to the composition to increase an immune response. Adjuvants are well-known in the art.

Activation of a CD8+ and/or CD4+ T cells means causing T cells that have the ability to produce cytokines (e.g., IFN-γ) to actually produce one or more cytokine(s), or to increase their production of one or more cytokine(s). "Induction of CTL response" means causing potentially cytotoxic T lymphocytes to exhibit antigen specific cytotoxicity. "Antigen specific cytotoxicity" means cytotoxicity against a cell presenting an antigen that is associated with the antigen associated with the cancer that is greater than an antigen that is not associated with a cancer. "Cytotoxicity" refers to the ability of the cytotoxic T lymphocyte to kill a target cell. Such antigen-specific cytotoxicity can be at least about 3-fold, at least about 10-fold greater, at least about 100-fold greater or more than cytotoxicity against a cell not presenting the antigen not associated with the cancer. Antibody dependent cell-mediated cytotoxicity (ADCC) also includes activation of natural killer cells ("NK cells") which mediate cell killing via antibody binding. The IgG1 antibodies and antigen-binding fragments described herein can mediate ADCC via NK cells through the binding of endoglin.

B. Methods of Making and Expressing Humanized Anti-Endoglin Antibodies

A chimeric monoclonal antibody has been developed that binds endoglin. This antibody is designated TRC105 (also known as c-SN6j).

In one aspect, the antibodies and antigen-binding fragments thereof described herein were created by humanization of the $V_L$ and $V_H$ sequences of the chimeric monoclonal TRC105 antibody (SEQ ID NOS. 1 and 39, respectively).

Humanized immunoglobulins, including humanized antibodies, have been constructed by means of genetic engineering. Most humanized immunoglobulins that have been previously described have comprised a framework that is identical to the framework of a particular human immunoglobulin chain (i.e., an acceptor or recipient), and three CDRs from a non-human (i.e., donor) immunoglobulin chain. As described herein, humanization can also include criteria by which a limited number of amino acids in the framework of a humanized immunoglobulin chain are identified and chosen to be the same as the amino acids at those positions in the donor rather than in the acceptor, in order to increase or maintain the affinity of an antibody comprising the humanized immunoglobulin chain.

The present invention is based in part on the model that two contributing causes of the loss of affinity in prior means of producing humanized antibodies (using as examples mouse antibodies as the source of CDRs) are: (1) when the mouse CDRs are combined with a human framework, the amino acids in the frameworks close to the CDRs become human instead of mouse. Without intending to be bound by theory, these changed amino acids may slightly distort the CDRs (e.g., they may create different electrostatic or hydrophobic forces than in the donor mouse antibody, and the distorted-CDRs may not make as effective contacts with the antigen as the CDRs did in the donor antibody); (2) also, amino acids in the original mouse antibody that are close to, but not part of, the CDRs (i.e., still part of the framework), may make contacts with the antigen that contribute to affinity. These amino acids are lost when the antibody is humanized because, generally, all framework amino acids are made human. To circumvent these issues, and to produce humanized antibodies that have a very strong affinity for a desired antigen, humanized antibodies and antigen-binding fragments thereof can be constructed using one or more of the following principles.

One non-limiting principle is that, for example, as acceptor, a framework is used from a particular human immunoglobulin that is unusually homologous to the donor immunoglobulin to be humanized, or use a consensus framework from many human antibodies is used as an acceptor. For example, comparison of the sequence of a mouse heavy (or light) chain variable region against human heavy (or light) variable regions in a data bank (for example, the National Biomedical Research Foundation Protein Identification Resource or the protein sequence database of the National Center for Biotechnology Information—NCBI) shows that the extent of homology to different human regions can vary greatly, for example from about 40% to about 60%, about 70%, about 80% or higher. By choosing as the acceptor immunoglobulin one of the human heavy chain variable regions that is most homologous to the heavy chain variable region of the donor immunoglobulin, fewer amino acids will be changed in going from the donor immunoglobulin to the humanized immunoglobulin. By choosing as the acceptor immunoglobulin one of the human light chain variable regions that is most homologous to the light chain variable region of the donor immunoglobulin, fewer amino acids will be changed in going from the donor immunoglobulin to the humanized immunoglobulin. Generally, using such techniques, there is a reduced chance of changing an amino acid near one or more of the CDRs that distorts their conformation. Moreover, the precise overall shape of a humanized antibody comprising the humanized immunoglobulin chain may more closely resemble the shape of the donor antibody, thereby also reducing the chance of distorting the CDRs.

One can also use light and heavy chains from the same human antibody as acceptor sequences, to improve the likelihood that the humanized light and heavy chains will make favorable contacts with each other. Alternatively, one can also use light and heavy chains from different human antibody germline sequences as acceptor sequences; when such combinations are used, one can readily determine whether the $V_H$ and $V_L$ bind an epitope of interest using conventional assays (e.g., an ELISA). In one example, the human antibody will be chosen in which the light and heavy chain variable regions sequences, taken together, are overall most homologous to the donor light and heavy chain variable region sequences. Sometimes greater weight will be given to the heavy chain sequence. Regardless of how the acceptor immunoglobulin is chosen, higher affinity can, in some cases, be achieved by selecting a small number of amino acids in the framework of the humanized immunoglobulin chain to be the same as the amino acids at those positions in the donor rather than in the acceptor. Methods of affinity maturation are known in the art.

Humanized antibodies generally have at least three potential advantages over mouse or chimeric antibodies for use in human therapy. Because the effector portion of an antibody is human, it is believed to interact better with the other parts of the human immune system (e.g., destroy the target cells more efficiently by complement-dependent cytotoxicity (CDC) or antibody-dependent cellular cytotoxicity (ADCC)). Additionally, the human immune system should not recognize the framework or constant region of the humanized antibody as foreign, and therefore the antibody response against such an injected antibody should be less than against a totally foreign mouse antibody or a partially foreign chimeric antibody. Finally, mouse antibodies are known to have a half-life in the human circulation that is much shorter than the half-life of human antibodies. Humanized antibodies can, presumably, have a half-life more similar to naturally-occurring human antibodies, allowing smaller and less frequent doses to be given.

Humanization of antibodies and antigen-binding fragments thereof, can be accomplished via a variety of methods known in the art and described herein. Similarly, production of humanized antibodies can also be accomplished via methods known in the art and described herein.

Methods for modifications of framework regions are known in the art and are contemplated herein. Selection of one or more relevant framework amino acid positions to be altered depends on a variety of criteria. One criterion for selecting relevant framework amino acids to change can be the relative differences in amino acid framework residues between the donor and acceptor molecules. Selection of relevant framework positions to alter using this approach has the advantage of avoiding any subjective bias in residue determination or any bias in CDR binding affinity contribution by the residue.

Another criterion that can be used for determining the relevant amino acid positions to change can be, for example, selection of framework residues that are known to be important or to contribute to CDR conformation. For example, canonical framework residues are important for CDR conformation and/or structure. Targeting of a canonical framework residue as a relevant position to change can be used to identify a more compatible amino acid residue in context with its associated donor CDR sequence.

The frequency of an amino acid residue at a particular framework position is another criterion which can be used for selecting relevant framework amino acid positions to change. For example, comparison of the selected framework with other framework sequences within its subfamily can reveal residues that occur at minor frequencies at a particular position or positions. Positions harboring less abundant residues are similarly applicable for selection as a position to alter in the acceptor variable region framework.

The relevant amino acid positions to change also can be selected, for example, based on proximity to a CDR. In certain contexts, FR residues can participate in CDR conformation and/or antigen binding. Moreover, this criterion can similarly be used to prioritize relevant positions selected by other criteria described herein. Therefore, differentiating between residues proximal and distal to one or more CDRs represents one way to reduce the number of relevant positions to change.

Other criteria for selecting relevant amino acid framework positions to alter include, for example, residues that are known or predicted to reside in a three dimensional space near the antigen-CDR interface or predicted to modulate CDR activity. Similarly, framework residues that are known to, or predicted to, form contacts between the heavy ($V_H$) and light ($V_L$) chain variable region interface can be selected. Such framework positions can affect the conformation and/or affinity of a CDR by modulating the CDR binding pocket, antigen (epitope) interaction or the $V_H$ and $V_L$ interaction. Therefore, selection of these amino acid positions for constructing a diverse population for screening of binding activity can be used to identify framework changes which replace residues having detrimental effects on CDR conformation or compensate for detrimental effects of residues occurring elsewhere in the framework.

Other framework residues that can be selected for alteration include amino acid positions that are inaccessible to solvent. Such residues are generally buried in the variable region and are, therefore, capable of influencing the conformation of the CDR or $V_H$ and $V_L$ interactions. Solvent accessibility can be predicted, for example, from the relative hydrophobicity of the environment created by the amino acid side chains of the polypeptide and/or by known three-dimensional structural data.

Following selection of relevant amino acid positions in the donor CDRs, as well as any relevant amino acid positions in the framework regions desired to be varied, amino acid changes at some or all of the selected positions can be incorporated into encoding nucleic acids for the acceptor variable region framework and donor CDRs. Altered framework or CDR sequences can be individually made and tested, or can be sequentially or simultaneously combined and tested.

The variability at any or all of the altered positions can range from a few to a plurality of different amino acid residues, including all twenty naturally occurring amino acids or functional equivalents and analogues thereof. In some cases, non-naturally occurring amino acids may also be considered and are known in the art.

Selection of the number and location of the amino acid positions to vary is flexible and can depend on the intended use and desired efficiency for identification of the altered variable region having a desirable activity such as substantially the same or greater binding affinity compared to the donor variable region. In this regard, the greater the number of changes that are incorporated into an altered variable region population, the more efficient it is to identify at least one species that exhibits a desirable activity, for example, substantially the same or greater binding affinity as the donor. Alternatively, where the user has empirical or actual data to the affect that certain amino acid residues or positions contribute disproportionally to binding affinity, then it can be desirable to produce a limited population of altered variable regions which focuses on changes within or around those identified residues or positions.

For example, if CDR grafted variable regions are desired, a large, diverse population of altered variable regions can include all the non-identical framework region positions between the donor and acceptor framework and all single CDR amino acid position changes. Alternatively, a population of intermediate diversity can include subsets, for example, of only the proximal non-identical framework positions to be incorporated together with all single CDR amino acid position changes to, for example, increase affinity of the humanized antibodies or antigen binding fragments. The diversity of the above populations can be further increased by, for example, additionally including all pairwise CDR amino acid position changes. In contrast, populations focusing on predetermined residues or positions which incorporate variant residues at as few as one framework and/or one CDR amino acid position can similarly be constructed for screening and identification of an altered antibody variable region. As with the above populations, the diversity of such focused populations can be further increased by additionally expanding the positions selected for change to include other relevant positions in either or both of the framework and CDR regions. There are numerous other combinations ranging from few changes to many changes in either or both of the framework regions and CDRs that can additionally be employed, all of which will result in a population of altered variable regions that can be screened for the identification of at least one CDR grafted altered variable region having desired activity, for example, binding activity to endoglin. Those skilled in the art will know, or can determine, which selected residue positions in the framework or donor CDRs, or subsets thereof, can be varied to produce a population for screening and identification of an altered antibody of the invention given the teachings and guidance provided herein. Codons encoding amino acids are known in the art.

Another method of humanizing antibodies includes a method termed "superhumanization." Superhumanization involves the steps of obtaining a peptide sequence for a subject variable region encoded by a non-human mature antibody gene and identifying a first set of canonical CDR structure types for at least two CDRs within the non-human antibody variable region. Canonical CDR structure types are the structure types designated by Chothia (CITE). Chothia and coworkers found that critical portions of the CDRs of many antibodies adopt nearly identical peptide backbone conformations, despite great diversity at the level of amino acid sequence. Accordingly, Chothia defined for each CDR in each chain one or a few "canonical structures." Each canonical structure specifies primarily a set of peptide backbone torsion angles for a contiguous segment of amino acid residues forming a loop.

After the identification of the canonical CDR structure type, a library of peptide sequences for human antibody variable regions for human antibodies is also obtained. This library contains sequences for human germline variable regions as encoded by germline nucleic acid segments, and may include mature human antibody sequences. In either case, the method includes identifying canonical CDR structure types (i.e., a second set of canonical CDR structure types) for at least two CDRs for each sequence within the library of human variable region sequences. From this library there is selected a subset of candidate sequences by comparing the first set of canonical CDR structure types to the second set of canonical CDR structure types (i.e., comparing the mouse canonical CDR structure types to the human canonical CDR structure types at corresponding locations within the variable region) and selecting those human sequences where the second set of canonical CDR structure is the same as the first set of canonical CDR structure types for the CDR sequences at corresponding locations within the non-human and human variable regions, respectively. The method uses these candidate human variable region sequences as a basis for constructing a chimeric molecule that includes at least two of the CDR sequences from the non-human variable region (e.g., of the mouse CDRs) combined with the framework regions from candidate human variable region sequences. The result of the construction is that the chimeric antibody contains each of the non-human CDR sequences substituted for each of the human CDR sequences at corresponding locations in the variable regions so that the framework sequences in the chimeric antibody differs from the candidate human framework sequences.

The similarity to the subject CDRs of candidate human antibody sequences is assessed for each domain at two levels. Primarily, identical three-dimensional conformations of CDR peptide backbones are sought. Experimentally determined atomic coordinates of the subject CDRs are seldom available, hence three-dimensional similarity is approximated by determining Chothia canonical structure types of the subject CDRs and excluding from further consideration candidates possessing different canonical structures. Secondarily, residue-to-residue homology between subject CDRs and the remaining human candidate CDRs is considered, and the candidate with the highest homology is chosen.

Choosing highest homology is based on various criterion used to rank candidate human variable regions having the same canonical structure as the subject the non-human variable regions. The criterion for ranking members of the selected set may be by amino acid sequence identity or amino acid homology or both. Amino acid identity is simple a score of position by position matches of amino acid residues. Similarity by amino acid homology is position by position similarity in residue structure of character. Homology may be scored, for example, according to the tables and procedures described by Henikoff and Henikoff, (1992) Amino acid substitution matrices from protein blocks, *Proc. Natl. Acad. Sci. USA* 89: 10915-10919, or by the BLOSUM series described by Henikoff and Henikoff, (1996). The steps are as follows:

a) Determine the peptide sequences of the heavy and light chain variable domains of the subject antibody. These can be determined by any of several methods, such as DNA sequencing of the respective genes after conventional cDNA cloning; DNA sequencing of cloning products that have been amplified by the polymerase chain reaction from reverse transcripts or DNA of the subject hybridoma line; or peptide sequencing of a purified antibody protein.

b) Apply the Kabat numbering system (Kabat et al, Id. 1991) to the heavy and light chain sequences of the subject non-human antibody. Determine canonical structure types for each of the CDRs of the subject non-human antibody. This determination is made from examination of the peptide sequence in light of the guidelines discussed in Chothia and Lesk (1987), Chothia et al. (1992), Tomlinson et al. (1995), Martin and Thornton (1996), and Al-Lazikani et al. (1997).

The salient features of canonical structure determination for each of the CDRs are as follows. For heavy chain CDR1, three canonical structure types are currently known. Assignment of a new sequence is straightforward because each canonical structure type has a different number of residues. As described in Al-Lazikani et al. (1997), when Kabat numbering is assigned to the sequence, the numbering for residues 31-35 will be as follows for the respective canonical structures:

Canonical structure type 1: 31, 32, 33, 34, 35;
Canonical structure type 2: 31, 32, 33, 34, 35, 35a; and
Canonical structure type 3: 31, 32, 33, 34, 35, 35a, 35b.

For heavy chain CDR2, four canonical structure types are currently known. Several have unique numbers of residues, and are easily distinguished from their unique Kabat numbering of positions 52-56, viz.:

Canonical structure type 1: 52, 53, 54, 55, 56; and
Canonical structure type 4: 52, 52a, 52b, 52c, 53, 54, 55, 56.

Canonical structure types 2 and 3 for heavy chain CDR2 have equal numbers of residues, hence must be distinguished by clues within their sequence, as discussed by Chothia et al. (1992). The Kabat numbering of the segment containing these clues is: 52, 52a, 53, 54, 55. Canonical structure type 2 has Pro or Ser at position 52a and Gly or Ser at position 55, with no restriction at the other positions. Canonical structure type 3 has Gly, Ser, Asn, or Asp at position 54, with no restriction at the other positions. These criteria are sufficient to resolve the correct assignment in most cases. Additionally, framework residue 71 is commonly Ala, Val, Leu, Ile, or Thr for canonical structure type 2 and commonly Arg for canonical structure type 3.

Heavy chain CDR3 is the most diverse of all the CDRs. It is generated by genetic processes, some of a random nature, unique to lymphocytes. Consequently, canonical structures for CDR3 have been difficult to predict. In any case, human germline V gene segments do not encode any part of CDR3; because the V gene segments end at Kabat position 94, whereas positions 95 to 102 encode CDR3. For these reasons, canonical structures of CDR3 are generally not considered for choosing candidate human sequences.

For light chain CDR1, six canonical structure types are currently known for CDR1 in kappa chains. Each canonical structure type has a different number of residues, hence assignment of a canonical structure type to a new sequence is apparent from the Kabat numbering of residue positions 27-31:

Canonical structure type 1: 27, 29, 30, 31;
Canonical structure type 2: 27, 28, 29, 30, 31;
Canonical structure type 3: 27, 27a, 27b, 27c, 27d, 27e, 27f, 28, 29, 30, 31;
Canonical structure type 4: 27, 27a, 27b, 27c, 27d, 27e, 28, 29, 30, 31;
Canonical structure type 5: 27, 27a, 27b, 27c, 27d, 28, 29, 30, 31; and
Canonical structure type 6: 27, 27a, 28, 29, 30, 31.

For light chain CDR2, only a single canonical structure type is known for CDR2 in kappa chains, hence, barring exceptional subject antibody sequences, assignment is automatic. For light chain CDR3, up to six canonical structure types have been described for CDR3 in kappa chains, but three of these are rare. The three common ones can be distinguished by their length, reflected in Kabat numbering of residue positions 91-97:

Canonical structure type 1: 91, 92, 93, 94, 95, 96, 97 (also with an obligatory Pro at position 95 and Gln, Asn, or His at position 90):
Canonical structure type 3: 91, 92, 93, 94, 95, 97; and
Canonical structure type 5: 91, 92, 93, 94, 95, 96, 96a, 97.

After identifying the canonical CDR structure types of the subject non-human antibody, human genes of the same chain type (heavy or light) that have the same combination of canonical structure types as the subject antibody are identified to form a candidate set of human sequences. Most of these gene fragments have been discovered and have already been assigned to a canonical structure type (Chothia et al., 1992, Tomlinson et al., 1995).

For the heavy chain, conformity of CDR1 and CDR2 to the mouse canonical structure types is assessed, and genes that do not conform are excluded. For the light chain, conformity of CDR1 and CDR2 of each human sequence to the canonical structure types of the subject antibody is first assessed. The potential of residues 89-95 of a candidate Vk gene to form a CDR3 of the same canonical structure type as the subject antibody is assessed, by positing a fusion of the gene with a J region and applying criteria for CDR3 canonical CDR structure type determination to the fused sequence, and non-conforming sequences are excluded.

Alternatively, when a variable domain of the subject antibody is of a canonical structure type not available in the human genome, human germline V genes that have three-dimensionally similar, but not identical, canonical structure types are considered for comparison. Such a circumstance often occurs with kappa chain CDR1 in murine antibodies, including two of the examples described below. All 6 possible canonical structure types have been observed at this CDR in murine antibodies, whereas the human genome encodes only canonical types 2, 3, 4 and 6. In these circumstances, a canonical CDR structure type having length of amino acid residues within two of the length of the amino acid residues of the subject non-human sequence may selected for the comparison. For example, where a type 1 canonical structure is found in the subject antibody, human Vk sequences with canonical structure type 2 are used for comparison. Where a type 5 canonical structure is found in the murine antibody, human Vk sequences with either canonical structure type 3 or 4 are be used for comparison.

Mature, rearranged human antibody sequences can be considered for the sequence comparison. Such consideration might be warranted under a variety of circumstances, including but not limited to instances where the mature human sequence (1) is very close to germline; (2) is known not to be immunogenic in humans; or (3) contains a canonical structure type identical to that of the subject antibody, but not found in the human germline.

For each of the candidate V genes with matching canonical structure types, residue to residue sequence identity and/or homology with the subject sequence is also evaluated to rank the candidate human sequences. For example, the residues evaluated are as follows: (1) Kappa (K) light chain CDR amino acid residue positions are CDR1 (26-32), CDR2 (50-52), CDR3 (91-96); and (2) heavy chain CDR amino acid residue positions are CDR1 (31-35) and CDR2 (50-60). Additionally, heavy chain CDR3 amino acid residue positions 95 to 102 can also be considered.

Residue-to-residue homology is first scored by the number of identical amino acid residues between the subject and the candidate human sequences. The human sequence used for subsequent construction of a converted antibody is chosen from among the 25 percent of candidates with the highest score. When appropriate, such as when several candidate sequences have similar identity scores, similarity between non-identical amino acid residues may be additionally considered as needed. Aliphatic-with-aliphatic, aromatic-with-aromatic, or polar-with-polar matches between subject and object residues are added to the scores. In another example, quantitative evaluation of sequence homology may be performed using amino acid substitution matrices such as the BLOSUM62 matrix of Henikoff and Henikoff.

An object sequence for the framework region C-terminal to CDR3 sequence can be selected from the set of known human germline J segments. A J peptide sequence is selected by evaluating residue to residue homology for each J segment for sequence positions for which CDR3 and J overlap, using the scoring criteria specified for the evaluation of candidate V genes as mentioned above. The J gene segment peptide sequence used for subsequent construction of a converted antibody is chosen from among the 25 percent of candidates with the highest score.

As an example, the chimeric variable chain contains at least two CDRs from a subject non-human sequence, and framework sequences from a candidate human sequence. In another example, chimeric light chain contains three CDRs from a subject non-human sequence and framework sequences from a candidate human sequence. In additional examples, a chimeric heavy chain contains at least two CDRs of a subject heavy chain, and framework sequence of a candidate human heavy chain, or a chimeric heavy chin contains each of the CDRs from the subject heavy chain and framework sequences of a candidate human heavy chain. In still another example, a chimeric antibody heavy chain contains CDRs 1 and 2 from a subject non-human sequence and residues 50-60 for CDR3 and residues 61-65 of a CDR from the candidate human heavy chain, along with the framework sequences of the candidate human sequence. In another example, a chimeric heavy chain sequence contains each CDR from the subject non-human sequence; frameworks sequences 27-30 form the subject sequence, and the framework sequences from the candidate sequences. In all cases however, the chimeric antibody molecule contains no more than 10 amino acid residues in the framework sequence that differ from those in the framework sequence of the candidate human variable ration.

When increased affinity of a humanized antibody is desired, residues within the CDRs of a converted antibody may be additionally substituted with other amino acids. Typically, no more than four amino acid residues in a CDR are changed, and most typically no more than two residues in the CDR will be changed, except for heavy chain CDR2, where as many as 10 residues may be changed. Changes in affinity can be measured by conventional methods such as those described herein (e.g., Biacore).

The methods of superhumanizing antibodies are described in more detail in U.S. Pat. No. 6,881,557 which is hereby incorporated by reference in its entirety.

Humanized antibodies and antigen-binding fragments can be constructed and produced using conventional techniques known in the art. In addition, recombinantly prepared antibodies can often be produced in large quantities, particularly when utilizing high level expression vectors.

Antibodies can be sequenced using conventional techniques known in the art. In one aspect, the amino acid sequences of one or more of the CDRs is inserted into a synthetic sequence of, for example, a human antibody (or antigen-binding fragment thereof) framework to create a human antibody that could limit adverse side reactions of treating a human patient with a non-human antibody. The amino acid sequences of one or more of the CDRs can also be inserted into a synthetic sequence of, for example, into a binding protein such as an AVIMER™ to create a construct for administration to a human patient. Such techniques can be modified depending on the species of animal to be treated. For example, for veterinary uses, an antibody, antigen-binding fragment or binding protein can be synthesized for administration of a non-human (e.g., a primate, a cow, a horse, etc.).

In another aspect, using art-recognized techniques such as those provided and incorporated herein, nucleotides encoding amino acid sequences of one or more of the CDRs can inserted, for example, by recombinant techniques in restriction endonuclease sites of an existing polynucleotide that encodes an antibody, antigen-binding fragment or binding protein.

For expression, an expression system is one which utilizes the GS system (Lonza) using a glutamine synthetase gene as the selectable marker. Briefly, a transfection is performed in CHO cells by electroporation (250V) using the GS system (Lonza) using the glutamine synthetase gene as the selectable marker. Wild type CHO cells are grown in DMEM (Sigma) containing 10% dialyzed Fetal Calf Serum (FCS) with 2 mM glutamine. $6 \times 10^7$ CHO cells are transfected with 300 µg of linearized DNA by electroporation. After electroporation the cells are resuspended in DMEM with glutamine and plated out into 36×96-well plates (50 µl/well), and incubated at 37° C. in 5% $CO_2$. The following day, 150 of selective medium (DMEM without glutamine) is added. After approximately 3 weeks the colonies are screened by ELISA (see below) using an irrelevant antibody as a negative control. All colonies producing >20 µg/ml are expanded into 24-well plates and then into duplicate T25 flasks.

For high level production, the most widely used mammalian expression system is one which utilizes the gene amplification procedure offered by dihydrofolate reductase deficient ("dhfr-") Chinese hamster ovary cells. The system is well known to the skilled artisan. The system is based upon the dihydrofolate reductase "dhfr" gene, which encodes the DHFR enzyme, which catalyzes conversion of dihydrofolate to tetrahydrofolate. In order to achieve high production, dhfr-CHO cells are transfected with an expression vector containing a functional DHFR gene, together with a gene that encodes a desired protein. In this case, the desired protein is recombinant antibody heavy chain and/or light chain.

By increasing the amount of the competitive DHFR inhibitor methotrexate (MTX), the recombinant cells develop resistance by amplifying the dhfr gene. In standard cases, the amplification unit employed is much larger than the size of the dhfr gene, and as a result the antibody heavy chain is co-amplified.

When large scale production of the protein, such as the antibody chain, is desired, both the expression level and the stability of the cells being employed are taken into account. In long term culture, recombinant CHO cell populations lose homogeneity with respect to their specific antibody productivity during amplification, even though they derive from a single, parental clone.

The present application provides an isolated polynucleotide (nucleic acid) encoding an antibody or antigen-binding fragment as described herein, vectors containing such polynucleotides, and host cells and expression systems for transcribing and translating such polynucleotides into polypeptides.

The present application also provides constructs in the form of plasmids, vectors, transcription or expression cassettes which comprise at least one polynucleotide as above.

The present application also provides a recombinant host cell which comprises one or more constructs as above. A nucleic acid encoding any antibody or antigen-binding fragments thereof described herein as provided itself forms an aspect of the present application, as does a method of production of the antibody or antigen-binding fragments thereof described herein which method comprises expression from encoding nucleic acid therefrom. Expression can conveniently be achieved by culturing under appropriate conditions recombinant host cells containing the nucleic acid. Following production by expression, an antibody or antigen-binding fragment can be isolated and/or purified using any suitable technique, then used as appropriate. Antibodies described herein have been engineered with particular features in mind to reduce their immunogenicity to prevent human anti-mouse antibody (HAMA) reactions while retaining specificity and avidity.

Specific antibodies, antigen-binding fragments, and encoding nucleic acid molecules and vectors described herein can be provided isolated and/or purified, e.g., from their natural environment, in substantially pure or homogeneous form. In the case of nucleic acid, free or substantially free of nucleic acid or genes origin other than the sequence encoding a polypeptide with the required function. Nucleic acid can comprise DNA or RNA and can be wholly or partially synthetic. Methods of purification are well known in the art.

Systems for cloning and expression of a polypeptide in a variety of different host cells are well known. Suitable host cells include bacterial cells, mammalian cells, yeast cells and baculovirus systems. Mammalian cell lines available in the art for expression of a heterologous polypeptide include Chinese hamster ovary cells, HeLa cells, baby hamster kidney cells, NS0 mouse myeloma cells and many others. A common bacterial host is *E. coli*.

The expression of antibodies and antibody fragments in prokaryotic cells such as *E. coli* is well established in the art. For a review, see, for example Plückthun, A., *Bio/Technology* 9: 545-551 (1991). Expression in eukaryotic cells in culture is also available to those skilled in the art as an option for production of the antibodies and antigen-binding fragments described herein, see for recent reviews, for example Raff, M. E., (1993) *Curr. Opinion Biotech.* 4: 573-576; Trill J. J., et al. (1995) *Curr. Opinion Biotech* 6: 553-560, each of which is which is incorporated herein by reference in its entirety.

Suitable vectors can be chosen or constructed, containing appropriate regulatory sequences, including promoter sequences, terminator sequences, polyadenylation sequences, enhancer sequences, marker genes and other sequences as appropriate. Vectors can be plasmids, viral e.g., 'phage, or phagemid, as appropriate. For further details see, for example, Molecular Cloning: a Laboratory Manual: 2nd Ed., Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Short Protocols in Molecular Biology, Second Edition, Ausubel et al. Eds., John Wiley & Sons, 1992. The methods disclosures of Sambrook et al. and Ausubel et al. are incorporated herein by reference in their entirety and are well known in the art.

Thus, a further aspect provides a host cell containing nucleic acid as disclosed herein. A still further aspect provides a method comprising introducing such nucleic acid into a host cell. The introduction can employ any available technique. For eukaryotic cells, suitable techniques can include, for example, calcium phosphate transfection, DEAE Dextran, electroporation, liposome-mediated transfection and transduction using retrovirus or other virus, e.g., vaccinia or, for insect cells, baculovirus. For bacterial cells, suitable techniques can include, for example, calcium chloride transformation, electroporation and transfection using bacteriophage.

The introduction can be followed by causing or allowing expression from the nucleic acid, e.g., by culturing host cells under conditions for expression of the gene.

In one embodiment, the nucleic acid is integrated into the genome (e.g., chromosome) of the host cell. Integration can be promoted by inclusion of sequences which promote recombination with the genome, in accordance with standard techniques. Ig enhances can be initialized as needed to maximize expression.

The present application also provides a method which comprises using a construct as stated above in an expression system in order to express the antibodies or antigen-binding fragments thereof as above.

The present application also relates to isolated nucleic acids, such as recombinant DNA molecules or cloned genes, or degenerate variants thereof, mutants, analogs, or fragments thereof, which encode an antibody or antigen-binding sequence described herein that binds endoglin.

In one aspect, the present application provides a nucleic acid which codes for an antibody or antigen-binding fragment thereof as described herein which binds endoglin.

In a further embodiment, the full DNA sequence of the recombinant DNA molecule or cloned gene of an antibody or antigen-binding fragment described herein can be operatively linked to an expression control sequence which can be introduced into an appropriate host. The application accordingly extends to unicellular hosts transformed with the cloned gene or recombinant DNA molecule comprising a DNA sequence encoding the $V_H$ and/or $V_L$, or portions thereof, of the antibody.

Another feature is the expression of the DNA sequences disclosed herein. As is well known in the art, DNA sequences can be expressed by operatively linking them to an expression control sequence in an appropriate expression vector and employing that expression vector to transform an appropriate unicellular host.

Such operative linking of a DNA sequence to an expression control sequence, of course, includes, if not already part of the DNA sequence, the provision of an initiation codon, ATG, in the correct reading frame upstream of the DNA sequence.

Polynucleotides and vectors can be provided in an isolated and/or a purified form (e.g., free or substantially free of polynucleotides of origin other than the polynucleotide encoding a polypeptide with the required function). As used herein, "substantially pure," and "substantially free" refer to a solution or suspension containing less than, for example, about 20% or less extraneous material, about 10% or less extraneous material, about 5% or less extraneous material, about 4% or less extraneous material, about 3% or less extraneous material, about 2% or less extraneous material, or about 1% or less extraneous material.

A wide variety of host/expression vector combinations can be employed in expressing the DNA sequences of this invention. Useful expression vectors, for example, can consist of segments of chromosomal, non-chromosomal and synthetic DNA sequences. Suitable vectors include, but are not limited to, derivatives of SV40 and known bacterial plasmids, e.g., *E. coli* plasmids col E1, Pcr1, Pbr322, Pmb9 and their derivatives, plasmids such as RP4; phage DNAs, e.g., the numerous derivatives of phage k, e.g., NM989, and other phage DNA, e.g., M13 and filamentous single stranded phage DNA; yeast plasmids such as the 2u plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Also provided herein is a recombinant host cell which comprises one or more polynucleotide constructs. A polynucleotide encoding an antibody or antigen-binding fragment as provided herein forms an aspect of the present application, as does a method of production of the antibody or antigen-binding fragment which method comprises expression from the polynucleotide. Expression can be achieved, for example, by culturing under appropriate conditions recombinant host cells containing the polynucleotide. An antibody or antigen-binding fragment can then be isolated and/or purified using any suitable technique, and used as appropriate.

Any of a wide variety of expression control sequences—sequences that control the expression of a DNA sequence operatively linked to it—can be used in these vectors to express the DNA sequences. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast alpha-mating factors, and other sequences known to control the expression of genes of prokaryotic or eukaryotic cells or their viruses, and various combinations thereof.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary (CHO) cells, HeLa cells, baby hamster kidney cells, NS0 mouse myeloma cells and many others. A common, bacterial host can be, for example, *E. coli*.

The expression of antibodies or antigen-binding fragments in prokaryotic cells, such as *E. coli*, is well established in the art. For a review, see for example Plückthun, A., *Bio/Technology* 9: 545-551 (1991). Expression in eukaryotic cells in culture is also available to those skilled in the art (Raff, M. E., (1993) *Curr. Opinion Biotech*. 4: 573-576; Trill J. J. et al., (1995) *Curr. Opinion Biotech* 6: 553-560).

A wide variety of unicellular host cells are also useful in expressing the DNA sequences. These hosts include well-known eukaryotic and prokaryotic hosts, such as strains of *E. coli, Pseudomonas, Bacillus, Streptomyces*, fungi such as yeasts, and animal cells, such as CHO, YB/20, NS0, SP2/0, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences. Neither will all hosts function equally well with the same expression system. However, one skilled in the art will be able to select the proper vectors, expression control sequences, and hosts without undue experimentation to accomplish the desired expression without departing from the scope of this application. For example, in selecting a vector, the host must be considered because the vector must function in it. The vector's copy number, the ability to control that copy number, and the expression of any other proteins encoded by the vector, such as antibiotic markers, will also be considered. One of ordinary skill in the art can select the proper vectors, expression control sequences, and hosts to accomplish the desired expression without departing from the scope of this application. For example, in selecting a vector, the host is considered because the vector functions in it. The vector's copy number, the ability to control that copy number, and the expression of any other proteins encoded by the vector, such as antibiotic markers, can also be considered.

The present application also provides constructs in the form of plasmids, vectors, transcription or expression cassettes as described elsewhere herein which comprise at least one polynucleotide as above. Suitable vectors can be chosen or constructed, containing appropriate regulatory sequences, including promoter sequences, terminator sequences, polyadenylation sequences, enhancer sequences, selectable markers and other sequences as appropriate. Vectors can be plasmids, viral e.g., phage, phagemid, etc., as appropriate. For further details see, for example, Molecular Cloning: a Laboratory Manual: 2nd Ed., Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Short Protocols in Molecular Biology, Second Edition, Ausubel et al. Eds., John Wiley & Sons, 1992. The methods and disclosures of Sambrook et al. and Ausubel et al. are incorporated herein by reference.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

A further aspect provides a host cell containing one or more polynucleotides as disclosed herein. Yet a further aspect provides a method of introducing such one or more polynucleotides into a host cell, any available technique. For eukaryotic cells, suitable techniques can include, for example, calcium phosphate transfection, DEAE Dextran, electroporation, liposome-mediated transfection and transduction using retrovirus or other virus (e.g., vaccinia) or, for insect cells, baculovirus. For bacterial cells, suitable techniques can include, for example calcium chloride transformation, electroporation and transfection using bacteriophages.

The introduction can be followed by causing or allowing expression from the one or more polynucleotides, e.g., by culturing host cells under conditions for expression of one or more polypeptides from one or more polynucleotides. Inducible systems can be used and expression induced by addition of an activator.

In one embodiment, the polynucleotides can be integrated into the genome (e.g., chromosome) of the host cell. Integration can be promoted by inclusion of sequences which promote recombination with the genome, in accordance with standard techniques. In another embodiment, the nucleic acid is maintained on an episomal vector in the host cell.

Methods are provided herein which include using a construct as stated above in an expression system in order to express a specific polypeptide.

Considering these and other factors, a person skilled in the art will be able to construct a variety of vector/expression control sequence/host combinations that will express the DNA sequences on fermentation or in large scale animal culture.

A polynucleotide encoding an antibody, antigen-binding fragment, or a binding protein can be prepared recombinantly/synthetically in addition to, or rather than, cloned. The polynucleotide can be designed with the appropriate codons for the antibody, antigen-binding fragment, or a binding protein. In general, one will select preferred codons for an intended host if the sequence will be used for expression. The complete polynucleotide can be assembled from overlapping oligonucleotides prepared by standard methods and assembled into a complete coding sequence. See, e.g., Edge, *Nature*, 292:756 (1981); Nambair et al., *Science*, 223:1299 (1984); Jay et al., *J. Biol. Chem.*, 259: 6311 (1984).

A general method for site-specific incorporation of unnatural amino acids into proteins is described in Christopher J. Noren, Spencer J. Anthony-Cahill, Michael C. Griffith, Peter G. Schultz, *Science*, 244:182-188 (April 1989). This method can be used to create analogs with unnatural amino acids.

As mentioned above, a DNA sequence encoding an antibody or antigen-binding fragment thereof can be prepared synthetically rather than cloned. The DNA sequence can be designed with the appropriate codons for the antibody or antigen-binding fragment amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, *Nature*, 292:756 (1981); Nambair et al., *Science*, 223:1299 (1984); Jay et al., *J. Biol. Chem.*, 259:6311 (1984), each of which is which is incorporated herein by reference in its entirety.

C. In Silico Analysis of Immunogenicity

If needed, an antibody or an antigen binding fragment thereof described herein can be assessed for immunogenicity and, as needed, be deimmunized (i.e., the antibody is made less immuno reactive by altering one or more T cell epitopes). Analysis of immunogenicity and T-cell epitopes present in the humanized anti-endoglin antibodies and antigen-binding fragments described herein can be carried out via the use of software and specific databases. Exemplary software and databases include iTope™ developed by Antitope of Cambridge, England. iTope™ is an in silico technology for analysis of peptide binding to human MHC class II alleles.

The iTope™ software predicts peptide binding to human MHC class II alleles and thereby provides an initial screen for the location of such "potential T cell epitopes." iTope™ software predicts favorable interactions between amino acid side chains of a peptide and specific binding pockets within the binding grooves of 34 human MHC class II alleles. The location of key binding residues is achieved by the in silico generation of 9 mer peptides that overlap by one amino acid spanning the test antibody variable region sequence. Each 9 mer peptide can be tested against each of the 34 MHC class II allotypes and scored based on their potential "fit" and interactions with the MHC class II binding groove. Peptides that produce a high mean binding score (>0.55 in the iTope™ scoring function) against >50% of the MHC class II alleles are considered as potential T cell epitopes. In such regions, the core 9 amino acid sequence for peptide binding within the MHC class II groove is analyzed to determine the MHC class II pocket residues (P1, P4, P6, P7 and P9) and the possible T cell receptor (TCR) contact residues (P-1, P2, P3, P5, P8).

After identification of any T-cell epitopes, amino acid residue changes, substitutions, additions, and/or deletions can be introduced to remove the identified T-cell epitope. Such changes can be made so as to preserve antibody structure and function while still removing the identified epitope. Exemplary changes can include, but are not limited to, conservative amino acid changes.

Techniques exploiting soluble complexes of recombinant MHC molecules in combination with synthetic peptides have come into use. These reagents and procedures may be used to identify the presence of T-cell clones from peripheral blood samples from human or experimental animal subjects that are able to bind particular MHC-peptide complexes and are not adapted for the screening multiple potential epitopes to a wide diversity of MHC allotypes.

Biological assays of T-cell activation remain the best practical option to providing a reading of the ability of a test peptide/protein sequence to evoke an immune response. Examples of this kind of approach include the use of T-cell proliferation assays to the bacterial protein staphylokinase, followed by epitope mapping using synthetic peptides to stimulate T-cell lines. Similarly, T-cell proliferation assays using synthetic peptides of the tetanus toxin protein have resulted in definition of immunodominant epitope regions of the toxin. In one embodiment, T-cell epitopes in a test protein may be determined using isolated sub-sets of human immune cells, promoting their differentiation in vitro and culture of the cells in the presence of synthetic peptides of interest and measurement of any induced proliferation in the cultured T-cells. Other techniques may also be used. Such a technique involves careful application of cell isolation techniques and cell culture with multiple cytokine supplements to obtain the desired immune cell sub-sets (dendritic cells, CD4+ and or CD8+ T-cells). In another embodiment, the presence of T cell epitopes in an antibody may be determined by adding the antibody to isolated sub-sets of human immune cells, and assessing their differentiation in vitro and measuring any induced proliferation in the cultured T cells.

In silico techniques to define MHC class II ligands for multiple proteins of therapeutic interest may also be utilized. However, for reasons such as the requirement for proteolytic processing and other physiologic steps leading to the presentation of immunogenic peptides in vivo, a sub-set of the entire repertoire of peptides definable by computer-based schemes may have ultimate biological relevance. Thus, ex vivo human T-cell activation assays may be used to identify the regions within the protein sequence of a polypeptide that are able to support T-cell activation and are thereby most biologically relevant to the problem of immunogenicity in this protein. As used herein, "T-cell epitope" refers to an amino acid sequence which is able to bind MHC class II, able to stimulate T-cells and/or also to bind (without necessarily measurably activating) T-cells in complex with MHC class II.

According to a method disclosed herein, synthetic peptides or whole antibodies are tested for their ability to evoke a proliferative response in human T-cells cultured in vitro. The T-cells are present within a peripheral blood mononuclear cell (PBMC) layer readily obtainable by well known means from whole blood samples. Moreover, the PBMC preparation contains physiological ratios of T-cells and antigen presenting cells and is, therefore, a good source of materials with which to conduct a surrogate immune reaction in vitro. In the operation of such an assay, a stimulation index approaching or exceeding 2.0 is a useful measure of induced proliferation. However, the stimulation index may be different depending upon the antibody, or antigen-binding fragment thereof, and may be established with reference to a baseline for each antibody, or antigen-binding fragment thereof, and corresponding peptide library. In one example of such testing, the stimulation index (SI) may be conventionally derived by division of the proliferation score (e.g., counts per minute of radioactivity if using for example $^3$H-thymidine incorporation) measured to the test peptide by the score measured in cells not contacted with a test peptide. Peptides which evoke no response may give a SI=1.0 although SI values in the range 0.8-1.2 may also be unremarkable. A number of technical procedures can be built into the operation of such assays in order to ensure confidence in the recorded scores. Typically all determinations are made at least in triplicate and the mean score may be computed. Where a computed SI=>2.0, individual scores of the triplicate can be examined for evidence of outlying data. Test peptides are contacted with cells in at least two different concentrations and the concentrations would typically span a minimum two-fold concentration difference. Such a concentration range provides an off-set to the kinetic dimension to the assay and may be useful where a single time point determination, for example at day plus 7, is being conducted. In some assays, multiple time course determinations may be conducted and these too may be made using peptide immunogen provided at a minimum of two different concentrations. Similarly the inclusion of control peptides for which there is expectation that the majority of PBMC donor samples will be responsive may be included in each assay plate. The influenza haemagglutinin peptide 307-309, sequence PKYVKQNTLKLA (SEQ ID NO: 104); and the Chlamydia HSP 60 peptide sequence KVVDQIKKISK-PVQH (SEQ ID NO: 105) are examples of control peptides to be used in such an assay. Alternatively, or in addition, assays could also use a potent whole protein antigen, such as hemocyanin from Keyhole Limpet, to which all PBMC samples would be expected to exhibit an SI significantly greater than 2.0. Other control antigens for such use will be well-known in the art.

The methods disclosed herein can provide an epitope map of antibodies, or antigen-binding fragments thereof, where the map has relevance to a wide spectrum of possible MHC allotypes. The map may be sufficiently representative to allow the design or selection of a modified protein for which the ability of the protein to evoke a T-cell driven immune response may be eliminated or at least ameliorated for the majority of patients to whom the protein is likely to be administered. Amelioration can refer to a reduction in an immune response (i.e., reduced immunogenicity) compared to an unmodified protein (e.g., about 1.5 fold less, about 2 fold less, about 5 fold less, about 10 fold less, about 20 fold less, about 50 fold less, about 100 fold less, about 200 fold less, about 500 fold less or more, or any range therein). Alternatively, antibodies, or antigen-binding fragments thereof, with reduced immunogenicity can refer to a percent reduction in its ability to elicit an immune response compared to an unmodified protein (e.g., about 1% less, about 2% less, about 3% less, about 4% less, about 5% less, about 10% less, about 20% less, about 50% less, about 100% less, and any range therein). Accordingly in the practice of the screening process, PBMC derived T-cells from naive donors are collected from a pool of donors of sufficient immunological diversity to provide a sample of at least greater than 90% of the MHC class II repertoire (HLA-DR) extant in the human population. Where a naive T-cell response is to be detected to a given synthetic peptide (or antibody), the peptide (or antibody) in practice is contacted with PBMC preparations derived from multiple donors in isolation; the numbers of donors (or "donor pool" size), is for practical purposes not likely to be less than 20 unrelated individuals and all samples in the donor pool may be pre-selected according to their MHC class II haplotype.

As used herein, the term "naive donor" refers to a subject that has not been previously exposed to antibodies, or antigen-binding fragments thereof, described herein either environmentally, by vaccination, or by other means such as, for example, blood transfusions.

When screening for T-cell epitopes, T-cells can be provided from a peripheral blood sample from a multiplicity of different healthy donors but who have not been in receipt of the protein therapeutically. If needed, patient blood samples can be tested for the presence of a particular polypeptide using conventional assays such as an ELISA which uses antibodies to identify the presence or absence of one or more polypeptides. The assay is conducted using PBMC cultured in vitro using conventional procedures known in the art and involves contacting the PBMC with synthetic peptide species representative of the protein of interest (i.e., a library), or a whole protein, such as an antibody and following a suitable period of incubation, measurement of induced T cell activation such as cellular proliferation. Measurement can be by any suitable means and may, for example, be conducted using $H^3$-thymidine incorporation whereby the accumulation of $H^3$ into cellular material is readily measured using laboratory instruments. The degree of cellular proliferation for each combination of PBMC sample and synthetic peptide or whole protein can be examined relative to that seen in an untreated PBMC sample. Reference may also be made to the proliferative response seen following treatment with a peptide or peptides or whole proteins for which there is an expected proliferative effect. In this regard, it is advantageous to use a peptide or whole protein with known broad MHC restriction and especially peptide epitopes with MHC restriction to the DP or DQ isotypes, although the invention is not limited to the use of such restricted peptides or proteins. Such peptides have been described above, for example, with respect to influenza haemagglutinin and chlamydia HSP60.

In one non-limiting example, T-cell epitopes are mapped and subsequently modified using the methods described herein. To facilitate assembly of an epitope map, a library of synthetic peptides is produced. Each of the peptides is 15 amino acid residues in length and each overlapped the next peptide in the series by 12 amino acid residues; i.e., each successive peptide in the series incrementally added a further 3 amino acids to the analysis. In this way, any given adjacent pair of peptides mapped 18 amino acids of contiguous sequence. One method for defining a T-cell map using naive T-cell assays is illustrated in the Examples below. Each of the peptides identified via the method to define a T-cell map are suggested to be able to bind MHC class II and engage at least one cognate TCR with sufficient affinity to evoke a proliferative burst detectable in the assay system.

In another non-limiting example, the potential of an antibody to be processed to generate T-cell epitopes that bind MHC class II and engage at least one cognate TCR with sufficient affinity to evoke a proliferative burst detectable in the assay system is assessed.

The molecules described herein can be prepared in any of several ways including the use of recombinant methods. The protein sequences and information provided herein can be used to deduce a polynucleotide (DNA) encoding an amino acid sequence. This can be achieved for example using computer software tools such as the DNASTAR® software suite [DNASTAR® Inc, Madison, Wis., USA] or similar. Any such polynucleotide encoding the polypeptides or significant homologues, variants, truncations, elongations, or further modifications thereof, are contemplated herein.

Provided herein are methods of mapping (identifying) T-cell epitopes and modifying the epitopes such that the modified sequence reduces (partially or completely) induction of a T-helper response. Modification includes amino acid substitutions, deletions, or insertion made in codons of a polynucleotide encoding modified polypeptides to affect similar changes. Codons encoding amino acid residues are well known in the art. It is possible to use recombinant DNA methods to achieve directed mutagenesis of the target sequences and many such techniques are available, described herein, and known in the art such as described above. In general, the technique of site-specific mutagenesis is well known. Briefly, a bacteriophage vector that produces a single stranded template for oligonucleotide directed PCR mutagenesis is employed. Phage vectors (e.g., M13) are commercially available and their use is generally well known in the art. Similarly, double stranded plasmids are also routinely employed in site directed mutagenesis, which eliminates the step of transferring the polynucleotide of interest from a phage to a plasmid. Synthetic oligonucleotide primers bearing the desired mutated sequence can be used to direct the in vitro synthesis of modified (desired mutant) DNA from this template and the heteroduplex DNA is used to transform competent E. coli for the growth selection and identification of desired clones. Alternatively, a pair of primers can be annealed to two separate strands of a double stranded vector to simultaneously synthesize both corresponding complementary strands with the desired mutation(s) in a PCR reaction.

In one embodiment, the Quick Change site-directed mutagenesis method using plasmid DNA templates may be employed. PCR amplification of the plasmid template containing the insert target gene of insert is achieved using two synthetic oligonucleotide primers containing the desired mutation. The oligonucleotide primers, each complementary to opposite strands of the vector, are extended during temperature cycling by mutagenesis-grade Pfu Turbo DNA polymerase. On incorporation of the oligonucleotide primers, a mutated plasmid containing staggered nicks is generated. Amplified un-methylated products are treated with Dpn I to digest methylated parental DNA template and select for the newly synthesized DNA containing mutations. Since DNA isolated from most E. coli strains is dam methylated, it is susceptible to Dpn I digestion, which is specific for methylated and hemi-methylated DNA. The reaction products are transformed into high efficiency strains of E. coli to obtain plasmids containing the desired modifications. Additional methods for introducing amino acid modifications into a polypeptide are well known in the art and can also be used herein.

Suitable modifications to a protein may include amino acid substitution of particular residues or combinations of residues. For the elimination of T-cell epitopes, amino acid substitutions are made at appropriate points or amino acid residues within an amino acid sequence predicted to achieve reduction or elimination of the activity of the T-cell epitope. In practice, an appropriate point or amino acid residue will preferably equate to an amino acid residue binding within one of the pockets provided within the MHC class II binding groove. Such modifications may alter binding within the first pocket of the cleft at the so-called "P1" or "P1 anchor" position of the peptide. The quality of binding interaction between the P1 anchor residue of the peptide and the first pocket of the MHC class II binding groove is recognized as being a major determinant of overall binding affinity for the whole peptide. An appropriate substitution at this position of the amino acid sequence will generally incorporate an amino acid residue less readily accommodated within the pocket (e.g., substitution to a more hydrophilic residue). Amino acid residues in the peptide at positions equating to binding within other pocket regions within the MHC binding cleft are also considered and fall under the scope of the present.

It is understood that single amino acid modifications within a given potential T-cell epitope represent one route by which one or more T-cell epitopes may be eliminated. Combinations of modifications within a single epitope may be contemplated and can be appropriate where individually defined epitopes are in overlap with each other. Moreover, amino acid modifications (either singly within a given epitope or in combination within a single epitope) may be made at positions not equating to the "pocket residues" with respect to the MHC class II binding groove, but at any point within the amino acid sequence. Modifications may be made with reference to a homologous structure or structural method produced using in silico techniques known in the art and described herein may be based on known structural features of the polypeptide. A change (modification) may be contemplated to restore structure or biological activity of the variant molecule. Such compensatory changes and changes may also include deletion or addition (insertion) of particular amino acid residues from a polypeptide. Additionally, modifications can be made that alter the structure and/or reduce the biological activity of the molecule and also eliminate a T-cell epitope, thus reducing the immunogenicity of the molecule. All types of modifications are contemplated herein.

An additional means of removing epitopes from protein molecules is the concerted use of a naive T-cell activation assay scheme as outlined herein together with an in silico tool developed according to the scheme described in WO 02/069232 which is also incorporated fully herein by reference. The software simulates the process of antigen presentation at the level of the polypeptide-MHC class II binding interaction to provide a binding score for any given polypeptide sequence. Such a score is determined for many of the predominant MHC class II allotypes extant in the population. As this scheme is able to test any polypeptide sequence, the consequences of amino acid substitutions additions or deletions with respect to the ability of a polypeptide to interact with a MHC class II binding groove can be predicted. Consequently new sequence compositions can be designed which contain reduced numbers of amino acids able to interact with a MHC class II and thereby function as immunogenic T-cell epitopes. Where the biological assay using any one given donor sample can assess binding to a maximum of four DR allotypes, the in silico process can test a same polypeptide sequence using >40 allotypes simultaneously. In practice this approach is able to direct the design of new sequence variants which are altered in their ability to interact with multiple MHC allotypes. As will be clear to one in the art, multiple alternative sets of substitutions could be arrived at which achieve the objective of removing undesired epitopes. The resulting sequences would however be recognized to be closely homologous with the specific compositions disclosed herein and therefore fall within the scope of the present application.

A combined approach of using an in silico tool for the identification of MHC class II ligands and design of sequence analogues lacking MHC class II ligands, in concert with epitope mapping and re-testing optionally using biologically based assays of T-cell activation is an additional method and embodiment of the present application. The general method according to this embodiment comprises the following steps:

i) use of naive T-cell activation assays and synthetic peptides collectively encompassing the protein sequence of interest to identify epitope regions capable of activating T-cells;

ii) use of a computational scheme simulating the binding of the peptide ligand with one or more MHC allotypes to analyze the epitope regions identified in step (i) and thereby identify MHC class II ligands within the epitope region;

iii) use of a computational scheme simulating the binding of the peptide ligand with one or more MHC allotypes to identify sequence analogues of the MHC ligands encompassed within the epitope region(s) which no longer bind MHC class II or bind with lowered affinity to a lesser number of MHC allotypes and, optionally, iv) use of naive T-cell activation assays and synthetic peptides encompassing entirely or in collection encompassing the epitope regions identified within the protein of interest and testing the sequence analogues in naive T-cell activation assay in parallel with the wild-type (parental) sequences.

In one embodiment, a method of making a modified antibody, or antigen-binding fragment thereof, exhibiting reduced immunogenicity compared to an unmodified antibody, or antigen-binding fragment thereof, comprises identifying at least one T-cell epitope within the amino acid sequence of an antibody, or antigen-binding fragment thereof, and modifying at least one amino acid residue within at least one identified T-cell epitope.

In another embodiment, a modified antibody, or antigen-binding fragment thereof, exhibiting reduced immunogenicity compared to an unmodified antibody, or antigen-binding fragment thereof, is produced by a process of identifying at least one T-cell epitope within the amino acid sequence of an antibody, or antigen-binding fragment thereof, and modifying at least epitope one amino acid residue within at least one identified T-cell epitope.

In yet another embodiment, a method of selecting a modified antibody, or antigen-binding fragment thereof, that exhibits reduced immunogenicity compared to an unmodified antibody, or antigen-binding fragment thereof, comprises identifying at least one T-cell epitope within the amino acid sequence of a antibody, or antigen-binding fragment thereof, modifying at least one amino acid residue within at least one identified T-cell epitope, and selecting a modified antibody, or antigen-binding fragment thereof, that exhibits reduced immunogenicity compared to an unmodified antibody, or antigen-binding fragment thereof.

T-cell epitopes described herein can be further characterized by the regions of the. Such regions include the epitope core, the N-terminus and the C-terminus. As used herein "epitope core" refers to the core 9-mer amino acid sequences of the T-cell epitopes. The epitope core can further include 0, 1, 2, or 3 amino acid residues adjacent to the core 9-mer amino acid sequence on the N-terminus and/or the C-terminus. Thus the epitope core, in certain embodiments, can range in length from about 9 amino acids up to about 15 amino acids.

As used herein, "N-terminus" refers to the amino acids adjacent to the N-terminus of the epitope core and includes at least 1, 2, 3, 4, 5, 6, 7, 8 or 9 amino acids adjacent to and upstream of the N-terminus of the epitope core.

As used herein, "C-terminus" refers to the amino acids adjacent to the C-terminus of the epitope core and includes at least 1, 2, 3, 4, 5, 6, 7, 8, or 9 amino acids adjacent to and downstream of the C-terminus of the epitope core.

In one embodiment, a modified antibody, or antigen-binding fragment thereof, contains one or more modifications. In one embodiment, a modified antibody, or antigen-binding fragment thereof, contains two modifications. In one embodiment, a modified antibody, or antigen-binding fragment thereof, contains three modifications. In one embodiment, a modified antibody, or antigen-binding fragment thereof, contains four modifications. In one embodiment, a modified antibody, or antigen-binding fragment thereof, contains five modifications. In one embodiment, a modified antibody, or antigen-binding fragment thereof, contains six modifications. In one embodiment, a modified antibody, or antigen-binding fragment thereof, contains seven modifications. In one embodiment, a modified antibody, or antigen-binding fragment thereof, contains eight modifications. In one embodiment, a modified antibody, or antigen-binding fragment thereof, contains nine modifications. In one embodiment, a modified antibody, or antigen-binding fragment thereof, contains ten modifications. In one embodiment, a modified antibody, or antigen-binding fragment thereof, contains up to twenty modifications.

Provided herein is an antibody, or antigen-binding fragment thereof, comprising a light chain variable region having an amino acid sequence set forth as SEQ ID NO: 93 (VK1AA) and a heavy chain variable region having an amino acid sequence set forth as SEQ ID NO: 89 (VH1A2).

Provided herein is a humanized and deimmunized antibody, or antigen-binding fragment thereof, comprising a heavy chain variable region having an amino acid sequence set forth as any one of SEQ ID NOS: 88, 89, 90, 91 and 92.

Provided herein is a humanized and deimmunized antibody, or antigen-binding fragment thereof, comprising a light chain variable region having an amino acid sequence set forth as any one of SEQ ID NOS: 93, 94, 95, 96, 97, 100, 102, and 103.

Provided herein is a humanized and deimmunized antibody, or antigen-binding fragment thereof, that binds endoglin, comprising a heavy chain variable region having an amino acid sequence set forth as SEQ ID NO: 89 and a light chain variable region having an amino acid sequence set forth as SEQ ID NO: 93, wherein:

(i) the heavy chain variable region further comprises one or more modifications selected from the group consisting of a substitution of glycine (G) by alanine (A) or serine (S) at position 49; a substitution of alanine (A) by isoleucine (I) at position 51; a substitution of lysine (K) by arginine (R) or asparagine (Q) at position 52b; a substitution of leucine (L) by valine (V) at position 78 utilizing the Kabat numbering system; and (ii) the light chain variable region further comprises one or more modifications selected from the group consisting of a substitution of methionine (M) by leucine (L) at position 4; a substitution of alanine (A) by valine (V) at position 19; a substitution of threonine (T) by serine (S) at position 22; a substitution of alanine (A) by isoleucine (I) at position 48; and a substitution of threonine (T) by serine (S) at position 51 utilizing the Kabat numbering system Provided herein is a humanized and deimmunized antibody, or antigen-binding fragment thereof comprising a heavy chain variable region having an amino acid sequence set forth as SEQ ID NO: 88, 89, 90, 91 and 92; and a light chain variable region having an amino acid sequence set forth as SEQ ID NO: 93, 95, 96, 97, 100, 102, or 103.

In addition to the aforementioned examples and embodiments, a modified a humanized and deimmunized antibody, or antigen-binding fragment thereof, with one or more amino acid modifications in one or more T-cell epitopes are contemplated herein. In one non-limiting example, provided herein are antibodies, or antigen-binding fragments thereof, having at least one modification in at least one T-cell epitope. In another non-limiting example, provided herein are antibodies, or antigen-binding fragments thereof, having at least one amino acid modification in 1, 2, 3, 4, 5, 6, or 7 of the T-cell epitopes described herein. Additional non-limiting examples include antibodies, or antigen-binding fragments thereof, having more than one amino acid modification in more than one T-cell epitope. Any combination of the amino acid modifications in any number of the antibodies, or antigen-binding fragments thereof, T-cell epitopes described above are contemplated herein.

T-Cell Epitopes and Allotype Frequency

Individual epitopes found within antigens can be preferentially presented by specific MHC class II allotypes, and similarly other specific epitopes within the same antigen may not be presented on MHC class II molecules at all. Such associations of particular epitopes with specific MHC class II molecules have been shown to depend upon the MHC class II allotype of the individual. The association of a specific epitope with a specific allotype can also be considered when modifying antibodies, or antigen-binding fragments thereof, for the removal of T-cell epitopes. Such considerations can allow for the highly specific modification of an antibody, or antigen-binding fragment thereof, for specific allotypes (e.g., for specific populations of subjects having certain MHC class II allotypes). The MHC class II allotype of a subject or subjects can be easily determined by genotyping methods known in the art, and the association of T-cell epitopes with the given allotype thus easily identified, for consideration in modification of antibodies, or antigen-binding fragments thereof, tailored to that allotype. Identification of associations between T-cell epitopes and MHC class II allotypes are described in more detail in the examples below. Contemplated herein are modified antibodies, or antigen-binding fragments thereof, that have T-cell epitope modifications tailored to the MHC class II associations identified for the given epitopes.

D. Anti-Endoglin Antibodies

Simultaneous incorporation of all of the FR and/or CDR encoding nucleic acids and all of the selected amino acid position changes can be accomplished by a variety of methods known to those skilled in the art, including for example, recombinant and chemical synthesis. For example, simultaneous incorporation can be accomplished by, for example, chemically synthesizing the nucleotide sequence for the acceptor variable region, fused together with the donor CDR encoding nucleic acids, and incorporating at the positions selected for harboring variable amino acid residues a plurality of corresponding amino acid codons.

One can recognize that the a humanized and deimmunized antibodies and antigen-binding fragments thereof generated using the methods described herein can be tested using the assays provided herein or known in the art for the ability to bind to endoglin using conventional methods including, but not limited to, ELISA. Affinity of antibodies described herein can also be determined using conventional methods including, but not limited to, Biacore or surface plasmon resonance. The activity of the antibodies may tested using a competitive assay such as described in the Examples, to determine if the antibodies inhibit BMP9 function. Cell signaling pathways to assess the activity of, for example Smad 1/5/8 are known in the art and are contemplated for use herein.

The antibodies and antigen binding fragments thereof described herein were constructed by humanization of the $V_H$ and $V_L$ sequences of the TRC105 antibody. To accomplish this humanization, a 3-dimensional model of the $V_H$ and $V_L$ chains of TRC105 was created and analyzed. The $V_H$ and $V_L$ sequences were then compared individually to a database of human germline sequences, from which human $V_H$ and $V_L$ sequences were chosen based on their homology to the $V_H$ and $V_L$ sequences of TRC105. The human $V_L$ sequence chosen for humanization was O2/O12 (VK1-39) (SEQ ID NO. 2). O2/O12 has a sequence identity with TRC105 of 65% and the gene is highly expressed in the human germline repertoire. The human $V_H$ sequence chosen for humanization was VH3-15 (SEQ ID NO. 40). VH3-15 has sequence identity with TRC105 of 70% and is expressed with reasonable frequency in the human germline repertoire. The amino acid positions which were different between TRC105 and the human sequences were examined in the 3D model of TRC105 to determine which substitutions would be considered for modification. Amino acid selection criteria based on the 3D model analysis included, but was not limited to, for example, steric effects related to the amino acid, relative charge of the amino acid, and the location of the amino acid within the variable heavy and/or light chains. The identified and proposed substitutions for the human framework regions are incorporated into the O2 and VH3-15 human framework regions, and the CDRs of TRC105 are grafted into the corresponding O2 and VH3-15 human framework regions resulting in a multitude of humanized antibodies or antigen-binding fragments. Additionally, the FR-4 of the light chain is derived from human J germline sequence Jk4. Similarly, the FR-4 of the heavy chain is derived from human J germline sequence JH4.

Antibodies and antigen-binding fragments thereof can have a variable heavy ($V_H$) chain, a variable light ($V_L$) chain, both, or binding portions thereof. In one embodiment, the $V_H$ chain has an amino acid sequence set forth as any of SEQ ID NOS: 41-43, or a binding portion thereof. Such $V_H$ chains can have framework regions sequences set forth as any of SEQ ID NOS: 44-62. In another embodiment, the $V_L$ chain has an amino acid sequence set forth as any of SEQ ID NOS: 3-5, or a binding portion thereof. Such V$_L$ chains can have framework regions sequences set forth as any of SEQ ID NOS: 6-38.

Provided herein is an antibody, or antigen-binding fragment thereof, comprising a light chain variable region having an amino acid sequence set forth as SEQ ID NO: 3 and a heavy chain variable region having an amino acid sequence set forth as SEQ ID NO: 41.

Provided herein is an antibody, or antigen-binding fragment thereof, comprising a light chain variable region having an amino acid sequence set forth as SEQ ID NO: 3 and a heavy chain variable region having an amino acid sequence set forth as SEQ ID NO: 41, wherein: the heavy chain variable region further comprises one or more modifications selected from the group consisting of a substitution of glycine (G) by alanine (A) at position 49; a substitution of asparagine (N) by serine (S) at position 76; a substitution of threonine (T) by arginine (R) at position 77; a substitution of leucine (L) by valine (V) at position 78; a substitution of asparagine (N) by isoleucine (I) at position 82a; a substitution of valine (V) by isoleucine (I) or leucine (L) at position 89; a substitution of threonine (T) by arginine (R) or glycine (G) at position 94; a substitution of leucine (L) by threonine (T) at position 108; a substitution of valine (V) by leucine (L) at position 109; and a substitution of serine (S) by alanine (A) at position 113 utilizing the Kabat numbering system; and the light chain variable region further comprises one or more modifications selected from the group consisting of a substitution of aspartic acid (D) by glutamine (Q) at position 1; a substitution of glutamine (Q) by valine (V) at position 3; a substitution of methionine (M) by leucine (L) at position 4; a substitution of threonine (T) by serine (S) at position 5; a substitution of tyrosine (Y) by phenylalanine (F) at position 36; a substitution of leucine (L) by proline (P) at position 46; a substitution of leucine (L) by tryptophan (W) at position 47; a substitution of serine (S) by valine (V) or alanine (A) at position 60; a substitution of aspartic acid (D) by serine (S) at position 70; a substitution of phenylalanine (F) by tyrosine (Y) at position 71; a substitution of glutamine (G) by alanine (A) at position 100; and a substitution of isoleucine (I) by leucine (L) at position 106 utilizing the Kabat numbering system.

Provided herein is an antibody, or antigen-binding fragment thereof, that binds endoglin comprising a heavy chain variable region having an amino acid sequence set forth as SEQ ID NO: 41, 42, or 43; and a light chain variable region having an amino acid sequence set forth as SEQ ID NO: 3, 4, or 5. An antibody, or antigen-binding fragment thereof, can comprise a heavy chain variable region having an amino acid sequence set forth as SEQ ID NO: 41 and a light chain variable region having an amino acid sequence set forth as SEQ ID NO: 3. An antibody, or antigen-binding fragment thereof, can comprise a heavy chain variable region having an amino acid sequence set forth as SEQ ID NO: 41 and a light chain variable region having an amino acid sequence set forth as SEQ ID NO: 4. An antibody, or antigen-binding fragment thereof, can comprise a heavy chain variable region having an amino acid sequence set forth as SEQ ID NO: 41 and a light chain variable region having an amino acid sequence set forth as SEQ ID NO: 5. An antibody, or antigen-binding fragment thereof, can comprise a heavy chain variable region having an amino acid sequence set forth as SEQ ID NO: 42 and a light chain variable region having an amino acid sequence set forth as SEQ ID NO: 3. An antibody, or antigen-binding fragment thereof, can comprise a heavy chain variable region having an amino acid sequence set forth as SEQ ID NO: 42 and a light chain variable region having an amino acid sequence set forth as SEQ ID NO: 4. An antibody, or antigen-binding fragment thereof, can comprise a heavy chain variable region having an amino acid sequence set forth as SEQ ID NO: 42 and a light chain variable region having an amino acid sequence set forth as SEQ ID NO: 5. An antibody, or antigen-binding fragment thereof, can comprise a heavy chain variable region having an amino acid sequence set forth as SEQ ID NO: 43 and a light chain variable region having an amino acid sequence set forth as SEQ ID NO: 3. An antibody, or antigen-binding fragment thereof, can comprise a heavy chain variable region having an amino acid sequence set forth as SEQ ID NO: 43 and a light chain variable region having an amino acid sequence set forth as SEQ ID NO: 4. An antibody, or antigen-binding fragment thereof, can comprise a heavy chain variable region having an amino acid sequence set forth as SEQ ID NO: 43 and a light chain variable region having an amino acid sequence set forth as SEQ ID NO: 5.

In any of such embodiments, a heavy chain variable region can further comprise one or more modifications selected from the group consisting of: a substitution of asparagine (N) by serine (S) at position 76; a substitution of threonine (T) by arginine (R) at position 77; a substitution of asparagine (N) by isoleucine (I) at position 82a; a substitution of valine (V) by isoleucine (I) or leucine (L) at position 89; a substitution of threonine (T) by glycine (G) at position 94; a substitution of leucine (L) by threonine (T) at position 108; a substitution of valine (V) by leucine (L) at position 109; and a substitution of serine (S) by alanine (A) a position 113; and the light chain variable region can further comprise one or more modifications selected from the group consisting of: a substitution of aspartic acid (D) by glutamine (Q) at position 1; a substitution of glutamine (Q) by valine (V) at position 3; a substitution of threonine (T) by serine (S) at position 5; a substitution of tyrosine (Y) by phenylalanine (F) a position 36; a substitution of serine (S) by valine (V) or alanine (A) at position 60; a substitution of aspartic acid (D) by serine (S) at position 70; a substitution of glycine (G) by alanine (A) at position 100, and a substitution of isoleucine (I) by leucine (L) at position 106 utilizing the Kabat numbering system.

Provided herein is an antibody, or antigen-binding fragment thereof, that binds endoglin, comprising a heavy chain variable region and a light chain variable region, wherein said heavy chain variable region comprises:

(i) a CDR1 of SEQ ID NO: 66, a CDR2 of SEQ ID NO: 67, and a CDR3 of SEQ ID NO: 68;

(ii) a heavy chain FR1 having the amino acid sequence of SEQ ID NO: 44 or the amino acid sequence of SEQ ID NO: 44 except for one or more conservative substitutions;

(iii) a heavy chain FR2 having the amino acid sequence of SEQ ID NO: 45 or the amino acid sequence of SEQ ID NO: 45 except for a substitution of glycine (G) by alanine (A) at position 49 utilizing the Kabat numbering system; and (iv) a heavy chain FR3 having the amino acid sequence of SEQ ID NO: 47 or the amino acid sequence of SEQ ID NO: 47 except for one or more substitutions selected from the group consisting of:

(a) a substitution of asparagine (N) by serine (S) at position 76;

(b) a substitution of threonine (T) by arginine (R) at position 77;

(c) a substitution of leucine (L) by valine (V) at position 78;

(d) a substitution of asparagine (N) by isoleucine (I) at position 82a;

(e) a substitution of valine (V) by isoleucine (I) or leucine (L) at position 89; and
(f) a substitution of threonine (T) by arginine (R) or glycine (G) at position 94 utilizing the Kabat numbering system; and
(v) a heavy chain FR4 having the amino acid sequence of SEQ ID NO: 56 or the amino acid sequence of SEQ ID NO: 56 except for one or more substitutions selected from the group consisting of:
   (a) a substitution of leucine (L) by threonine (T) at position 108;
   (b) a substitution of valine (V) by leucine (L) at position 109; and
   (c) a substitution of serine (S) by alanine (A) at position 113 utilizing the Kabat numbering system;
and said light chain variable region comprises:
(i) a CDR1 of SEQ ID NO: 63, a CDR2 of SEQ ID NO: 64, and a CDR3 of SEQ ID NO: 65;
(ii) a light chain FR1 having the amino acid sequence of SEQ ID NO: 6 or the amino acid sequence of SEQ ID NO: 6 except for one or more substitutions selected from the group consisting of:
   (a) a substitution of aspartic acid (D) by glutamine (Q) at position 1;
   (b) a substitution of glutamine (Q) by valine (V) at position 3;
   (c) a substitution of methionine (M) by leucine (L) at position 4; and
   (d) a substitution of threonine (T) by serine (S) at position 5; utilizing the Kabat numbering system; and
(iii) a light chain FR2 having the amino acid sequence of SEQ ID NO: 20 or the amino acid sequence of SEQ ID NO: 20 except for one or more substitutions selected from the group consisting of:
   (a) a substitution of tyrosine (Y) by phenylalanine (F) at position 36;
   (b) a substitution of leucine (L) by proline (P) at position 46; and
   (c) a substitution of leucine (L) by tryptophan (W) at position 47 utilizing the Kabat numbering system; and
(iv) a light chain FR3 having the amino acid sequence of SEQ ID NO: 28 or the amino acid sequence of SEQ ID NO: 28 except for one or more substitutions selected from the group consisting of:
   (a) a substitution of serine (S) by valine (V) or alanine (A) at position 60;
   (b) a substitution of aspartic acid (D) by serine (S) at position 70; and
   (b) a substitution of phenylalanine (F) by tyrosine (Y) at position 71 utilizing the Kabat numbering system; and
(v) a light chain FR4 having the amino acid sequence of SEQ ID NO: 35 or the amino acid sequence of SEQ ID NO: 35 except for one or more substitutions selected from the group consisting of:
   (a) a substitution of glycine (G) by alanine (A) at position 100; and
   (b) a substitution of isoleucine (I) by leucine (L) at position 106 utilizing the Kabat numbering system.

An antibody, or antigen-binding fragment thereof, provided herein can comprise a heavy chain variable region CDR1 having an amino acid sequence as set forth in SEQ ID NO: 66, a heavy chain variable region CDR2 having an amino acid sequence as set forth in SEQ ID NO: 67, a heavy chain variable region CDR3 having an amino acid sequence as set forth in SEQ ID NO: 68, a light chain variable region CDR1 having an amino acid sequence as set forth in SEQ ID NO: 63, a light chain variable region CDR2 having an amino acid sequence as set forth in SEQ ID NO: 64, and a light chain variable region CDR3 having an amino acid sequence as set forth in SEQ ID NO: 65.

In one embodiment, the antibody, or antigen-binding fragment thereof binds endoglin and comprises a heavy chain variable region FR1 having an amino acid sequence as set forth in SEQ ID NO: 44; a heavy chain variable region FR2 having an amino acid sequence as set forth in SEQ ID NO: 45; a heavy chain variable region FR3 having an amino acid sequence as set forth in SEQ ID NO: 47; a heavy chain variable region FR4 having an amino acid sequence as set forth in SEQ ID NO: 56.

In another embodiment, the antibody, or antigen-binding fragment thereof binds endoglin and comprises a heavy chain variable region FR1 having an amino acid sequence as set forth in SEQ ID NO: 44; a heavy chain variable region FR2 having an amino acid sequence as set forth in SEQ ID NO: 46; a heavy chain variable region FR3 having an amino acid sequence as set forth in SEQ ID NO: 48; a heavy chain variable region FR4 having an amino acid sequence as set forth in SEQ ID NO: 56.

In another embodiment, the antibody, or antigen-binding fragment thereof, comprises a light chain variable region FR1 having an amino acid sequence as set forth in SEQ ID NO: 6; a light chain variable region FR2 having an amino acid sequence as set forth in SEQ ID NO: 20; a light chain variable region FR3 having an amino acid sequence as set forth in SEQ ID NO: 28; and a light chain variable region FR4 having an amino acid sequence as set forth in SEQ ID NO: 35.

In another embodiment, the antibody, or antigen-binding fragment thereof binds endoglin and comprises a light chain variable region FR1 having an amino acid sequence as set forth in SEQ ID NO: 6; a light chain variable region FR2 having an amino acid sequence as set forth in SEQ ID NO: 21; a light chain variable region FR3 having an amino acid sequence as set forth in SEQ ID NO: 29; and a light chain variable region FR4 having an amino acid sequence as set forth in SEQ ID NO: 35.

In another embodiment, the antibody, or antigen-binding fragment thereof binds endoglin and comprises a light chain variable region FR1 having an amino acid sequence as set forth in SEQ ID NO: 7; a light chain variable region FR2 having an amino acid sequence as set forth in SEQ ID NO: 21; a light chain variable region FR3 having an amino acid sequence as set forth in SEQ ID NO: 29; and a light chain variable region FR4 having an amino acid sequence as set forth in SEQ ID NO: 35.

Provided herein is an antibody, or antigen-binding fragment thereof, comprising a heavy chain variable region having an amino acid sequence set forth as SEQ ID NO: 42 and a light chain variable region having an amino acid sequence set forth as SEQ ID NO: 4.

Provided herein is an antibody, or antigen-binding fragment thereof, that binds endoglin, comprising a light chain variable region having an amino acid sequence set forth as SEQ ID NO: 4 and a heavy chain variable region having an amino acid sequence set forth as SEQ ID NO: 42, wherein: said heavy chain variable region further comprises one or more modifications selected from the group consisting of a substitution of glycine (G) by alanine (A) at position 49; a substitution of asparagine (N) by serine (S) at position 76; a substitution of threonine (T) by arginine (R) at position 77; a substitution of leucine (L) by valine (V) at position 78; a substitution of asparagine (N) by isoleucine (I) at position 82a; a substitution of valine (V) by isoleucine (I) or leucine (L) at position 89; a substitution of arginine (R) by threonine (T) or glycine (G) at position 94; a substitution of leucine (L) by threonine (T) at position 108; a substitution of valine (V) by leucine (L) at position 109; and a substitution of serine (S) by alanine (A) at position 113 utilizing the Kabat numbering system; and the light chain variable region further comprises one or more modifications selected from the group consisting of a substitution of aspartic acid (D) by glutamine (Q) at position 1; a substitution of glutamine (Q) by valine (V) at position 3; a substitution of methionine (M) by leucine (L) at position 4; a substitution of threonine (T) by serine (S) at position 5; a substitution of tyrosine (Y) by phenylalanine (F) at position 36; a substitution of proline (P) by leucine (L) at position 46; a substitution of tryptophan (W) by leucine (L) at position 47; a substitution of serine (S) by valine (V) or alanine (A) at position 60; a substitution of aspartic acid (D) by serine (S) at position 70; a substitution of tyrosine (Y) by phenylalanine (F) at position 71; a substitution of glutamine (G) by alanine (A) at position 100; and a substitution of isoleucine (I) by leucine (L) at position 106 utilizing the Kabat numbering system Provided herein is an antibody, or antigen-binding fragment thereof, that binds endoglin, comprising a heavy chain variable region and a light chain variable region, wherein said heavy chain variable region comprises:
(i) a CDR1 of SEQ ID NO: 66, a CDR2 of SEQ ID NO: 67, and a CDR3 of SEQ ID NO: 68;
(ii) a heavy chain FR1 having the amino acid sequence of SEQ ID NO: 44 or the amino acid sequence of SEQ ID NO: 44 except for one or more conservative substitutions;
(iii) a heavy chain FR2 having the amino acid sequence of SEQ ID NO: 45 or the amino acid sequence of SEQ ID NO: 45 except for a substitution of glycine (G) by alanine (A) at position 49 utilizing the Kabat numbering system; and
(iv) a heavy chain FR3 having the amino acid sequence of SEQ ID NO: 47 or the amino acid sequence of SEQ ID NO: 47 except for one or more substitutions selected from the group consisting of:
   (a) a substitution of asparagine (N) by serine (S) at position 76;
   (b) a substitution of threonine (T) by arginine (R) at position 77;
   (c) a substitution of leucine (L) by valine (V) at position 78;
   (d) a substitution of asparagine (N) by isoleucine (I) at position 82a;
   (e) a substitution of valine (V) by isoleucine (I) or leucine (L) at position 89; and
   (f) a substitution of arginine (R) by threonine (T) or glycine (G) at position 94 utilizing the Kabat numbering system; and
(v) a heavy chain FR4 having the amino acid sequence of SEQ ID NO: 56 or the amino acid sequence of SEQ ID NO: 56 except for one or more substitutions selected from the group consisting of:
   (a) a substitution of leucine (L) by threonine (T) at position 108;
   (b) a substitution of valine (V) by leucine (L) at position 109; and
   (c) a substitution of serine (S) by alanine (A) at position 113 utilizing the Kabat numbering system;
and said light chain variable region comprises:
(i) a CDR1 of SEQ ID NO: 63, a CDR2 of SEQ ID NO: 64, and a CDR3 of SEQ ID NO: 65;
(ii) a light chain FR1 having the amino acid sequence of SEQ ID NO: 6 or the amino acid sequence of SEQ ID NO: 6 except for one or more substitutions selected from the group consisting of:
   (a) a substitution of aspartic acid (D) by glutamine (Q) at position 1;
   (b) a substitution of glutamine (Q) by valine (V) at position 3;
   (c) a substitution of methionine (M) by leucine (L) at position 4; and
   (d) a substitution of threonine (T) by serine (S) at position 5; utilizing the Kabat numbering system; and
(iii) a light chain FR2 having the amino acid sequence of SEQ ID NO: 21 or the amino acid sequence of SEQ ID NO: 20 except for one or more substitutions selected from the group consisting of:
   (a) a substitution of tyrosine (Y) by phenylalanine (F) at position 36;
   (b) a substitution of proline (P) by leucine (L) at position 46; and
   (c) a substitution of tryptophan (W) by leucine (L) at position 47 utilizing the Kabat numbering system; and
(iv) a light chain FR3 having the amino acid sequence of SEQ ID NO: 29 or the amino acid sequence of SEQ ID NO: 28 except for one or more substitutions selected from the group consisting of:
   (a) a substitution of serine (S) by valine (V) or alanine (A) at position 60;
   (b) a substitution of aspartic acid (D) by serine (S) at position 70; and
   (b) a substitution of tyrosine (Y) by phenylalanine (F) at position 71 utilizing the Kabat numbering system; and
(v) a light chain FR4 having the amino acid sequence of SEQ ID NO: 35 or the amino acid sequence of SEQ ID NO: 35 except for one or more substitutions selected from the group consisting of:
   (a) a substitution of glycine (G) by alanine (A) at position 100; and
   (b) a substitution of isoleucine (I) by leucine (L) at position 106 utilizing the Kabat numbering system.

A substantial portion of a variable domain will include three CDR regions, together with their intervening framework regions. The portion can also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of humanized endoglin antibodies and antigen-binding fragments described herein made by recombinant DNA techniques can result in the introduction of N- or C-terminal residues encoded by linkers introduced to facilitate cloning or other manipulation steps. Other manipulation steps include the introduction of linkers to join variable domains to further protein sequences including immunoglobulin heavy chains, other variable domains (for example in the production of diabodies) or protein labels as discussed in more detail below.

Humanized endoglin CDR3 regions having amino acid sequences substantially as set out as the CDR3 regions of the antibodies described herein will be carried in a structure which allows for binding of the CDR3 regions to endoglin. The structure for carrying the CDR3s can be of an antibody heavy or light chain sequence or substantial portion thereof in which the CDR3 regions are located at locations corresponding to the CDR3 region of naturally-occurring $V_H$ and $V_L$ antibody variable domains encoded by rearranged immunoglobulin genes.

In one non-limiting example, provided herein are antibodies or antigen binding fragments thereof containing a variable heavy chain having a CDR3 which has an amino acid sequence set forth as SEQ ID NO: 68 and/or a variable light chain having a CDR3 which has an amino acid sequence set forth as SEQ ID NO: 65. In one embodiment, the variable heavy chain has an amino acid sequence set forth as SEQ ID NO: 40 except for a substitution of the CDR3 by the CDR3 amino sequence set forth as SEQ ID NO: 68. In another embodiment, the variable light chain has an amino acid sequence set forth as SEQ ID NO: 2 except for a substitution of the CDR3 by the CDR3 amino acid sequence set forth as SEQ ID NO: 65. Additionally, such CDR3 containing variable regions/chains can comprise one or more FR amino acid sequences set forth as, for example, described above (or such FRs containing one or more additional modifications), where the antibodies or antigen binding fragments have 3 CDRs and 4 FRs in each of the VH and VL regions, have specific binding activity for endoglin. Additionally, various antibody J segments can also be substituted within these variable regions for further variation within the variable region chains.

Provided herein are neutralizing antibodies or antigen-binding fragments that bind to endoglin and modulate the activity of endoglin or inhibit binding of BMP9 to a TGF beta receptor.

In one aspect, the antigen-binding fragment of any one of the humanized antibodies described above is a Fab, a Fab', a Fd, a F(ab')₂, a Fv, a scFv, a single chain binding polypeptide (e.g., a scFv with Fc portion) or any other functional fragment thereof as described herein.

Antibodies or antigen-binding fragments described herein are useful in detection or diagnostic applications as described in more detail below.

Antibodies, or antigen-binding fragments thereof, described herein can be further modified to alter the specific properties of the antibody while retaining the desired functionality, if needed. For example, in one embodiment, the compound can be modified to alter a pharmacokinetic property of the compound, such as in vivo stability, solubility, bioavailability or half-life. Antibodies, or antigen-binding fragments thereof, described herein can further comprise a therapeutic moiety, a detectable moiety, or both, for use in diagnostic and/or therapeutic applications.

TABLE 1

In one aspect, variable heavy and light chains described herein can also be created by further replacing FR4 sequences. In one embodiment, heavy chain FR4 sequences can be substituted for one of the following:

| SEQ ID NO: | Kabat-Number | 103 | 104 | 105 | 106 | 107 | 108 | 109 | 110 | 111 | 112 | 113 |
|---|---|---|---|---|---|---|---|---|---|---|---|---|
| 76 | FRM4 from JH1, JH4 or JH5 | W | G | Q | G | T | L | V | T | V | S | S |
| 77 | FRM4 from JH2 | W | G | R | G | T | L | V | T | V | S | S |
| 78 | FRM4 from JH3 | W | G | Q | G | T | M | V | T | V | S | S |
| 79 | FRM4 from JH6 | W | G | Q | G | T | T | V | T | V | S | S |

TABLE 2

In one embodiment, light chain FR4 sequences can be substituted for one of the following:

| SEQ ID NO: | Kabat Number | 98 | 99 | 100 | 101 | 102 | 103 | 104 | 105 | 106 | 107 |
|---|---|---|---|---|---|---|---|---|---|---|---|
| 80 | JK1 | F | G | Q | G | T | K | V | E | I | K |
| 81 | JK2 | F | G | Q | G | T | K | L | E | I | K |
| 82 | JK3 | F | G | P | G | T | K | V | D | I | K |
| 83 | JK4 | F | G | G | G | T | K | V | E | I | K |
| 84 | JK5 | F | G | Q | G | T | R | L | E | I | K |

Further provided herein are humanized versions of anti-endoglin antibodies alternatively named "superhumanized" anti-endoglin antibodies or antigen-binding fragments thereof. Such superhumanized antibodies, or antigen-binding fragments thereof, can comprise a light chain variable region having an amino acid sequence set forth as SEQ ID NOS: 71 or 72 and a heavy chain variable region having an amino acid sequence set forth as SEQ ID NO: 75.

In another aspect, the present application provides a humanized antibody capable of competing with a humanized anti-endoglin antibody or antigen-binding described herein under conditions in which at least 5% of an antibody having the $V_H$ and $V_L$ sequences of the antibody is blocked from binding to endoglin by competition with such an antibody in an ELISA assay.

Antibodies, or antigen-binding fragments thereof, described herein can also be used as immunoconjugates. As used herein, for purposes of the specification and claims, immunoconjugates refer to conjugates comprised of the humanized anti-endoglin antibodies or fragments thereof according to the present invention and at least one therapeutic label. Such antitumor agents are known in the art and include, but not limited to, toxins, drugs, enzymes, cytokines, radionuclides, and photodynamic agents. Toxins include, but are not limited to, ricin A chain, mutant Pseudomonas exotoxins, diphtheria toxoid, streptonigrin, boamycin, saporin, gelonin, and pokeweed antiviral protein. Drugs include daunorubicin, methotrexate, and calicheamicins. Radionuclides include radiometals. Cytokines include, but are not limited to, transforming growth factor (TGF)-β, interleukins, interferons, and tumor necrosis factors. Photodynamic agents include, but are not limited to, porphyrins and their derivatives. Additional therapeutic labels will be known in the art and are also contemplated herein. The methods for complexing the anti-endoglin mAbs or a fragment thereof with at least one antitumor agent are well known to those skilled in the art (i.e., antibody conjugates as reviewed by Ghetie et al., 1994, *Pharmacol. Ther.* 63:209-34). Such methods may utilize one of several available heterobifunctional reagents used for coupling or linking molecules. Additional radionuclides are further described herein along with additional methods for linking molecules, such as therapeutic labels.

Antibodies, or antigen-binding fragments thereof, can be modified using techniques known in the art for various purposes such as, for example, by addition of polyethylene glycol (PEG). PEG modification (PEGylation) can lead to one or more of improved circulation time, improved solubility, improved resistance to proteolysis, reduced antigenicity and immunogenicity, improved bioavailability, reduced toxicity, improved stability, and easier formulation (for a review see, Francis et al., *International Journal of Hematology* 68:1-18, 1998).

In the case of an antigen-binding fragment which does not contain an Fc portion, an Fc portion can be added to (e.g., recombinantly) the fragment, for example, to increase half-life of the antigen-binding fragment in circulation in blood when administered to a patient. Choice of an appropriate Fc region and methods of to incorporate such fragments are known in the art. Incorporating a Fc region of an IgG into a polypeptide of interest so as to increase its circulatory half-life, but so as not to lose its biological activity can be accomplished using conventional techniques known in the art such as, for example, described in U.S. Pat. No. 6,096,871, which is hereby incorporated by reference in its entirety. Fc portions of antibodies can be further modified to increase half-life of the antigen-binding fragment in circulation in blood when administered to a patient. Modifications can be determined using conventional means in the art such as, for example, described in U.S. Pat. No. 7,217,798, which is hereby incorporated by reference in its entirety.

Other methods of improving the half-life of antibody-based fusion proteins in circulation are also known such as, for example, described in U.S. Pat. Nos. 7,091,321 and 6,737,056, each of which is hereby incorporated by reference. Additionally, antibodies and antigen-binding fragments thereof may be produced or expressed so that they do not contain fucose on their complex N-glycoside-linked sugar chains. The removal of the fucose from the complex N-glycoside-linked sugar chains is known to increase effector functions of the antibodies and antigen-binding fragments, including but not limited to, antibody dependent cell-mediated cytotoxicity (ADCC) and complement dependent cytotoxicity (CDC). Similarly, antibodies or antigen-binding fragments thereof that can bind endoglin can be attached at their C-terminal end to all or part of an immunoglobulin heavy chain derived from any antibody isotype, e.g., IgG, IgA, IgE, IgD and IgM and any of the isotype sub-classes, particularly IgG1, IgG2b, IgG2a, IgG3 and IgG4.

Additionally, the antibodies or antigen-binding fragments described herein can also be modified so that they are able to cross the blood-brain barrier. Such modification of the antibodies or antigen-binding fragments described herein allows for the treatment of brain diseases such as glioblastoma multiforme (GBM). Exemplary modifications to allow proteins such as antibodies or antigen-binding fragments to cross the blood-brain barrier are described in US Patent Application Publication 2007/0082380 which is hereby incorporated by reference in its entirety.

Glycosylation of immunoglobulins has been shown to have significant effects on their effector functions, structural stability, and rate of secretion from antibody-producing cells (Leatherbarrow et al., Mol. Immunol. 22:407 (1985)). The carbohydrate groups responsible for these properties are generally attached to the constant (C) regions of the antibodies. For example, glycosylation of IgG at asparagine 297 in the $C_H2$ domain is required for full capacity of IgG to activate the classical pathway of complement-dependent cytolysis (Tao and Morrison, J. Immunol. 143:2595 (1989)). Glycosylation of IgM at asparagine 402 in the $C_H3$ domain is necessary for proper assembly and cytolytic activity of the antibody (Muraoka and Shulman, J. Immunol. 142:695 (1989)). Removal of glycosylation sites as positions 162 and 419 in the $C_H1$ and $C_H3$ domains of an IgA antibody led to intracellular degradation and at least 90% inhibition of secretion (Taylor and Wall, *Mol. Cell. Biol.* 8:4197 (1988)). Additionally, antibodies and antigen-binding fragments thereof may be produced or expressed so that they do not contain fucose on their complex N-glycoside-linked sugar chains. The removal of the fucose from the complex N-glycoside-linked sugar chains is known to increase effector functions of the antibodies and antigen-binding fragments, including but not limited to, antibody dependent cell-mediated cytotoxicity (ADCC) and complement dependent cytotoxicity (CDC). These "defucosylated" antibodies and antigen-binding fragments may be produced through a variety of systems utilizing molecular cloning techniques known in the art, including but not limited to, transgenic animals, transgenic plants, or cell-lines that have been genetically engineered so that they no longer contain the enzymes and biochemical pathways necessary for the inclusion of a fucose in the complex N-glycoside-linked sugar chains (also known as fucosyltransferase knock-out animals, plants, or cells). Non-limiting examples of cells that can be engineered to be fucosyltransferase knock-out cells include CHO cells, SP2/0 cells, NS0 cells, and YB2/0 cells.

Glycosylation of immunoglobulins in the variable (V) region has also been observed. Sox and Hood reported that about 20% of human antibodies are glycosylated in the V region (*Proc. Natl. Acad. Sci. USA* 66:975 (1970)). Glycosylation of the V domain is believed to arise from fortuitous occurrences of the N-linked glycosylation signal Asn-Xaa-Ser/Thr in the V region sequence and has not been recognized in the art as playing a role in immunoglobulin function.

Glycosylation at a variable domain framework residue can alter the binding interaction of the antibody with antigen. The present invention includes criteria by which a limited number of amino acids in the framework or CDRs of a humanized immunoglobulin chain are chosen to be mutated (e.g., by substitution, deletion, or addition of residues) in order to increase the affinity of an antibody.

Affinity for binding a pre-determined polypeptide antigen can, generally, be modulated by introducing one or more mutations into the V region framework, typically in areas adjacent to one or more CDRs and/or in one or more framework regions. Typically, such mutations involve the introduction of conservative amino acid substitutions that either destroy or create the glycosylation site sequences but do not substantially affect the hydropathic structural properties of the polypeptide. Typically, mutations that introduce a proline residue are avoided. Glycosylation of antibodies and antigen-binding fragments thereof is further described in U.S. Pat. No. 6,350,861, which is incorporated by reference herein with respect to glycosylation.

Antibodies, or antigen-binding fragments thereof, can be formulated for short-term delivery or extended (long term) delivery.

Antibodies, or antigen-binding fragments thereof, that bind to endoglin can also be used for purification of endoglin and/or to detect endoglin levels in a sample or patient to detect or diagnose a disease or disorder associated with endoglin as described in more detail below.

Humanized antibodies, antigen-binding fragments, and binding proteins which bind endoglin generated using such methods can be tested for one or more of their binding affinity, avidity, and neutralizing capabilities. Useful humanized antibodies, antigen-binding fragments, and binding proteins can be used to administer a patient to prevent, inhibit, manage or treat a fibrotic condition disease or disorder.

Provided herein are methods of identifying humanized antibodies or antigen-binding fragments thereof that bind to endoglin. Antibodies and antigen-binding fragments can be evaluated for one or more of binding affinity, association rates, disassociation rates and avidity. In one aspect, antibodies can be evaluated for their ability to neutralize the activity of endoglin or a polypeptide in which the endoglin binding sequence is present. Measurement binding affinity, association rates, disassociation rates and avidity can be accomplished using art-recognized assays including (Surface Plasmon Resonance), but not limited to, an enzyme-linked-immunosorbent assay (ELISA), Scatchard Analysis, BIACORE analysis, etc., as well as other assays commonly used and known to those of ordinary skill in the art.

Measurement of binding of antibodies to endoglin and/or the ability of the antibodies and antigen-binding fragments thereof, for example, to inhibit fibrosis, can be determined using, for example, an enzyme-linked-immunosorbent assay (ELISA), a competitive binding assay, an ELISPOT assay, or any other useful assay known in the art. These assays are commonly used and well-known to those of ordinary skill in the art.

In one non-limiting embodiment, an ELISA assay can be used to measure the binding capability of specific antibodies or antigen-binding fragments that bind to endoglin.

Assays, such as an ELISA, also can be used to identify antibodies or antigen-binding fragments thereof which exhibit increased specificity in comparison to other antibodies or antigen-binding fragments thereof. Assays, such as an ELISA, also can be used to identify antibodies or antigen-binding fragments thereof with bind to epitopes across one or more polypeptides and across one or more species of endoglin. The specificity assay can be conducted by running parallel ELISAs in which a test antibodies or antigen-binding fragments thereof is screened concurrently in separate assay chambers for the ability to bind one or more epitopes on different species of the polypeptide containing the endoglin epitopes to identify antibodies or antigen-binding fragments thereof that bind to endoglin. Another technique for measuring apparent binding affinity familiar to those of skill in the art is a surface plasmon resonance technique (analyzed on a BIACORE® 2000 system) (Liljeblad, et al., *Glyco. J.* 2000, 17:323-329). Standard measurements and traditional binding assays are described by Heeley, R. P., *Endocr. Res.* 2002, 28:217-229.

Competitive binding assays for assessing disruption of BMP9 binding to a TGF-beta receptor as described in the Examples may also be used to assess their ability to treat, inhibit, or ameliorate fibrosis.

Humanized and deimmunized antibodies described herein can also be assayed for their ability to treat fibrosis. Any suitable assay known to one of skill in the art can be used to monitor such effects. Several such techniques are described herein. In one example, the antibodies and antigen-binding fragments described herein are assayed for their ability to bind endoglin. In another example, affinity constants for the antibodies and antigen-binding fragments described herein are determined by surface plasmon resonance (SPR).

II. Compositions

Each of the compounds described herein can be used as a composition when combined with an acceptable carrier or excipient. Such compositions are useful for in vitro or in vivo analysis or for administration to a subject in vivo or ex vivo for treating a subject with the disclosed compounds.

Thus pharmaceutical compositions can include, in addition to active ingredient, a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration.

Pharmaceutical formulations comprising a protein of interest, e.g., an antibody or antigen-binding fragment, identified by the methods described herein can be prepared for storage by mixing the protein having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are those that are non-toxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN®, PLURONICS® or polyethylene glycol (PEG).

Other reagents that may be included in a composition described herein are contemplated in International Application No. PCT/US2013/058265, filed Sep. 5, 2013, which is hereby incorporated by reference is its entirety.

Acceptable carriers are physiologically acceptable to the administered patient and retain the therapeutic properties of the compounds with/in which it is administered. Acceptable carriers and their formulations are and generally described in, for example, Remington's pharmaceutical Sciences (18th Edition, ed. A. Gennaro, Mack Publishing Co., Easton, Pa. 1990). One exemplary carrier is physiological saline. The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject compounds from the administration site of one organ, or portion of the body, to another organ, or portion of the body, or in an in vitro assay system. Each carrier is acceptable in the sense of being compatible with the other ingredients of the formulation and not injurious to a subject to whom it is administered. Nor should an acceptable carrier alter the specific activity of the subject compounds.

In one aspect, provided herein are pharmaceutically acceptable or physiologically acceptable compositions including solvents (aqueous or non-aqueous), solutions, emulsions, dispersion media, coatings, isotonic and absorption promoting or delaying agents, compatible with pharmaceutical administration. Pharmaceutical compositions or pharmaceutical formulations therefore refer to a composition suitable for pharmaceutical use in a subject. The pharmaceutical compositions and formulations include an amount of a compound described herein and a pharmaceutically or physiologically acceptable carrier.

Compositions can be formulated to be compatible with a particular route of administration (i.e., systemic or local). Thus, compositions include carriers, diluents, or excipients suitable for administration by various routes.

In another embodiment, the compositions can further comprise, if needed, an acceptable additive in order to improve the stability of the compounds in composition and/or to control the release rate of the composition. Acceptable additives do not alter the specific activity of the subject compounds. Exemplary acceptable additives include, but are not limited to, a sugar such as mannitol, sorbitol, glucose, xylitol, trehalose, sorbose, sucrose, galactose, dextran, dextrose, fructose, lactose and mixtures thereof. Acceptable additives can be combined with acceptable carriers and/or excipients such as dextrose. Alternatively, exemplary acceptable additives include, but are not limited to, a surfactant such as polysorbate 20 or polysorbate 80 to increase stability of the peptide and decrease gelling of the solution. The surfactant can be added to the composition in an amount of 0.01% to 5% of the solution. Addition of such acceptable additives increases the stability and half-life of the composition in storage.

The pharmaceutical composition can be administered, for example, by injection, including, but not limited to, subcutaneous, subcutaneous, intravitreal, intradermal, intravenous, intra-arterial, intraperitoneal, or intramuscular injection. Excipients and carriers for use in formulation of compositions for each type of injection are contemplated herein. The following descriptions are by example only and are not meant to limit the scope of the compositions. Compositions for injection include aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyetheylene glycol, and the like), and suitable mixtures thereof. Fluidity can be maintained, for example, by the use of a coating such as lecithin, by the maintenance of the required particle size in the case of dispersion and by the use of surfactants. Antibacterial and antifungal agents include, for example, parabens, chlorobutanol, phenol, ascorbic acid and thimerosal. Isotonic agents, for example, sugars, polyalcohols such as manitol, sorbitol, and sodium chloride may be included in the composition. The resulting solutions can be packaged for use as is, or lyophilized; the lyophilized preparation can later be combined with a sterile solution prior to administration. For intravenous, injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as needed. Sterile injectable solutions can be prepared by incorporating an active ingredient in the required amount in an appropriate solvent with one or a combination of ingredients enumerated above, as required, followed by filtered sterilization. Generally, dispersions are prepared by incorporating the active ingredient into a sterile vehicle which contains a basic dispersion medium and the required other ingredients from those enumerated above. In the case of sterile powders for the preparation of sterile injectable solutions, the preferred methods of preparation are vacuum drying and freeze drying which yields a powder of the active ingredient plus any additional desired ingredient from a previously sterile-filtered solution thereof.

Compositions can be conventionally administered intravitreally, sub-cutaneous, or via intravitreal implant.

Compositions can be conventionally administered intravenously, such as by injection of a unit dose, for example. For injection, an active ingredient can be in the form of a parenterally acceptable aqueous solution which is substantially pyrogen-free and has suitable pH, isotonicity and stability. One can prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required. Additionally, compositions can be administered via aerosolization.

In one embodiment, the composition is lyophilized, for example, to increase shelf-life in storage. When the compositions are considered for use in medicaments or any of the methods provided herein, it is contemplated that the composition can be substantially free of pyrogens such that the composition will not cause an inflammatory reaction or an unsafe allergic reaction when administered to a human patient. Testing compositions for pyrogens and preparing compositions substantially free of pyrogens are well understood to one or ordinary skill of the art and can be accomplished using commercially available kits.

Acceptable carriers can contain a compound that stabilizes, increases or delays absorption or clearance. Such compounds include, for example, carbohydrates, such as glucose, sucrose, or dextrans; low molecular weight proteins; compositions that reduce the clearance or hydrolysis of peptides; or excipients or other stabilizers and/or buffers. Agents that delay absorption include, for example, aluminum monostearate and gelatin. Detergents can also be used to stabilize or to increase or decrease the absorption of the pharmaceutical composition, including liposomal carriers. To protect from digestion the compound can be complexed with a composition to render it resistant to acidic and enzymatic hydrolysis, or the compound can be complexed in an appropriately resistant carrier such as a liposome. Means of protecting compounds from digestion are known in the art (see, e.g., Fix (1996) *Pharm Res.* 13:1760 1764; Samanen (1996) *J. Pharm. Pharmacol.* 48:119 135; and U.S. Pat. No. 5,391,377, describing lipid compositions for oral delivery of therapeutic agents).

The phrase "pharmaceutically acceptable" refers to molecular entities and compositions that are physiologically tolerable and do not typically produce an allergic or similar untoward reaction, such as gastric upset, dizziness and the like, when administered to a human.

The term "unit dose" when used in reference to a therapeutic composition refers to physically discrete units suitable as unitary dosage for humans, each unit containing a predetermined quantity of active material calculated to produce the desired therapeutic effect in association with the required diluent; i.e., carrier, or vehicle.

The compositions can be administered in a manner compatible with the dosage formulation, and in a therapeutically effective amount. The quantity to be administered depends on the subject to be treated, capacity of the subject's immune system to utilize the active ingredient, and degree of binding capacity desired. Precise amounts of active ingredient required to be administered depend on the judgment of the practitioner and are peculiar to each individual. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations in the blood are contemplated.

One embodiment contemplates the use of the compositions described herein to make a medicament for treating a condition, disease or disorder described herein. Medicaments can be formulated based on the physical characteristics of the patient/subject needing treatment, and can be formulated in single or multiple formulations based on the stage of the condition, disease or disorder. Medicaments can be packaged in a suitable package with appropriate labels for the distribution to hospitals and clinics wherein the label is for the indication of treating a subject having a disease described herein. Medicaments can be packaged as a single or multiple units. Instructions for the dosage and administration of the compositions can be included with the packages as described below. The invention is further directed to medicaments of a humanized and deimmunized anti-endoglin antibody or antigen binding fragment thereof described hereinabove and a pharmaceutically acceptable carrier.

Provided herein are compositions of humanized and deimmunized antibodies and antigen-binding fragments thereof that bind endoglin and include those such as described elsewhere herein. Humanized and deimmunized antibodies and antigen-binding fragments thereof as described herein can be used for the treatment, inhibition, or amelioration of fibrosis.

A composition (an antibody or an antigen-binding fragment described herein) can be administered alone or in combination with a second composition either simultaneously or sequentially dependent upon the condition to be treated. In one embodiment, a second therapeutic treatment is a fibrotic inhibitor (as described herein). When two or more compositions are administered, the compositions can be administered in combination (either sequentially or simultaneously). For example a combination treatment could include perfinedone or a VEGF receptor tyrosine kinase inhibitor. It would be understood that other art-recognized drugs or compounds could be administered with the antibodies described herein in combination therapy. A composition can be administered in a single dose or multiple doses.

In one embodiment of the present invention, the compositions are formulated to be free of pyrogens such that they are acceptable for administration to human patients. Testing compositions for pyrogens and preparing pharmaceutical compositions free of pyrogens are well understood to one of ordinary skill in the art.

One embodiment of the present invention contemplates the use of any of the compositions of the present invention to make a medicament for treating a disorder of the present invention. Medicaments can be formulated based on the physical characteristics of the patient/subject needing treatment, and can be formulated in single or multiple formulations based on the disorder. Medicaments of the present invention can be packaged in a suitable pharmaceutical package with appropriate labels for the distribution to hospitals and clinics wherein the label is for the indication of treating a disorder as described herein in a subject. Medicaments can be packaged as a single or multiple units. Instructions for the dosage and administration of the pharmaceutical compositions of the present invention can be included with the pharmaceutical packages.

III. Methods of Use

Provided herein is a method of inducing a response in a patient (human or non-human) by administering to the patient a composition of a humanized and deimmunized antibody or antigen-binding fragment thereof that preferentially binds to endoglin. The binding site to which the antibody binds can be a continuous or conformation/discontinuous epitope.

An effective response of the present invention is achieved when the patient experiences partial or total alleviation or reduction of signs or symptoms of illness, and specifically includes, without limitation, prolongation of survival. The expected progression-free survival times may be measured in months to years, depending on prognostic factors including the number of relapses, stage of disease, and other factors. Prolonging survival includes without limitation times of at least 1 month (mo), about at least 2 mos., about at least 3 mos., about at least 4 mos., about at least 6 mos., about at least 1 year, about at least 2 years, about at least 3 years, etc. Overall survival can be also measured in months to years. Alternatively, an effective response may be that a patient's symptoms remain static. Further indications of treatment of indications are described in more detail below.

Compositions of antibodies and antigen-binding fragments described herein can be used as non-therapeutic agents (e.g., as affinity purification agents). Generally, in one such embodiment, a protein of interest is immobilized on a solid phase such a Sephadex resin or filter paper, using conventional methods known in the art. The immobilized protein is contacted with a sample containing the target of interest (or fragment thereof) to be purified, and thereafter the support is washed with a suitable solvent that will remove substantially all the material in the sample except the target protein, which is bound to the immobilized antibody. Finally, the support is washed with another suitable solvent, such as glycine buffer, pH 5.0, which will release the target protein. In addition to purification, compositions can be used for treatment of fibrosis.

The term "contacting" as used herein refers to adding together a solution or composition of a compound with a liquid medium bathing the polypeptides, cells, tissue or organ from an organism. Alternately, "contacting" refers to mixing together a solution or composition of a compound, with a liquid such as blood, serum, or plasma derived from an organism. For in vitro applications, a composition can also comprise another component, such as dimethyl sulfoxide (DMSO). DMSO facilitates the uptake of the compounds or solubility of the compounds. The solution comprising the test compound may be added to the medium bathing the cells, tissues, or organs, or mixed with another liquid such as blood, by utilizing a delivery apparatus, such as a pipette-based device or syringe-based device. For in vivo applications, contacting can occur, for example, via administration of a composition to a patient by any suitable means; compositions with pharmaceutically acceptable excipients and carriers have been described in more detail above.

A "subject" (e.g., a mammal such as a human or a non-human animal such as a primate, rodent, cow, horse, llama, alpaca, pig, sheep, etc.) according to one embodiment of the present application, is a mammal who exhibits one or more clinical manifestations and/or symptoms of fibrosis. In certain situations, the patient may be asymptomatic and yet still have clinical manifestations of fibrosis. An antibody or antigen-binding fragment thereof can be conjugated to a therapeutic moiety or be a fusion protein containing a therapeutic moiety. Affinity tags such as, for example, His6 tags (SEQ ID NO: 85) are conventional in the art.

Antibodies or antigen-binding fragments thereof provided herein are such that they can be conjugated or linked to a therapeutic moiety and/or an affinity tag. Methods for conjugating or linking polypeptides are well known in the art. Associations (binding) between compounds and labels include any means known in the art including, but not limited to, covalent and non-covalent interactions, chemical conjugation as well as recombinant techniques.

A. Binding of Endoglin and Fibrosis

Endoglin (CD105) is expressed on the cell surface as a 180 kDa homodimeric transmembrane protein. The external domain binds TGF-β1 and -3 isoforms with high affinity (50 nM), and the transmembrane and the intracellular domains of CD105 share a 71% sequence similarity with beta glycan. The human CD105 gene is located on chromosome 9q34, identified using fluorescence in situ hybridization, and the coding region contains 14 exons, and two different isoforms (L and S) of CD105 with capacity to bind TGF-β have been characterized. The L-CD105 consists of 633 amino acid residues with 47 amino acid residues in the cytoplasmic tail as opposed to the S-CD105, which consists of 600 amino acid residues with a 14 amino acid cytoplasmic tail. However, L-CD105 is the predominant form. CD105 is constitutively phosphorylated in endothelial cells, mainly on serine and threonine residues, and this phosphorylation is due to the constitutively active TGF-β RII within the cell. The human CD105 amino acid sequence contains the tripeptide arginine-glycine-aspartic acid (RGD) located in an exposed region of the extracellular domain. The RGD peptide is a key recognition structure found on ECM proteins such as fibronectin, vitronectin, von Willebrand factor (vWF), type I collagen, and fibrinogen and is recognized by cell surface integrins.

CD105 is a member of the TGF-β receptor family that is expressed by proliferating endothelial cells. Normal levels of CD105 are needed for endothelial cell proliferation. CD105 expression is increased by cellular hypoxia through the production of hypoxia-inducible factor-1-α (HIF-1-α) and protects hypoxic cells from apoptosis. Several functions of CD105 are associated with TGF-β signaling. TGF-β signals through heterodimeric receptors consisting of serine kinases, receptor I (RI), and receptor II (RII). Binding of TGF-β to the external domains of the receptor unmasks the cytoplasmic RII kinase activity that phosphorylates the TGF-β RI, which can then interact with downstream signalers such as the Smad proteins. CD105 forms part of the TGF-β receptor complex but it can exist independently on the cell surface. In endothelial cells, binding of TGF-β to endoglin and the RI and RII receptors inhibits cell proliferation through the phosphorylation of the SMAD 2 and 3 intracellular proteins (Nolan-Stevaux, 2012) Thus, CD105 modulates TGF-β functions via interaction with TGF-β RI and TGF-β RII and modifies the phosphorylation of downstream Smad proteins.

CD105 also binds other growth factors such as activin A and bone morphogenic proteins (BMP)-10, -9, -7 and -2. Binding of BMP-9 to a complex consisting of endoglin, the BMP receptor II and ALK1 is critical to the process of SMAD 1/5/8 phosphorylation that is required for the proliferation of endothelial cells into blood vessels (i.e., the process of angiogenesis [Nolan-Stevaux, 2012]. Antibodies that bind to endoglin to inhibit angiogenesis inhibit BMP binding. TRC105 binds to the endoglin orphan domain to competitively inhibit BMP binding and inhibit SMAD 1/5/8 phosphorylation and inhibit angiogenesis. Antibodies that do not inhibit BMP binding do not inhibit angiogenesis in primary endothelial cells.

The sequences of human and mouse CD105 are not identical. TRC105 binds to human endoglin and competitively inhibits human BMP binding. TRC105 also binds to mouse endoglin. However, TRC105 dose not prevent the binding of mouse BMP to mouse endoglin. The antibody M1043 binds to mouse endoglin to competitively inhibit mouse BMP binding. M1043 therefore can be used in mouse models to mimic the expected effects of TRC105 in humans.

In addition to their use for purification of endoglin, these humanized and deimmunized antibodies are useful for detection and diagnostic purposes as well as therapeutic purposes. The antibodies provided herein can be used for the formulation of medicaments for the treatment a variety of fibrotic conditions and diseases.

Murine monoclonal antibodies (mAbs) have been raised against endoglin which modulate endoglin activity an. These murine antibodies are described in U.S. Pat. Nos. 5,928,641, 6,200,566, 6,190,660, and 7,097,836, each of which is hereby incorporated in their entirety. Additionally, the ex vivo and in vivo efficiency of a number of these antibodies has been demonstrated; monoclonal antibodies that bind endoglin are of interest as endoglin modulating compounds. Therapeutic use of murine antibodies is not feasible, however, as administration of the murine antibodies have a number of limitations, including immunogenicity in, for example, the form of human anti-mouse antibodies (HAMA).

"Fibrosis" is used herein to refer to abnormal accumulation of fibrous tissue that can occur as a part of the wound-healing process in damaged tissue. Such tissue damage may result from physical injury, inflammation, infection, exposure to toxins, and other causes. Examples of fibrosis include, but are not limited to, dermal scar formation, keloids, liver fibrosis, pulmonary fibrosis, kidney fibrosis, cardiac fibrosis, scleroderma, and glomerulosclerosis. Other fibrotic conditions and disease are discussed in more detail below.

The term "fibrosis inhibitory composition" refers to a composition which inhibits a fibrosis-mediated process.

Fibroblast differentiation is associated with a variety of fibrotic diseases including but not limited to scleroderma, keloid scarring, rheumatoid arthritis, lupus, nephrogenic fibrosing dermopathy, and idiopathic pulmonary fibrosis. They play a role in the formation of fibrotic lesions after *Schistosoma japonicum* infection in mice and are also implicated in fibrosis associated with autoimmune diseases.

Fibroblasts have also been implicated in pathogenic fibrosis associated with radiation damage, Lyme disease and pulmonary fibrosis, as well as stromal remodeling in pancreatitis and stromal fibrosis, whereas lack of such fibroblasts is associated with pancreatic tumors and adenocarcinomas. Fibrosis additionally occurs in asthma patients and possibly other pulmonary diseases such as chronic obstructive pulmonary disease when fibrocytes undergo further differentiation into myofibroblasts. Fibrosis involves the unchecked proliferation and differentiation of fibroblasts.

C. Treatment, Inhibition or Amelioration of Fibrosis with Humanized and Deimmunized Anti-Endoglin Antibodies CD105 acts to modulate signaling of multiple kinase receptor complexes of the TGF-β superfamily, including TGF-β receptors (TGF-βR), BMP receptors, activin receptor-like kinases (ALK) and activin receptors. In endothelial cells, TRC105 blocks BMP binding to human CD105 and causes the SMAD 1/5/8 pathway to be blocked or downregulated. Decreased phosphorylated SMAD 1/5/8 allows unopposed phospho-SMAD 2/3 signaling to restore a quiescent phenotype in human endothelial cells.

These observations led the present inventor to consider that antibodies to endoglin that inhibit the BMP signaling pathway could interrupt SMAD 1/5/8 signaling in fibroblasts to inhibit fibrosis. The importance of BMP signaling in promoting the process of fibrosis could be demonstrated in mouse models using the IgG1 antibody M1043. The treatment of human fibrosis could use the humanized and deimmunized antibody TRC205 (SEQ ID NO 89/SEQ ID NO 93; IgG4) to interrupt SMAD 1/5/8 signaling in human fibroblasts to inhibit fibrosis.

TRC205 has an advantage of being an IgG4 antibody and, therefore, will not engage natural killer (NK) and other effector cells that could cause inflammation that might promote fibrosis.

TRC105 and TRC205 would be expected to be active in mouse models through their ability to bind mouse endoglin and cause solubilization of the endoglin receptor. Soluble endoglin in plasma binds to BMP9 and makes BMP unavailable to bind to endoglin on the cell surface of fibroblasts and other cells, to initiate cell signaling. All three endoglin antibodies, M1043, TRC105 and TRC105, may also inhibit TGF-beta signaling through TGF-beta binding by soluble endoglin shed as a result of endoglin antibody binding to TGF-beta.

Provided herein are methods for treating, inhibiting, or ameliorating fibrosis comprising administering a composition comprising a humanized and deimmunized antibody or antigen-binding fragment described herein that binds to endoglin associated with the disease or disorder and prevents fibrosis (i.e., preventing, treating, ameliorating, or lessening the severity of fibrosis).

Provided herein are methods for treating, inhibiting, or ameliorating treating fibrosis, comprising administering a composition comprising a humanized and deimmunized antibody or antigen-binding fragment described herein that binds to endoglin treats fibrosis.

Provided herein are methods for treating, inhibiting, or ameliorating treating fibrosis, comprising administering a composition comprising a humanized and deimmunized antibody or antigen-binding fragment described herein that binds to a endoglin receptor and blocks BMP9 binding to endoglin.

Provided herein are methods for treating, inhibiting, or ameliorating treating fibrosis, comprising administering a composition comprising a humanized and deimmunized antibody or antigen-binding fragment described herein that binds to endoglin receptor and inhibits Smad 1/5/8 signaling.

As used herein, "amelioration" "inhibition," "treatment" and "treating" refer to, for example, stasis of symptoms, prolongation of survival, partial or full amelioration of symptoms, and partial or full eradication of a condition, disease or disorder associated with fibrosis.

In one embodiment, fibrosis is inhibited by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, following treatment with one or more doses of a humanized and deimmunized antibody compared to treatment with a placebo or compared to a subject that does not receive any treatment.

In another embodiment, symptoms of fibrosis may be ameliorated by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, following treatment with one or more doses of a humanized and deimmunized antibody compared to treatment with a placebo or compared to a subject that does not receive any treatment.

Treatment also refers to resolution of one or more symptoms of fibrosis. Treatment also refers to stasis of symptoms where fibrosis in a subject does not progress.

Pain associated with fibrosis may be reduced by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, following treatment with one or more doses of a humanized and deimmunized antibody compared to treatment with a placebo or compared to a subject that does not receive any treatment.

Other means of assessing patients for various fibrotic conditions and diseases are discussed below. In some instances, the tests described may be administered to determine the extent of treatment; a doctor may determine based upon the results of the tests whether to continue or discontinue treatment, increase or decrease dosage of the antibodies, or any combination thereof.

Compositions can be administered to a patient in a therapeutically effective amount, i.e., that are effective for producing some desired therapeutic effect by inhibiting fibrosis such as described herein which can be associated with endoglin, at a reasonable benefit/risk ratio applicable to any medical treatment. For the administration of the present compositions to human subjects, the compositions can be formulated by methodology known by one of ordinary skill in the art. A therapeutically effective amount is an amount achieves at least partially a desired therapeutic or prophylactic effect in an organ or tissue. The amount of a humanized and deimmunized anti-endoglin antibody or antigen binding fragment thereof necessary to bring about prevention and/or therapeutic treatment of fibrosis is not fixed per se. The amount of humanized and deimmunized anti-endoglin antibody or antigen binding fragment thereof administered may vary with the type of fibrosis, extensiveness of the fibrosis, and size of the mammal suffering from fibrosis. In one embodiment, two or more humanized anti-endoglin antibodies described herein are administered to a patient in combination. Combination includes concomitant or subsequent administration of the antibodies.

"Administering" is defined herein as a means providing the composition to the patient in a manner that results in the composition being inside the patient's body. Such an administration can be by any route including, without limitation, locally, regionally or systemically by subcutaneous, intravitreal, intradermal, intravenous, intra-arterial, intraperitoneal, or intramuscular administration (e.g., injection). "Concurrent administration" means administration within a relatively short time period from each other; such time period can be less than 2 weeks, less than 7 days, less than 1 day and could even be administered simultaneously.

Actual dosage levels of the active ingredients in the compositions can be varied so as to obtain an amount of the active ingredient that is effective to achieve the desired therapeutic response for a particular patient, composition, and mode of administration, without being toxic to the patient. The selected dosage level will depend upon a variety of factors including the activity of the particular compound employed, the route of administration, the time of administration, the rate of excretion of the particular compound being employed, the duration of the treatment, other drugs, compounds and/or materials used in combination with the particular composition employed, the age, sex, weight, condition, general health and prior medical history of the patient being treated, and like factors well known in the medical arts. The antibodies and antigen-binding fragments described herein can be administered to a subject in various dosing amounts and over various time frames. Non-limiting doses include about 0.01 mg/kg, about 0.05 mg/kg, about 0.1 mg/kg, about 0.5 mg/kg, about 1 mg/kg, about 5 mg/kg, about 10 mg/kg, about 20 mg/kg, about 30 mg/kg, about 40 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg per patient, or any integer in between. Additionally, the dose(s) of an antibody or antigen-binding fragment can be administered twice a week, weekly, every two weeks, every three weeks, every 4 weeks, every 6 weeks, every 8 weeks, every 12 weeks, or any combination of weeks therein. Dosing cycles are also contemplated such as, for example, administering antibodies or antigen-binding fragments thereof once or twice a week for 4 weeks, followed by two weeks without therapy. Additional dosing cycles including, for example, different combinations of the doses and weekly cycles described herein are also contemplated within the invention.

"Contacting" is defined herein as a means of bringing a composition as provided herein in physical proximity with a cell, organ, tissue or fluid as described herein. Contacting encompasses systemic or local administration of any of the compositions provided herein and includes, without limitation, in vitro, in vivo and/or ex vivo procedures and methods. "Combining" and "contacting" are used interchangeably herein and are meant to be defined in the same way.

A response is achieved when the patient experiences partial or total alleviation, or reduction of signs or symptoms of illness, and specifically includes, without limitation, prolongation of survival. The expected progression-free survival times can be measured in months to years, depending on prognostic factors including the number of relapses, stage of disease, and other factors. Prolonging survival includes without limitation times of at least 1 month (mo), about at least 2 months (mos.), about at least 3 mos., about at least 4 mos., about at least 6 mos., about at least 1 year, about at least 2 years, about at least 3 years, or more. Overall survival can also be measured in months to years. The patient's symptoms can remain static or can decrease.

A physician or veterinarian having ordinary skill in the art can readily determine and prescribe the effective amount (ED50) of the composition required. For example, the physician or veterinarian could start doses of the compounds employed in the composition at levels lower than that required in order to achieve the desired therapeutic effect and gradually increase the dosage until the desired effect is achieved. Alternatively, a dose can remain constant.

Compositions can be administered to a patient by any convenient route such as described above. Regardless of the route of administration selected, the compounds of the present invention, which can be used in a suitable hydrated form, and/or the compositions, are formulated into acceptable dosage forms such as described below or by other conventional methods known to those of skill in the art.

Antibodies can be combined with a therapeutic moiety using methods known in the art such as, for example, chemical conjugation, covalent or non-covalent bonds or recombinant techniques to create conjugates or fusion proteins such as described in more detail below. Alternatively, antibodies and/or other agents can be combined in separate compositions for simultaneous or sequential administration.

Toxicity and therapeutic efficacy of such ingredient can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. While compounds that exhibit toxic side effects may be used, care should be taken to design a delivery system that targets such compounds to the site of affected tissue in order to minimize potential damage to healthy cells and, thereby, reduce side effects.

Data obtained from cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration arrange that includes the $IC_{50}$ (i.e., the concentration of the test compound which achieves a half-maximal inhibition) as determined in cell culture. Levels in plasma can be measured, for example, by high performance liquid chromatography. Such information can be used to more accurately determine useful doses in humans.

The unique specificity of the antibodies which recognize (e.g., bind) an epitope on endoglin and provide therapeutic uses for fibrosis such as described herein.

In another aspect, methods are provided for inhibiting, treating, or ameliorating fibrosis in a subject in vivo, comprising administering to the subject an effective amount of an anti-endoglin antibody described herein.

Liver (Hepatic) Fibrosis

Fibrosis of the liver is implicated in the pathology of numerous hepatic diseases. As previously noted, fibrosis occurs as a complication of haemochromatosis, Wilson's disease, alcoholism, schistosomiasis, viral hepatitis, bile duct obstruction, exposure to toxins, and metabolic disorders. Left unchecked, hepatic fibrosis progresses to cirrhosis (defined by the presence of encapsulated nodules), liver failure, and death.

Liver (hepatic) fibrosis, for example, occurs as a part of the wound-healing response to chronic liver injury. Fibrosis occurs as a complication of haemochromatosis, Wilson's disease, alcoholism, schistosomiasis, viral hepatitis, bile duct obstruction, exposure to toxins, and metabolic disorders. This formation of scar tissue is believed to represent an attempt by the body to encapsulate the injured tissue. Liver fibrosis is characterized by the accumulation of extracellular matrix that can be distinguished qualitatively from that in normal liver. Left unchecked, hepatic fibrosis progresses to cirrhosis (defined by the presence of encapsulated nodules), liver failure, and death.

Liver fibrosis includes, but is not limited to, cirrhosis (e.g., primary biliary cirrhosis (PBC), biliary cirrhosis), and associated conditions such as chronic viral hepatitis, hepatitis C viral (HCV) infection, hepatitis B viral (HBV) infection, Alcoholic liver disease (ALD), Primary sclerosing cholangitis, Hereditary hemochromatosis, and Wilson's disease, non-alcoholic fatty liver disease (NAFLD), alcoholic steatohepatitis (ASH), non-alcoholic steatohepatitis (NASH), a Human Immunodeficiency Virus (HIV), schistosomiasis and autoimmune hepatitis.

Chronic insults to the liver from such sources as parasites and viral infection (e.g. HBV, HCV, HIV, schistosomiasis) or the long term stress from alcohol consumption typically result in remodeling of the liver, presumably to encapsulate the damaged area and protect the remaining liver tissue from damage. Liver fibrosis results in extracellular matrix changes, including 3-10 fold increases in total collagen content and replacement of the low density basement membrane with high-density matrix, which impair the metabolic and synthesis function of hepatocytes, hepatic stellate cells and endothelial cells.

Nonalcoholic steatohepatitis (NASH) is a common, often "silent" liver disease. It resembles alcoholic liver disease, but occurs in people who drink little or no alcohol. The major feature in NASH is fat in the liver, along with inflammation and damage. Most people with NASH feel well and are not aware that they have a liver problem. Nevertheless, NASH can be severe and can lead to cirrhosis, in which the liver is permanently damaged and scarred and no longer able to work properly.

The efficacy of administration of a composition described herein for treatment, inhibition or amelioration of NASH can be assessed using art recognized tests including, for example, those described in Example 11.

The efficacy of administration of a composition described herein for treatment, inhibition or amelioration of cirrhosis can be assessed using art recognized tests including, for example, ultrasound, elastography techniques, abdominal CT scan, liver/bile duct MRI (MRCP), serology tests for hepatitis viruses, testing for autoantibodies, and endoscopy (gastroscopy). The severity of cirrhosis can be classified with a Child-Pugh score which uses bilirubin, albumin, INR, presence and severity of ascites, and encephalopathy to classify patients in class A, B, or C. Class A has a favorable prognosis, while class C is at high risk of death. The Model for End-Stage Liver Disease (MELD) score and the Pediatric End-Stage Liver Disease (PELD) score may also be used to grade the severity of cirrhosis.

The compositions described herein are thus useful for treating, inhibiting, or ameliorating fibrotic liver diseases such as those described herein.

Kidney Fibrosis

Like liver fibrosis, kidney fibrosis can result from various diseases and insults to the kidneys. Examples of such diseases and insults include chronic kidney disease, metabolic syndrome, vesicoureteral reflux, tubulointerstitial renal fibrosis, diabetes (including diabetic nephropathy), and resultant glomerular nephritis (GN), including, but not limited to, focal segmental glomerulosclerosis and membranous glomerulonephritis, mesangiocapillary GN.

It has become recognized that metabolic syndrome is a cluster of abnormalities including diabetic hallmarks such as insulin resistance, as well as central or visceral obesity and hypertension. In nearly all cases, dysregulation of glucose results in the stimulation of cytokine release and upregulation of extracellular matrix deposition. Additional factors contributing to chronic kidney disease, diabetes, metabolic syndrome, and glomerular nephritis include hyperlipidemia, hypertension, and proteinuria, all of which result in further damage to the kidneys and further stimulate the extracellular matrix deposition. Thus, regardless of the primary cause, insults to the kidneys may result in kidney fibrosis and the concomitant loss of kidney function. The compositions described herein are thus useful for the prevention, treatment, and/or amelioration of fibrotic kidney diseases (chronic kidney disease, diabetic nephropathy, glomerular nephritis, metabolic syndrome), and such use is contemplated herein.

Kidney fibrosis includes, but is not limited to, diabetic nephropathy, vesicoureteral reflux, tubulointerstitial renal fibrosis, glomerulonephritis or glomerular nephritis (GN), focal segmental glomerulosclerosis, membranous glomerulonephritis, or mesangiocapillary GN.

The efficacy of administration of a composition described herein for treatment, inhibition or amelioration of including diabetic nephropathy can be assessed using art recognized tests including, for example, the measurement of urinary albumin. Normoalbuminuria refers to urinary albumin excretion <30 mg/24 h, it is the physiological state; Microalbuminuria refers to urinary albumin excretion in the range of 30-299 mg/24 h; and Clinical (overt) albuminuria refers to urinary albumin excretion ≥300 mg/24 h.

The efficacy of administration of a composition described herein for treatment, inhibition or amelioration of resultant glomerular nephritis (GN) can be assessed using art recognized tests including, for example, monitoring edema in a subject that has increased protein in the urine and decreased protein in the blood, with increased fat in the blood. Concentrations of proteins in urine, oncotic pressure of the blood and hyperlipidemia can also be monitored to assess treatment.

The efficacy of administration of a composition described herein for treatment, inhibition or amelioration of vesicoureteral reflux can be assessed using art recognized tests including, for example, Nuclear cystogram (RNC); Fluoroscopic voiding cystourethrogram (VCUG); Ultrasonic cystography; and ultrasound.

The efficacy of administration of a composition described herein for treatment, inhibition or amelioration of tubulointerstitial renal fibrosis can be assessed using art recognized tests including, for example, tests to assess hyperkalemia, metabolic acidosis, and kidney failure. Blood may be collected and tested for eosinophilia as about 23% of patients have eosinophilia. Urinary samples may also be assessed for eosinophiluria; isosthenuria; hematuria; sterile pyuria; and nephrotic-range proteinuria.

The compositions described herein are thus useful for treating, inhibiting, or ameliorating fibrotic kidney diseases such as those described herein.

Pulmonary Fibrosis

Pulmonary fibrosis refers to, for example, a respiratory disease in which scars are formed in the lung tissues, leading to serious breathing problems. Scar formation and the accumulation of excess fibrous connective tissue leads to thickening of the walls and causes reduced oxygen supply in the blood. Exemplary diseases include, but are not limited to, idiopathic pulmonary fibrosis (IPF), idiopathic interstitial pneumonia, and acute respiratory distress syndrome (ARDS). Lung fibrosis may also include, but not be limited to, cryptogenic fibrosing alveolitis, chronic fibrosing interstitial pneumonia, interstitial lung disease (ILD), chronic obstructive pulmonary disease (COPD), chronic asthma, and diffuse parenchymal lung disease (DPLD).

Chronic pulmonary fibrosis of known and idiopathic origin presents extraordinary clinical challenges for which treatment options show limited effectiveness or toxicity, and the median survival rate following diagnosis has changed little. Known profibrotic stimuli include radiation, inhaled mineral and organic particles, gaseous oxidants, pharmaceutics and infectious organisms, whereas debate persists regarding the identity of etiological factors that initiate the clinicopathologic entities of idiopathic interstitial pneumonias (TIP). TIP are a diverse group of disorders involving the distal pulmonary parenchyma, which share numerous features, but are felt to be sufficiently different to justify designation as separate disorders. Their pathogenesis remains unclear but is thought to center around an injury (or multiple injuries) to the lung followed by attempts to heal this injury. Fibroblastic foci, small aggregates of actively proliferating fibroblasts, are believed to represent the organization of prior foci of injury and indicate that fibrosis is active and ongoing.

Chronic pulmonary fibrosis results from scarring throughout the lungs which can be caused by many conditions including chronic inflammatory processes (sarcoidosis, Wegener's granulomatosis), infections, environmental agents (asbestos, silica, exposure to certain gases), exposure to ionizing radiation (such as radiation therapy to treat tumors of the chest), chronic conditions (lupus, rheumatoid arthritis), and even certain medications. In a condition known as hypersensitivity pneumonitis, fibrosis of the lung can develop following a heightened immune reaction to inhaled organic dusts or occupational chemicals. This condition most often results from inhaling dust contaminated with bacterial, fungal, or animal products.

The compositions described herein are thus useful for treating, inhibiting, or ameliorating fibrotic pulmonary diseases such as those described herein.

The efficacy of administration of a composition described herein can be assessed using art recognized tests including, for example, Spirometry. The modified British Medical Research Council questionnaire (mMRC) or COPD assessment test (CAT) are questionnaires that may be used to determine the severity of symptoms. Scores on CAT range from 0-40 with the higher the score, the more severe the disease. Spirometry may help to determine the severity of airflow limitation. This is typically based on the FEV1 or forced vital capacity (FVC) expressed as a percentage of the predicted "normal" for the person's age, gender, height and weight. Both the American and European guidelines recommended partly basing treatment recommendations on the FEV1. The GOLD guidelines suggest dividing people into four categories based on symptoms assessment and airflow limitation. Weight loss and muscle weakness, as well as the presence of other diseases, may also be assessed.

Recognition and monitoring of symptoms of idiopathic pulmonary fibrosis (IPF) can be used to determine efficacy of the compositions described herein. A chest x-ray may be utilized at various stages of treatment.

For subjects having acute respiratory distress syndrome (ARDS), an arterial blood gas analysis and chest X-ray may be used for monitoring.

Cardiac Fibrosis

Cardiac fibrosis includes, but is not limited to, congestive heart failure, heart failure with preserved ejection fraction, cardiomyopathy, post-myocardial infarction defects in heart function; atherosclerosis; rheumatoid arthritis; glaucoma; age-related macular degeneration (wet AMD and dry AMD); emphysema, multiple sclerosis; and chronic asthma may also be prevented, treated, or ameliorated with compositions of described herein. The pathological cardiac condition or disease may be hypertension, hypertensive heart disease (HHD), myocardial infarction (MI), acute myocardial infarction, atherosclerosis, or restenosis.

The efficacy of administration of a composition described herein for treatment, inhibition or amelioration of cardiac fibrosis may be assessed using one or more of the following: measuring cardiac output in the subject; measuring stroke volume in the subject; measuring mean systolic ejection rate in the subject; measuring systolic blood pressure in the subject; measuring left ventricular ejection fraction in the subject; determining stroke index in the subject; determining cardiac index in the subject; measuring left ventricular percent fractional shortening in the subject; measuring mean velocity of circumferential fiber shortening in the subject; measuring left ventricular inflow velocity pattern in the subject; measuring pulmonary venous flow velocity pattern in the subject; and/or measuring peak early diastolic velocity of the mitral annulus of the subject.

Exemplary experimental animal models for the testing the compositions described herein include, but are not limited to, a pressure overload-induced hypertrophy, an isoproterenol-induced cardiac hypertrophy model, an exercise-induced cardiac hypertrophy model, a high-salt diet-induced cardiac hypertrophy model, and a hormone-induced cardiac hypertrophy model.

The compositions described herein are thus useful for treating, inhibiting, or ameliorating cardiac kidney diseases such as those described herein.

Dermal Scar and Keloid Formation

Dermal scar and keloid formation are known to involve excessive collagen deposition and/or dysregulation of collagen deposition. This deviation from normal fibroblast remodeling of injured dermal tissue can result in thick and unsightly scarring. Keloids are known to be, in part, the result of dysregulated wound healing and subsequent elevated collagen deposition. Keloids, unlike the scars seen in normal wound healing, do not fade or regress over time. Though keloids are typically benign dermal tumors, they are unsightly and can accumulate into more problematic skin deformations and/or lesions. The accumulation of collagen in the skin is also implicated in scleroderma, a generalized term for numerous conditions of thickening or hardening of dermal tissue, where the common element is the overproduction or dysregulation of collagen in the dermal tissues by fibroblasts.

The compositions described herein are thus useful for treating, inhibiting, or ameliorating dermal scar and keloid formation.

Neurofibromatosis

Neurofibromatosis is a genetic disease that causes fibrotic tumors to form within nerve tissue anywhere in the body. Neurofibromatosis includes neurofibromatosis type 1, which is most common, neurofibromatosis type 2, and Schwannomatosis. The disease can be disfiguring due to the occurrence of multiple cutaneous and subcutaneous fibrotic lesions throughout the body. Benign tumors may affect hearing, sight, balance, strength and sensation. Neurofibromas may also degenerate into malignant tumors that are difficult to treat.

Provided herein are methods of treating, inhibiting, or ameliorating neurofibromatosis with a composition described herein.

Combination Therapy

One would understand that the anti-endoglin antibodies can be effective for treating fibrosis, it is contemplated herein that a subject can also be treated with one or more additional fibrotic inhibitors.

The term "fibrotic inhibitor" or "anti-fibrotic agent" is used herein, for purposes of the specification and claims, to mean a compound or molecule including, but not limited to, commercially available inhibitors. In one embodiment, the one or more additional anti-fibrotic agents or anti-fibrotic treatments include, but are not limited to, removal of the underlying cause (e.g., toxin or infectious agent), suppression of inflammation (using, e.g., corticosteroids such as Prednisone, IL-1 receptor antagonists, or other agents), down-regulation of stellate cell activation using, e.g., gamma interferon or antioxidants), promotion of matrix degradation, or promotion of stellate cell apoptosis.

IV. Packages and Kits

In still further embodiments, the present application concerns kits for use with the compounds described above. Humanized and deimmunized antibodies, or antigen-binding fragments, that bind endoglin can be provided in a kit. The kit can, optionally, include one or more anti-fibrotic reagents. The kits will thus comprise, in suitable container means, a composition comprising an antibody or antigen-binding fragment thereof that binds endoglin. The kit may comprise an antibody or antigen-binding fragment thereof that binds endoglin in suitable container means.

The container means of the kits will generally include at least one vial, test tube, flask, bottle, syringe and/or other container means, into which the at least one reagent can be placed, and/or preferably, suitably aliquoted. The kits can include a means for containing any reagent containers in close confinement for commercial sale. Such containers may include injection and/or blow-molded plastic containers into which the desired vials are retained. Kits can also include printed material for use of the materials in the kit.

Packages and kits can additionally include a buffering agent, a preservative and/or a stabilizing agent in a pharmaceutical formulation. Each component of the kit can be enclosed within an individual container and all of the various containers can be within a single package. Invention kits can be designed for cold storage or room temperature storage.

Additionally, the preparations can contain stabilizers to increase the shelf-life of the kits and include, for example, bovine serum albumin (BSA). Where the compositions are lyophilized, the kit can contain further preparations of solutions to reconstitute the lyophilized preparations. Acceptable reconstitution solutions are well known in the art and include, for example, pharmaceutically acceptable phosphate buffered saline (PBS).

Packages and kits can further include one or more components for an assay, such as, for example, an ELISA assay. Samples to be tested in this application include, for example, blood, plasma, and fresh or frozen tissue sections (e.g., lung, liver, kidney, cardiac, etc.), tissue secretions, urine, lymph, and products thereof. Packages and kits can further include one or more components for collection of a sample (e.g., a syringe, a cup, a swab, etc.).

Packages and kits can further include a label specifying, for example, a product description, mode of administration and/or indication of treatment. Packages provided herein can include any of the compositions as described herein. The package can further include a label for treating fibrosis.

The term "packaging material" refers to a physical structure housing the components of the kit. The packaging material can maintain the components sterilely and can be made of material commonly used for such purposes (e.g., paper, corrugated fiber, glass, plastic, foil, ampules, etc.). The label or packaging insert can include appropriate written instructions. Kits, therefore, can additionally include labels or instructions for using the kit components in any method of the invention. A kit can include a compound in a pack, or dispenser together with instructions for administering the compound in a method described herein.

Instructions can include instructions for practicing any of the methods described herein including treatment methods. Instructions can additionally include indications of a satisfactory clinical endpoint or any adverse symptoms that may occur, or additional information required by regulatory agencies such as the Food and Drug Administration for use on a human subject.

The instructions may be on "printed matter," e.g., on paper or cardboard within or affixed to the kit, or on a label affixed to the kit or packaging material, or attached to a vial or tube containing a component of the kit. Instructions may additionally be included on a computer readable medium, such as, for example, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

The embodiments of the compounds and methods of the present application are intended to be illustrative and not limiting. Modifications and variations can be made by persons skilled in the art in light of the above teachings specifically those that may pertain to alterations in the antibodies or antigen-binding fragments which bind endoglin surrounding the described modifications while maintaining near native functionally with respect to binding of endoglin. Therefore, it should be understood that changes may be made in the particular embodiments disclosed which are within the scope of what is described.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

The application may be better understood by reference to the following non-limiting examples, which are provided as exemplary embodiments of the application. The following examples are presented in order to more fully illustrate embodiments of the invention and should in no way be construed, however, as limiting the broad scope of the application.

Example 1

Generation and Binding of Anti-CD105 Humanized/Deimmunized Antibodies

Construction, Expression and Purification of Antibodies

All humanized/deimmunized VH and VK region genes were synthesized using a series of overlapping oligonucleotides that were annealed, ligated and PCR amplified to give full length synthetic V regions. The assembled variants were then cloned directly into Antitope Ltd.'s pANT expression vector system for IgG1 heavy chains and kappa light chains.

All combinations of humanized/deimmunized heavy and light chains (i.e., a total of 24 pairings) were stably transfected into NS0 cells via electroporation and selected using 200 nM methotrexate (Sigma Cat. No. M8407). Methotrexate-resistant colonies for each construct were tested for IgG expression levels using an IgG1 ELISA. The best expressing lines were selected and frozen under liquid nitrogen. Successful transfection and clone selection was achieved for all variants and expression levels of humanized and humanized/deimmunized antibody variants in saturated static cultures are shown in Table 1.

Twenty-four IgG1 variants were therefore purified from NS0 cell culture supernatants on a Protein A sepharose column (GE Healthcare Cat. No. 110034-93) and quantified by $OD_{280\ nm}$ using an extinction coefficient, $Ec_{(0.1\%)}=1.62$, based on the predicted amino acid sequence. Approximately 500 µg of each antibody variant was purified and lead variants were analyzed by reducing SDS-PAGE. Briefly, Coomassie blue stained reducing SDS-PAGE gel of lead antibody variants. 1 µg of each sample was loaded on a NuPage 4-12% Bis-Tris gel (Invitrogen Cat. No. NP0322BOX) and run at 200 V for 30 minutes. Marker was Bio-Rad Precision Plus (Cat. No. 161-073). Bands corresponding to the predicted sizes of the heavy and light chains were observed with no evidence of any contamination in any lane (data not shown).

ELISA Methodology

An ELISA was used to assay binding of humanized and humanized/deimmunized anti-endoglin antibodies to endoglin. Briefly, an ELISA was performed according to the following steps:

1. Coat a Nunc Maxisorp plate with MAB9811-01 (polyclonal anti-endoglin antibody) at 1500 ng/ml in PBS, 100 µl/well. Cover the plate with a sealer and incubate overnight (16-24 hours) at 4° C.

2. Wash the plate 2× with ~200 µl of PBS (without Tween).

3. Add 200 µl/well of BSA blocking solution (1% BSA) and incubate 60 minutes at room temperature.

4. Wash the plate 3× with PBS containing Tween (PBS-T) using the BioTek plate washer.

5. Add 100 µl/well of CD105 (R&D Systems Cat 1097-EN) at 100 ng/ml in PBS-T with 0.1% BSA and incubate 60 minutes at room temperature.

6. Wash the plate 3× with PBS-T using the BioTek plate washer.

7. In test wells: add 100 µl/well of anti-endoglin antibodies at 20, 10, 4, 2, 1, 0.5 and 0.2 ng/ml (diluted in PBS-T with 0.1% BSA and incubate 60 minutes at room temperature. In negative control wells: add 100 µl/well of isotype matched control antibody.

8. Wash the plate 3× with PBS-T using the BioTek plate washer.

9. Add 100 µl/well of Goat anti-Human IgG conjugated to HRP (Jackson Immunoresearch), diluted 1:10000 in PBS-T with 0.1% BSA to all wells; incubate 30-60 minutes at room temperature.

10. Wash the plate 5× with PBS-T using the BioTek plate washer.

11. Add 100 µl/well of TMB substrate solution and incubate uncovered in the dark for 15 minutes.

12. Stop the reaction by addition of 100 µl/well of TMB Stop Solution.

Samples are run in triplicate and the optical density is read to construct a standard curve and determine the binding constant. Statistical analysis is conducted using the Student's t-test or another standard test.

Competition ELISA

Antibodies were tested in a competition ELISA for binding to CD105 against biotinylated chimeric anti-CD105. Briefly, chimeric anti-CD105 was biotinylated using a micro-biotinylation kit (Sigma, Catalog No. BTAG-1KT) following the manufacturer's instructions. Nunc Immuno MaxiSorp 96-well flat-bottom microtiter plates were coated with mouse anti-human CD105 (Southern Biotechnologies, Catalog No. 9811-01) at 1.5 µg/mL in phosphate buffered saline (PBS) overnight at 4° C. The following day, 100 ng/ml human CD105 (R&D Systems, Catalog No. 1097-EN) in PBS/2% BSA was added to the pre-coated plate and incubated at room temperature for 1 hour. Varying concentrations of humanized/deimmunized anti-CD105 antibodies (4 µg/mL to 0.0018 µg/mL in three-fold dilutions) were mixed with a fixed concentration of biotinylated chimeric anti-CD105 antibody (6.25 ng/ml) and added to the plate. Binding of the biotinylated chimeric antibody was detected via streptavidin-HRP (Sigma, Catalog No. 55512) and TMB substrate (Sigma, Catalog No. T0440). OD450 nm values were measured on a Dynex MRX TCII plate reader. The results of the competition analysis are illustrated in FIG. 6. Curves were fitted through the straight line portion of each of the plots of absorbance against the log sample concentration and the equations of the lines were used to calculate the concentrations of humanized or humanized/deimmunized antibody required to inhibit biotinylated chimeric antibody binding to CD105 by 50% (IC50). To allow for comparisons within and between experiments, IC50 values of humanized or humanized/deimmunized variants were normalized against the reference antibody that was included on each plate to give a value for the fold difference. IC50 values are relative to chimeric anti-CD105 and are representative of three experiments. Summary ELISA data are presented in Table 1 of U.S. Pat. No. 8,221,753 and include antibody expression levels (µg/ml) as assayed in saturated static cultures.

Table 1 of U.S. Pat. No. 8,221,753 provided the characteristics of humanized and humanized/deimmunized antibody variants. IC50 values are relative to chimeric anti-endoglin antibody and are representative of three experiments. Antibody expression levels (µg/ml) were assayed in saturated static cultures. The level of deimmunization is represented by an arbitrary scale based upon the location in the epitopes of the mutations. Accordingly, the present inventors have demonstrated the successful preparation of humanized and deimmunized anti-endoglin antibodies.

Example 2

BIAcore (Surface Plasmon Resonance: SPR) Analysis of Humanized and Deimmunized Anti-Endoglin Antibody Binding Affinity of antibodies can be assessed using, for example, BIAcore analysis using standard protocols. Briefly, protein A is chemically coupled to a BIAcore CM5 chip, with the amount of protein A immobilized corresponding to 2000 RU. Subsequent steps are performed in a running buffer of 10 mM HEPES, 150 mM NaCl, 3 mM EDTA, 0.05% TWEEN, pH=7.4, at 25 degrees Celsius using a 10 Hz data collection rate. Anti-endoglin antibody (10 nM) is captured at a 10 μL/min flow rate by the immobilized protein A on the BIAcore chip: typically, capture times of 20, 40 and 80 seconds allow the capture of antibody densities corresponding to 130 RU, 330 RU and 570 RU, respectively. Start-up cycles are performed using running buffer at a flow rate of 40 μL/min, a contact time of 90 seconds and a dissociation time of 90 seconds. Sample cycles are performed using recombinant endoglin at concentrations ranging from 0 to 40 nM. Endoglin is passed over the BIAcore chip containing captured antibody at a flow rate of 40 μL/min with a contact time of 525 seconds and dissociation time of 2500 seconds. Eight sample cycles are typically performed at each antibody capture density. Regeneration of the chip is accomplished using 10 mM glycine pH=1.7. Data analysis is performed using BIAcore T100 Evaluation Software v1.1 Signals generated using BIAcore chips with different captured antibody densities are compared and data generated in the absence of recombinant endoglin are used to adjust for the intraassay blank signal. For fitting of the data, the $R_{max}$ is allowed to float to account for variation in capture levels of each antibody in each cycle. Data from each capture density is fitted simultaneously during analysis of each antibody. BIAcore data are presented in Table 2 for chimeric, humanized and deimmunized anti-endoglin antibodies, including $k_a$ (1/Ms), $k_d$ (1/s), $K_D$ (M) and $Chi^2$ ($RU^2$).

TABLE 2

| Anti-endoglin Antibody | $k_a$ ($\times 10^4$) | $k_d$ ($\times 10^{-5}$) | $K_D$ ($\times 10^{-10}$) | $Chi^2$ ($\times 10^{-2}$) |
|---|---|---|---|---|
| VK1AAVH1R | 6.40 | 3.41 | 5.33 | 6.84 |
| Chimeric | 5.47 | 3.28 | 6.00 | 6.78 |
| VK1AAVH1Q | 3.56 | 3.03 | 8.50 | 7.07 |
| VK1AAVH1A2 | 4.60 | 3.25 | 7.06 | 5.52 |

Table 2. BIAcore binding data for chimeric anti-endoglin antibody and humanized/deimmunized anti-endoglin antibodies VK1AAVH1R, VK1AAVH1Q and VK1AAVKVH1A2.

Example 3

Antibody Avidity and Number of Available Epitopes on Endoglin-Expressing Cells Antibody avidity and number of available epitopes on endoglin-expressing cells can be assessed utilizing Scatchard plot analyses using standard protocols.

Briefly, Scatchard plot analyses of direct binding of radiolabeled humanized anti-endoglin antibodies to endoglin-expressing KM-3 leukemia cells and sub-confluent proliferating HUVECs are carried out. The purified anti-endoglin antibodies are individually radiolabeled with $^{125}I$ using Iodo-Gen and according to standard methods known to those skilled in the art. The radiolabeled humanized anti-endoglin antibodies are assayed for the mean number of iodine atoms per IgG molecule. Titration experiments are carried out using a fixed amount (0.1 μg) of each $^{125}I$-labeled mAb and 2-fold serial increments of endoglin-expressing HUVEC cells to determine antigen-binding activity. Analysis of Scatchard plot of binding data is carried out according to known methods. An equilibrium constant and an average maximal number of mAb bound/cell are estimated by this analysis.

Example 4

Identification of T-Cell Epitopes in Humanized Anti-Endoglin Antibodies

Sequences of humanized variable regions were tested by iTope™ analysis. Humanized variable region sequences were divided into overlapping 9-15-mer peptides. The variable region sequences were analyzed for promiscuous high affinity binding to human WIC class II (potential T cell epitopes) using iTope™, an in silico analytic tool that determines the affinity of peptides for WIC Class II by computational analysis. Sequences with the lowest frequencies of potential T cell epitopes from the iTope™ analysis are identified as leads for generation of a humanized antibody. The selected humanized variable region sequences may redesigned through inclusion of mutations in order to remove potential T cell epitopes. Mutations are designed using iTope™ to reduce or eliminate MHC class II binding. Alternatively, germ-line human sequences can be substituted at sites of potential T cell epitopes or alternative sequences may be substituted.

FIGS. 19-23 of U.S. Pat. No. 8,221,753, which is hereby incorporated by reference is its entirety, present the predicted binding of 9 mer peptides for the humanized anti-endoglin antibody containing the light chain HuVK_v0 and the heavy chain HuVH_v0, noted in FIG. 3B of the present application.

Example 5

Design of Anti-CD105 Humanized/Deimmunized Antibodies

This example describes the design of therapeutic monoclonal, humanized-deimmunized antibodies targeting human CD105 that exhibit reduced immunogenicity.

The promiscuous high affinity WIC class II binding sequences identified using iTope™ (data not shown) were further analyzed by iTope™ in order to identify amino acid substitutions at key MHC class II pocket positions that would reduce or eliminate peptide binding to MHC class II. Since all the sequences overlapped CDRs, consideration was also given to the CDR location of the changes (potential antigen contact residues) and the physicochemical characteristics of the original and replacement amino acids. TCR contact residues and residues outside the main binding groove involved in the stabilization of peptide/WIC class II-TCR interactions were also considered for replacement.

In VHV1, a 9-mer peptide lying completely within CDR2 and starting at residue 51 was identified as a promiscuous high affinity MEW class II binding peptide. The most successful method for elimination of WIC class II binding is to target the first amino acid of the 9-mer (the pocket 1 or p1 position) where removal of the hydrophobic side-chain or replacement with a hydrophilic side-chain eliminates MHC class II binding. However, this type of radical amino acid replacement may not always be successful in retaining antibody affinity, hence secondary pocket positions (p4, p6, p7 or p9), alone or in combination, were also assessed. iTope™ analysis revealed that targeting the p4 position of this peptide by changing K52b to Q or R is predicted to significantly reduce MHC class II binding while replacement of I51 at p1 with A is predicted to remove binding entirely (See, Table 5 of U.S. Pat. No. 8,221,753).

Crystal structures of antibody/antigen complexes suggest that 151 may infrequently contact with antigen; however a radical change of I to A (a substitution for disrupting a p1 anchor position) at this position could affect the overall conformation of the CDR. Therefore, relatively conservative changes at K52b (p4 anchor position) were also included since this residue is solvent exposed but may not contact antigen. Finally, additional mutations lying outside the CDR were also designed (G49 to A or S) to assess the destabilizing effect on peptide/MHC class II/TCR interactions. Table 6 of U.S. Pat. No. 8,221,753 lists the humanized/deimmunized variant VH regions that were constructed; the SEQ ID NOS for the corresponding nucleotide and amino acid sequences are indicated next to the constructs.

Two promiscuous high affinity MEW class II binding peptides were identified in VKV2 and VKV1. The first, with a p1 anchor at V19, partially overlaps CDR1 and the second, with a p1 anchor at 148, overlaps CDR2. Both p1 anchors lie outside the CDRs and were targeted by mutation to A, which may completely remove MHC class II binding (Table 7). However, both these residues may be involved in the maintenance of the conformations of CDRs 1 and 2; therefore, additional mutations were designed that significantly reduced MHC class II binding (Table 7). In both cases, p4 residues were targeted by mutation of T to S. T22S also lies outside the CDR and is less likely to affect CDR conformation than V19A. T51 lies inside CDR2; however evidence from crystal structures of antibodies complexed with antigen suggests that this residue rarely contacts antigen. Table 6 of U.S. Pat. No. 8,221,753 lists humanized and humanized/deimmunized VK regions that were constructed.

Example 6

This example describes a method of screening anti-endoglin antibodies for T-cell epitopes. The interaction between MHC, polypeptide and T cell receptor (TCR) provides the structural basis for the antigen specificity of T cell recognition. T cell proliferation assays test the binding of polypeptides processed from antibodies to MHC and the recognition of MHC/polypeptide complexes by the TCR. In vitro T cell proliferation assays of the present example, involve the stimulation of peripheral blood mononuclear cells (PBMCs), containing antigen presenting cells (APCs) and T cells. Stimulation is conducted in vitro using intact anti-endoglin antibodies. Stimulated T cell proliferation is measured using $^3$H-thymidine ($^3$H-Thy) and the presence of incorporated $^3$H-Thymidine is assessed using scintillation counting of washed fixed cells.

All humanized and humanized/deimmunized VH and VK region genes were synthesized using a series of overlapping oligonucleotides that were annealed, ligated and PCR amplified to give full length synthetic V regions. The assembled variants were then cloned directly into Antitope Ltd.'s pANT expression vector system for IgG1 heavy chains and kappa light chains.

Purification of Antibodies

Anti-endoglin antibodies were purified from the supernatants of mammalian cultures by protein A chromatography. Buffer exchange and protein concentration was done using PBS pH=7.4. Anti-endoglin antibody was further purified by size exclusion chromatography using a Sephacryl S200 column (GE Healthcare, AMersham, UK). The major peak is collected, filter sterilized and shown to have endotoxin levels <5 EU/mg using an Endosafe-PTS (Charles River, Margate, UK). The purified antibodies are stored at 4 degrees Celsius. Final concentrations were determined by UV absorption using calculated molar extinction coefficients, where A280 1.0=1.62 mg/mL. Each antibody was then diluted to 100 μg/mL in AIMV culture medium.

Preparation and Selection of Donor PBMC

Peripheral Blood Mononuclear cells (PBMC) are isolated from healthy community donor buffy coats (from blood drawn within 24 hours) which are obtained from the UK National Blood Transfusion Service (Addenbrooke's Hospital, Cambridge, UK) according to approval granted by Addenbrooke's Hospital Local Research Ethics Committee. PBMC are isolated from buffy coats by Lymphoprep (Axis-shield, Dundee, Scotland) density centrifugation and CD8+ T cells are depleted using CD8+ RossetteSep™ (StemCell Technologies, Inc.). Donors are characterized by identifying HLA-DR haplotypes using a Biotest HLA SSP-PCR based tissue-typing kit (Biotest, Landsteinerstralβe, Denmark). T cell responses to a control antigen, Keyhole Limpet Haemocyanin (KLH) (Pierce, Rockford, Ill., USA) are determined for a positive control. PBMC were then frozen and stored in liquid nitrogen until required. When required for use, cells are thawed rapidly in a water bath at 37° C. before transferring to 10 ml pre-warmed AIM V medium.

A cohort of 20 donors is selected to best represent the number and frequency of HLA-DR allotypes expressed in the world population. Analysis of the allotypes expressed in the cohort against those expressed in the world population revealed that coverage of >80% is achieved and that all major HLA-DR alleles (individual allotypes with a frequency >5% expressed in the world population) are well represented. A summary of donor haplotypes is provided in FIG. 23, and a comparison of the frequency of donor allotypes used in the study versus those present in the world population is made.

PBMCs from each donor are thawed, counted and viability assessed. Cells were revived and resuspended in AIMV culture medium to 4-6×10$^6$ PBMC/mL. For each donor, bulk cultures were established in which a total of 1 mL proliferation cell stock was added to a 24-well plate. A total of 1 mL of each diluted test sample was added to the PBMC to give a final concentration of 50 μg/mL per antibody sample. For each donor, a positive control (cells incubated with 100 μg/mL KLH) and a negative control (cells incubated with culture media only) were also included. For the first 4 donors, an additional control was included to test for modulation of T cell responses by the test samples, where test sample and KLH were added to the PBMC. Comparison of these samples with KLH alone can be used to assess the effects of the test samples on proliferation. Cultures were incubated for a total of 8 days at 37 degrees Celsius with 5% carbon dioxide. On days 5, 6, 7 and 8, the cells in each well are gently resuspended and three 100 μL aliquots are transferred to individual wells of a round bottom 96 well plate. The cultures are pulsed with 1 μCi $^3$[H]-Thy (Perkin Elmer, Waltham, Mass.) in 100 μL AIMV culture medium and incubated for a further 18 hours before harvesting onto filter mats using a TomTec Mach III cell harvester. Counts per minute (cpm) for each well are determined by Meltilex™ (Perkin Elmer®, Waltham, Mass., USA) scintillation counting on a Microplate Beta Counter (Perkin Elmer®, Waltham, Mass., USA) in paralux, low background counting mode.

Results are expressed as stimulation indices, where the stimulation index (SI) is derived by division of the proliferation score (e.g., counts per minute of radioactivity) measured to the test anti-endoglin antibody by the score measured in cells not contacted with a test anti-endoglin antibody. All basal cpm for the control wells are above the minimum threshold for the assay of 150 cpm.

For proliferation assays, an empirical threshold of a stimulation index (SI) equal to or greater than 2 (SI≥2) has been previously established whereby samples inducing proliferative responses above this threshold are deemed positive (where included, borderline SIs≥1.90 are highlighted). Extensive assay development and previous studies have shown that this is the minimum signal to noise threshold allowing maximum sensitivity without detecting large numbers of false positive responses. Positive responses are defined by the following statistical and empirical thresholds:

1. Significance (p<0.05) of the response by comparing cpm of test wells against medium control wells using unpaired two sample student's t-test.
2. Stimulation index greater than 2 (SI≥2), where SI=mean of test wells (cpm)/mean medium control wells (cpm).

In addition, intra-assay variation is assessed by calculating the coefficient of variance and standard deviation (SD) of the raw data from replicate cultures.

Results for the EpiScreen time course proliferation assay with the anti-endoglin antibodies are shown in FIG. 24 of U.S. Pat. No. 8,221,753 and summarized in tabular form (Table 8 of U.S. Pat. No. 8,221,753). The chimeric antibody stimulated responses in 4 of 20 donors (20% of the study cohort) and, although two of the donor responses were borderline (1.92 and 1.95 for donors 11 and 17, respectively), they were significantly different from background (p<0.05). The humanized antibody VK1VH1 stimulated responses in 2 of 20 donors (10% of the study cohort) including one borderline response (1.91 for donor 20) that was significantly different from background (p<0.05). It is noteworthy that donors 11 and 20 responded to both of these antibodies suggesting that there could be a shared T cell epitope. In contrast, none of the donors in the study cohort responded positively to the deimmunized anti-endoglin antibody VK1AA VH1A2. Results with the control antigen KLH show that there was a good correlation between positive and negative results, indicating a high level of reproducibility in the assay.

Example 7

EpiScreen™ T Cell Epitope Mapping

EpiScreen™ is an ex vivo technology for measurement of T cell epitopes in whole antibodies or for mapping the sequence location of such T cell epitopes as described in more detail below.

EpiScreen™ Donor Selection

Peripheral Blood Mononuclear cells (PBMC) are isolated from healthy community donor buffy coats (from blood drawn within 24 hours) which are obtained from the UK National Blood Transfusion Service (Addenbrooke's Hospital, Cambridge, UK) according to approval granted by Addenbrooke's Hospital Local Research Ethics Committee. PBMC are isolated from buffy coats by Lymphoprep (Axis-shield, Dundee, Scotland) density centrifugation and CD8+ T cells are depleted using CD8+ RossetteSep™ (StemCell Technologies, Inc.). Donors are characterized by identifying HLA-DR haplotypes using a Biotest HLA SSP-PCR based tissue-typing kit (Biotest, Landsteinerstralβe, Denmark). T cell responses to a control antigen, e.g., Keyhole Limpet Haemocyanin (KLH) (Pierce, Rockford, USA) are also determined for a positive control. A cohort of 54 donors is selected to best represent the number and frequency of HLA-DR allotypes expressed in the world population. Analysis of the allotypes expressed in the cohort against those expressed in the world population revealed that coverage of >80% is achieved and that all major HLA-DR alleles (individual allotypes with a frequency >5% expressed in the world population) are well represented. A summary of donor haplotypes is provided, and a comparison of the frequency of donor allotypes used in the study versus those present in the world population is made.

Donor details and haplotypes. Donor responses (SI) to KLH are tested in two independent experiments. Test 1 is performed on freshly isolated PBMC and an antibody is the re-test in the current study. Responses that did not produce the same result (i.e., positive or negative) in both tests are highlighted. Donors with very low basal cpm (<150 cpm) are excluded from the analysis.

EpiScreen Analysis: Proliferation Assays

EpiScreen™ is used to test overlapping peptides derived from the sequence of chimeric, humanized and humanized/deimmunized antibodies. Overlapping peptides are designed. A series of 128×15-mer peptides overlapping by 12 amino acids are synthesized together with 1×14-mer and 1×11-mer and used to stimulate peripheral blood mononuclear cells (PBMC) derived from a cohort of 51 healthy donors using EpiScreen™ T cell epitope mapping. Individual peptides are tested in replicate cultures and responses are assessed using T cell proliferation assays to identify the precise location of epitopes. PBMC from each donor are thawed, counted and assessed for viability. Cells are revived in room temperature AIM V culture medium (Invitrogen, Carlsbad, Calif.) before adjusting the cell density to 2.5×10$^6$PBMC/ml (proliferation cell stock). Peptides are dissolved in DMSO (Sigma-Aldrich, St Louis, Mo., USA) to a final concentration of 10 mM. Peptide culture stocks are then prepared by diluting into AIM V culture medium to a final concentration of 5 For each peptide and each donor, sextuplicate cultures are established by adding 100 μl of the peptide culture stocks to 100 μl of proliferation cell stock in a flat bottomed 96 well plate. Both positive and negative control cultures are also established in sextuplicate. A total of 9×96 well plates are used for each donor, and each plate is sufficient to test 15 peptides with one negative control (carrier alone) in sextuplicate. On the final plate, a positive control is added.

Cultures are incubated for a total of 6 days before adding 0.5 μCi $^3$[H]-Thymidine (Perkin Elmer®, Waltham, Mass., USA) to each well. Cultures are incubated for a further 18 hours before harvesting onto filter mats using a TomTec Mach III cell harvester. Counts per minute (cpm) for each well are determined by Meltilex™ (Perkin Elmer®, Waltham, Mass., USA) scintillation counting on a Microplate Beta Counter (Perkin Elmer®, Waltham, Mass., USA) in paralux, low background counting mode.

For proliferation assays, an empirical threshold of a stimulation index (SI) equal to or greater than 2 (SI≥2) has been previously established whereby samples inducing proliferative responses above this threshold are deemed positive (where included, borderline SIs≥1.90 are highlighted). Extensive assay development and previous studies have shown that this is the minimum signal to noise threshold allowing maximum sensitivity without detecting large numbers of false positive responses. Positive responses are defined by the following statistical and empirical thresholds:

1. Significance (p<0.05) of the response by comparing cpm of test wells against medium control wells using unpaired two sample student's t-test.
2. Stimulation index greater than 2 (SI≥2), where SI=mean of test wells (cpm)/mean medium control wells (cpm).

In addition, intra-assay variation is assessed by calculating the coefficient of variance and standard deviation (SD) of the raw data from replicate cultures.

Proliferation assays are set up in sextuplicate cultures ("non-adjusted data"). To ensure that intra assay variability is low, data is also analyzed after removing the maximum and minimum cpm values ("adjusted data") and the SI of donor responses are compared using both data sets. Details of donor SIs from both adjusted and non-adjusted data sets are prepared. T cell epitopes are identified by calculating the average frequency of responses to all peptides in the study +2×SD (background response rate). Any peptide(s) that induced proliferation above this threshold is considered to contain a T cell epitope.

In Silico iTope™ Analysis of Peptides

The sequences of peptides that are positive in the proliferation assay are analyzed using Antitope's predictive iTope™ software. This software predicts favorable interactions between amino acid side chains of the peptide and specific binding pockets within the MEW class II binding groove. The location of key binding residues is determined by generating 10-mer peptides that overlapped by one amino acid spanning the long peptide sequence. Each 10-mer is tested against Antitope's database of MHC class II allotypes and scored based on their fit and interactions with the MEW class II molecules. Peptides that produced a high binding score against a large number of alleles are considered to contain the core 9-mer.

Identification of T Cell Epitopes

All peptides identified using the EpiScreen™ Analysis described above are successfully synthesized for testing against 51 healthy donors (54 donors are originally selected; donors may be excluded from the analysis due to low basal cpm, i.e., below the cut off value of 150 cpm). Positive responses are defined by donors that produced a significant (p<0.05) response with a SI≥2 to any given peptide. Borderline responses (a significant (p<0.05) response with an SI≥1.90) are also included. The outputs from non-adjusted and adjusted data analyses are compared to ensure that intra-assay variability is low and that positive responses are not the result of spurious proliferation in individual wells. The results from each analysis showed little difference between the methods; consequently, the T cell epitope map is compiled using the adjusted data analysis. Donor stimulation indices from both non-adjusted and adjusted analyses are prepared. T cell epitopes are identified by calculating the average frequency of the responses to all peptides in the study plus twice the standard deviation (termed 'background response rate'). This is calculated to be 5.6% and is the equivalent of inducing a positive response in three or more donors. Peptides inducing proliferative responses above this threshold are considered to contain a T cell epitope.

Immunogenicity Testing of Lead Variants Using EpiScreen™

Lead variants are purified and compared against the wild-type polypeptide using EpiScreen™ time course T cell assays. A large number of healthy donors representing the world population according to expression of HLA allotypes are selected from a donor library as described above. Donors are stimulated with each protein in separate bulk cultures containing $2\text{-}4\times10^6$ CD8$^+$ T cell depleted PBMC. Replicate samples (of T blasts) are removed from bulk cultures on days 5-8, and proliferation along with IL-2 secretion (ELISPOT) is assessed. To further validate the assessment between wild type and variants, the study cohort is supplemented with responding donors from the EpiScreen™ T cell epitope mapping study (provided sufficient numbers of CD8$^+$ T cell depleted PBMC remain).

In order to confirm loss of immunogenicity in lead variants, an analysis of T cell immunogenicity by EpiScreen™ time course T cell assays is undertaken as follows:

(i) Buffy coats from healthy donors (with >80% DRB 1 allotypic coverage for world population) are used to isolate PBMC which contain physiological levels of APC and CD4+ T cells;

(ii) Each donor is tested against positive control antigens including keyhole limpet haemocyanin (a potent neoantigen);

(iii) CD8+ T cells are depleted to exclude the detection of MEW class I restricted T cell responses;

(iv) Lead variants and wild-type polypeptides are compared against each other to evaluate relative capacity to activate T cells CD4+ T cells;

(v) Data is analyzed using previously validated assay parameters with positive responses of SI>2 supported by additional information including statistical and frequency analysis;

(vi) Data from EpiScreen™ time course T cell assays provides information on the magnitude and kinetics of T cell responses to individual molecules;

(vii) Any remaining PBMC from donors that produce positive responses is archived and is available for use in repeat testing studies; and (viii) An assessment is made of association between donor allotype and responses to wild-type polypeptide and any responses to variant leads.

Example 8

In Vivo Efficacy Study of M1043 in a Carbon Tetrachloride-Induced Liver Fibrosis Model The purpose of this example is to examine the effects of M1043 Antibody that binds to mouse endoglin to competitively inhibit mouse BMP binding to mouse endoglin in a carbon tetrachloride-induced liver fibrosis model.

```
M1043 heavy chain variable region
                                      (SEQ ID NO: 124)
QVQLQQSGAELVKPGSSVKISCKASGYTFTSYDMHWIKQQPGNGLE

WIGWIYPGNGNTKYNQKFNGKATLTADKSSSTAYMQLSSLTSEDSA

VYFCARGKFGVGDYWGQGVMVTVSS

M1043 light chain variable region
                                      (SEQ ID NO: 125)
DTVLTQSPALAVSPGERVSISCRASEGVNSYMHWYQQKPGQQPKLL

IYIASNLASGVPARFSGSGSGTDFTLTIDPVEADDTATYFCQQSWN

DPYTFGAGTKLELKR
```

Materials And Methods

Test Substances

M1043 Antibody was provided by TRACON Pharmaceuticals, Inc. Isotype-matched antibody (rat IgG1) was purchased from Bio X cell (Cat# BE0088). Dosing solution was prepared by diluting the stock solution of isotype-matched antibody or M1043 Antibody with vehicle (sterilized Phosphate Buffered Saline (PBS)).

Animals

Seven-week-old female C57BL/6J mice (17~21 g) were obtained from Japan SLC (Japan).

Animals were housed and fed with normal diet (CE-2; CLEA Japan, Japan) under conventional conditions. All animals used in this study were cared for following guidelines;

1. Act on Welfare and Management of Animals (Ministry of the Environment, Act No. 105 of Oct. 1, 1973)
2. Standards Relating to the Care and Management of Laboratory Animals and Relief of Pain (Notice No. 88 of the Ministry of the Environment, Apr. 28, 2006)
3. Guidelines for Proper Conduct of Animal Experiments (Science Council of Japan, Jun. 1, 2006)

Environment

The animals were maintained in a specific pathogen-free (SPF) facility under controlled conditions of temperature (23±2° C.), humidity (45±10%), lighting (12-hour artificial light and dark cycles; light from 8:00 to 20:00) and air exchange. A high pressure was maintained in the experimental room to prevent contamination of the facility.

Animal Housing

The animals were housed in polycarbonate cages KN-600 (Natsume Seisakusho, Japan) with a maximum of 4 mice per cage. Sterilized Paper-Clean (Japan SLC) was used for bedding and replaced once a week.

Food and Drink

Sterilized normal diet was provided ad libitum, being placed in a metal lid on the top of the cage. Distilled water was also provided ad libitum from a water bottle equipped with a rubber stopper and a sipper tube. Water bottles were replaced once weekly, cleaned, sterilized in an autoclave and reused.

Animal and Cage Identification

Mice were identified by numbers engraved on earrings. Each cage was also given a specific identification code.

Randomization

Mice were divided into 3 groups of 8 mice based on their body weight on the day before the start of the treatment (day 13).

Induction of $CCl_4$-Induced Liver Fibrosis Model

Mice were intraperitoneally administered 5% $CCl_4$ (Sigma-Aldrich, USA) in mineral oil (Sigma-Aldrich) in a volume of 100 μL twice a week (day 0, 4, 7, 11, 14, 18, 21 and 25) after acclimation.

Routes of Drug Administration

Isotype-matched antibody and M1043 Antibody were administered by intravenously route in a volume of 5 mL/kg.

Treatment Dose

Isotype-matched antibody and M1043 Antibody were administered to the mice twice weekly at a dose of 10 mg/kg twice weekly.

Individual body weight was measured daily. Survival, clinical signs and behavior of mice was also monitored daily.

Plasma Specimen Collection

The blood samples were collected in polypropylene tubes with anticoagulant (Novo-Heparin; Mochida Pharmaceutical, Japan) and centrifuged at 1,000×g for 15 minutes at 4° C. The supernatant was collected and stored at −80° C.

Tissue Specimen Collection

Fresh and frozen liver specimens were collected using conventional techniques.

Histological Analyses

To visualize collagen deposition, sections were cut from paraffin blocks of left lateral liver tissue prefixed in Bouin's solution and stained with picro-Sirius red solution (Waldeck, Germany). For quantitative analysis of fibrosis area, bright field images of Sirius red-stained section were randomly captured using a digital camera (DFC280; Leica Microsystems, Germany) at 100-fold magnification, and the Sirius red-stained positive areas in 5 field/section were measured using ImageJ software (National Institute of Health, USA). The quantification was done in a blinded fashion.

Statistical Tests

Statistical analyses were performed using Bonferroni Multiple comparison test on GraphPad Prism 4 (GraphPad Software, USA). P values<0.05 were considered statistically significant. Results were expressed as mean±SD.

Experimental Design and Treatment

Treatment groups were separated as follows:

Group 1: Disease-Control

Eight $CCl_4$-induced liver fibrosis model mice were kept without any treatment until day 28.

Group 2: Isotype Matched Antibody

Eight $CCl_4$-induced liver fibrosis model mice were intravenously administered vehicle supplemented with isotype-matched antibody at a dose of 10 mg/kg twice weekly at day 14, 17, 21 and 24.

Group 3: Antibody A

Eight CCl4-induced liver fibrosis model mice were intravenously administered vehicle supplemented with M1043 Antibody at a dose of 10 mg/kg twice weekly at day 14, 17, 21 and 24. All animals were sacrificed on day 28.

Table 3 summarizes the treatment schedule:

| Group | No. mice | Test substance | Dose (mg/kg) | Volume (mL/kg) | Regimen |
|---|---|---|---|---|---|
| 1 | 8 | Disease Control | 0 | — | — |
| 2 | 8 | Isotype-Matched Antibody | 10 | 5 | IV, twice weekly, Day 14, 17, 21 and 24 |
| 3 | 8 | M1043 Antibody | 10 | 5 | IV, twice weekly, Day 14, 17, 21 and 24 |

Animal Monitoring and Sacrifice

The viability, clinical signs and behavior were monitored every day. Body weight was recorded daily during the treatment period. Animals were sacrificed by exsanguination through the heart puncture under ether anesthesia (Wako Pure Chemical Industries, Japan).

Results

Figure 10:
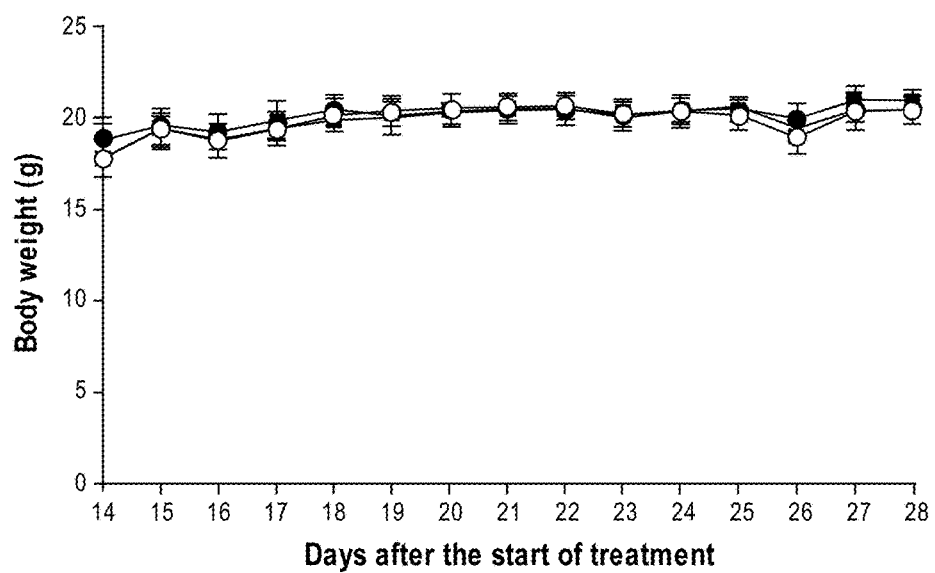
FIG. 10 illustrates body weight changes of mice in an in vivo Carbon Tetrachloride-induced Liver Fibrosis Model in disease-control animals, in animals treated with an isotype-matched antibody, and in animals treated with M1043 Antibody.
Figures 12A, 12B:
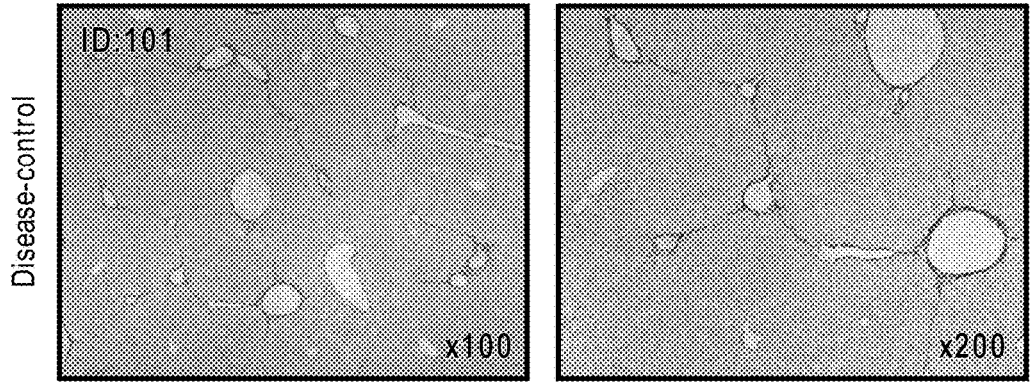
FIGS. 12A-F are representative photomicrographs of Sirius red-stained liver sections.
Figures 12C, 12D:
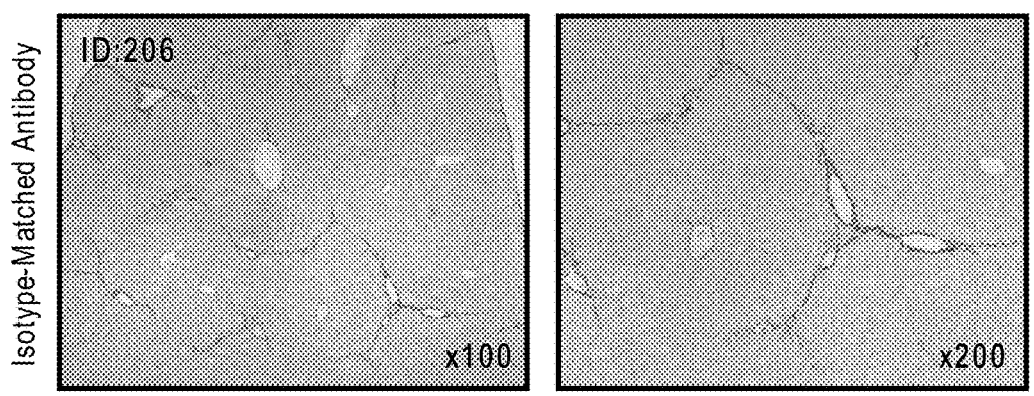
Figures 12E, 12F:
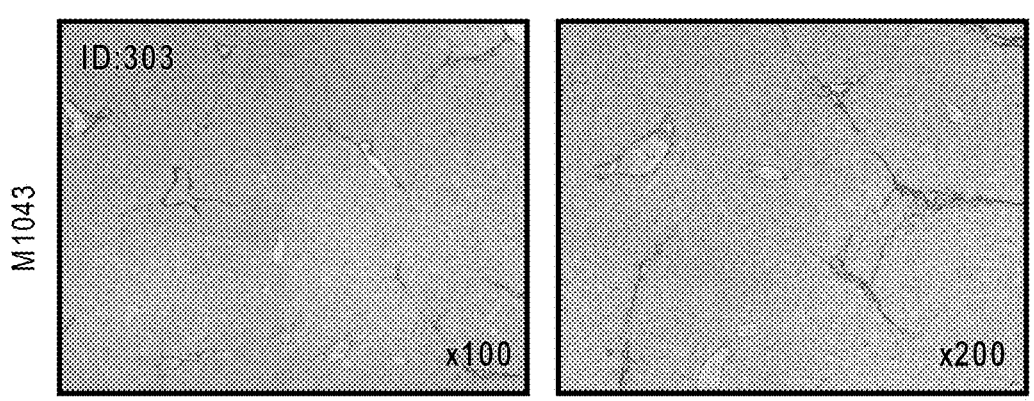
Figure 13:
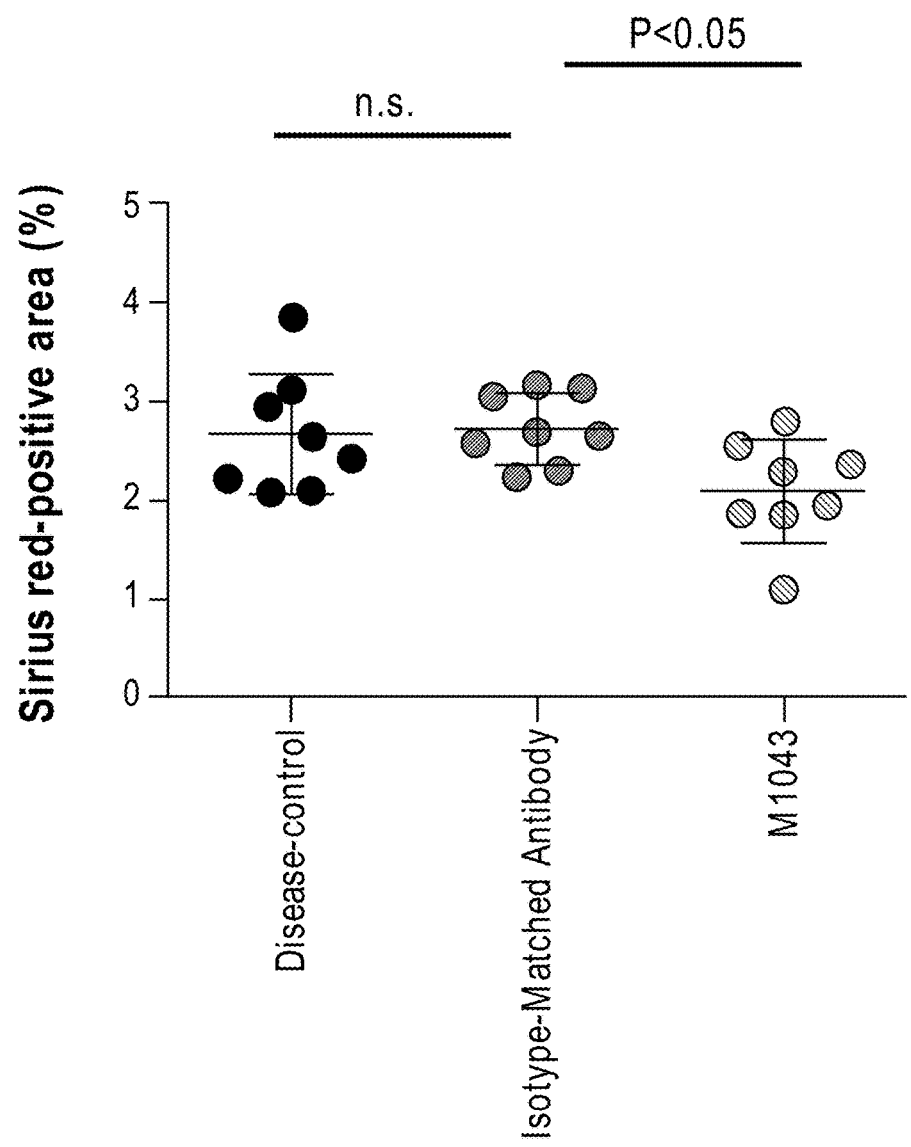
FIG. 13 is a graph illustrating the liver fibrotic area (% Sirius red-positive area) in disease-control animals, in animals treated with an isotype-matched antibody, and in animals treated with M1043 Antibody.

Body weight changes and general condition (FIG. 10)

There were no significant differences either between the isotype-matched antibody and disease control groups or between isotype-matched antibody and M1043 Antibody groups.

In the present study, none of the animals showed deterioration in general condition.

Body Weight on the Day of Sacrifice (FIG. 11A and Table 4)

There were no significant differences either between the Isotype-matched antibody and disease control groups or between isotype-matched antibody and M1043 Antibody groups.

Liver Weight (FIG. 11B and Table 4)

The isotype-matched antibody group showed a significant decrease in mean liver weight compared with the disease-control group. There was no significant difference in mean body weight between the isotype-matched antibody group and the M1043 Antibody group.

TABLE 4

Body weight and liver weight

| Parameter (mean ± SD) | Disease-control (n = 8) | Isotype-Matched Antibody (n = 8) | M1043 Antibody (n = 8) |
|---|---|---|---|
| Body weight (g) | 20.9 ± 0.7 | 20.6 ± 0.8 | 20.5 ± 0.7 |
| Liver weight (mg) | 1058 ± 57 | 877 ± 96 | 896 ± 48 |

Histological Analyses

Sirius red staining (FIGS. 12A-F, FIG. 13 and Table 5) was conducted using the protocol described above.

Extensive collagen deposition and bridging fibrosis were evident in the liver sections from the isotype-matched antibody and disease control groups. M1043 Antibody group showed a lower collagen deposition with less frequent formation of bridging fibrosis than the isotype-matched antibody and disease control groups.

The percentage of fibrosis area (Sirius red-positive area) significantly decreased in the M1043 Antibody group compared with the isotype-matched antibody group (P<0.05).

TABLE 5

Fibrosis area

| Parameter (mean ± SD) | Disease control (n = 8) | Isotype-Matched Antibody (n = 8) | M1043 Antibody (n = 8) |
|---|---|---|---|
| Sirius red-positive area (%) | 2.66 ± 0.61 | 2.70 ± 0.36 | 2.07 ± 0.52 |

Conclusion

In the present study, Antibody M1043 treatment showed a significant reduction of collagen deposition as evidenced by Sirius red positive area. Furthermore, no abnormal findings were observed in the antibody treatment group. These results suggested that M1043 Antibody treatment has anti-fibrosis efficacy without significant side effects.

Example 9

In Vivo Efficacy Study of M1043 and TRC105 in Bleomycin-Induced Pulmonary Fibrosis The purpose of this study was to examine the effects of M1043 that competitively inhibits mouse BMP binding to mouse endoglin and antibody TRC105 that binds mouse endoglin but does not inhibit mouse BMP binding to mouse endoglin in a bleomycin-(BLM)-induced model of pulmonary fibrosis.

Protocol

Pathogen-free 7 weeks old female C57BL/6J mice were obtained from Japan SLC, Inc. (Japan). At day 0, 60 mice were induced to develop pulmonary fibrosis by a single intratracheal administration of bleomycin sulphate (BLM, Nippon Kayaku, Japan) in saline at a dose of 3 mg/kg, in a volume of 50 μL per animal using Microsprayer® (Penn-Century, USA).

BLM-induced pulmonary fibrosis model mice were randomized into 4 groups of 12 mice based on the body weight on the day before the start of treatment.

Individual body weight were measured daily during the experimental period.

Survival, clinical signs and behavior of mice were monitored daily.

Groups:

Group 1 (Disease-control): Twelve BLM-induced pulmonary fibrosis model mice were kept without any treatment until day 20.

Group 2 (Isotype-Matched Antibody): Twelve BLM-induced pulmonary fibrosis model mice were intravenously administered vehicle (Phosphate buffered saline) supplemented with isotype-matched antibody [rat IgG1 from Bio-Excel catalog BE0088 (25 mg)] at a dose of 10 mg/kg twice weekly at day 7, 10, 14 and 17.

Group 3 (M1043 Antibody): Twelve BLM-induced pulmonary fibrosis model mice were intravenously administered vehicle supplemented with M1043 at a dose of 10 mg/kg twice weekly at day 7, 10, 14 and 17.

Group 4 (TRC105 human/mouse chimeric antibody): Twelve BLM-induced pulmonary fibrosis model mice were intravenously administered vehicle supplemented with TRC105 at a dose of 10 mg/kg twice weekly at day 7, 10, 14 and 17.

Group 5 (BIBF1120 inhibitor for Idiopathic Pulmonary Fibrosis—positive control, Boehringer Ingelheim): Twelve BLM-induced pulmonary fibrosis model mice were orally administered 1% CMC supplemented with BIBF1120 at a dose of 100 mg/kg once daily from day 7 to 21.

Mice in all groups were terminated for the following assays at day 21.

Sample Collection and Results

Figure 14A:
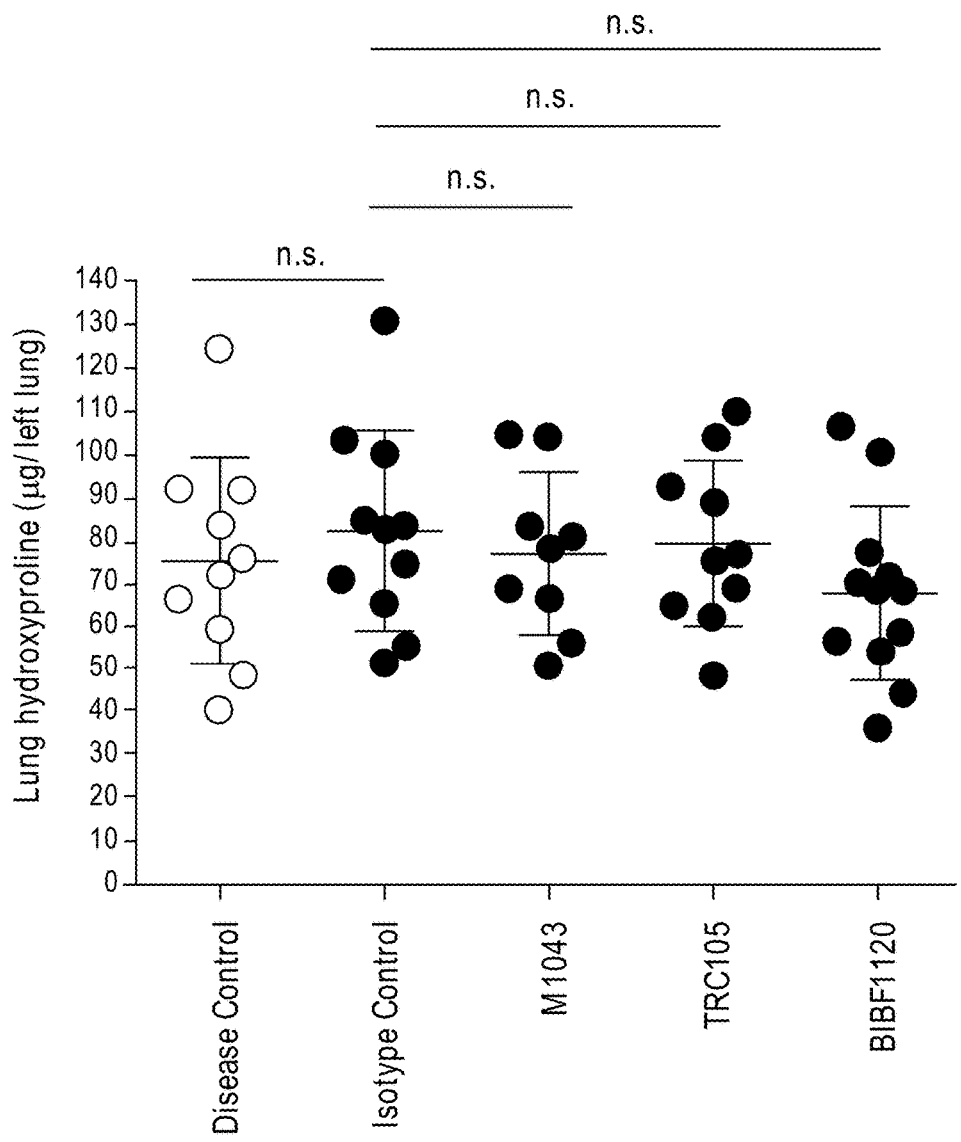
FIGS. 14A-E. Results of the bleomycin induced pulmonary fibrosis model.

Biochemical analysis (by examiners unaware of treatment assignment); lung hydroxyproline was quantified by a hydrolysis method. See, FIG. 14A.

Figure 14B:
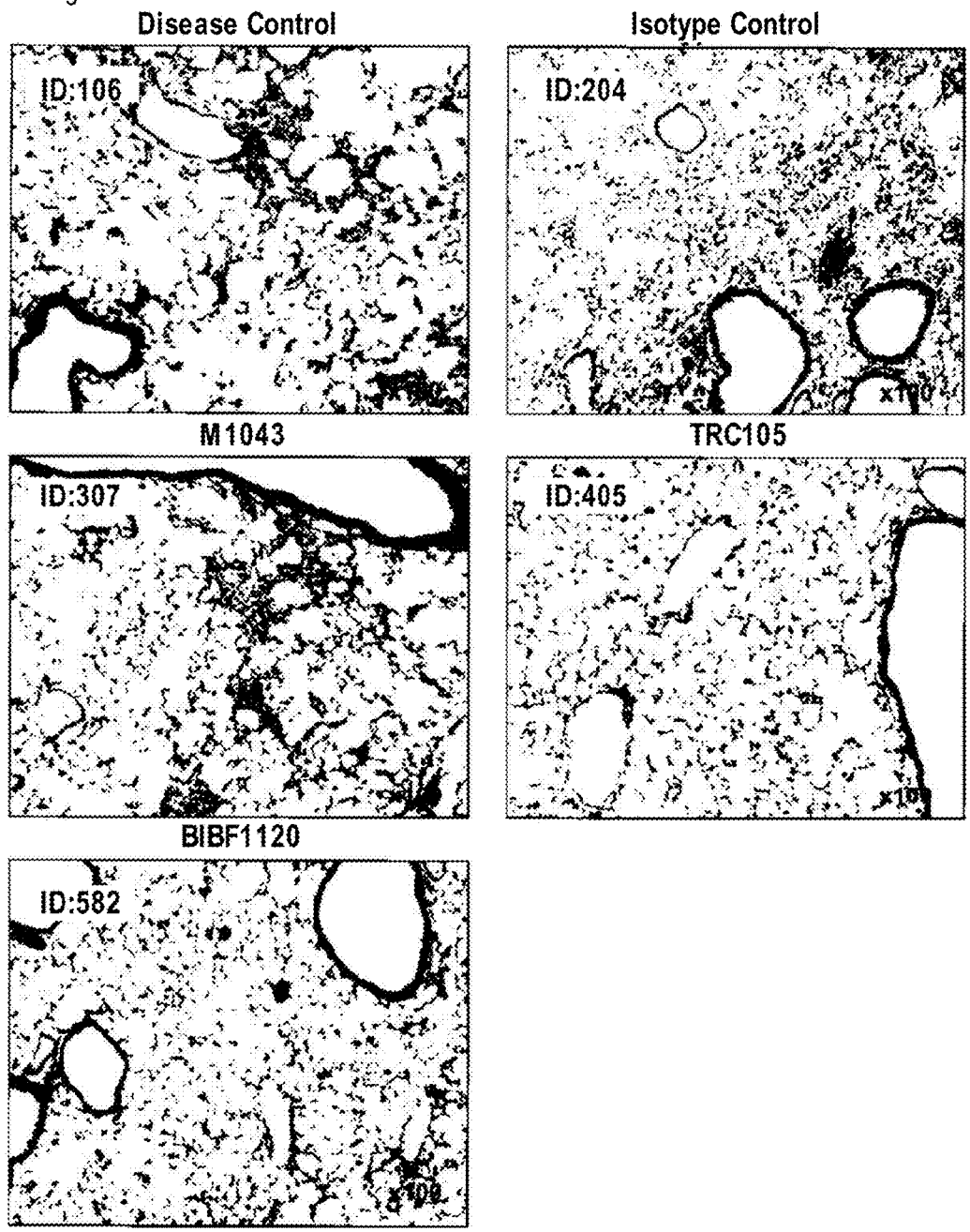

Histological analysis of lung sections was conducted by practitioners who are not aware of the Group identity. Masson's Trichrome staining is conducted and an Ashcroft Score estimate was determined. See, FIG. 14B.

Figure 14C:
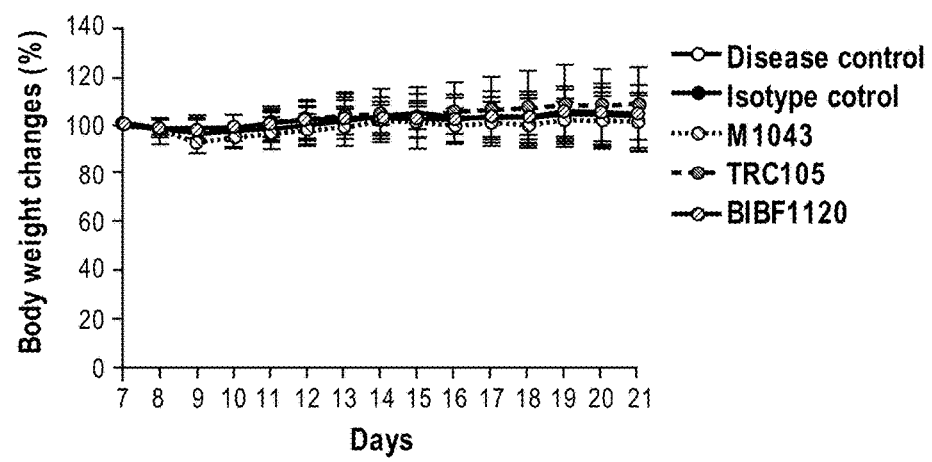

There were no significant differences in body weight between the five treatment groups by Bonferroni Multiple Comparison Testing (p>0.05 comparing the isotype control antibody group versus each other group). See, FIG. 14C.

Figure 14D:
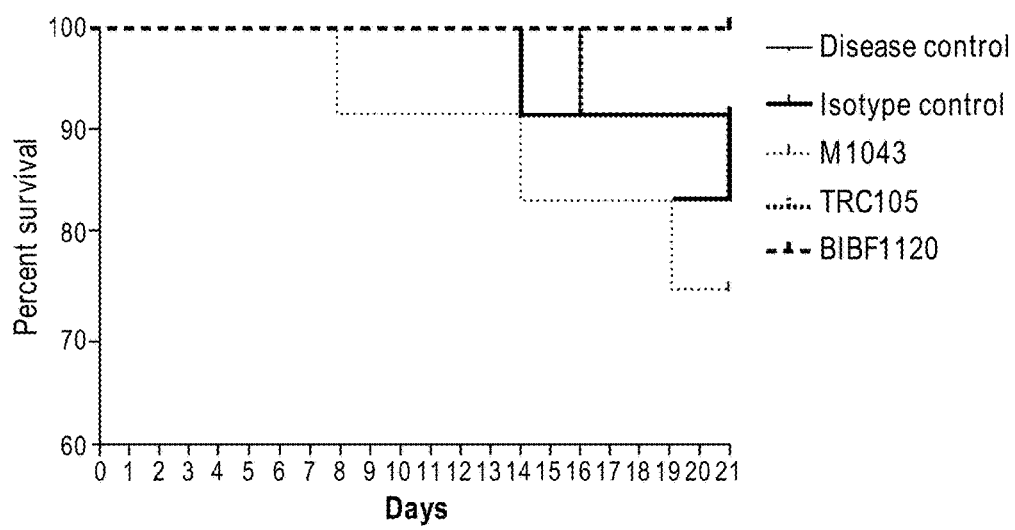

There were no significant differences in survival between the five treatment groups by Bonferroni Multiple Comparison Testing (p>0.05 comparing the isotype control antibody group versus each other group). See, FIG. 14D.

Figure 14E:
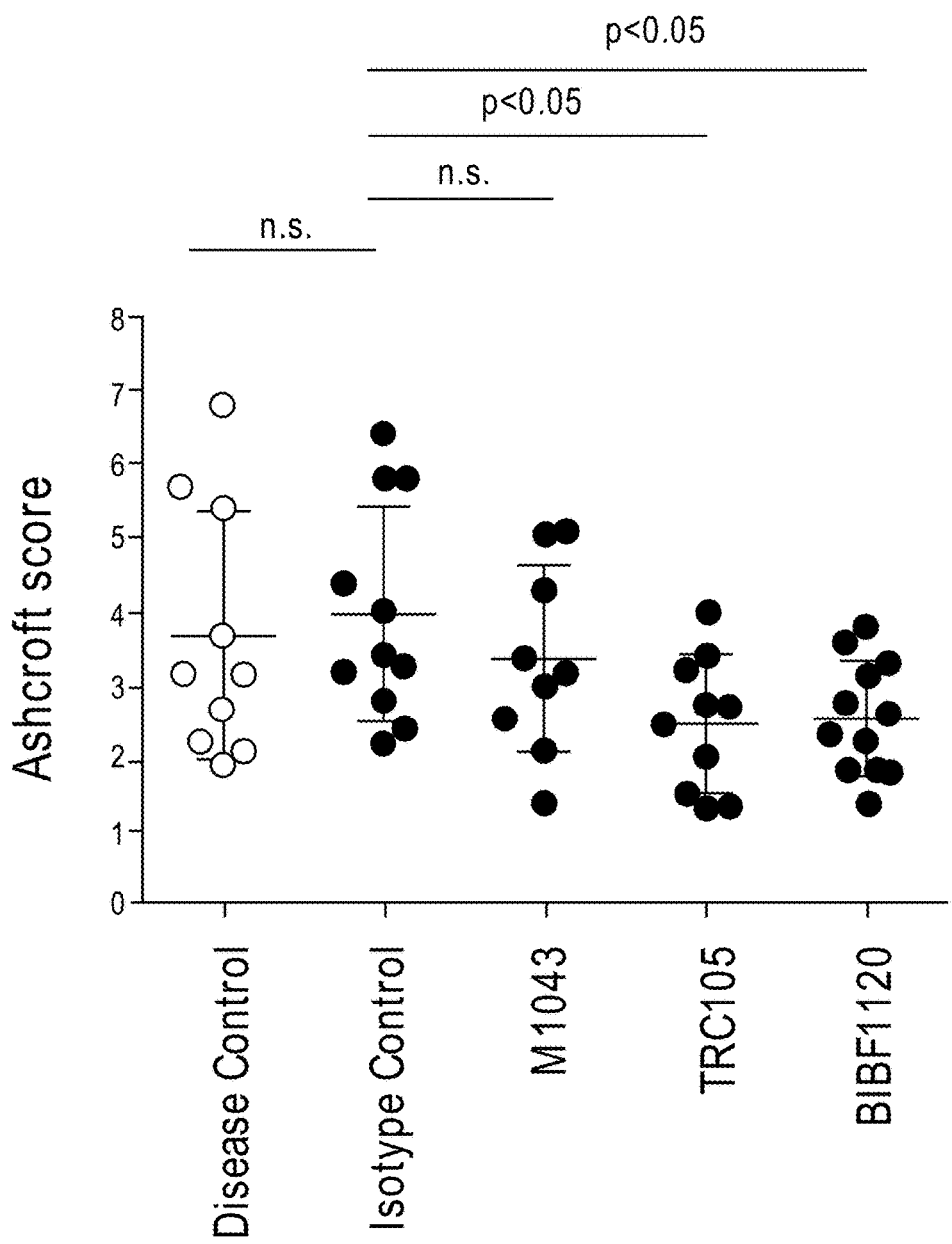

Ashcroft scores are presented in FIG. 14E. There was no significant difference in Ashcroft score between the isotype-control antibody group and the disease control group. There was no significant difference in Ashcroft score between the isotype-control antibody group and the M1043 treated group. Ashcroft score in the TRC105 antibody treated group was significantly lower than the isotype-control antibody group. Ashcroft score in the BIBF1120 treated group was significantly lower than the isotype-control antibody group Statistical tests were performed using Bonferroni Multiple Comparison Test. P values<0.05 were considered statistically significant.

Example 10

In Vivo Efficacy Study of M1043, TRC105 and TRC205 in a Model of Non-Alcoholic Steatohepatitis (NASH)

The purpose of this study was to examine the protective effects of endoglin antibodies on a murine model of NASH. Test articles included M1043, a rat IgG1 antibody that competitively inhibits mouse BMP binding to mouse endoglin; TRC105, a human murine chimeric IgG1 antibody that binds murine endoglin to cause endoglin to be shed into plasma where it may bind BMP and TGF-beta, but does not directly inhibit murine BMP binding to murine endoglin; and TRC205, a human deimmunized IgG4 antibody that binds murine endoglin to cause endoglin to be shed into plasma where it may bind BMP and TGF-beta, but does not directly inhibit murine BMP binding to murine endoglin.

Protocol

Pathogen-free 14-day-pregnant C57BL/6 mice were obtained from Japan SLC, Inc. (Japan).

NASH was established by a single subcutaneous injection of STZ (Sigma, USA) after birth and feeding with a high fat diet (HFD; CLEA Japan, Japan) ad libitum after 4 weeks of age (day 28±2).

Randomization of mice into 6 groups of 10 mice was done at 9 weeks of age (day 63±2), the day before the start of treatment.

Individual body weight was measured daily during the treatment period.

Survival, clinical signs and behavior of mice were monitored daily.

Groups:

Group 1 (non-Diseased control; Normal-Vehicle Group): Ten mice were fed ad libitum and be intravenously administered vehicle (Phosphate buffered saline) twice weekly at day 63, 66, 70, 73, 77, 80

Group 2 (Disease-control; NASH-Vehicle Group): Ten NASH mice were fed with HFD ad libitum and intravenously administered vehicle (Phosphate buffered saline) twice weekly at day 63, 66, 70, 73, 77 and 80.

Group 3 (Positive control; Temlisartan Group): Ten NASH mice were be orally administered pure water supplemented with telmisartan at a dose of 10 mg/kg once daily from day 63 to 84.

Group 4 (Antibody M1043: M1043 Group): Ten NASH mice were intravenously administered vehicle supplemented with Antibody M1043 at a dose of 10 mg/kg twice weekly at day 63, 66, 70, 73, 77 and 80.

Group 5 (Antibody TRC105; TRC105 Group): Ten NASH mice were intravenously administered vehicle supplemented with Antibody TRC105 at a dose of 10 mg/kg twice weekly at day 63, 66, 70, 73, 77 and 80.

Group 6 (Antibody TRC205; TRC205 Group): Ten NASH mice were intravenously administered vehicle supplemented with Antibody TRC205 at a dose of 10 mg/kg twice weekly at days 63, 66, 70, 73, 77 and 80.

Mice in all groups were terminated for the following assays at 12 weeks of age.

Sample Collection and Analysis

H&E staining of liver tissue was conducted to estimate NAFLD Activity score.

TABLE 6

Components of NAFLD Activity Score (NAS) and Fibrosis Staging

| Item | Score | Extent | Definition and Comment |
|---|---|---|---|
| NAS Components | | | |
| Steatosis | 0 | <5% | Refers to amount of surface area involved by steatosis as evaluated on low to medium power examination; minimal steatosis (<5%) receives a score of 0 to avoid giving excess weight to biopsies with very little fatty change |
| | 1 | 5-33% | |
| | 2 | >33-66% | |
| | 3 | >66% | |
| Lobular Inflammation | 0 | No foci | Acidophil bodies are not included in this assessment, nor is portal inflammation |
| | 1 | foci/200x | |
| | 2 | 2-4 foci/200x | |
| | 3 | foci/200x | |
| Hepatocyte Ballooning | 0 | None | |
| | 1 | Few balloon cells | The term "few" means rare but definite ballooned hepatocytes as well as cases that are diagnostically borderline |
| | 2 | Many cells/prominent ballooning | Most cases with prominent ballooning also had Mallory's hyalin, but Mallory's hyaline is not scored separately for the NAS |
| Fibrosis Stage (Evaluated separately from NAS) | | | |
| Fibrosis | 0 | None | |
| | 1 | Perisinusoidal or periportal | |
| | 1A | Mild, zone 3, perisinusoidal | "delicate" fibrosis |
| | 1B | Moderate, zone 3, perisinusoidal | "dense" fibrosis |
| | 1C | Portal/periportal | This category is included to accommodate cases with portal and/or periportal fibrosis without accompanying pericellular/perisinusoidal fibrosis |
| | 2 | Perisinusoidal and portal/periportal | |
| | 3 | Bridging fibrosis | |
| | 4 | Cirrhosis | |

Total NAS score represents the sum of scores for steatosis, lobular inflammation, and ballooning, and ranges from 0-8. Diagnosis of NASH (or, alternatively, fatty liver not diagnostic of NASH) should be made first, then NAS is used to grade activity. In the reference study, NAS scores of 0-2 occurred in cases largely considered not diagnostic of NASH, scores of 3-4 were evenly divided among those considered not diagnostic, borderline, or positive for NASH. Scores of 5-8 occurred in cases that were largely considered diagnostic of NASH.

NAFLD scores are presented in Table 7.

TABLE 7

NAFLD Activity score

| Group | n | Steatosis | | | | Lobular inflammation | | | | Hepatocyte ballooning | | | NAS (mean ± SD) |
|---|---|---|---|---|---|---|---|---|---|---|---|---|---|
| | | 0 | 1 | 2 | 3 | 0 | 1 | 2 | 3 | 0 | 1 | 2 | |
| Normal-Vehicle | 10 | 10 | — | — | — | 10 | — | — | — | 10 | — | — | 0.0 ± 0.0 |
| NASH-Vehicle | 9 | — | 6 | 3 | — | — | 1 | 6 | 2 | — | — | 9 | 5.4 ± 0.5 |
| Telmisartan | 9 | — | 9 | — | — | 3 | 4 | 2 | — | 1 | 3 | 5 | 3.3 ± 1.2 |
| TRC105 | 8 | 1 | 6 | 1 | — | — | 1 | 5 | 2 | 3 | — | 5 | 4.4 ± 1.4 |
| TRC205 | 9 | — | 6 | 3 | — | 5 | — | 4 | — | 1 | 4 | 4 | 3.6 ± 1.1 |
| M1043 | 8 | — | 6 | 2 | — | 1 | 1 | 6 | — | 2 | 2 | 4 | 4.1 ± 1.0 |

| Item | Score | Extent |
|---|---|---|
| Steatosis | 0 | <5% |
| | 1 | 5-33% |
| | 2 | >33-66% |
| | 3 | >66% |
| Lobular Inflammation | 0 | No Foci |
| | 1 | <2 foci/200x |
| | 2 | 2-4 foci/200x |
| | 3 | >4 foci/200x |
| Hepatocyte Ballooning | 0 | None |
| | 1 | Few balloon cells |
| | 2 | Many cells/prominent ballooning |

Liver sections from the NASH-Vehicle group exhibited severe micro- and macrovesicular fat deposition, hepatocellular ballooning and inflammatory cell infiltration. The NASH-Vehicle group showed a significant increase in NAS compared with the Normal-Vehicle group. The Telmisartan (positive control group), TRC205 and M1043 groups showed significant decreases in NAS compared with the NASH-Vehicle group. The TRC105 group tended to decrease in NAS compared with the NASH-Vehicle group.

F4/80 is a mature macrophage marker. Liver sections from the NASH-Vehicle group showed an increased number and size of F4/80-positive cells in the liver lobule compared with the Normal-Vehicle group. Lower F4/80-positive signals and positive cells were observed in the TRC105, TRC205 and M1043 groups compared with the NASH-Vehicle group. No obvious changes were observed in the Telmisartan group compared with the NASH-Vehicle group.

Sirius-Red Staining

Sirius-red staining was conducted to estimate the percentage of fibrosis area. Liver sections from the NASH-Vehicle group exhibited collagen deposition in the pericentral region of liver lobule. The NASH-Vehicle group showed a significant increase in Sirius red-positive area compared with the Normal-Vehicle group. The Telmisartan group showed a significant decrease in Sirius red-positive area compared with the NASH-Vehicle group. There were no significant differences in Sirius red-positive area between the NASH-Vehicle group and any of the treatment groups. See, e.g., Table 8.

TABLE 8

Histology analysis

| Parameter (mean ± SD) | Normal-Vehicle (n = 10) | NASH-Vehicle (n = 9) | Telmisartan (n = 9) | TRC105 (n = 8) | TRC205 (n = 9) | M1043 (n = 8) |
|---|---|---|---|---|---|---|
| Sirius red-positive area (%) | 0.30 ± 0.06 | 0.98 ± 0.21 | 0.67 ± 0.12 | 0.92 ± 0.20 | 0.93 ± 0.14 | 0.86 ± 0.30 |

Biochemistry

Several serum proteins were quantified to assess the damage to liver parenchyma (Table 9).

TABLE 9

Biochemistry

| Parameter (mean ± SD) | Normal-Vehicle (n = 10) | NASH-Vehicle (n = 9) | Telmisartan (n = 9) | TRC105 (n = 8) | TRC205 (n = 9) | M1043 (n = 8) |
|---|---|---|---|---|---|---|
| Serum ALT (U/L) | 15 ± 3 | 48 ± 21 | 29 ± 15 | 62 ± 57 | 28 ± 16 | 24 ± 4 |
| Serum AST (U/L) | 61 ± 21 | 126 ± 52 | 113 ± 32 | 204 ± 205 | 83 ± 41 | 76 ± 24 |

TABLE 9-continued

Biochemistry

| Parameter (mean ± SD) | Normal-Vehicle (n = 10) | NASH-Vehicle (n = 9) | Telmisartan (n = 9) | TRC105 (n = 8) | TRC205 (n = 9) | M1043 (n = 8) |
| --- | --- | --- | --- | --- | --- | --- |
| Serum ALP (U/L) | 339 ± 62 | 420 ± 121 | 444 ± 134 | 291 ± 119 | 264 ± 63 | 358 ± 129 |
| Liver triglyceride (mg/g liver) | 5.9 ± 1.0 | 44.2 ± 6.9 | 23.5 ± 10.6 | 31.1 ± 20.3 | 29.3 ± 9.4 | 22.4 ± 5.4 |

The NASH-Vehicle group showed a significant increase in serum alanine aminotransferase (ALT) levels compared with the Normal-Vehicle group. The Telmisartan, TRC205 and M1043 groups tended to decrease in serum alanine aminotransferase levels compared with the NASH-Vehicle group. There was no significant difference in serum alanine aminotransferase levels between the NASH-Vehicle group and the TRC105 group.

The NASH-Vehicle group tended to increase in serum aspartate aminotransferase (AST) levels compared with the Normal-Vehicle group. The TRC205 and M1043 groups tended to decrease in serum aspartate aminotransferase levels compared with the NASH-Vehicle group. There were no significant differences in serum aspartate aminotransferase levels between the NASH-Vehicle group and any of the other groups.

The TRC205 group showed a significant decrease in serum alkaline phosphatase (ALP) levels compared with the NASH-Vehicle group. The TRC105 group tended to decrease in serum alkaline phosphatase levels compared with the NASH-Vehicle group. There were no significant differences in serum alkaline phosphatase levels between the NASH-Vehicle group and any of the other groups.

The NASH-Vehicle group showed a significant increase in liver triglyceride contents compared with the Normal-Vehicle group. The Telmisartan, TRC205 and M1043 groups showed significant decreases in liver triglyceride contents compared with the NASH-Vehicle group. The TRC105 group tended to decrease in liver triglyceride contents compared with the NASH-Vehicle group.

Gene Expression

Gene expression of several genes implicated in liver injury and fibrosis were assessed. See, e.g., Table 10.

Tissue inhibitor of metalloproteinase-1 mRNA expression levels tended to increase in the NASH-Vehicle group compared with the Normal-Vehicle group. Tissue inhibitor of metalloproteinase-1 mRNA expression levels tended to decrease in the TRC205 group compared with the NASH-Vehicle group. Tissue inhibitor of metalloproteinase-1 mRNA expression levels was significantly up-regulated in the TRC105 group compared with the NASH-Vehicle group. There were no significant differences in Tissue inhibitor of metalloproteinase-1 mRNA expression levels between the NASH-Vehicle group and any of the other groups.

Tumor necrosis factor-alpha mRNA expression levels tended to increase in the NASH-Vehicle group compared with the Normal-Vehicle group. Tumor necrosis factor-alpha mRNA expression levels tended to increase in the TRC205 group compared with the NASH-Vehicle group. Tumor necrosis factor-alpha mRNA expression levels was significantly up-regulated in the TRC105 group compared with the NASH-Vehicle group. There were no significant differences in Tumor necrosis factor-alpha mRNA expression levels between the NASH-Vehicle group and any of the other groups.

Macrophage chemoattractant protein-1 mRNA expression levels tended to increase in the NASH-Vehicle group compared with the Normal-Vehicle group. Macrophage chemoattractant protein-1 mRNA expression levels tended to decrease in the Telmisartan group compared with the NASH-Vehicle group. There were no significant differences in macrophage chemoattractant protein-1 mRNA expression levels between the NASH-Vehicle group and any of the other groups.

TABLE 10

Gene expression analyses

| Parameter (mean ± SD) | Normal-Vehicle (n = 10) | NASH-Vehicle (n = 9) | Telmisartan (n = 9) | TRC105 (n = 8) | TRC205 (n = 9) | M1043 (n = 8) |
| --- | --- | --- | --- | --- | --- | --- |
| TNF-α | 1.0 ± 0.5 | 4.1 ± 1.6 | 3.2 ± 2.3 | 12.9 ± 9.5 | 6.2 ± 2.4 | 4.4 ± 1.9 |
| MCP-1 | 1.0 ± 0.5 | 4.7 ± 2.8 | 1.5 ± 1.1 | 5.7 ± 4.2 | 9.3 ± 9.1 | 3.2 ± 2.4 |
| Alpha-SMA | 1.0 ± 0.3 | 2.2 ± 1.1 | 0.7 ± 0.3 | 1.7 ± 0.7 | 1.1 ± 0.3 | 1.7 ± 0.4 |
| TIMP-1 | 1.0 ± 0.2 | 8.9 ± 3.9 | 5.8 ± 3.7 | 25.4 ± 23.0 | 6.0 ± 2.6 | 7.6 ± 3.3 |

Alpha-smooth muscle actin mRNA expression levels was significantly up-regulated in the NASH-Vehicle group compared with the Normal-Vehicle group. Alpha-smooth muscle actin mRNA expression levels was significantly down-regulated in the Telmisartan and TRC205 groups compared with the NASH-Vehicle group. There were no significant differences in Alpha-smooth muscle actin mRNA expression levels between the NASH-Vehicle group and any of the treatment groups.

Liver Weight

The NASH-Vehicle group showed a significant increase in mean liver weight compared with the Normal-Vehicle group. The Telmisartan group showed a significant decrease in mean liver weight compared with the NASH-Vehicle group. The M1043 group tended to decrease in mean liver weight compared with the NASH-Vehicle group. There were no significant differences in mean liver weight between the NASH-Vehicle group and any of the other groups.

The NASH-Vehicle group showed a significant increase in mean liver-to-body weight ratio compared to the Normal-Vehicle group. The Telmisartan and M1043 groups showed significant decreases in mean liver-to-body weight ratio compared with the NASH-Vehicle group. The TRC205 group tended to decrease in mean liver-to-body weight ratio compared with the NASH-Vehicle group. There was no significant difference in mean liver-to-body weight ratio between the NASH-Vehicle group and the TRC205 group.

Statistical Tests

Statistical tests were performed using Bonferroni Multiple Comparison Test. P values<0.05 were considered statistically significant.

In the study, the improvement in serum ALT and AST levels indicate that TRC205 and M1043 ameliorated hepatocellular injury and inflammation. TRC205 and M1043 groups showed reductions in inflammatory cell infiltration in the liver, which resulted in the decrease of the lobular inflammation score of NAS and F4/80 immunostaining. Together these results suggest that TRC205 and M1043 possess hepatoprotective and anti-inflammatory properties against NASH. Further, of particular note is the significant reduction of total NAS in the TRC205 and M1043 groups. NAS is one of the clinical endpoints for assessing the activity of NASH, and is the key preclinical endpoint in the study. TRC205 and M1043 showed significant reductions of NAS.

Example 11

Figure 15:
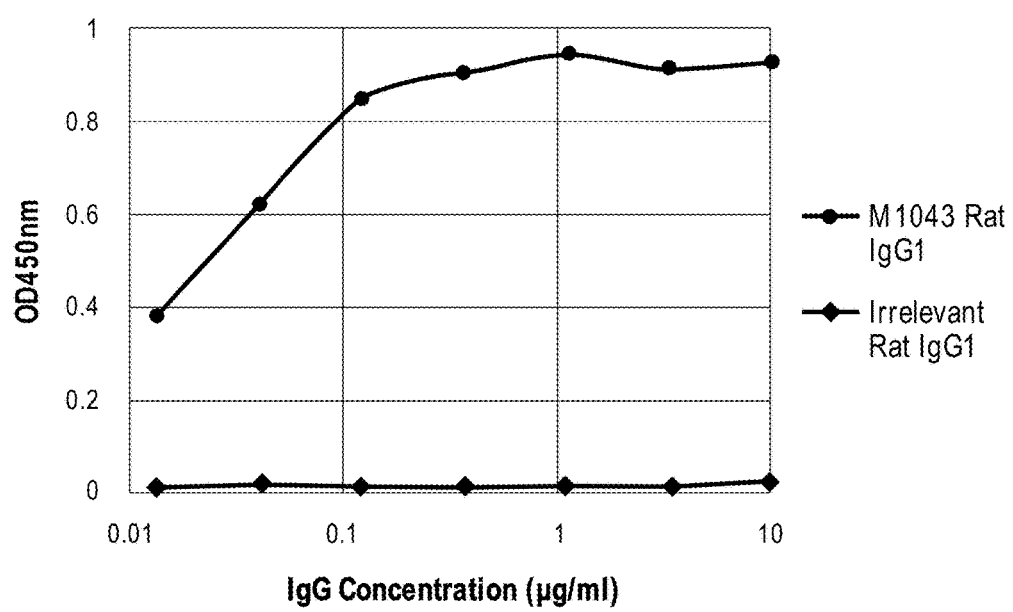
FIG. 15: ELISA was established to determine the binding of M1043 antibody to mouse endoglin was determined by ELISA.

An ELISA was established to determine the binding of M1043 antibody to mouse endoglin as follows: Nunc Immuno MaxiSorp 96 well flat bottom plates (Fisher, Cat. No. DIS-971-030J) were coated with mouse endoglin (R&D Systems, Cat. No. 1320-EN-025) at 1 µg/ml in PBS overnight at 4° C. The following day the plate was washed three times with PBST before blocking with PBST/3% Marvel at room temperature for 1 hour. After blocking, the plate was washed three times with PBST, and varying concentrations (10 µg/ml to 0.014 µg/ml in three-fold serial dilutions) of either M1043 or an irrelevant rat IgG1 (Affymetrix, Cat. No. 14-4301) in PBST/3% Marvel were added to the plate and incubated for 1 hour at room temperature. Binding of the antibodies was detected via anti-rat IgG peroxidase (Sigma, Cat. No. A9037) and TMB single solution substrate (Invitrogen, Cat. No. 00-2023). The reaction was stopped by adding 3 M HCl and OD450 nm values were measured on a Dynex MRX TCII plate reader. The results of the binding ELISA are shown in FIG. 15. The results show that the M1043 antibody binds specifically to mouse endoglin since no binding was observed with the isotype matched irrelevant antibody.

Figure 16:
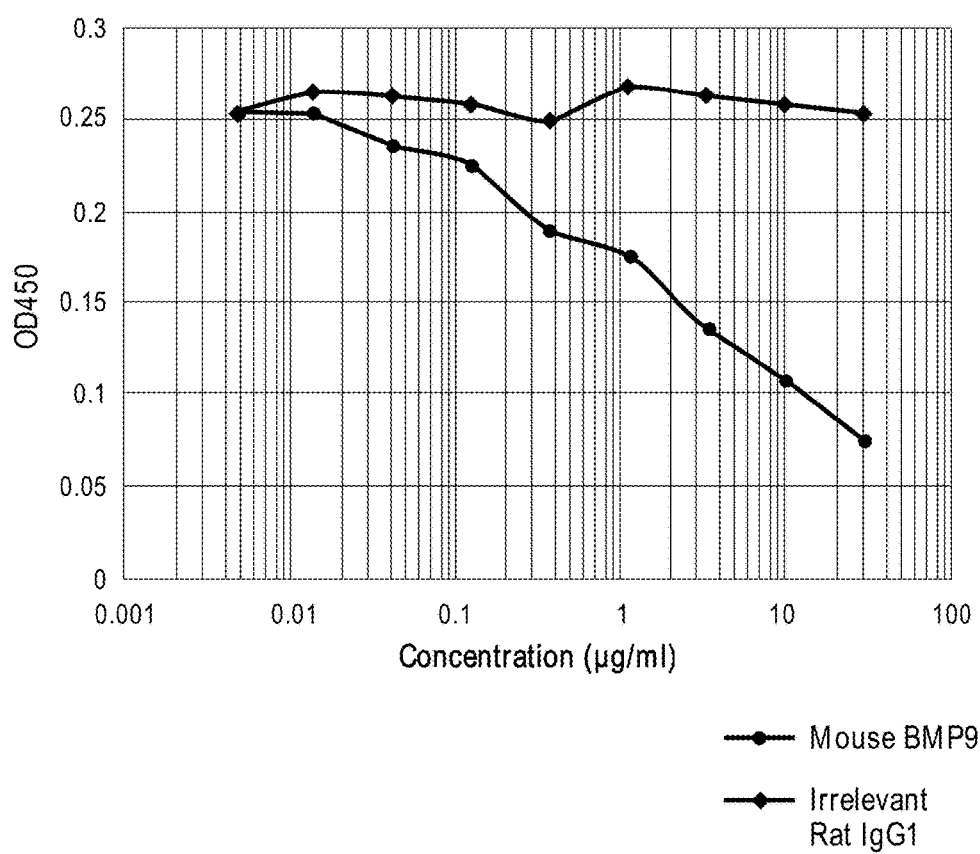
FIG. 16: Competition ELISA of biotinylated M1043 with BMP9 binding to endoglin. A dilution series of BMP9 was competed against a fixed concentration of biotinylated M1043 for binding to endoglin. Rat IgG1 was used as a negative control. Bound biotinylated M1043 antibody was detected with streptavidin-HRP conjugate and TMB substrate.

The ability of mouse BMP9 to compete with the rat antibody M1043 for binding to mouse endoglin was determined by competition ELISA as follows: 200 µg of M1043 antibody was biotinylated with a Lightning-Link biotinylation kit (Innova Biosciences, Cat. No. 704-0010) according to the manufacturers recommendations. Nunc Immuno MaxiSorp 96 well flat bottom plates (Fisher Cat. No. DIS-971-030J) were coated with mouse endoglin (R&D Systems, Cat. No. 1320-EN-025) at 1 µg/ml in PBS overnight at 4° C. The following day the plate was washed three times with PBST before blocking with PBST/3% Marvel at room temperature for 1 hour. A threefold dilution series (30 µg/ml to 0.004 µg/ml) of mouse BMP9 (R&D Systems, Cat. No. 5566-BP-010) or an irrelevant rat IgG1 was mixed with a fixed concentration of biotinylated M1043 (40 ng/ml), added to the plate and incubated for 1 hour at room temperature. Binding of the biotinylated antibody was detected via streptavidin-HRP (Sigma, Cat. No. 55512) and TMB substrate (Sigma, Cat. No. T0440). OD450 nm values were measured on a Dynex MRX TCII plate reader. The results of this competition ELISA are shown in FIG. 16. The results show that mouse BMP9 competed with biotinylated M1043 for binding to mouse endoglin whereas an irrelevant molecule did not.

Example 12

Figure 17:
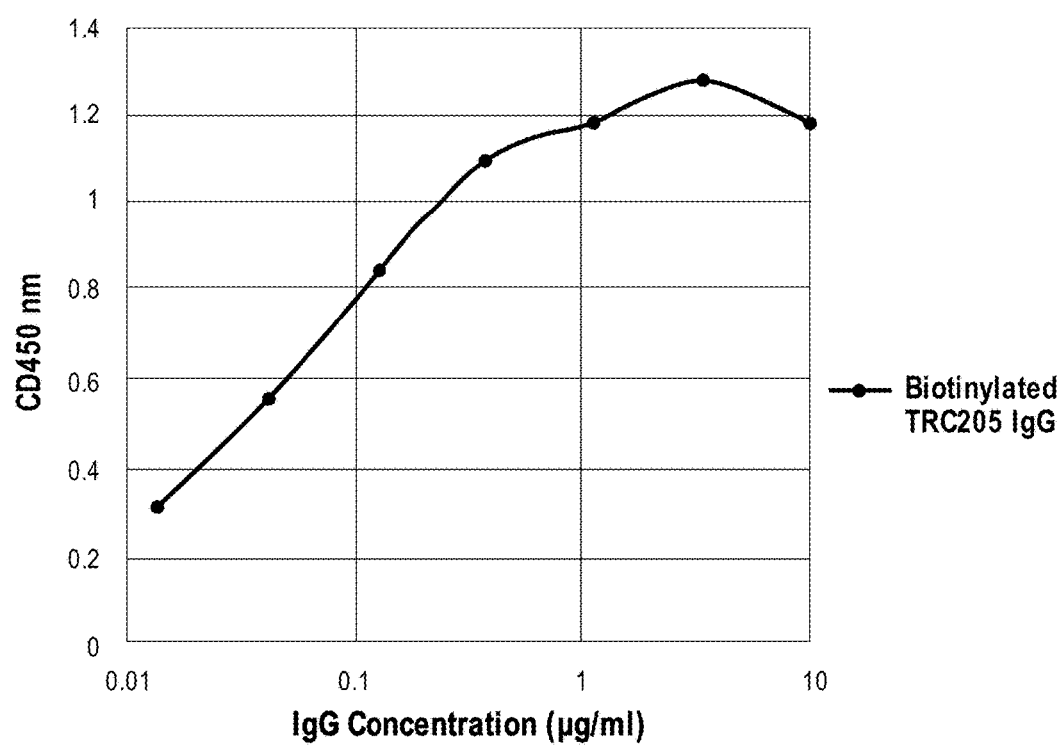
FIG. 17. The binding of biotinylated TRC205 antibody to human CD105 was determined by ELISA.

An ELISA was established to determine the binding of biotinylated TRC205 antibody to human CD105 as follows: The TRC205 antibody (SEQ ID NO 89/SEQ ID NO 93; IgG4) was biotinylated using a Lightning-Link Biotin Conjugation Kit (Type A) (Innova Biosciences Cat. No. 704-0010) according to the manufacturer's instructions. Nunc Immuno MaxiSorp 96 well flat bottom plates (Fisher Cat. No. DIS-971-030J) were coated with mouse anti-human CD105 (Southern Biotechnologies Cat. No. 9811-01) at 1.5 µg/ml in PBS overnight at +4° C. The following day, 100 ng/ml human CD105 (R&D Systems Cat. No. 1097-EN) in PBS/2% BSA was added to the pre-coated plate and incubated at room temperature for 1 hour. After washing three times with PBST, a three-fold dilution series of biotinylated TRC205 antibody (10 µg/ml to 0.014 µg/ml) in PBST/2% BSA was added in duplicate to the plate. Following incubation for 1 hour at room temperature, the plate was washed three times with PBST and binding of the biotinylated TRC205 antibody was detected using streptavidin-HRP (Sigma Cat. No. 55512) and TMB substrate (Sigma Cat. No. T0440). OD450 nm values were measured on a Dynex MRX TCII plate reader. From the binding curve, the EC50 value was calculated to be 46 ng/ml (FIG. 17).

Figure 18:
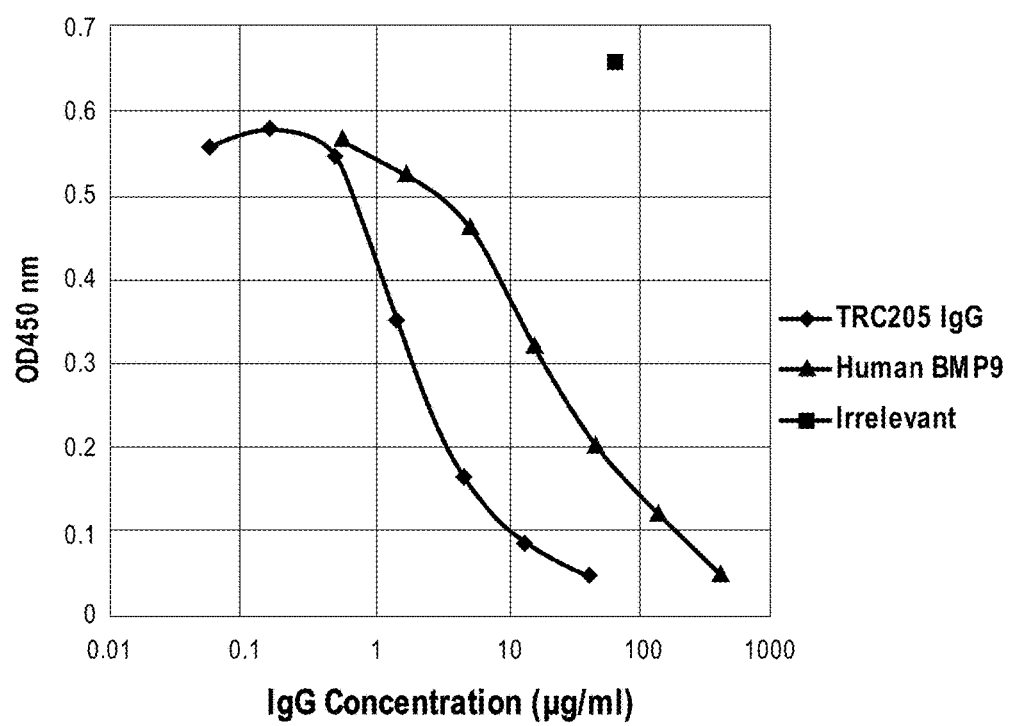
FIG. 18. The ability of human BMP9 to compete with the TRC205 antibody for binding to human CD105 was determined by competition ELISA.

The ability of human BMP9 to compete with the TRC205 antibody for binding to human CD105 was determined by competition ELISA as follows: Nunc Immuno MaxiSorp 96 well flat bottom plates (Fisher Cat. No. DIS-971-030J) were coated with mouse anti-human CD105 (Southern Biotechnologies Cat. No. 9811-01) at 1.5 µg/ml in PBS overnight at +4° C. The following day, 100 ng/ml human CD105 (R&D Systems Cat. No. 1097-EN) in PBS/2% BSA was added to the pre-coated plate and incubated at room temperature for 1 h. After washing three times with PBST, a three-fold dilution series of either human BMP9 (R&D Systems Cat. No. 3209-BP-010) (413 nM to 0.56 nM), or unlabelled TRC205 antibody (40 nM to 0.05 nM) or a single concentration of an irrelevant antibody (66 nM) was mixed with a fixed concentration of biotinylated TRC205 antibody (55 ng/ml) and added to the plate. Following incubation for 1 hour at room temperature, the plate was washed three times with PBST and binding of the biotinylated TRC205 antibody was detected using streptavidin-HRP (Sigma Cat. No. 55512) and TMB substrate (Sigma Cat. No. T0440). OD450 nm values were measured on a Dynex MRX TCII plate reader. From the resultant competition curves (FIG. 18), the IC50 values were calculated as 1.7 nM (0.26 µg/ml) and 14.6 nM (0.35 µg/ml) for TRC205 antibody and BMP9 respectively.

Example 13

A cell based assay was established to demonstrate that antibody TRC205 inhibits the phosphorylation of SMAD 1/5/8 in human fibroblasts. A Meso Scale Discovery (MSD)

capture ELISA assay was developed to detect phosphorylated SMAD1 and total SMAD1 in protein extracts.

Fifty high density 96-well plates will be custom-coated by MSD using 500 mg of a monoclonal anti-SMAD1 antibody (Santa Cruz #sc-81378). Two different detection antibodies will be used to detect phosphorylated SMAD1/5/8 (Cell Signaling Technology #9511) and total SMAD1 (Cell Signaling Technology #9743). Detection will be conducted using the recommended MSD's protocol and buffers. In brief, fibroblasts will be lifted with Accutase (Invitrogen #A1110501), washed 2× in PBS and plated in a 96-well plate at 2500 cells/well in 25 ml of media. After 3 hours of serum starvation, antibodies will be added to the wells in 25 ml of media. After 1 hour, 2.5 ml of BMP9 (2 ng/ml) will be added to each well. After 30 min, cells will be lyzed with 50 ml of MSD lysis buffer 2× (150 mM NaCl, 20 mM Tris, pH 7.5, 1 mM EDTA, 1 mM EGTA, 1% Triton™ X-100, supplemented with phosphatase and protease inhibitors) and kept frozen at −20 degrees Centigrade.

Forty (40) ml of lysate will be used for the MSD assay (per the manufacturer's instructions). MSD plates will be washed on an ELx405 Select CW plate washer (from Biotek) and the signal will be read on a Sector Imager 6000 (from Meso Scale Discovery).

The primary end point will be a change in the ratio of phosphorylated SMAD 1 protein divided by total SMAD1 in response to BMP-9 stimulation, between fibroblasts treated with antibody TRC105 or antibody TRC205 compared to fibroblasts treated with an antibody that does not bind to human endoglin.

Example 14

A phase 3 study will be conducted in which approximately 600 patients with idiopathic pulmonary fibrosis will be randomly assigned to receive either oral pirfenidone (2403 mg per day) or an anti-endoglin antibody for 52 weeks. The primary end point will be a change in forced vital capacity (FVC) or death at week 52. Secondary end points include, for example, the 6-minute walk distance, progression-free survival, extension of life, dyspnea, and/or death from any cause or from idiopathic pulmonary fibrosis. Other assessments can include the occurrence of adverse events between the two treatment arms.

Example 15

A Phase 3 study will be conducted in which approximately 100 patients aged 3-25 years with neurofibromas and imaging evidence of tumor progression. Patients will be randomized in a double-blinded fashion to receive an endoglin antibody or placebo (phase A) and crossed over to the opposite treatment arm at the time of tumor progression (phase B). Neurofibroma volumes will be measured with MRI, and progression was defined as ≥20% volume increase. Time to progression (TTP) in phase A will be the primary endpoint, and the trial will be powered to detect whether endoglin antibody doubled TTP compared with placebo. Toxicity, response, and quality of life will also be monitored.

While certain embodiments of the present application have been shown and described herein, it will be obvious that such embodiments are provided by way of example only. Numerous variations, changes, and substitutions may occur to those skilled in the art without departing from the invention; it should be understood that various alternatives to the embodiments described herein may be employed in practicing the methods described herein.

What is claimed is:

1. A method of treating or inhibiting a myelofibrosis or a neurofibromatosis in a subject in need thereof, comprising administering to the subject a composition that comprises an antibody, or antigen-binding fragment thereof, that binds endoglin, that comprises a heavy chain variable region having an amino acid sequence set forth as SEQ ID NO: 89 and a light chain variable region having an amino acid sequence set forth as SEQ ID NO: 93, and a pharmaceutically acceptable excipient, whereby the myelofibrosis or the neurofibromatosis is treated or inhibited.

2. The method of claim 1, wherein the antigen-binding fragment is a Fab fragment, a Fab' fragment, a F(ab')$_2$ fragment, an Fv fragment, an scFv fragment, or a single chain binding polypeptide.

3. The method of claim 1, wherein the antibody, or antigen-binding fragment thereof, is further labeled with a therapeutic label.

4. The method of claim 1, wherein the fibrosis is a neurofibromatosis that is a neurofibromatosis type 1 or a neurofibromatosis type 2.

5. The method of claim 1, further comprising administering to the subject one or more fibrosis inhibitors.

6. The method of claim 5, wherein the anti-endoglin antibody, or antigen-binding fragment and the one or more fibrosis inhibitors are administered to the subject at the same site.

7. The method of claim 5, wherein the anti-endoglin antibody, or antigen-binding fragment and the one or more fibrosis inhibitors are administered to the subject at different sites.

8. The method of claim 5, wherein the anti-endoglin antibody, or antigen-binding fragment and the one or more fibrosis inhibitors are administered to the subject sequentially.

9. The method of claim 5, wherein the anti-endoglin antibody, or antigen-binding fragment and the one or more fibrosis inhibitors are administered to the subject concurrently.

10. The method of claim 1, wherein the antibody or antigen-binding fragment thereof is administered to the subject in an amount of about 0.01 mg/kg, about 0.05 mg/kg, about 0.1 mg/kg, about 0.5 mg/kg, about 1 mg/kg, about 5 mg/kg, about 10 mg/kg, about 20 mg/kg, about 30 mg/kg, about 40 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, or about 200 mg/kg per subject.

11. A method of treating or inhibiting a myelofibrosis or a neurofibromatosis in a subject in need thereof, comprising administering to the subject a composition comprising an antibody, or antigen-binding fragment thereof, that binds endoglin, that comprises a heavy chain variable region having an amino acid sequence set forth as SEQ ID NO: 89 with one or more modifications selected from the group consisting of a substitution of glycine (G) by alanine (A) or serine (S) at position 49; a substitution of alanine (A) by isoleucine (I) at position 51; a substitution of lysine (K) by arginine (R) or glutamine (Q) at position 54; a substitution of leucine (L) by valine (V) at position 81; and a light chain variable region having an amino acid sequence set forth as SEQ ID NO: 93 with one or more modifications selected from the group consisting of a substitution of methionine (M) by leucine (L) at position 4; a substitution of alanine (A) by valine (V) at position 19; a substitution of threonine (T) by serine (S) at position 22; a substitution of alanine (A) by isoleucine (I) at position 48; and a substitution of threonine (T) by serine (S) at position 51; and a pharmaceutically acceptable excipient, whereby the myelofibrosis or the neurofibromatosis is treated or inhibited.

12. The method of claim 11, wherein the antibody, or antigen-binding fragment thereof, comprises a heavy chain variable region having an amino acid sequence set forth as SEQ ID NO: 88, 89, 90, 91 or 92; and a light chain variable region having an amino acid sequence set forth as SEQ ID NO: 93, 94, 95, 96, 97, 100, 102, or 103.

13. The method of claim 11, wherein the antibody, or antigen-binding fragment thereof, comprises a heavy chain variable region having an amino acid sequence set forth as SEQ ID NO: 89, and a light chain variable region having an amino acid sequence set forth as SEQ ID NO: 94, 95, 96, 97, 100, 102, or 103.

14. The method of claim 11, wherein the fibrosis is a neurofibromatosis that is a neurofibromatosis type 1 or a neurofibromatosis type 2.

15. The method of claim 11, further comprising administering to the subject one or more fibrosis inhibitors.

16. The method of claim 11, wherein the antibody or antigen-binding fragment thereof is administered to the subject in an amount of about 0.01 mg/kg, about 0.05 mg/kg, about 0.1 mg/kg, about 0.5 mg/kg, about 1 mg/kg, about 5 mg/kg, about 10 mg/kg, about 20 mg/kg, about 30 mg/kg, about 40 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, or about 200 mg/kg per subject.

* * * * *

SEQUENCE LISTING

```
<160> NUMBER OF SEQ ID NOS: 126

<210> SEQ ID NO 1
<211> LENGTH: 106
<212> TYPE: PRT
<213> ORGANISM: Mus sp.

<400> SEQUENCE: 1

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105

<210> SEQ ID NO 2
<211> LENGTH: 107
<212> TYPE: PRT
<213> ORGANISM: Homo sapiens
```

```
<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 3
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 4
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

His Trp Tyr Gln Gln Lys Pro Gly Lys Ala Pro Lys Pro Trp Ile Tyr
        35                  40                  45

Ala Thr Ser Asn Leu Ala Ser Gly Val Pro Ser Arg Phe Ser Gly Ser
    50                  55                  60
```

```
Gly Ser Gly Thr Asp Tyr Thr Leu Thr Ile Ser Ser Leu Gln Pro Glu
 65                  70                  75                  80

Asp Phe Ala Thr Tyr Tyr Cys Gln Gln Trp Ser Ser Asn Pro Leu Thr
                 85                  90                  95

Phe Gly Gly Gly Thr Lys Val Glu Ile Lys
            100                 105

<210> SEQ ID NO 5
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Gln Leu Thr Gln Ser Pro Ser Ser Leu Ser Ala Ser Val Gly
 1               5                  10                  15

Asp Arg Val Thr Ile Thr Cys Arg Ala Ser Ser Val Ser Tyr Met
             20                  25                  30

His Trp Tyr Gln Gln Lys Pro Gly Lys Ala Pro Lys Pro Trp Ile Tyr
         35                  40                  45

Ala Thr Ser Asn Leu Ala Ser Gly Val Pro Ser Arg Phe Ser Gly Ser
     50                  55                  60

Gly Ser Gly Thr Asp Tyr Thr Leu Thr Ile Ser Ser Leu Gln Pro Glu
 65                  70                  75                  80

Asp Phe Ala Thr Tyr Tyr Cys Gln Gln Trp Ser Ser Asn Pro Leu Thr
                 85                  90                  95

Phe Gly Gly Gly Thr Lys Val Glu Ile Lys
            100                 105

<210> SEQ ID NO 6
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Ile Gln Met Thr Gln Ser Pro Ser Ser Leu Ser Ala Ser Val Gly
 1               5                  10                  15

Asp Arg Val Thr Ile Thr Cys
             20

<210> SEQ ID NO 7
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Ile Gln Leu Thr Gln Ser Pro Ser Ser Leu Ser Ala Ser Val Gly
 1               5                  10                  15

Asp Arg Val Thr Ile Thr Cys
             20

<210> SEQ ID NO 8
<211> LENGTH: 23
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 8

Gln Ile Gln Met Thr Gln Ser Pro Ser Ser Leu Ser Ala Ser Val Gly
1               5                  10                  15

Asp Arg Val Thr Ile Thr Cys
            20

<210> SEQ ID NO 9
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Ile Val Met Thr Gln Ser Pro Ser Ser Leu Ser Ala Ser Val Gly
1               5                  10                  15

Asp Arg Val Thr Ile Thr Cys
            20

<210> SEQ ID NO 10
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Ile Gln Met Ser Gln Ser Pro Ser Ser Leu Ser Ala Ser Val Gly
1               5                  10                  15

Asp Arg Val Thr Ile Thr Cys
            20

<210> SEQ ID NO 11
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Ile Val Met Ser Gln Ser Pro Ser Ser Leu Ser Ala Ser Val Gly
1               5                  10                  15

Asp Arg Val Thr Ile Thr Cys
            20

<210> SEQ ID NO 12
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Ile Val Leu Thr Gln Ser Pro Ser Ser Leu Ser Ala Ser Val Gly
1               5                  10                  15

Asp Arg Val Thr Ile Thr Cys
```

<210> SEQ ID NO 13
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Ile Val Leu Ser Gln Ser Pro Ser Ser Leu Ser Ala Ser Val Gly
1               5                   10                  15

Asp Arg Val Thr Ile Thr Cys
            20

<210> SEQ ID NO 14
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Ile Gln Leu Ser Gln Ser Pro Ser Ser Leu Ser Ala Ser Val Gly
1               5                   10                  15

Asp Arg Val Thr Ile Thr Cys
            20

<210> SEQ ID NO 15
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Ile Val Met Thr Gln Ser Pro Ser Ser Leu Ser Ala Ser Val Gly
1               5                   10                  15

Asp Arg Val Thr Ile Thr Cys
            20

<210> SEQ ID NO 16
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Ile Gln Leu Thr Gln Ser Pro Ser Ser Leu Ser Ala Ser Val Gly
1               5                   10                  15

Asp Arg Val Thr Ile Thr Cys
            20

<210> SEQ ID NO 17
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 17

Gln Ile Gln Met Ser Gln Ser Pro Ser Ser Leu Ser Ala Ser Val Gly
1               5                   10                  15

Asp Arg Val Thr Ile Thr Cys
            20

<210> SEQ ID NO 18
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Ile Val Leu Thr Gln Ser Pro Ser Ser Leu Ser Ala Ser Val Gly
1               5                   10                  15

Asp Arg Val Thr Ile Thr Cys
            20

<210> SEQ ID NO 19
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Ile Gln Leu Ser Gln Ser Pro Ser Ser Leu Ser Ala Ser Val Gly
1               5                   10                  15

Asp Arg Val Thr Ile Thr Cys
            20

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Trp Tyr Gln Gln Lys Pro Gly Lys Ala Pro Lys Leu Leu Ile Tyr
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Trp Tyr Gln Gln Lys Pro Gly Lys Ala Pro Lys Pro Trp Ile Tyr
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 22

Trp Tyr Gln Gln Lys Pro Gly Lys Ala Pro Lys Pro Leu Ile Tyr
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Trp Tyr Gln Gln Lys Pro Gly Lys Ala Pro Lys Leu Trp Ile Tyr
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Trp Phe Gln Gln Lys Pro Gly Lys Ala Pro Lys Leu Leu Ile Tyr
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Trp Phe Gln Gln Lys Pro Gly Lys Ala Pro Lys Pro Leu Ile Tyr
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Trp Phe Gln Gln Lys Pro Gly Lys Ala Pro Lys Leu Trp Ile Tyr
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Trp Phe Gln Gln Lys Pro Gly Lys Ala Pro Lys Pro Trp Ile Tyr
1               5                   10                  15

<210> SEQ ID NO 28
<211> LENGTH: 32
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 28

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 29
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gly Val Pro Ser Arg Phe Ser Gly Ser Gly Ser Gly Thr Asp Tyr Thr
1               5                   10                  15

Leu Thr Ile Ser Ser Leu Gln Pro Glu Asp Phe Ala Thr Tyr Tyr Cys
            20                  25                  30

<210> SEQ ID NO 30
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gly Val Pro Val Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 31
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gly Val Pro Ala Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 32
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gly Val Pro Val Arg Phe Ser Gly Ser Gly Ser Gly Thr Asp Tyr Thr
1               5                   10                  15

Leu Thr Ile Ser Ser Leu Gln Pro Glu Asp Phe Ala Thr Tyr Tyr Cys
```

<210> SEQ ID NO 33
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gly Val Pro Ala Arg Phe Ser Gly Ser Gly Ser Gly Thr Asp Tyr Thr
1               5                   10                  15

Leu Thr Ile Ser Ser Leu Gln Pro Glu Asp Phe Ala Thr Tyr Tyr Cys
            20                  25                  30

<210> SEQ ID NO 34
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gly Val Pro Ser Arg Phe Ser Gly Ser Gly Ser Gly Thr Ser Phe Thr
1               5                   10                  15

Leu Thr Ile Ser Ser Leu Gln Pro Glu Asp Phe Ala Thr Tyr Tyr Cys
            20                  25                  30

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Phe Gly Gly Gly Thr Lys Val Glu Ile Lys
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Phe Gly Ala Gly Thr Lys Val Glu Ile Lys
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Phe Gly Gly Gly Thr Lys Val Glu Leu Lys
1               5                   10

-continued

```
<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Phe Gly Ala Gly Thr Lys Val Glu Leu Lys
1               5                   10

<210> SEQ ID NO 39
<211> LENGTH: 118
<212> TYPE: PRT
<213> ORGANISM: Mus sp.

<400> SEQUENCE: 39

Glu Val Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
                20                  25                  30

Trp Met Asp Trp Val Arg Gln Ser Pro Glu Lys Gly Leu Glu Trp Val
            35                  40                  45

Ala Glu Ile Arg Ser Lys Ala Ser Asn His Ala Thr Tyr Tyr Ala Glu
        50                  55                  60

Ser Val Lys Gly Arg Phe Thr Ile Ser Arg Asp Asp Ser Lys Ser Ser
65                  70                  75                  80

Val Tyr Leu Gln Met Asn Ser Leu Arg Ala Glu Asp Thr Gly Ile Tyr
                85                  90                  95

Tyr Cys Thr Arg Trp Arg Arg Phe Phe Asp Ser Trp Gly Gln Gly Thr
            100                 105                 110

Thr Leu Thr Val Ser Ser
        115

<210> SEQ ID NO 40
<211> LENGTH: 115
<212> TYPE: PRT
<213> ORGANISM: Homo sapiens

<400> SEQUENCE: 40

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
                20                  25                  30

Trp Met Ser Trp Val Arg Gln Ala Pro Gly Lys Gly Leu Glu Trp Val
            35                  40                  45

Gly Arg Ile Lys Ser Lys Thr Asp Gly Gly Thr Thr Asp Tyr Ala Ala
        50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Tyr Phe Asp Tyr Trp Gly Gln Gly Thr Leu Val Thr
            100                 105                 110

Val Ser Ser
        115

<210> SEQ ID NO 41
```

```
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Gly Glu Ile Arg Ser Lys Ala Ser Asn His Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Trp Arg Arg Phe Phe Asp Ser Trp Gly Gln Gly Thr
            100                 105                 110

Leu Val Thr Val Ser Ser
        115

<210> SEQ ID NO 42
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Gly Glu Ile Arg Ser Lys Ala Ser Asn His Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Arg Trp Arg Arg Phe Phe Asp Ser Trp Gly Gln Gly Thr
            100                 105                 110

Leu Val Thr Val Ser Ser
        115

<210> SEQ ID NO 43
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43
```

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
                20                  25                  30

Trp Met Asp Trp Val Arg Gln Ala Pro Gly Lys Gly Leu Glu Trp Val
            35                  40                  45

Ala Glu Ile Arg Ser Lys Ala Ser Asn His Ala Thr Tyr Tyr Ala Glu
        50                  55                  60

Ser Val Lys Gly Arg Phe Thr Ile Ser Arg Asp Asp Ser Lys Asn Thr
65                  70                  75                  80

Val Tyr Leu Gln Met Asn Ser Leu Lys Thr Glu Asp Thr Ala Val Tyr
                85                  90                  95

Tyr Cys Thr Arg Trp Arg Arg Phe Phe Asp Ser Trp Gly Gln Gly Thr
            100                 105                 110

Leu Val Thr Val Ser Ser
        115
```

<210> SEQ ID NO 44
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
                20                  25                  30
```

<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

```
Trp Val Arg Gln Ala Pro Gly Lys Gly Leu Glu Trp Val Gly
1               5                   10
```

<210> SEQ ID NO 46
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

```
Trp Val Arg Gln Ala Pro Gly Lys Gly Leu Glu Trp Val Ala
1               5                   10
```

<210> SEQ ID NO 47
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Arg Phe Thr Ile Ser Arg Asp Asp Ser Lys Asn Thr Leu Tyr Leu Gln
1               5                   10                  15

Met Asn Ser Leu Lys Thr Glu Asp Thr Ala Val Tyr Tyr Cys Thr Thr
            20                  25                  30

<210> SEQ ID NO 48
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Arg Phe Thr Ile Ser Arg Asp Asp Ser Lys Asn Thr Val Tyr Leu Gln
1               5                   10                  15

Met Asn Ser Leu Lys Thr Glu Asp Thr Ala Val Tyr Tyr Cys Thr Arg
            20                  25                  30

<210> SEQ ID NO 49
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Arg Phe Thr Ile Ser Arg Asp Asp Ser Lys Asn Thr Val Tyr Leu Gln
1               5                   10                  15

Met Asn Ser Leu Lys Thr Glu Asp Thr Ala Val Tyr Tyr Cys Thr Thr
            20                  25                  30

<210> SEQ ID NO 50
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Arg Phe Thr Ile Ser Arg Asp Asp Ser Lys Ser Thr Leu Tyr Leu Gln
1               5                   10                  15

Met Asn Ser Leu Lys Thr Glu Asp Thr Ala Val Tyr Tyr Cys Thr Thr
            20                  25                  30

<210> SEQ ID NO 51
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Arg Phe Thr Ile Ser Arg Asp Asp Ser Lys Asn Arg Leu Tyr Leu Gln
1               5                   10                  15

Met Asn Ser Leu Lys Thr Glu Asp Thr Ala Val Tyr Tyr Cys Thr Thr
            20                  25                  30

<210> SEQ ID NO 52
<211> LENGTH: 32
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 52

Arg Phe Thr Ile Ser Arg Asp Asp Ser Lys Asn Thr Leu Tyr Leu Gln
1               5                   10                  15

Met Ile Ser Leu Lys Thr Glu Asp Thr Ala Val Tyr Tyr Cys Thr Thr
            20                  25                  30

<210> SEQ ID NO 53
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Arg Phe Thr Ile Ser Arg Asp Asp Ser Lys Asn Thr Leu Tyr Leu Gln
1               5                   10                  15

Met Arg Phe Thr Ile Ser Arg Asp Asp Ser Ile Tyr Tyr Cys Thr Thr
            20                  25                  30

<210> SEQ ID NO 54
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Arg Phe Thr Ile Ser Arg Asp Asp Ser Lys Asn Thr Leu Tyr Leu Gln
1               5                   10                  15

Met Arg Phe Thr Ile Ser Arg Asp Asp Ser Leu Tyr Tyr Cys Thr Thr
            20                  25                  30

<210> SEQ ID NO 55
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Arg Phe Thr Ile Ser Arg Asp Asp Ser Lys Asn Thr Leu Tyr Leu Gln
1               5                   10                  15

Met Asn Ser Leu Lys Thr Glu Asp Thr Ala Val Tyr Tyr Cys Thr Gly
            20                  25                  30

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Trp Gly Gln Gly Thr Leu Val Thr Val Ser Ser
1               5                   10
```

```
<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Trp Gly Gln Gly Thr Thr Val Thr Val Ser Ser
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Trp Gly Gln Gly Thr Leu Leu Thr Val Ser Ser
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Trp Gly Gln Gly Thr Leu Val Thr Val Ser Ala
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Trp Gly Gln Gly Thr Thr Val Thr Val Ser Ala
1               5                   10

<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Trp Gly Gln Gly Thr Leu Leu Thr Val Ser Ala
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62
```

Trp Gly Gln Gly Thr Thr Leu Thr Val Ser Ser
1               5                   10

<210> SEQ ID NO 63
<211> LENGTH: 10
<212> TYPE: PRT
<213> ORGANISM: Mus sp.

<400> SEQUENCE: 63

Arg Ala Ser Ser Ser Val Ser Tyr Met His
1               5                   10

<210> SEQ ID NO 64
<211> LENGTH: 7
<212> TYPE: PRT
<213> ORGANISM: Mus sp.

<400> SEQUENCE: 64

Ala Thr Ser Asn Leu Ala Ser
1               5

<210> SEQ ID NO 65
<211> LENGTH: 9
<212> TYPE: PRT
<213> ORGANISM: Mus sp.

<400> SEQUENCE: 65

Gln Gln Trp Ser Ser Asn Pro Leu Thr
1               5

<210> SEQ ID NO 66
<211> LENGTH: 5
<212> TYPE: PRT
<213> ORGANISM: Mus sp.

<400> SEQUENCE: 66

Asp Ala Trp Met Asp
1               5

<210> SEQ ID NO 67
<211> LENGTH: 19
<212> TYPE: PRT
<213> ORGANISM: Mus sp.

<400> SEQUENCE: 67

Glu Ile Arg Ser Lys Ala Ser Asn His Ala Thr Tyr Tyr Ala Glu Ser
1               5                   10                  15

Val Lys Gly

<210> SEQ ID NO 68
<211> LENGTH: 7
<212> TYPE: PRT
<213> ORGANISM: Mus sp.

<400> SEQUENCE: 68

Trp Arg Arg Phe Phe Asp Ser
1               5

<210> SEQ ID NO 69
<211> LENGTH: 107
<212> TYPE: PRT
<213> ORGANISM: Homo sapiens

<400> SEQUENCE: 69

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105
```

<210> SEQ ID NO 70
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Met
            20                  25                  30

His Trp Tyr Gln Gln Lys Pro Gly Gln Ala Pro Arg Leu Leu Ile Tyr
        35                  40                  45

Ala Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Ser Ser Asn Pro Leu Thr
                85                  90                  95

Phe Gly Gly Gly Thr Lys Val Glu Ile Lys
            100                 105
```

<210> SEQ ID NO 71
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Met
            20                  25                  30

His Trp Tyr Gln Gln Lys Pro Gly Gln Ala Pro Arg Pro Trp Ile Tyr
        35                  40                  45

Ala Thr Ser Asn Leu Ala Ser Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80
```

```
Asp Phe Ala Val Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 72
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Met
            20                  25                  30

His Trp Tyr Gln Gln Lys Pro Gly Gln Ala Pro Arg Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 73
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg Tyr Phe Asp Tyr Trp Gly Gln Gly Thr Leu Val Thr
            100                 105                 110

Val Ser Ser
        115

<210> SEQ ID NO 74
<211> LENGTH: 118
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 74

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asp Ala
            20                  25                  30

Trp Met Asp Trp Val Arg Gln Ala Ser Gly Lys Gly Leu Glu Trp Val
        35                  40                  45

Gly Glu Ile Arg Ser Lys Ala Ser Asn His Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg Trp Arg Arg Phe Phe Asp Ser Trp Gly Gln Gly Thr
            100                 105                 110

Leu Val Thr Val Ser Ser
        115
```

<210> SEQ ID NO 75
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asp Ala
            20                  25                  30

Trp Met Asp Trp Val Arg Gln Ala Ser Gly Lys Gly Leu Glu Trp Val
        35                  40                  45

Ala Glu Ile Arg Ser Lys Ala Ser Asn His Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Val Tyr Leu Gln Met Asn Ser Leu Lys Thr Glu Asp Thr Ala Val Tyr
                85                  90                  95

Tyr Cys Thr Arg Trp Arg Arg Phe Phe Asp Ser Trp Gly Gln Gly Thr
            100                 105                 110

Leu Val Thr Val Ser Ser
        115
```

<210> SEQ ID NO 76
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

```
Trp Gly Gln Gly Thr Leu Val Thr Val Ser Ser
1               5                   10
```

<210> SEQ ID NO 77
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Trp Gly Arg Gly Thr Leu Val Thr Val Ser Ser
1               5                   10

<210> SEQ ID NO 78
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Trp Gly Gln Gly Thr Met Val Thr Val Ser Ser
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Trp Gly Gln Gly Thr Thr Val Thr Val Ser Ser
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Phe Gly Gln Gly Thr Lys Val Glu Ile Lys
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Phe Gly Gln Gly Thr Lys Leu Glu Ile Lys
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 82

Phe Gly Pro Gly Thr Lys Val Asp Ile Lys
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Phe Gly Gly Gly Thr Lys Val Glu Ile Lys
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Phe Gly Gln Gly Thr Arg Leu Glu Ile Lys
1               5                   10

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 85

His His His His His His
1               5

<210> SEQ ID NO 86
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Asp or Gln
<220> FEATURE:
<221> NAME/KEY: MOD_RES
<222> LOCATION: (3)..(3)
<223> OTHER INFORMATION: Gln or Val
<220> FEATURE:
<221> NAME/KEY: MOD_RES
<222> LOCATION: (4)..(4)
<223> OTHER INFORMATION: Met or Leu
<220> FEATURE:
<221> NAME/KEY: MOD_RES
<222> LOCATION: (5)..(5)
<223> OTHER INFORMATION: Thr or Ser
<220> FEATURE:
<221> NAME/KEY: MOD_RES
<222> LOCATION: (35)..(35)
<223> OTHER INFORMATION: Tyr or Phe
<220> FEATURE:
<221> NAME/KEY: MOD_RES
<222> LOCATION: (45)..(45)
<223> OTHER INFORMATION: Pro or Leu
```

```
<220> FEATURE:
<221> NAME/KEY: MOD_RES
<222> LOCATION: (46)..(46)
<223> OTHER INFORMATION: Trp or Leu
<220> FEATURE:
<221> NAME/KEY: MOD_RES
<222> LOCATION: (59)..(59)
<223> OTHER INFORMATION: Ser, Val or Ala
<220> FEATURE:
<221> NAME/KEY: MOD_RES
<222> LOCATION: (69)..(69)
<223> OTHER INFORMATION: Asp or Ser
<220> FEATURE:
<221> NAME/KEY: MOD_RES
<222> LOCATION: (70)..(70)
<223> OTHER INFORMATION: Tyr or Phe
<220> FEATURE:
<221> NAME/KEY: MOD_RES
<222> LOCATION: (99)..(99)
<223> OTHER INFORMATION: Gly or Ala
<220> FEATURE:
<221> NAME/KEY: MOD_RES
<222> LOCATION: (105)..(105)
<223> OTHER INFORMATION: Ile or Leu

<400> SEQUENCE: 86

Xaa Ile Xaa Xaa Xaa Gln Ser Pro Ser Ser Leu Ser Ala Ser Val Gly
1               5                   10                  15

Asp Arg Val Thr Ile Thr Cys Arg Ala Ser Ser Val Ser Tyr Met
            20                  25                  30

His Trp Xaa Gln Gln Lys Pro Gly Lys Ala Pro Lys Xaa Xaa Ile Tyr
        35                  40                  45

Ala Thr Ser Asn Leu Ala Ser Gly Val Pro Xaa Arg Phe Ser Gly Ser
50                  55                  60

Gly Ser Gly Thr Xaa Xaa Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Xaa Gly Thr Lys Val Glu Xaa Lys
            100                 105

<210> SEQ ID NO 87
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (49)..(49)
<223> OTHER INFORMATION: Gly or Ala
<220> FEATURE:
<221> NAME/KEY: MOD_RES
<222> LOCATION: (79)..(79)
<223> OTHER INFORMATION: Asn or Ser
<220> FEATURE:
<221> NAME/KEY: MOD_RES
<222> LOCATION: (80)..(80)
<223> OTHER INFORMATION: Thr or Arg
<220> FEATURE:
<221> NAME/KEY: MOD_RES
<222> LOCATION: (81)..(81)
<223> OTHER INFORMATION: Leu or Val
<220> FEATURE:
<221> NAME/KEY: MOD_RES
<222> LOCATION: (86)..(86)
<223> OTHER INFORMATION: Asn or Ile
<220> FEATURE:
<221> NAME/KEY: MOD_RES
<222> LOCATION: (95)..(95)
```

<223> OTHER INFORMATION: Val, Ile or Leu
<220> FEATURE:
<221> NAME/KEY: MOD_RES
<222> LOCATION: (100)..(100)
<223> OTHER INFORMATION: Arg, Thr or Gly
<220> FEATURE:
<221> NAME/KEY: MOD_RES
<222> LOCATION: (113)..(113)
<223> OTHER INFORMATION: Leu or Thr
<220> FEATURE:
<221> NAME/KEY: MOD_RES
<222> LOCATION: (114)..(114)
<223> OTHER INFORMATION: Val or Leu
<220> FEATURE:
<221> NAME/KEY: MOD_RES
<222> LOCATION: (118)..(118)
<223> OTHER INFORMATION: Ser or Ala

<400> SEQUENCE: 87

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Xaa Glu Ile Arg Ser Lys Ala Ser Asn His Ala Thr Tyr Tyr Ala Glu
 50                  55                  60

Ser Val Lys Gly Arg Phe Thr Ile Ser Arg Asp Asp Ser Lys Xaa Xaa
65                  70                  75                  80

Xaa Tyr Leu Gln Met Xaa Ser Leu Lys Thr Glu Asp Thr Ala Xaa Tyr
                85                  90                  95

Tyr Cys Thr Xaa Trp Arg Arg Phe Phe Asp Ser Trp Gly Gln Gly Thr
            100                 105                 110

Xaa Xaa Thr Val Ser Xaa
        115

<210> SEQ ID NO 88
<211> LENGTH: 118
<212> TYPE: PRT
<213> ORGANISM: Artificial Sequence
<220> FEATURE:
<223> OTHER INFORMATION: Description of Artificial Sequence: Synthetic
      VH_v1(A) polypeptide

<400> SEQUENCE: 88

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Ala Glu Ile Arg Ser Lys Ala Ser Asn His Ala Thr Tyr Tyr Ala Glu
 50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Arg Trp Arg Arg Phe Phe Asp Ser Trp Gly Gln Gly Thr
            100                 105                 110

Leu Val Thr Val Ser Ser
        115

```
<210> SEQ ID NO 89
<211> LENGTH: 118
<212> TYPE: PRT
<213> ORGANISM: Artificial Sequence
<220> FEATURE:
<223> OTHER INFORMATION: Description of Artificial Sequence: Synthetic
      VH_v1(A2) polypeptide

<400> SEQUENCE: 89

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Gly Glu Ala Arg Ser Lys Ala Ser Asn His Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Arg Trp Arg Arg Phe Phe Asp Ser Trp Gly Gln Gly Thr
            100                 105                 110

Leu Val Thr Val Ser Ser
        115

<210> SEQ ID NO 90
<211> LENGTH: 118
<212> TYPE: PRT
<213> ORGANISM: Artificial Sequence
<220> FEATURE:
<223> OTHER INFORMATION: Description of Artificial Sequence: Synthetic
      VH_v1(Q) polypeptide

<400> SEQUENCE: 90

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Gly Glu Ile Arg Ser Gln Ala Ser Asn His Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Arg Trp Arg Arg Phe Phe Asp Ser Trp Gly Gln Gly Thr
            100                 105                 110

Leu Val Thr Val Ser Ser
        115

<210> SEQ ID NO 91
<211> LENGTH: 118
<212> TYPE: PRT
<213> ORGANISM: Artificial Sequence
<220> FEATURE:
<223> OTHER INFORMATION: Description of Artificial Sequence: Synthetic
      VH_v1(R) polypeptide
```

-continued

<400> SEQUENCE: 91

```
Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Asp Ala
            20                  25                  30
Trp Met Asp Trp Val Arg Gln Ala Pro Gly Lys Gly Leu Glu Trp Val
        35                  40                  45
Gly Glu Ile Arg Ser Arg Ala Ser Asn His Ala Thr Tyr Tyr Ala Glu
    50                  55                  60
Ser Val Lys Gly Arg Phe Thr Ile Ser Arg Asp Asp Ser Lys Asn Thr
65                  70                  75                  80
Leu Tyr Leu Gln Met Asn Ser Leu Lys Thr Glu Asp Thr Ala Val Tyr
                85                  90                  95
Tyr Cys Thr Arg Trp Arg Arg Phe Phe Asp Ser Trp Gly Gln Gly Thr
            100                 105                 110
Leu Val Thr Val Ser Ser
        115
```

<210> SEQ ID NO 92
<211> LENGTH: 118
<212> TYPE: PRT
<213> ORGANISM: Artificial Sequence
<220> FEATURE:
<223> OTHER INFORMATION: Description of Artificial Sequence: Synthetic
    VH_v1(S) polypeptide

<400> SEQUENCE: 92

```
Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Asp Ala
            20                  25                  30
Trp Met Asp Trp Val Arg Gln Ala Pro Gly Lys Gly Leu Glu Trp Val
        35                  40                  45
Ser Glu Ile Arg Ser Lys Ala Ser Asn His Ala Thr Tyr Tyr Ala Glu
    50                  55                  60
Ser Val Lys Gly Arg Phe Thr Ile Ser Arg Asp Asp Ser Lys Asn Thr
65                  70                  75                  80
Leu Tyr Leu Gln Met Asn Ser Leu Lys Thr Glu Asp Thr Ala Val Tyr
                85                  90                  95
Tyr Cys Thr Arg Trp Arg Arg Phe Phe Asp Ser Trp Gly Gln Gly Thr
            100                 105                 110
Leu Val Thr Val Ser Ser
        115
```

<210> SEQ ID NO 93
<211> LENGTH: 106
<212> TYPE: PRT
<213> ORGANISM: Artificial Sequence
<220> FEATURE:
<223> OTHER INFORMATION: Description of Artificial Sequence: Synthetic
    VK_v1(AA) polypeptide

<400> SEQUENCE: 93

```
Asp Ile Gln Met Thr Gln Ser Pro Ser Ser Leu Ser Ala Ser Val Gly
1               5                   10                  15
Asp Arg Ala Thr Ile Thr Cys Arg Ala Ser Ser Ser Val Ser Tyr Met
            20                  25                  30
His Trp Tyr Gln Gln Lys Pro Gly Lys Ala Pro Lys Pro Trp Ala Tyr
```

```
              35                  40                  45
Ala Thr Ser Asn Leu Ala Ser Gly Val Pro Ser Arg Phe Ser Gly Ser
         50                  55                  60

Gly Ser Gly Thr Asp Tyr Thr Leu Thr Ile Ser Ser Leu Gln Pro Glu
 65                  70                  75                  80

Asp Phe Ala Thr Tyr Tyr Cys Gln Gln Trp Ser Ser Asn Pro Leu Thr
                 85                  90                  95

Phe Gly Gly Gly Thr Lys Val Glu Ile Lys
            100                 105

<210> SEQ ID NO 94
<211> LENGTH: 106
<212> TYPE: PRT
<213> ORGANISM: Artificial Sequence
<220> FEATURE:
<223> OTHER INFORMATION: Description of Artificial Sequence: Synthetic
      VK_v2(AA) polypeptide

<400> SEQUENCE: 94

Asp Ile Gln Leu Thr Gln Ser Pro Ser Ser Leu Ser Ala Ser Val Gly
 1               5                  10                  15

Asp Arg Ala Thr Ile Thr Cys Arg Ala Ser Ser Val Ser Tyr Met
             20                  25                  30

His Trp Tyr Gln Gln Lys Pro Gly Lys Ala Pro Lys Pro Trp Ala Tyr
         35                  40                  45

Ala Thr Ser Asn Leu Ala Ser Gly Val Pro Ser Arg Phe Ser Gly Ser
     50                  55                  60

Gly Ser Gly Thr Asp Tyr Thr Leu Thr Ile Ser Ser Leu Gln Pro Glu
 65                  70                  75                  80

Asp Phe Ala Thr Tyr Tyr Cys Gln Gln Trp Ser Ser Asn Pro Leu Thr
                 85                  90                  95

Phe Gly Gly Gly Thr Lys Val Glu Ile Lys
            100                 105

<210> SEQ ID NO 95
<211> LENGTH: 106
<212> TYPE: PRT
<213> ORGANISM: Artificial Sequence
<220> FEATURE:
<223> OTHER INFORMATION: Description of Artificial Sequence: Synthetic
      VK_v2(AA) polypeptide

<400> SEQUENCE: 95

Asp Ile Gln Leu Thr Gln Ser Pro Ser Ser Leu Ser Ala Ser Val Gly
 1               5                  10                  15

Asp Arg Ala Thr Ile Thr Cys Arg Ala Ser Ser Val Ser Tyr Met
             20                  25                  30

His Trp Tyr Gln Gln Lys Pro Gly Lys Ala Pro Lys Pro Trp Ile Tyr
         35                  40                  45

Ala Ser Ser Asn Leu Ala Ser Gly Val Pro Ser Arg Phe Ser Gly Ser
     50                  55                  60

Gly Ser Gly Thr Asp Tyr Thr Leu Thr Ile Ser Ser Leu Gln Pro Glu
 65                  70                  75                  80

Asp Phe Ala Thr Tyr Tyr Cys Gln Gln Trp Ser Ser Asn Pro Leu Thr
                 85                  90                  95

Phe Gly Gly Gly Thr Lys Val Glu Ile Lys
            100                 105
```

-continued

<210> SEQ ID NO 96
<211> LENGTH: 106
<212> TYPE: PRT
<213> ORGANISM: Artificial Sequence
<220> FEATURE:
<223> OTHER INFORMATION: Description of Artificial Sequence: Synthetic
      VK_v2(SA) polypeptide

<400> SEQUENCE: 96

Asp Ile Gln Leu Thr Gln Ser Pro Ser Leu Ser Ala Ser Val Gly
1               5                   10                  15

Asp Arg Val Thr Ile Ser Cys Arg Ala Ser Ser Val Ser Tyr Met
                20                  25                  30

His Trp Tyr Gln Gln Lys Pro Gly Lys Ala Pro Lys Pro Trp Ala Tyr
            35                  40                  45

Ala Thr Ser Asn Leu Ala Ser Gly Val Pro Ser Arg Phe Ser Gly Ser
        50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 97
<211> LENGTH: 106
<212> TYPE: PRT
<213> ORGANISM: Artificial Sequence
<220> FEATURE:
<223> OTHER INFORMATION: Description of Artificial Sequence: Synthetic
      VK_v2(SS) polypeptide

<400> SEQUENCE: 97

Asp Ile Gln Leu Thr Gln Ser Pro Ser Leu Ser Ala Ser Val Gly
1               5                   10                  15

Asp Arg Val Thr Ile Ser Cys Arg Ala Ser Ser Val Ser Tyr Met
                20                  25                  30

His Trp Tyr Gln Gln Lys Pro Gly Lys Ala Pro Lys Pro Trp Ile Tyr
            35                  40                  45

Ala Ser Ser Asn Leu Ala Ser Gly Val Pro Ser Arg Phe Ser Gly Ser
        50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 98
<211> LENGTH: 330
<212> TYPE: PRT
<213> ORGANISM: Artificial Sequence
<220> FEATURE:
<223> OTHER INFORMATION: Description of Artificial Sequence: Synthetic
      IgG1(m3)_constant_region polypeptide

<400> SEQUENCE: 98

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 99
<211> LENGTH: 107
<212> TYPE: PRT
<213> ORGANISM: Artificial Sequence
<220> FEATURE:
<223> OTHER INFORMATION: Description of Artificial Sequence: Synthetic
      CK_constant_region polypeptide

<400> SEQUENCE: 99

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
```

```
                50                  55                  60
Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

<210> SEQ ID NO 100
<211> LENGTH: 106
<212> TYPE: PRT
<213> ORGANISM: Artificial Sequence
<220> FEATURE:
<223> OTHER INFORMATION: Description of Artificial Sequence: Synthetic
      97 with L4M polypeptide

<400> SEQUENCE: 100

```
Asp Ile Gln Met Thr Gln Ser Pro Ser Ser Leu Ser Ala Ser Val Gly
 1               5                  10                  15

Asp Arg Val Thr Ile Ser Cys Arg Ala Ser Ser Ser Val Ser Tyr Met
                20                  25                  30

His Trp Tyr Gln Gln Lys Pro Gly Lys Ala Pro Lys Pro Trp Ile Tyr
             35                  40                  45

Ala Ser Ser Asn Leu Ala Ser Gly Val Pro Ser Arg Phe Ser Gly Ser
 50                  55                  60

Gly Ser Gly Thr Asp Tyr Thr Leu Thr Ile Ser Ser Leu Gln Pro Glu
 65                  70                  75                  80

Asp Phe Ala Thr Tyr Tyr Cys Gln Gln Trp Ser Ser Asn Pro Leu Thr
                 85                  90                  95

Phe Gly Gly Gly Thr Lys Val Glu Ile Lys
            100                 105
```

<210> SEQ ID NO 101
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

```
Asp Ile Gln Leu Thr Gln Ser Pro Ser Ser Leu Ser Pro Trp Ile Tyr
 1               5                  10                  15

Ala Thr Ser Asn Leu Ala Ser Tyr Thr Leu Thr Ile Ser Ser Leu Gln
                20                  25                  30
```

<210> SEQ ID NO 102
<211> LENGTH: 106
<212> TYPE: PRT
<213> ORGANISM: Artificial Sequence
<220> FEATURE:
<223> OTHER INFORMATION: Description of Artificial Sequence: Synthetic
      95 with L4M polypeptide

<400> SEQUENCE: 102

```
Asp Ile Gln Met Thr Gln Ser Pro Ser Ser Leu Ser Ala Ser Val Gly
 1               5                  10                  15

Asp Arg Ala Thr Ile Thr Cys Arg Ala Ser Ser Ser Val Ser Tyr Met
                20                  25                  30

His Trp Tyr Gln Gln Lys Pro Gly Lys Ala Pro Lys Pro Trp Ile Tyr
             35                  40                  45
```

```
Ala Ser Ser Asn Leu Ala Ser Gly Val Pro Ser Arg Phe Ser Gly Ser
         50                  55                  60

Gly Ser Gly Thr Asp Tyr Thr Leu Thr Ile Ser Ser Leu Gln Pro Glu
 65                  70                  75                  80

Asp Phe Ala Thr Tyr Tyr Cys Gln Gln Trp Ser Ser Asn Pro Leu Thr
                 85                  90                  95

Phe Gly Gly Gly Thr Lys Val Glu Ile Lys
            100                 105

<210> SEQ ID NO 103
<211> LENGTH: 106
<212> TYPE: PRT
<213> ORGANISM: Artificial Sequence
<220> FEATURE:
<223> OTHER INFORMATION: Description of Artificial Sequence: Synthetic
      96 with L4M polypeptide

<400> SEQUENCE: 103

Asp Ile Gln Met Thr Gln Ser Pro Ser Ser Leu Ser Ala Ser Val Gly
 1               5                  10                  15

Asp Arg Val Thr Ile Ser Cys Arg Ala Ser Ser Ser Val Ser Tyr Met
             20                  25                  30

His Trp Tyr Gln Gln Lys Pro Gly Lys Ala Pro Lys Pro Trp Ala Tyr
         35                  40                  45

Ala Thr Ser Asn Leu Ala Ser Gly Val Pro Ser Arg Phe Ser Gly Ser
     50                  55                  60

Gly Ser Gly Thr Asp Tyr Thr Leu Thr Ile Ser Ser Leu Gln Pro Glu
 65                  70                  75                  80

Asp Phe Ala Thr Tyr Tyr Cys Gln Gln Trp Ser Ser Asn Pro Leu Thr
                 85                  90                  95

Phe Gly Gly Gly Thr Lys Val Glu Ile Lys
            100                 105

<210> SEQ ID NO 104
<211> LENGTH: 12
<212> TYPE: PRT
<213> ORGANISM: Influenza A virus

<400> SEQUENCE: 104

Pro Lys Tyr Val Lys Gln Asn Thr Leu Lys Leu Ala
 1               5                  10

<210> SEQ ID NO 105
<211> LENGTH: 15
<212> TYPE: PRT
<213> ORGANISM: Chlamydia sp.

<400> SEQUENCE: 105

Lys Val Val Asp Gln Ile Lys Lys Ile Ser Lys Pro Val Gln His
 1               5                  10                  15

<210> SEQ ID NO 106
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Trp Val Gly Glu Ile Arg Ser Lys Ala Ser Asn His Ala Thr
```

```
1               5                  10
```

<210> SEQ ID NO 107
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

```
Trp Val Gly Glu Ile Arg Ser Gln Ala Ser Asn His Ala Thr
1               5                   10
```

<210> SEQ ID NO 108
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

```
Trp Val Gly Glu Ile Arg Ser Arg Ala Ser Asn His Ala Thr
1               5                   10
```

<210> SEQ ID NO 109
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

```
Trp Val Gly Glu Ala Arg Ser Lys Ala Ser Asn His Ala Thr
1               5                   10
```

<210> SEQ ID NO 110
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

```
Asp Arg Val Thr Ile Thr Cys Arg Ala Ser Ser Ser Val
1               5                   10
```

<210> SEQ ID NO 111
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

```
Asp Arg Val Thr Ile Ser Cys Arg Ala Ser Ser Ser Val
1               5                   10
```

<210> SEQ ID NO 112
<211> LENGTH: 13
<212> TYPE: PRT
<213> ORGANISM: Artificial Sequence
<220> FEATURE:
<223> OTHER INFORMATION: Description of Artificial Sequence: Synthetic

```
                                      peptide

<400> SEQUENCE: 112

Asp Arg Ala Thr Ile Thr Cys Arg Ala Ser Ser Ser Val
1               5                   10

<210> SEQ ID NO 113
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Pro Trp Ile Tyr Ala Thr Ser Asn Leu Ala Ser Gly Val
1               5                   10

<210> SEQ ID NO 114
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Pro Trp Ile Tyr Ala Ser Ser Asn Leu Ala Ser Gly Val
1               5                   10

<210> SEQ ID NO 115
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Pro Trp Ala Tyr Ala Thr Ser Asn Leu Ala Ser Gly Val
1               5                   10

<210> SEQ ID NO 116
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (49)..(49)
<223> OTHER INFORMATION: Gly, Ala or Ser
<220> FEATURE:
<221> NAME/KEY: MOD_RES
<222> LOCATION: (51)..(51)
<223> OTHER INFORMATION: Ala or Ile
<220> FEATURE:
<221> NAME/KEY: MOD_RES
<222> LOCATION: (54)..(54)
<223> OTHER INFORMATION: Lys, Gln or Arg
<220> FEATURE:
<221> NAME/KEY: MOD_RES
<222> LOCATION: (81)..(81)
<223> OTHER INFORMATION: Leu or Val

<400> SEQUENCE: 116

Glu Val Gln Leu Val Glu Ser Gly Gly Gly Leu Val Lys Pro Gly Gly
1               5                   10                  15
```

```
Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Xaa Glu Xaa Arg Ser Xaa Ala Ser Asn His Ala Thr Tyr Tyr Ala Glu
 50              55                  60

Ser Val Lys Gly Arg Phe Thr Ile Ser Arg Asp Asp Ser Lys Asn Thr
 65                  70                  75                  80

Xaa Tyr Leu Gln Met Asn Ser Leu Lys Thr Glu Asp Thr Ala Val Tyr
                 85                  90                  95

Tyr Cys Thr Arg Trp Arg Arg Phe Phe Asp Ser Trp Gly Gln Gly Thr
            100                 105                 110

Leu Val Thr Val Ser Ser
            115

<210> SEQ ID NO 117
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Met or Leu
<220> FEATURE:
<221> NAME/KEY: MOD_RES
<222> LOCATION: (19)..(19)
<223> OTHER INFORMATION: Ala or Val
<220> FEATURE:
<221> NAME/KEY: MOD_RES
<222> LOCATION: (22)..(22)
<223> OTHER INFORMATION: Thr or Ser
<220> FEATURE:
<221> NAME/KEY: MOD_RES
<222> LOCATION: (47)..(47)
<223> OTHER INFORMATION: Ala or Ile
<220> FEATURE:
<221> NAME/KEY: MOD_RES
<222> LOCATION: (50)..(50)
<223> OTHER INFORMATION: Thr or Ser

<400> SEQUENCE: 117

Asp Ile Gln Xaa Thr Gln Ser Pro Ser Ser Leu Ser Ala Ser Val Gly
 1               5                  10                  15

Asp Arg Xaa Thr Ile Xaa Cys Arg Ala Ser Ser Ser Val Ser Tyr Met
            20                  25                  30

His Trp Tyr Gln Gln Lys Pro Gly Lys Ala Pro Lys Pro Trp Xaa Tyr
        35                  40                  45

Ala Xaa Ser Asn Leu Ala Ser Gly Val Pro Ser Arg Phe Ser Gly Ser
 50                  55                  60

Gly Ser Gly Thr Asp Tyr Thr Leu Thr Ile Ser Ser Leu Gln Pro Glu
 65                  70                  75                  80

Asp Phe Ala Thr Tyr Tyr Cys Gln Gln Trp Ser Ser Asn Pro Leu Thr
                 85                  90                  95

Phe Gly Gly Gly Thr Lys Val Glu Ile Lys
            100                 105

<210> SEQ ID NO 118
<211> LENGTH: 34
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 118

Trp Val Ala Glu Ile Arg Ser Lys Ala Ser Asn Val Tyr Leu Gln Met
1               5                   10                  15

Asn Ser Leu Lys Val Tyr Tyr Cys Thr Arg Trp Arg Phe Phe Asp
            20                  25                  30

Ser Trp

<210> SEQ ID NO 119
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 119
gaggtgcagc tggtggagtc tggaggaggc ttagtacagc ctggaagttc cctgaaactc      60
tcatgtgtag cttctggatt cactttcagt aactatggca tgaactggat tcgacaggct    120
ccaaagaagg ggctggaatg gataacattg atttattatg atagtagtaa caagtactat    180
gtagactctg tgaagggtcg attcaccatc tccagagaca attctaagaa caccctgtac    240
ctggaaatga acagtctgag atctgaggac acagccatgt attactgtgc aaaagagggc    300
tgggagctcg gttactttga ttactggggc caaggagtca tggtcacagt ctcctca      357

<210> SEQ ID NO 120
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 120

Glu Val Gln Leu Val Glu Ser Gly Gly Gly Leu Val Gln Pro Gly Ser
1               5                   10                  15

Ser Leu Lys Leu Ser Cys Val Ala Ser Gly Phe Thr Phe Ser Asn Tyr
            20                  25                  30

Gly Met Asn Trp Ile Arg Gln Ala Pro Lys Lys Gly Leu Glu Trp Ile
        35                  40                  45

Thr Leu Ile Tyr Tyr Asp Ser Ser Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Ser Glu Asp Thr Ala Met Tyr Tyr Cys
                85                  90                  95

Ala Lys Glu Gly Trp Glu Leu Gly Tyr Phe Asp Tyr Trp Gly Gln Gly
            100                 105                 110

Val Met Val Thr Val Ser Ser
        115

<210> SEQ ID NO 121
<211> LENGTH: 324
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 121

```
gacatccaga tgacacagtc tcctgcctcc ctgtctgcat ctctggaaga agttgtcacc    60
atcacatgcc aggcaagcca ggacattggt aattccgtat catggtatca gcagaaacca   120
gggaaatctc ctcagttcct gatccatagt gcaaccagct ggcagatgg ggtcccatca    180
aggttcagcg gcagtagatc tggcacacag tattctctca agatcaatag actacaggtt   240
gaagattctg gaatctatta ctgtctacag cattatagta ctccattcac gttcggctca   300
gggacgaagt tggaaataaa acgg                                          324
```

<210> SEQ ID NO 122
<211> LENGTH: 108
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 122

```
Asp Ile Gln Met Thr Gln Ser Pro Ala Ser Leu Ser Ala Ser Leu Glu
1               5                   10                  15
Glu Val Val Thr Ile Thr Cys Gln Ala Ser Gln Asp Ile Gly Asn Ser
            20                  25                  30
Val Ser Trp Tyr Gln Lys Pro Gly Lys Ser Pro Gln Phe Leu Ile
        35                  40                  45
His Ser Ala Thr Ser Leu Ala Asp Gly Val Pro Ser Arg Phe Ser Gly
    50                  55                  60
Ser Arg Ser Gly Thr Gln Tyr Ser Leu Lys Ile Asn Arg Leu Gln Val
65                  70                  75                  80
Glu Asp Ser Gly Ile Tyr Tyr Cys Leu Gln His Tyr Ser Thr Pro Phe
                85                  90                  95
Thr Phe Gly Ser Gly Thr Lys Leu Glu Ile Lys Arg
            100                 105
```

<210> SEQ ID NO 123
<211> LENGTH: 351
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 123

```
caggtgcagc tgcagcaatc tggggctgaa ctagtgaagc ctgggtcctc agtgaaaatt    60
tcctgcaagg cttctggcta cacattcacc agttacgata tgcactggat aaaacagcag   120
cctggaaatg gccttgagtg gattgggtgg atttatcctg gaaatggtaa tactaagtac   180
aatcaaaagt tcaatgggaa ggcaacactc actgcagaca atcctccag cacagcctat   240
atgcagctca gcagcctgac atctgaggac tctgcagtct atttctgtgc aagagggaaa   300
ttcgggggtag gggattactg gggccaagga gtcatggtca cagtctcctc a           351
```

<210> SEQ ID NO 124
<211> LENGTH: 117
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 124

Gln Val Gln Leu Gln Gln Ser Gly Ala Glu Leu Val Lys Pro Gly Ser
1               5                   10                  15

Ser Val Lys Ile Ser Cys Lys Ala Ser Gly Tyr Thr Phe Thr Ser Tyr
                20                  25                  30

Asp Met His Trp Ile Lys Gln Gln Pro Gly Asn Gly Leu Glu Trp Ile
            35                  40                  45

Gly Trp Ile Tyr Pro Gly Asn Gly Asn Thr Lys Tyr Asn Gln Lys Phe
    50                  55                  60

Asn Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Lys Phe Gly Val Gly Asp Tyr Trp Gly Gln Gly Val Met
            100                 105                 110

Val Thr Val Ser Ser
        115

<210> SEQ ID NO 125
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125
gacactgtac tgacccagtc tcctgctttg ctgtgtctc aggagagag ggtttccatc      60 tcctgtaggg ccagtgaagg ggtcaattca tatatgcact ggtaccaaca gaaaccagga    120
cagcaaccca aactcctcat ctatatagca tcaaacctag catctggggt ccctgccagg    180
ttcagtggca gtgggtctgg gacagacttc accctcacca ttgatcctgt ggaggctgat    240
gacactgcaa cctatttctg tcagcagagt tggaatgatc cgtacacgtt tggagctggg    300
accaagctgg aactgaaacg g                                              321

<210> SEQ ID NO 126
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Asp Thr Val Leu Thr Gln Ser Pro Ala Leu Ala Val Ser Pro Gly Glu
1               5                   10                  15

Arg Val Ser Ile Ser Cys Arg Ala Ser Glu Gly Val Asn Ser Tyr Met
                20                  25                  30

His Trp Tyr Gln Gln Lys Pro Gly Gln Gln Pro Lys Leu Leu Ile Tyr
            35                  40                  45

Ile Ala Ser Asn Leu Ala Ser Gly Val Pro Ala Arg Phe Ser Gly Ser
    50                  55                  60

```
-continued

Gly Ser Gly Thr Asp Phe Thr Leu Thr Ile Asp Pro Val Glu Ala Asp
 65                  70                  75                  80

Asp Thr Ala Thr Tyr Phe Cys Gln Gln Ser Trp Asn Asp Pro Tyr Thr
                 85                  90                  95

Phe Gly Ala Gly Thr Lys Leu Glu Leu Lys Arg
                100             105
```